US008623829B2

(12) United States Patent
Tsunoda et al.

(10) Patent No.: US 8,623,829 B2
(45) Date of Patent: Jan. 7, 2014

(54) PEPTIDE VACCINES FOR CANCERS EXPRESSING TUMOR-ASSOCIATED ANTIGENS

(75) Inventors: Takuya Tsunoda, Kawasaki (JP); Ryuji Ohsawa, Kawasaki (JP); Sachiko Yoshimura, Kawasaki (JP)

(73) Assignee: Oncotherapy Science, Inc. (JP)

( * ) Notice: Subject to any disclaimer, the term of this patent is extended or adjusted under 35 U.S.C. 154(b) by 0 days.

(21) Appl. No.: 13/464,831

(22) Filed: May 4, 2012

(65) Prior Publication Data

US 2012/0321649 A1 Dec. 20, 2012

Related U.S. Application Data

(60) Division of application No. 12/542,638, filed on Aug. 17, 2009, now Pat. No. 8,383,590, which is a continuation-in-part of application No. PCT/JP2008/000290, filed on Feb. 21, 2008.

(60) Provisional application No. 60/902,949, filed on Feb. 21, 2007, provisional application No. 61/089,973, filed on Aug. 19, 2008.

(51) Int. Cl.
*A61K 38/00* (2006.01)

(52) U.S. Cl.
USPC ........... 514/19.2; 530/326; 530/327; 530/328

(58) Field of Classification Search
None
See application file for complete search history.

(56) References Cited

U.S. PATENT DOCUMENTS

| 5,525,488 | A | 6/1996 | Mason et al. |
|---|---|---|---|
| 6,664,232 | B1 | 12/2003 | Itoh et al. |
| 6,783,961 | B1 | 8/2004 | Edwards et al. |
| 6,830,885 | B1 | 12/2004 | Lanctot et al. |
| 7,531,300 | B2 | 5/2009 | Nakamura et al. |
| 7,727,714 | B2 | 6/2010 | Nakamura et al. |
| 8,143,228 | B2 | 3/2012 | Mabjeesh |
| 2003/0013649 | A1 | 1/2003 | Rosen et al. |
| 2003/0082758 | A1 | 5/2003 | Rosen et al. |
| 2003/0086934 | A1 | 5/2003 | Botstein et al. |
| 2003/0124579 | A1 | 7/2003 | Mack et al. |
| 2003/0194704 | A1 | 10/2003 | Penn et al. |
| 2003/0232350 | A1 | 12/2003 | Afar et al. |
| 2005/0214836 | A1 | 9/2005 | Nakamura et al. |
| 2005/0259483 | A1 | 11/2005 | Nakamura et al. |
| 2005/0260639 | A1 | 11/2005 | Nakamura et al. |
| 2006/0024692 | A1 | 2/2006 | Nakamura et al. |
| 2006/0093617 | A1 | 5/2006 | Buyse et al. |
| 2006/0105333 | A1 | 5/2006 | Nakamura et al. |
| 2006/0194199 | A1 | 8/2006 | Nakamura et al. |
| 2006/0199179 | A1 | 9/2006 | Nakamura et al. |
| 2007/0014787 | A1 | 1/2007 | Ruben et al. |
| 2007/0015271 | A1 | 1/2007 | Rosen et al. |
| 2007/0253954 | A1 | 11/2007 | Nakamura et al. |
| 2009/0062512 | A1 | 3/2009 | Hildebrand et al. |
| 2009/0162361 | A1 | 6/2009 | Nakamura et al. |
| 2009/0169572 | A1 | 7/2009 | Nakatsuru et al. |
| 2009/0175844 | A1 | 7/2009 | Nakamura et al. |
| 2009/0191211 | A1 | 7/2009 | Nakatsuru et al. |
| 2009/0202576 | A1 | 8/2009 | Tahara et al. |
| 2009/0208514 | A1 | 8/2009 | Nakamura et al. |
| 2009/0215683 | A1 | 8/2009 | Nakamura et al. |
| 2009/0286856 | A1 | 11/2009 | Nakamura et al. |
| 2009/0312264 | A1 | 12/2009 | Itoh et al. |
| 2009/0317392 | A1 | 12/2009 | Nakamura et al. |
| 2010/0009920 | A1 | 1/2010 | Nakamura et al. |
| 2010/0204060 | A1 | 8/2010 | Nakamura et al. |
| 2012/0014996 | A1 | 1/2012 | Nakamura et al. |
| 2012/0264634 | A1 | 10/2012 | Amersdorfer et al. |

FOREIGN PATENT DOCUMENTS

| CN | 1073878 | A | 7/1993 |
|---|---|---|---|
| CN | 1362263 | A | 8/2002 |
| CN | 1469926 | A | 1/2004 |
| CN | 1781934 | A | 6/2006 |
| CN | 1872877 | A | 12/2006 |
| EP | 01/29221 | A2 | 12/1984 |
| EP | 0222491 | A1 | 5/1987 |
| EP | 0546787 | A2 | 6/1993 |
| EP | 1022286 | A1 | 7/2000 |

(Continued)

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Essell (J. NIH Res. 1995 7:46).*
Spitler (Cancer Biotherapy, 1995, 10:1-3).*
Boon (Adv. Can. Res. 1992 58:177-210).*
Burgess et al, Journal of Cell Biology vol. 111 Nov. 1990 2129-2138.*
Lazar et al Molecular and Cellular Biology Mar. 1988 vol. 8 No. 3 1247-1252.*

(Continued)

*Primary Examiner* — Sheela J. Huff
(74) *Attorney, Agent, or Firm* — Kilpatrick Townsend & Stockton LLP

(57) ABSTRACT

The present invention provides peptides having an amino acid sequence as set forth in SEQ ID NO: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288, as well as peptides having the above-mentioned amino acid sequences in which 1, 2, or several (e.g., up to 5) amino acids are substituted, deleted, or added, provided the peptides possess cytotoxic T cell inducibility. The present invention also provides drugs for treating or preventing a disease associated with over-expression of the CDH3, EPHA4, ECT2, HIG2, INHBB, KIF20A, KNTC2, TTK and/or URLC10, e.g. cancers containing as an active ingredient one or more of these peptides. The peptides of the present invention find further utility as vaccines.

4 Claims, 20 Drawing Sheets

(56) References Cited

FOREIGN PATENT DOCUMENTS

| | | |
|---|---|---|
| EP | 1757306 A1 | 2/2007 |
| EP | 1972639 A2 | 9/2008 |
| EP | 1983003 A2 | 10/2008 |
| EP | 2080812 A1 | 7/2009 |
| RU | 2283130 C2 | 9/2006 |
| TW | 2005/02247 | 1/2005 |
| WO | 95/28484 A1 | 10/1995 |
| WO | 98/45433 A1 | 10/1998 |
| WO | 01/29221 A | 4/2001 |
| WO | 01/44291 A2 | 6/2001 |
| WO | 01/62776 | 8/2001 |
| WO | 01/64835 A2 | 9/2001 |
| WO | 01/72295 A2 | 10/2001 |
| WO | 02/08765 | 1/2002 |
| WO | 02/30268 | 4/2002 |
| WO | 02/078524 A2 | 10/2002 |
| WO | WO 02/086443 A2 | 10/2002 |
| WO | 02/102235 A2 | 12/2002 |
| WO | 03/080640 A1 | 10/2003 |
| WO | WO 2004/001072 A2 | 12/2003 |
| WO | WO 2004/007770 A2 | 1/2004 |
| WO | WO 2004/024952 A1 | 3/2004 |
| WO | 2004/030615 | 4/2004 |
| WO | WO 2004/031410 A2 | 4/2004 |
| WO | WO 2004/031412 A2 | 4/2004 |
| WO | WO 2004/031413 A2 | 4/2004 |
| WO | WO 2004/031414 A2 | 4/2004 |
| WO | 2004/055050 A2 | 7/2004 |
| WO | 2004/058153 A2 | 7/2004 |
| WO | 2005/001138 | 1/2005 |
| WO | 2005/016962 A2 | 2/2005 |
| WO | 2005/109258 A2 | 3/2005 |
| WO | WO 2005/019475 A2 | 3/2005 |
| WO | WO 2005/028676 A2 | 3/2005 |
| WO | WO 2005/083086 A2 | 9/2005 |
| WO | WO 2005/090572 A2 | 9/2005 |
| WO | 2005/097189 A1 | 10/2005 |
| WO | 2005/118626 A2 | 12/2005 |
| WO | 2006/038208 A2 | 4/2006 |
| WO | 2006/058496 A1 | 6/2006 |
| WO | 2005/091734 A2 | 8/2006 |
| WO | WO 2006/085684 A2 | 8/2006 |
| WO | WO 2006/090810 A2 | 8/2006 |
| WO | 2006/093337 | 9/2006 |
| WO | 2007/018047 A1 | 2/2007 |
| WO | WO 2007/013480 A2 | 2/2007 |
| WO | WO 2007/013575 A2 | 2/2007 |
| WO | WO 2007/013665 A2 | 2/2007 |
| WO | WO 2007/013671 A2 | 2/2007 |
| WO | 2007/064743 A2 | 6/2007 |
| WO | WO 2007/102383 A1 | 9/2007 |
| WO | WO 2007/102525 A1 | 9/2007 |
| WO | 2007121147 A1 | 10/2007 |
| WO | 2007/150077 A2 | 12/2007 |
| WO | WO 2008/072777 A2 | 6/2008 |
| WO | WO 2008/102557 A1 | 8/2008 |
| WO | WO 2008/102906 A1 | 8/2008 |
| WO | WO 2009/016691 A1 | 2/2009 |
| WO | WO 2009/025116 A1 | 2/2009 |
| WO | 2010/021112 A1 | 2/2010 |
| WO | 2011/039289 A1 | 4/2011 |

OTHER PUBLICATIONS

Adams, et al., "Prediction of binding to MHC class I molecules," *J Immunol Methods*, vol. 185(2), pp. 181-190 (Sep. 25, 1995).

Ashida, S., et al., "Molecular Features of the Transition from Prostatic Intraepithelial Neoplasia (PIN) to Prostate Cancer: Genome-wide Gene-expression Profiles of Prostate Cancers and PINs," *Cancer Research*, vol. 64(17), pp. 5963-5972 (Sep. 1, 2004).

Bachinsky, et al., "Mapping and binding analysis of peptides derived from the tumor-associated antigen survivin for eight HLA alleles," *Cancer Immun.*, vol. 5:6. 9 pages (Mar. 22, 2005).

Belli, et al., "Vaccination of Metastatic Melanoma Patients With Autologous Tumor-Derived Heat Shock Protein gp96-Peptide Complexes: Clinical and Immunologic Findings," *J Clin. Oncol.*, vol. 20(20), pp. 4169-4180 (Oct. 15, 2002).

Belokoneva, "Immunity Retro Style," *Science and Life*, No. 1, pp. 45-48 (2004).

Bienz, M., et al., "Linking Colorectal Cancer to Wnt Signaling," *Cell*, vol. 103(2), pp. 311-320 (Oct. 13, 2000).

Boon, "Tumor Antigens Recognized by Cytolytic T Lymphocytes: Present Perspectives for Specific Immunotherapy," *Int J Cancer*, vol. 54(2), pp. 177-180 (May 8, 1993).

Boon, et al., "Human Tumor Antigens Recognized by T Lymphocytes," *J Exp Med.*, vol. 183(3), pp. 725-729 (Mar. 1, 1996).

Brown et al., "Activins are Critical Modulators of Growth and Survival," 2003, *Mol. Endocrinol*, 17, pp. 2404-2417.

Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).

Coulie, et al, "Cytolytic T-cell responses of cancer patients vaccinated with a MAGE antigen," *Immunol Rev.*, vol. 188, pp. 33-42 (Oct. 2002).

Fujie, et al., "A Mage-1 Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).

GenBank Accession No. EAW83239.1, 3 pgs., downloaded from http://www.ncbi.nlm.nih.gov/protein/EAW83239.1 (Dec. 18, 2006).

Gross, D., et al., "High vaccination efficiency of low-affinity epitopes in antitumor immunotherapy," *J. Clin. Invest.*, vol. 113(3), pp. 425-433 (Feb. 2004.

Harada, M., et al., "Kinesin superfamily protein-derived peptides with the ability to induce glioma-reactive cytotoxic T lymphocytes in human leukocyte antigen-A24+ glioma patients," *Oncology Reports*, vol. 17(3), pp. 629-636 (Mar. 2007).

Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).

Hoffman, et al., "The Ability of Variant Peptides to Reverse the Nonresponsiveness of T Lymphocytes to the Wild-Type Sequence p53264-272 Epitope," *J Immunol.*, vol. 168(3), pp. 1338-1347 (Feb. 1, 2002).

Hung, et al., "Molecular profiling of bladder cancer: Involvement of the TGF-β pathway in bladder cancer progression," *Cancer Lett.*, vol. 265(1), pp. 27-38 (Jun. 28, 2008, Epub May 13, 2008).

Ishikawa, N., et al., "Cancer-Testis Antigen Lymphocyte Antigen 6 Complex Locus K Is a Serologic Biomarker and a Therapeutic Target for Lung and Esophageal Carcinomas," *Cancer Res.*, vol. 67(24), pp. 11601-11611 (Dec. 15, 2007).

Kikuchi, et al., "Identification of a SART-1-Dervied Peptide Capable of Inducing HLA-A24-Restricted and Tumor-Specific Cytotoxic T Lymphocytes," *Int J Cancer*, vol. 81(3), pp. 459-466 (May 5, 1999).

Kondo, A., et al., "Prominent Roles of Secondary Anchor Residues in Peptide Binding to HLA-A24 Human Class I Molecules," *J. Immunol.*, vol. 155(9), pp. 4307-4312 (Nov. 1, 1995).

Kubo, R., et al., "Definition of Specific Peptide Motifs for Four Major HLA-A Alleles," *J. Immunol.*, vol. 152(8), pp. 3913-3924 (Apr. 15, 1994).

Kuzushima, et al., "Efficient identification of HLA-A*2402-restricted cytomegalovirus-specific CD8+ T-cell epitopes by a computer algorithm and an enzyme-linked immunospot assay," *Blood*, vol. 98(6), pp. 1872-1881 (Sep. 15, 2001).

Lin, Y.-M., et al., "Molecular diagnosis of colorectal tumors by expression profiles of 50 genes expressed differentially in adenomas and carcinomas," *Oncogene*, vol. 21(26), pp. 4120-4128 (Jun. 13, 2002).

Mylonas, et al., "Inhibin/activin subunits beta-A (-βA) and beta-B (-βB) are differentially localised in normal, hyperplastic and malignant human endometrial tissue," *Acta Histochem.*, vol. 108(1), pp. 1-11 (2006, Epub Jan. 19, 2006).

Oiso, et al., "A Newly Identified Mage-3-Dervied Epitope Recognized by HLA-A24-Restricted Cytotoxic T Lymphocytes," *Int J Cancer*, vol. 81(3), pp. 387-394 (May 5, 1999).

Okabe, H., et al., "Genome-wide Analysis of Gene Expression in Human Hepatocellular Carcinomas Using cDNA Microarray: Identification of Genes Involved in Viral Carcinogenesis and Tumor Progression," *Cancer Res.*, vol. 61(5), pp. 2129-2137 (Mar. 1, 2001).

(56) References Cited

OTHER PUBLICATIONS

Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).
Protein Sequence Analysis, http://vitalonic.narod.ru/biochem/index.html (English Translation at http://molbiol.ru/eng/scripts/01_18.html) (2006).
Protocol of Oral Hearing issued in related Russian Application No. 2009135020/10(049325) based on International Patent Application No. PCT/JP2008/000290, filed Feb. 21, 2008.
Robertson et al, "Inhibin/activin and ovarian cancer," 2004, *Endocr. Relat. Cancer*, 11, pp. 35-49.
Rosenberg, et al., "Cancer immunotherapy: moving beyond current vaccines," *Nat Med.*, vol. 10(9), pp. 909-915 (Sep. 2004).
Schueler-Furman, et al., "Structure-based prediction of binding peptides to MHC class I molecules: Application to a broad range of MHC alleles," *Protein Sci.*, vol. 9(9), pp. 1838-1846 (Sep. 2000).
Stevanovic, et al., "Identification of Tumour-Associated T-Cell Epitopes for Vaccine Development," *Nat Rev Cancer*, vol. 2(7), pp. 514-520 (Jul. 2002).
Suda, T., et al., "Identification of human leukocyte antigen-A24-restricted epitope peptides derived from gene products upregulated in lung and esophageal cancers as novel targets for immunotherapy," *Cancer Science*, vol. 98(11), pp. 1803-1808 (Nov. 2007).
Suda, T., et al., "Identification of secernin 1 as a novel immunotherapy target for gastric cancer using the expression profiles of cDNA microarray," *Cancer Science*, vol. 97(5), pp. 411-419 (May 2006).
Supplementary European Search Report issued on Jan. 30, 2012, filed in related European Patent Application No. EP09808047.
Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).
U.S. Appl. No. 11/913,147, filed Oct. 30, 2007, 239 pgs.
U.S. Appl. No. 12/671,447, filed Jul. 6, 2010, 103 pgs.
U.S. Appl. No. 12/673,451, filed Feb. 2, 2010, 131 pgs.
U.S. Appl. No. 12/903,961, filed Oct. 13, 2010, 46 pgs.
U.S. Appl. No. 13/001,869, which is a U.S. National Phase of PCT/JP2009/003009, filed Jun. 30, 2009, 63 pgs.
U.S. Appl. No. 13/002,977, filed Sep. 16, 2011, 66 pages.
U.S. Appl. No. 13/059,617, 44 pages, filed Jun. 16, 2011.
U.S. Appl. No. 13/059,617, filed Jun. 16, 2011, 39 pages.
U.S. Appl. No. 13/059,618, filed Jun. 9, 2011, 43 pages.
U.S. Appl. No. 13/080,461, filed Apr. 5, 2011, 75 pgs.
U.S. Appl. No. 13/125,548, filed Jul. 6, 2011, 54 pages.
U.S. Appl. No. 13/224,102, filed Sep. 1, 2011, 82 pages.
U.S. Appl. No. 13/246,639, filed Sep. 27, 2011, 164 pages.
U.S. Appl. No. 13/320,022, which is a U.S. National Stage of PCT/JP2010/003166, filed May 10, 2010, 66 pages.
U.S. Appl. No. 13/464,831, 162 pages, filed May 4, 2012.
U.S. Appl. No. 13/519,127, which is a U.S. National Stage of PCT/JP2009/007333, 59 pages, filed Dec. 28, 2009.
Van Der Burg, et al., "Immunogenicity of Peptides Bound to MHC Class I Molecules Depends on the MHC-Peptide Complex Stability," *J Immunol.*, vol. 156(9), pp. 3308-3314 (May 1, 1996).
Vissers, et al., "The Renal Cell Carcinoma-associated Antigen G250 Encodes a Human Leukocyte Antigen (HLA)-A2.1-restricted Epitope Recognized by a Cytotoxic T Lymphocytes," *Cancer Res.*, vol. 59(21), pp. 5554-5559 (Nov. 1, 1999).
Worbs, et al., "Expression of the inhibin/activin subunits (-α, -βA, and -βB) in normal and carcinogenic endometrial tissue: Possible immunohistochemical differentiation markers," *Oncol Rep.*, vol. 17(1), pp. 97-104 (Jan. 2007).
Ying, et al., "Synthesis of Human Inhibin βB Fragments, Preparation and Generation of Monoclonal Antibodies Against Human Inhibin βB Subunits," Yao Hsueh Hsueh Pao—*Acta Pharmaceutica* Sinica, Yao Xuebao, CN, vol. 35(7), pp. 505-507 (Jul. 1, 2000).

Zaremba, S., et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).
Allan, et al., "Membrane motors," *Curr Opin Cell Biol.*, vol. 11(4), pp. 476-482 (Aug. 1999).
Andre, et al., "Exosomes as Potent Cell-Free Peptide-Based Vaccine. I. Dendritic Cell-Derived Exosomes Transfer Functional MHC Class I/Peptide Complexes to Dendritic Cells," *J Immunol.*, vol. 172(4), pp. 2126-2136 (Feb. 15, 2004).
Dionne, et al., "Her-2/*neu* altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).
Echard, et al., "Interaction of a Golgi-Associated Kinesin-Like Protein with Rab6," et al., *Science*, vol. 279(5350), pp. 580-585 (Jan. 23, 1998).
Eloubeidi, et al., "Prognostic factors for survival in pancreatic cancer: a population-based study," *Am J Surg.*, vol. 192(3), pp. 322-329 (Sep. 2006).
Escudier, et al., "Vaccination of metastatic melanoma patients with autologous dendritic cell (DC) derived-exosomes: results of the first phase I clinical trial," *J Transl Med.*, vol. 3(1):10, 13 pages (Mar. 2, 2005).
Falk, et al., "Allele-specific motifs revealed by sequencing of self-peptide eluted from MHC molecules," *Nature*, vol. 351(6324), pp. 290-296 (May 23, 1991).
Goonetilleke, et al., "Nationwide questionnaire survey of the contemporary surgical management of pancreatic cancer in the United Kingdom &* Ireland," *Int J Surg.*, vol. 5(3), pp. 147-151 (Jun. 2007, Epub Oct. 24, 2006).
Hirokawa, et al., "Kinesin and dynein superfamily proteins in organelle transport and cell division," *Curr Opin Cell Biol.*, vol. 10(1), pp. 60-73 (Feb. 1998).
Hoffman, et al., "The Ability of Variant Peptides to Reverse the Nonresponsiveness of T Lymphocytes to the Wild-type Sequence $p53_{264-272}$ Epitope," *J Immunol.*, vol. 168(3), pp. 1338-1347 (Feb. 1, 2002).
Imai, et al., "Identification of a novel tumor-associated antigen, RAB6KIFL, as a candidate of target for immunotherapy of pancreatic cancer," *Abstract of the Annual Meeting of the Japanese Society of Immunology*, #1-H-W15-1-0/P, vol. 38, p. 101 (2008).
Lockhart, et al., "Treatment for Pancreatic Cancer: Current Therapy and Continued Progress," *Gastroenterology*, vol. 128(6), pp. 1642-1654 (May 2005).
Rammensee, et al., "MHC ligands and peptide motifs: first listing," *Immunogenetics*, vol. 41(4), pp. 178-228 (1995).
Sener, et al., "Pancreatic Cancer: A Report of Treatment and Survival Trends for 100,313 Patients Diagnosed from 1985-1995, Using the National Cancer Database," *J Am Coll Surg.*, vol. 189(1), pp. 1-7 (Jul. 1999).
Smeenk, et al., "Survival after surgical management of pancreatic adenocarcinoma: does curative and radical surgery truly exist?" *Langenbecks Arch Surg.*, vol. 390(2), pp. 94-103 (Apr. 2005, Epub May 14, 2004).
Taniuchi, et al., "Identification and functional analysis of RAB6KIFL Up-regulated in pancreatic cancer," *Abstract of the Annual Meeting of the Japanese Cancer Association*, W-135, vol. 63, p. 79 (2004).
Taniuchi, et al., "Down-regulation of RAB6KIFL/KIF20A, a Kinesin Involved with Membrane Trafficking of Discs Large Homologue 5, Can Attenuate Growth of Pancreatic Cancer," *Cancer Res.*, vol. 65(1), pp. 105-112 (Jan. 1, 2005).
Yeo, et al., "Pancreaticoduodenectomy for Cancer of the Head of the Pancreas," *Ann Surg.*, vol. 221(6), pp. 721-731, discussion pp. 731-733 (Jun. 1995).
U.S. Appl. No. 13/536,327, 204 pages, filed Jun. 28, 2012.
Decision on Grant of Russian Patent Application No. 2009135020/10, 8 pages, application filed on Feb. 21, 2008.
U.S. Appl. No. 13/638,272, which is a U.S. National Stage of PCT/JP2011/001909, filed Mar. 30, 2011, 70 pages.
Kono, et al., "Multicenter, phase II clinical trial of cancer vaccination for advanced esophageal cancer with three peptides derived from novel cancer-testis antigens," *J Transl Med.*, vol. 10:141, 9 pages (Jul. 9, 2012).

(56) References Cited

OTHER PUBLICATIONS

De Nooij-Van, et al., "Characterization of the Human LY-6 Antigens, the Newly Annotated Member LY-6K Included, As Molecular Markers for Head-and-Neck Squamous Cell Carcinoma," *Int J Cancer*, vol. 103(6), pp. 768-774 (Mar. 1, 2003).

Dionne, et al., "Functional characterization of CTL against gp100 altered peptide ligands," *Cancer Immunol Immunother.*, vol. 52(4), pp. 199-206 (Apr. 2003, Epub Feb. 18, 2003).

Ishizaki, et al., "Inhibition of Tumor Growth with Antiangiogenic Cancer Vaccine Using Epitope Peptides Derived from Human Vascular Endothelial Growth Factor Receptor 1," *Clin Cancer Res.*, vol. 12(19), pp. 5841-5849 (Oct. 1, 2006).

Kono, et al. "Vaccination with multiple peptides derived from novel cancer-testis antigens can induce specific T-cell responses and clinical responses in advanced esophageal cancer," *Cancer Sci.*, vol. 100(8), pp. 1502-1509 (Aug. 2009, Epub May. 14, 2009).

Tahara, et al., "Translation Research of cancer vaccine therapy by novel antigen peptides," *Japanese Cancer Association Symposium* (Feb. 7, 2006).

Tsunoda, et al., "Phase I clinical trial of epitope peptides based vaccine with novel tumor associate antigen, RNF43 and URLC10, found by genome-wide exploration using cDNA Microarray Profiling (GET-MAP) against colorectal cancer and esophageal cancer patients," *Annual Report 2005, Institute of Medical Science, University of Tokyo*, No. 5, p. 247 (2006).

Extended European Search Report for European Application No. 12175482.4, 5 pages, dated Jul. 31, 2013.

Extended European Search Report for European Application No. 12175487.3, 6 pages, dated Aug. 7, 2013.

Extended European Search Report mailed on Sep. 23, 2013 for European Application No. EP12175488.1 15 pages.

Komori et al., "Identification of HLA-A2- or HLA-A24-Restricted CTL Eptitopes Possibly Useful for Flypican-3-Specific Immunotherapy of Hepatocellular Carcinoma", 2006; *Clin Cancer Res*; vol. 12, pp. 2689-2697.

Hayama, S., et al., "Activation of CDCA1-KNTC2, Members of Centromere Protein Complex, Involved in Pulmonary Carcinogenesis," *Cancer Research*, Vol. 66 (21), pp.10339-10348 (Nov. 1, 2006).

\* cited by examiner a  CDH3-A24-10-248 b  CDH3-A24-10-332 c  CDH3-A24-10-470 d  CDH3-A24-9-513 e  CDH3-A24-9-406 f  HIG2-A24-10-7
CTL line

HIG2-A24-10-7 #7 LD#134
HIG2-A24-10-7 #7 g  HIG2-A24-10-18
CTL line

HIG2-A24-18-7 #7 LD#63 h  HIG2-A02-9-15
CTL line

HIG2-A02-9-15 (Endo assay- COS7)

d  INHBB-A24-10-305 e INHBB-A24-10-7 f INHBB-A24-10-212 a TTK-A02-9-278 b TTK-A02-9-462

TTK-A02-9-462 LD#4-72

TTK-A02-9-462 LD#4-56

TTK-A02-9-462 Endo assay – COS7 transfectant

TTK-A02-9-719 Endo assay – COS7 transfectant c TTK-A02-9-719

CTL clone LD#6 a URLC10-A02-9-58 b URLC10-A02-9-206    c URLC10-A02-9-212 d URLC10-A02-10-211

Continuation of d
CTL line stimulated by URLC10-A02-10-211 recognized endogenously URLC10 expressed target cells with HLA-A02

INHBB-A02 ELISPOT data

INHBB-A02 CTL line

SEQUENCE LISTING

```
<160> NUMBER OF SEQ ID NOS: 436

<210> SEQ ID NO 1
<211> LENGTH: 3649
<212> TYPE: DNA
<213> ORGANISM: Homo sapiens
<220> FEATURE:
<221> NAME/KEY: CDS
<222> LOCATION: (508)..(2997)

<400> SEQUENCE: 1
cccgctgtag ccgcgtgtgg gaggacgcac gggcctgctt caaagctttg ggataacagc      60
gcctccgggg gataatgaat gcggagcctc cgttttcagt cgacttcaga tgtgtctcca     120
cttttttccg ctgtagccgc aaggcaagga aacatttctc ttcccgtact gaggaggctg     180
aggagtgcac tgggtgttct tttctcctct aacccagaac tgcgagacag aggctgagtc     240
cctgtaaaga acagctccag aaaagccagg agagcgcagg agggcatccg ggaggccagg     300
aggggttcgc tggggcctca accgcaccca catcggtccc acctgcgagg gggcgggacc     360
tcgtggcgct ggaccaatca gcacccacct gcgctcacct ggcctcctcc cgctggctcc     420
cgggggctgc ggtgctcaaa ggggcaagag ctgagcggaa caccggcccg ccgtcgcggc     480
agctgcttca cccctctctc tgcagcc atg ggg ctc cct cgt gga cct ctc gcg     534
                              Met Gly Leu Pro Arg Gly Pro Leu Ala
                               1               5 tct ctc ctc ctt ctc cag gtt tgc tgg ctg cag tgc gcg gcc tcc gag     582
Ser Leu Leu Leu Leu Gln Val Cys Trp Leu Gln Cys Ala Ala Ser Glu
 10                  15                  20                  25 ccg tgc cgg gcg gtc ttc agg gag gct gaa gtg acc ttg gag gcg gga     630
Pro Cys Arg Ala Val Phe Arg Glu Ala Glu Val Thr Leu Glu Ala Gly
                 30                  35                  40 ggc gcg gag cag gag ccc ggc cag gcg ctg ggg aaa gta ttc atg ggc     678
Gly Ala Glu Gln Glu Pro Gly Gln Ala Leu Gly Lys Val Phe Met Gly
             45                  50                  55 tgc cct ggg caa gag cca gct ctg ttt agc act gat aat gat gac ttc     726
Cys Pro Gly Gln Glu Pro Ala Leu Phe Ser Thr Asp Asn Asp Asp Phe
         60                  65                  70 act gtg cgg aat ggc gag aca gtc cag gaa aga agg tca ctg aag gaa     774
Thr Val Arg Asn Gly Glu Thr Val Gln Glu Arg Arg Ser Leu Lys Glu
     75                  80                  85 agg aat cca ttg aag atc ttc cca tcc aaa cgt atc tta cga aga cac     822
Arg Asn Pro Leu Lys Ile Phe Pro Ser Lys Arg Ile Leu Arg Arg His
 90                  95                 100                 105
```

```
aag aga gat tgg gtg gtt gct cca ata tct gtc cct gaa aat ggc aag      870
Lys Arg Asp Trp Val Val Ala Pro Ile Ser Val Pro Glu Asn Gly Lys
            110                 115                 120 ggt ccc ttc ccc cag aga ctg aat cag ctc aag tct aat aaa gat aga      918
Gly Pro Phe Pro Gln Arg Leu Asn Gln Leu Lys Ser Asn Lys Asp Arg
125                 130                 135 gac acc aag att ttc tac agc atc acg ggg ccg ggg gca gac agc ccc      966
Asp Thr Lys Ile Phe Tyr Ser Ile Thr Gly Pro Gly Ala Asp Ser Pro
        140                 145                 150 cct gag ggt gtc ttc gct gta gag aag gag aca ggc tgg ttg ttg ttg     1014
Pro Glu Gly Val Phe Ala Val Glu Lys Glu Thr Gly Trp Leu Leu Leu
            155                 160                 165 aat aag cca ctg gac cgg gag gag att gcc aag tat gag ctc ttt ggc     1062
Asn Lys Pro Leu Asp Arg Glu Glu Ile Ala Lys Tyr Glu Leu Phe Gly
170                 175                 180                 185 cac gct gtg tca gag aat ggt gcc tca gtg gag gac ccc atg aac atc     1110
His Ala Val Ser Glu Asn Gly Ala Ser Val Glu Asp Pro Met Asn Ile
                190                 195                 200 tcc atc atc gtg acc gac cag aat gac cac aag ccc aag ttt acc cag     1158
Ser Ile Ile Val Thr Asp Gln Asn Asp His Lys Pro Lys Phe Thr Gln
            205                 210                 215 gac acc ttc cga ggg agt gtc tta gag gga gtc cta cca ggt act tct     1206
Asp Thr Phe Arg Gly Ser Val Leu Glu Gly Val Leu Pro Gly Thr Ser
        220                 225                 230 gtg atg cag gtg aca gcc acg gat gag gat gat gcc atc tac acc tac     1254
Val Met Gln Val Thr Ala Thr Asp Glu Asp Asp Ala Ile Tyr Thr Tyr
235                 240                 245 aat ggg gtg gtt gct tac tcc atc cat agc caa gaa cca aag gac cca     1302
Asn Gly Val Val Ala Tyr Ser Ile His Ser Gln Glu Pro Lys Asp Pro
250                 255                 260                 265 cac gac ctc atg ttc acc att cac cgg agc aca ggc acc atc agc gtc     1350
His Asp Leu Met Phe Thr Ile His Arg Ser Thr Gly Thr Ile Ser Val
                270                 275                 280 atc tcc agt ggc ctg gac cgg gaa aaa gtc cct gag tac aca ctg acc     1398
Ile Ser Ser Gly Leu Asp Arg Glu Lys Val Pro Glu Tyr Thr Leu Thr
            285                 290                 295 atc cag gcc aca gac atg gat ggg gac ggc tcc acc acc acg gca gtg     1446
Ile Gln Ala Thr Asp Met Asp Gly Asp Gly Ser Thr Thr Thr Ala Val
        300                 305                 310 gca gta gtg gag atc ctt gat gcc aat gac aat gct ccc atg ttt gac     1494
Ala Val Val Glu Ile Leu Asp Ala Asn Asp Asn Ala Pro Met Phe Asp
315                 320                 325 ccc cag aag tac gag gcc cat gtg cct gag aat gca gtg ggc cat gag     1542
Pro Gln Lys Tyr Glu Ala His Val Pro Glu Asn Ala Val Gly His Glu
330                 335                 340                 345 gtg cag agg ctg acg gtc act gat ctg gac gcc ccc aac tca cca gcg     1590
Val Gln Arg Leu Thr Val Thr Asp Leu Asp Ala Pro Asn Ser Pro Ala
                350                 355                 360 tgg cgt gcc acc tac ctt atc atg ggc ggt gac gac ggg gac cat ttt     1638
Trp Arg Ala Thr Tyr Leu Ile Met Gly Gly Asp Asp Gly Asp His Phe
            365                 370                 375 acc atc acc acc cac cct gag agc aac cag ggc atc ctg aca acc agg     1686
Thr Ile Thr Thr His Pro Glu Ser Asn Gln Gly Ile Leu Thr Thr Arg
        380                 385                 390 aag ggt ttg gat ttt gag gcc aaa aac cag cac acc ctg tac gtt gaa     1734
Lys Gly Leu Asp Phe Glu Ala Lys Asn Gln His Thr Leu Tyr Val Glu
395                 400                 405 gtg acc aac gag gcc cct ttt gtg ctg aag ctc cca acc tcc aca gcc     1782
Val Thr Asn Glu Ala Pro Phe Val Leu Lys Leu Pro Thr Ser Thr Ala
410                 415                 420                 425
```

```
acc ata gtg gtc cac gtg gag gat gtg aat gag gca cct gtg ttt gtc     1830
Thr Ile Val Val His Val Glu Asp Val Asn Glu Ala Pro Val Phe Val
            430                 435                 440 cca ccc tcc aaa gtc gtt gag gtc cag gag ggc atc ccc act ggg gag     1878
Pro Pro Ser Lys Val Val Glu Val Gln Glu Gly Ile Pro Thr Gly Glu
            445                 450                 455 cct gtg tgt gtc tac act gca gaa gac cct gac aag gag aat caa aag     1926
Pro Val Cys Val Tyr Thr Ala Glu Asp Pro Asp Lys Glu Asn Gln Lys
            460                 465                 470 atc agc tac cgc atc ctg aga gac cca gca ggg tgg cta gcc atg gac     1974
Ile Ser Tyr Arg Ile Leu Arg Asp Pro Ala Gly Trp Leu Ala Met Asp
        475                 480                 485 cca gac agt ggg cag gtc aca gct gtg ggc acc ctc gac cgt gag gat     2022
Pro Asp Ser Gly Gln Val Thr Ala Val Gly Thr Leu Asp Arg Glu Asp
490                 495                 500                 505 gag cag ttt gtg agg aac aac atc tat gaa gtc atg gtc ttg gcc atg     2070
Glu Gln Phe Val Arg Asn Asn Ile Tyr Glu Val Met Val Leu Ala Met
                510                 515                 520 gac aat gga agc cct ccc acc act ggc acg gga acc ctt cta cta aca     2118
Asp Asn Gly Ser Pro Pro Thr Thr Gly Thr Gly Thr Leu Leu Leu Thr
                525                 530                 535 ctg att gat gtc aat gac cat ggc cca gtc cct gag ccc cgt cag atc     2166
Leu Ile Asp Val Asn Asp His Gly Pro Val Pro Glu Pro Arg Gln Ile
            540                 545                 550 acc atc tgc aac caa agc cct gtg cgc cag gtg ctg aac atc acg gac     2214
Thr Ile Cys Asn Gln Ser Pro Val Arg Gln Val Leu Asn Ile Thr Asp
            555                 560                 565 aag gac ctg tct ccc cac acc tcc cct ttc cag gcc cag ctc aca gat     2262
Lys Asp Leu Ser Pro His Thr Ser Pro Phe Gln Ala Gln Leu Thr Asp
570                 575                 580                 585 gac tca gac atc tac tgg acg gca gag gtc aac gag gaa ggt gac aca     2310
Asp Ser Asp Ile Tyr Trp Thr Ala Glu Val Asn Glu Glu Gly Asp Thr
                590                 595                 600 gtg gtc ttg tcc ctg aag aag ttc ctg aag cag gat aca tat gac gtg     2358
Val Val Leu Ser Leu Lys Lys Phe Leu Lys Gln Asp Thr Tyr Asp Val
                605                 610                 615 cac ctt tct ctg tct gac cat ggc aac aaa gag cag ctg acg gtg atc     2406
His Leu Ser Leu Ser Asp His Gly Asn Lys Glu Gln Leu Thr Val Ile
            620                 625                 630 agg gcc act gtg tgc gac tgc cat ggc cat gtc gaa acc tgc cct gga     2454
Arg Ala Thr Val Cys Asp Cys His Gly His Val Glu Thr Cys Pro Gly
            635                 640                 645 ccc tgg aag gga ggt ttc atc ctc cct gtg ctg ggg gct gtc ctg gct     2502
Pro Trp Lys Gly Gly Phe Ile Leu Pro Val Leu Gly Ala Val Leu Ala
650                 655                 660                 665 ctg ctg ttc ctc ctg ctg gtg ctg ctt ttg ttg gtg aga aag aag cgg     2550
Leu Leu Phe Leu Leu Leu Val Leu Leu Leu Val Arg Lys Lys Arg
                670                 675                 680 aag atc aag gag ccc ctc cta ctc cca gaa gat gac acc cgt gac aac     2598
Lys Ile Lys Glu Pro Leu Leu Leu Pro Glu Asp Asp Thr Arg Asp Asn
                685                 690                 695 gtc ttc tac tat ggc gaa gag ggg ggt ggc gaa gag gac cag gac tat     2646
Val Phe Tyr Tyr Gly Glu Glu Gly Gly Gly Glu Glu Asp Gln Asp Tyr
            700                 705                 710 gac atc acc cag ctc cac cga ggt ctg gag gcc agg ccg gag gtg gtt     2694
Asp Ile Thr Gln Leu His Arg Gly Leu Glu Ala Arg Pro Glu Val Val
            715                 720                 725 ctc cgc aat gac gtg gca cca acc atc atc ccg aca ccc atg tac cgt     2742
Leu Arg Asn Asp Val Ala Pro Thr Ile Ile Pro Thr Pro Met Tyr Arg
730                 735                 740                 745
```

```
cct cgg cca gcc aac cca gat gaa atc ggc aac ttt ata att gag aac    2790
Pro Arg Pro Ala Asn Pro Asp Glu Ile Gly Asn Phe Ile Ile Glu Asn
            750                 755                 760 ctg aag gcg gct aac aca gac ccc aca gcc ccg ccc tac gac acc ctc    2838
Leu Lys Ala Ala Asn Thr Asp Pro Thr Ala Pro Pro Tyr Asp Thr Leu
            765                 770                 775 ttg gtg ttc gac tat gag ggc agc ggc tcc gac gcc gcg tcc ctg agc    2886
Leu Val Phe Asp Tyr Glu Gly Ser Gly Ser Asp Ala Ala Ser Leu Ser
            780                 785                 790 tcc ctc acc tcc tcc gcc tcc gac caa gac caa gat tac gat tat ctg    2934
Ser Leu Thr Ser Ser Ala Ser Asp Gln Asp Gln Asp Tyr Asp Tyr Leu
            795                 800                 805 aac gag tgg ggc agc cgc ttc aag aag ctg gca gac atg tac ggt ggc    2982
Asn Glu Trp Gly Ser Arg Phe Lys Lys Leu Ala Asp Met Tyr Gly Gly
810             815                 820                 825 ggg gag gac gac tag gcggcctgcc tgcagggctg ggaccaaac gtcaggccac     3037
Gly Glu Asp Asp agagcatctc caaggggtct cagttccccc ttcagctgag gacttcggag cttgtcagga   3097
agtggccgta gcaacttggc ggagacaggc tatgagtctg acgttagagt ggtggcttcc   3157
ttagcctttc aggatggagg aatgtgggca gtttgacttc agcactgaaa acctctccac   3217
ctgggccagg gttgcctcag aggccaagtt tccagaagcc tcttacctgc cgtaaaatgc   3277
tcaaccctgt gtcctgggcc tgggcctgct gtgactgacc tacagtggac tttctctctg   3337
gaatggaacc ttcttaggcc tcctggtgca acttaatttt ttttttttaat gctatcttca   3397 aaacgttaga gaaagttctt caaaagtgca gcccagagct gctgggccca ctggccgtcc   3457
tgcatttctg gtttccagac cccaatgcct cccattcgga tggatctctg cgttttata    3517 ctgagtgtgc ctaggttgcc ccttattttt tattttccct gttgcgttgc tatagatgaa   3577
gggtgaggac aatcgtgtat atgtactaga actttttat taaagaaact tttcccagaa    3637
aaaaaaaaaa aa                                                       3649

<210> SEQ ID NO 2
<211> LENGTH: 829
<212> TYPE: PRT
<213> ORGANISM: Homo sapiens

<400> SEQUENCE: 2

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
        35                  40                  45

Gln Ala Leu Gly Lys Val Phe Met Gly Cys Pro Gly Gln Glu Pro Ala
    50                  55                  60

Leu Phe Ser Thr Asp Asn Asp Phe Thr Val Arg Asn Gly Glu Thr
65                  70                  75                  80

Val Gln Glu Arg Arg Ser Leu Lys Glu Arg Asn Pro Leu Lys Ile Phe
            85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140
```

```
Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
            165                 170                 175

Glu Ile Ala Lys Tyr Glu Leu Phe Gly His Ala Val Ser Glu Asn Gly
        180                 185                 190

Ala Ser Val Glu Asp Pro Met Asn Ile Ser Ile Val Thr Asp Gln
    195                 200                 205

Asn Asp His Lys Pro Lys Phe Thr Gln Asp Thr Phe Arg Gly Ser Val
210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
        355                 360                 365

Met Gly Gly Asp Asp Gly Asp His Phe Thr Ile Thr Thr His Pro Glu
370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
        435                 440                 445

Val Gln Glu Gly Ile Pro Thr Gly Glu Pro Val Cys Val Tyr Thr Ala
450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
        515                 520                 525

Thr Gly Thr Gly Thr Leu Leu Leu Thr Leu Ile Asp Val Asn Asp His
530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575
```

```
Ser Pro Phe Gln Ala Gln Leu Thr Asp Asp Ser Asp Ile Tyr Trp Thr
            580                 585                 590

Ala Glu Val Asn Glu Glu Gly Asp Thr Val Val Leu Ser Leu Lys Lys
        595                 600                 605

Phe Leu Lys Gln Asp Thr Tyr Asp Val His Leu Ser Leu Ser Asp His
        610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
            645                 650                 655

Leu Pro Val Leu Gly Ala Val Leu Ala Leu Leu Phe Leu Leu Leu Val
            660                 665                 670

Leu Leu Leu Leu Val Arg Lys Lys Arg Lys Ile Lys Glu Pro Leu Leu
        675                 680                 685

Leu Pro Glu Asp Asp Thr Arg Asp Asn Val Phe Tyr Tyr Gly Glu Glu
        690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
            725                 730                 735

Thr Ile Ile Pro Thr Pro Met Tyr Arg Pro Arg Pro Ala Asn Pro Asp
            740                 745                 750

Glu Ile Gly Asn Phe Ile Ile Glu Asn Leu Lys Ala Ala Asn Thr Asp
        755                 760                 765

Pro Thr Ala Pro Pro Tyr Asp Thr Leu Leu Val Phe Asp Tyr Glu Gly
        770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
            805                 810                 815

Lys Lys Leu Ala Asp Met Tyr Gly Gly Gly Glu Asp Asp
        820                 825

<210> SEQ ID NO 3
<211> LENGTH: 3107
<212> TYPE: DNA
<213> ORGANISM: Homo sapiens
<220> FEATURE:
<221> NAME/KEY: CDS
<222> LOCATION: (34)..(2994)

<400> SEQUENCE: 3
aagcggcagg agcagcgttg gcaccggcga acc atg gct ggg att ttc tat ttc     54
                                    Met Ala Gly Ile Phe Tyr Phe
                                      1               5 gcc cta ttt tcg tgt ctc ttc ggg att tgc gac gct gtc aca ggt tcc    102
Ala Leu Phe Ser Cys Leu Phe Gly Ile Cys Asp Ala Val Thr Gly Ser
         10                  15                  20 agg gta tac ccc gcg aat gaa gtt acc tta ttg gat tcc aga tct gtt    150
Arg Val Tyr Pro Ala Asn Glu Val Thr Leu Leu Asp Ser Arg Ser Val
     25                  30                  35 cag gga gaa ctt ggg tgg ata gca agc cct ctg gaa gga ggg tgg gag    198
Gln Gly Glu Leu Gly Trp Ile Ala Ser Pro Leu Glu Gly Gly Trp Glu
 40                  45                  50                  55 gaa gtg agt atc atg gat gaa aaa aat aca cca atc cga acc tac caa    246
Glu Val Ser Ile Met Asp Glu Lys Asn Thr Pro Ile Arg Thr Tyr Gln
                 60                  65                  70
```

```
gtg tgc aat gtg atg gaa ccc agc cag aat aac tgg cta cga act gat    294
Val Cys Asn Val Met Glu Pro Ser Gln Asn Asn Trp Leu Arg Thr Asp
            75                  80                  85 tgg atc acc cga gaa ggg gct cag agg gtg tat att gag att aaa ttc    342
Trp Ile Thr Arg Glu Gly Ala Gln Arg Val Tyr Ile Glu Ile Lys Phe
            90                  95                 100 acc ttg agg gac tgc aat agt ctt ccg ggc gtc atg ggg act tgc aag    390
Thr Leu Arg Asp Cys Asn Ser Leu Pro Gly Val Met Gly Thr Cys Lys
           105                 110                 115 gag acg ttt aac ctg tac tac tat gaa tca gac aac gac aaa gag cgt    438
Glu Thr Phe Asn Leu Tyr Tyr Tyr Glu Ser Asp Asn Asp Lys Glu Arg
120                 125                 130                 135 ttc atc aga gag aac cag ttt gtc aaa att gac acc att gct gct gat    486
Phe Ile Arg Glu Asn Gln Phe Val Lys Ile Asp Thr Ile Ala Ala Asp
                140                 145                 150 gag agc ttc acc caa gtg gac att ggt gac aga atc atg aag ctg aac    534
Glu Ser Phe Thr Gln Val Asp Ile Gly Asp Arg Ile Met Lys Leu Asn
                155                 160                 165 acc gag atc cgg gat gta ggg cca tta agc aaa aag ggg ttt tac ctg    582
Thr Glu Ile Arg Asp Val Gly Pro Leu Ser Lys Lys Gly Phe Tyr Leu
                170                 175                 180 gct ttt cag gat gtg ggg gcc tgc atc gcc ctg gta tca gtc cgt gtg    630
Ala Phe Gln Asp Val Gly Ala Cys Ile Ala Leu Val Ser Val Arg Val
185                 190                 195 ttc tat aaa aag tgt cca ctc aca gtc cgc aat ctg gcc cag ttt cct    678
Phe Tyr Lys Lys Cys Pro Leu Thr Val Arg Asn Leu Ala Gln Phe Pro
200                 205                 210                 215 gac acc atc aca ggg gct gat acg tct tcc ctg gtg gaa gtt cga ggc    726
Asp Thr Ile Thr Gly Ala Asp Thr Ser Ser Leu Val Glu Val Arg Gly
                220                 225                 230 tcc tgt gtc aac aac tca gaa gag aaa gat gtg cca aaa atg tac tgt    774
Ser Cys Val Asn Asn Ser Glu Glu Lys Asp Val Pro Lys Met Tyr Cys
                235                 240                 245 ggg gca gat ggt gaa tgg ctg gta ccc att ggc aac tgc cta tgc aac    822
Gly Ala Asp Gly Glu Trp Leu Val Pro Ile Gly Asn Cys Leu Cys Asn
                250                 255                 260 gct ggg cat gag gag cgg agc gga gaa tgc caa gct tgc aaa att gga    870
Ala Gly His Glu Glu Arg Ser Gly Glu Cys Gln Ala Cys Lys Ile Gly
265                 270                 275 tat tac aag gct ctc tcc acg gat gcc acc tgt gcc aag tgc cca ccc    918
Tyr Tyr Lys Ala Leu Ser Thr Asp Ala Thr Cys Ala Lys Cys Pro Pro
280                 285                 290                 295 cac agc tac tct gtc tgg gaa gga gcc acc tcg tgc acc tgt gac cga    966
His Ser Tyr Ser Val Trp Glu Gly Ala Thr Ser Cys Thr Cys Asp Arg
                300                 305                 310 ggc ttt ttc aga gct gac aac gat gct gcc tct atg ccc tgc acc cgt   1014
Gly Phe Phe Arg Ala Asp Asn Asp Ala Ala Ser Met Pro Cys Thr Arg
                315                 320                 325 cca cca tct gct ccc ctg aac ttg att tca aat gtc aac gag aca tct   1062
Pro Pro Ser Ala Pro Leu Asn Leu Ile Ser Asn Val Asn Glu Thr Ser
                330                 335                 340 gtg aac ttg gaa tgg agt agc cct cag aat aca ggt ggc cgc cag gac   1110
Val Asn Leu Glu Trp Ser Ser Pro Gln Asn Thr Gly Gly Arg Gln Asp
345                 350                 355 att tcc tat aat gtg gta tgc aag aaa tgt gga gct ggt gac ccc agc   1158
Ile Ser Tyr Asn Val Val Cys Lys Lys Cys Gly Ala Gly Asp Pro Ser
            360                 365                 370                 375 aag tgc cga ccc tgt gga agt ggg gtc cac tac acc cca cag cag aat   1206
Lys Cys Arg Pro Cys Gly Ser Gly Val His Tyr Thr Pro Gln Gln Asn
                380                 385                 390
```

```
ggc ttg aag acc acc aaa gtc tcc atc act gac ctc cta gct cat acc      1254
Gly Leu Lys Thr Thr Lys Val Ser Ile Thr Asp Leu Leu Ala His Thr
            395                 400                 405 aat tac acc ttt gaa atc tgg gct gtg aat gga gtg tcc aaa tat aac      1302
Asn Tyr Thr Phe Glu Ile Trp Ala Val Asn Gly Val Ser Lys Tyr Asn
            410                 415                 420 cct aac cca gac caa tca gtt tct gtc act gtg acc acc aac caa gca      1350
Pro Asn Pro Asp Gln Ser Val Ser Val Thr Val Thr Thr Asn Gln Ala
        425                 430                 435 gca cca tca tcc att gct ttg gtc cag gct aaa gaa gtc aca aga tac      1398
Ala Pro Ser Ser Ile Ala Leu Val Gln Ala Lys Glu Val Thr Arg Tyr
440                 445                 450                 455 agt gtg gca ctg gct tgg ctg gaa cca gat cgg ccc aat ggg gta atc      1446
Ser Val Ala Leu Ala Trp Leu Glu Pro Asp Arg Pro Asn Gly Val Ile
                460                 465                 470 ctg gaa tat gaa gtc aag tat tat gag aag gat cag aat gag cga agc      1494
Leu Glu Tyr Glu Val Lys Tyr Tyr Glu Lys Asp Gln Asn Glu Arg Ser
            475                 480                 485 tat cgt ata gtt cgg aca gct gcc agg aac aca gat atc aaa ggc ctg      1542
Tyr Arg Ile Val Arg Thr Ala Ala Arg Asn Thr Asp Ile Lys Gly Leu
            490                 495                 500 aac cct ctc act tcc tat gtt ttc cac gtg cga gcc agg aca gca gct      1590
Asn Pro Leu Thr Ser Tyr Val Phe His Val Arg Ala Arg Thr Ala Ala
        505                 510                 515 ggc tat gga gac ttc agt gag ccc ttg gag gtt aca acc aac aca gtg      1638
Gly Tyr Gly Asp Phe Ser Glu Pro Leu Glu Val Thr Thr Asn Thr Val
520                 525                 530                 535 cct tcc cgg atc att gga gat ggg gct aac tcc aca gtc ctt ctg gtc      1686
Pro Ser Arg Ile Ile Gly Asp Gly Ala Asn Ser Thr Val Leu Leu Val
                540                 545                 550 tct gtc tcg ggc agt gtg gtg ctg gtg gta att ctc att gca gct ttt      1734
Ser Val Ser Gly Ser Val Val Leu Val Val Ile Leu Ile Ala Ala Phe
            555                 560                 565 gtc atc agc cgg aga cgg agt aaa tac agt aaa gcc aaa caa gaa gcg      1782
Val Ile Ser Arg Arg Arg Ser Lys Tyr Ser Lys Ala Lys Gln Glu Ala
            570                 575                 580 gat gaa gag aaa cat ttg aat caa ggt gta aga aca tat gtg gac ccc      1830
Asp Glu Glu Lys His Leu Asn Gln Gly Val Arg Thr Tyr Val Asp Pro
        585                 590                 595 ttt acg tac gaa gat ccc aac caa gca gtg cga gag ttt gcc aaa gaa      1878
Phe Thr Tyr Glu Asp Pro Asn Gln Ala Val Arg Glu Phe Ala Lys Glu
600                 605                 610                 615 att gac gca tcc tgc att aag att gaa aaa gtt ata gga gtt ggt gaa      1926
Ile Asp Ala Ser Cys Ile Lys Ile Glu Lys Val Ile Gly Val Gly Glu
                620                 625                 630 ttt ggt gag gta tgc agt ggg cgt ctc aaa gtg cct ggc aag aga gag      1974
Phe Gly Glu Val Cys Ser Gly Arg Leu Lys Val Pro Gly Lys Arg Glu
            635                 640                 645 atc tgt gtg gct atc aag act ctg aaa gct ggt tat aca gac aaa cag      2022
Ile Cys Val Ala Ile Lys Thr Leu Lys Ala Gly Tyr Thr Asp Lys Gln
            650                 655                 660 agg aga gac ttc ctg agt gag gcc agc atc atg gga cag ttt gac cat      2070
Arg Arg Asp Phe Leu Ser Glu Ala Ser Ile Met Gly Gln Phe Asp His
        665                 670                 675 ccg aac atc att cac ttg gaa ggc gtg gtc act aaa tgt aaa cca gta      2118
Pro Asn Ile Ile His Leu Glu Gly Val Val Thr Lys Cys Lys Pro Val
680                 685                 690                 695 atg atc ata aca gag tac atg gag aat ggc tcc ttg gat gca ttc ctc      2166
Met Ile Ile Thr Glu Tyr Met Glu Asn Gly Ser Leu Asp Ala Phe Leu
                700                 705                 710
```

```
agg aaa aat gat ggc aga ttt aca gtc att cag ctg gtg ggc atg ctt      2214
Arg Lys Asn Asp Gly Arg Phe Thr Val Ile Gln Leu Val Gly Met Leu
            715                 720                 725 cgt ggc att ggg tct ggg atg aag tat tta tct gat atg agc tat gtg      2262
Arg Gly Ile Gly Ser Gly Met Lys Tyr Leu Ser Asp Met Ser Tyr Val
            730                 735                 740 cat cgt gat ctg gcc gca cgg aac atc ctg gtg aac agc aac ttg gtc      2310
His Arg Asp Leu Ala Ala Arg Asn Ile Leu Val Asn Ser Asn Leu Val
745                 750                 755 tgc aaa gtg tct gat ttt ggc atg tcc cga gtg ctt gag gat gat ccg      2358
Cys Lys Val Ser Asp Phe Gly Met Ser Arg Val Leu Glu Asp Asp Pro
760                 765                 770                 775 gaa gca gct tac acc acc agg ggt ggc aag att cct atc cgg tgg act      2406
Glu Ala Ala Tyr Thr Thr Arg Gly Gly Lys Ile Pro Ile Arg Trp Thr
            780                 785                 790 gcg cca gaa gca att gcc tat cgt aaa ttc aca tca gca agt gat gta      2454
Ala Pro Glu Ala Ile Ala Tyr Arg Lys Phe Thr Ser Ala Ser Asp Val
            795                 800                 805 tgg agc tat gga atc gtt atg tgg gaa gtg atg tcg tac ggg gag agg      2502
Trp Ser Tyr Gly Ile Val Met Trp Glu Val Met Ser Tyr Gly Glu Arg
            810                 815                 820 ccc tat tgg gat atg tcc aat caa gat gtg att aaa gcc att gag gaa      2550
Pro Tyr Trp Asp Met Ser Asn Gln Asp Val Ile Lys Ala Ile Glu Glu
825                 830                 835 ggc tat cgg tta ccc cct cca atg gac tgc ccc att gcg ctc cac cag      2598
Gly Tyr Arg Leu Pro Pro Pro Met Asp Cys Pro Ile Ala Leu His Gln
840                 845                 850                 855 ctg atg cta gac tgc tgg cag aag gag agg agc gac agg cct aaa ttt      2646
Leu Met Leu Asp Cys Trp Gln Lys Glu Arg Ser Asp Arg Pro Lys Phe
            860                 865                 870 ggg cag att gtc aac atg ttg gac aaa ctc atc cgc aac ccc aac agc      2694
Gly Gln Ile Val Asn Met Leu Asp Lys Leu Ile Arg Asn Pro Asn Ser
            875                 880                 885 ttg aag agg aca ggg acg gag agc tcc aga cct aac act gcc ttg ttg      2742
Leu Lys Arg Thr Gly Thr Glu Ser Ser Arg Pro Asn Thr Ala Leu Leu
            890                 895                 900 gat cca agc tcc cct gaa ttc tct gct gtg gta tca gtg ggc gat tgg      2790
Asp Pro Ser Ser Pro Glu Phe Ser Ala Val Val Ser Val Gly Asp Trp
905                 910                 915 ctc cag gcc att aaa atg gac cgg tat aag gat aac ttc aca gct gct      2838
Leu Gln Ala Ile Lys Met Asp Arg Tyr Lys Asp Asn Phe Thr Ala Ala
920                 925                 930                 935 ggt tat acc aca cta gag gct gtg gtg cac gtg aac cag gag gac ctg      2886
Gly Tyr Thr Thr Leu Glu Ala Val Val His Val Asn Gln Glu Asp Leu
            940                 945                 950 gca aga att ggt atc aca gcc atc acg cac cag aat aag att ttg agc      2934
Ala Arg Ile Gly Ile Thr Ala Ile Thr His Gln Asn Lys Ile Leu Ser
            955                 960                 965 agt gtc cag gca atg cga acc caa atg cag cag atg cac ggc aga atg      2982
Ser Val Gln Ala Met Arg Thr Gln Met Gln Gln Met His Gly Arg Met
            970                 975                 980 gtt ccc gtc tga gccagtactg aataaactca aaactcttga aattagttta          3034
Val Pro Val
        985 cctcatccat gcactttaat tgaagaactg cactttttt acttcgtctt cgccctctga    3094 aattaaagaa atg                                                       3107

<210> SEQ ID NO 4
<211> LENGTH: 986
<212> TYPE: PRT
```

<213> ORGANISM: Homo sapiens

<400> SEQUENCE: 4

```
Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
            20                  25                  30

Leu Leu Asp Ser Arg Ser Val Gln Gly Glu Leu Gly Trp Ile Ala Ser
        35                  40                  45

Pro Leu Glu Gly Gly Trp Glu Glu Val Ser Ile Met Asp Glu Lys Asn
    50                  55                  60

Thr Pro Ile Arg Thr Tyr Gln Val Cys Asn Val Met Glu Pro Ser Gln
65                  70                  75                  80

Asn Asn Trp Leu Arg Thr Asp Trp Ile Thr Arg Glu Gly Ala Gln Arg
                85                  90                  95

Val Tyr Ile Glu Ile Lys Phe Thr Leu Arg Asp Cys Asn Ser Leu Pro
            100                 105                 110

Gly Val Met Gly Thr Cys Lys Glu Thr Phe Asn Leu Tyr Tyr Tyr Glu
        115                 120                 125

Ser Asp Asn Asp Lys Glu Arg Phe Ile Arg Glu Asn Gln Phe Val Lys
    130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
            180                 185                 190

Ala Leu Val Ser Val Arg Val Phe Tyr Lys Lys Cys Pro Leu Thr Val
        195                 200                 205

Arg Asn Leu Ala Gln Phe Pro Asp Thr Ile Thr Gly Ala Asp Thr Ser
    210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
            260                 265                 270

Cys Gln Ala Cys Lys Ile Gly Tyr Tyr Lys Ala Leu Ser Thr Asp Ala
        275                 280                 285

Thr Cys Ala Lys Cys Pro Pro His Ser Tyr Ser Val Trp Glu Gly Ala
    290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
            340                 345                 350

Asn Thr Gly Gly Arg Gln Asp Ile Ser Tyr Asn Val Val Cys Lys Lys
        355                 360                 365

Cys Gly Ala Gly Asp Pro Ser Lys Cys Arg Pro Cys Gly Ser Gly Val
    370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
```

```
                    405                 410                 415
Asn Gly Val Ser Lys Tyr Asn Pro Asn Pro Asp Gln Ser Val Ser Val
            420                 425                 430
Thr Val Thr Thr Asn Gln Ala Ala Pro Ser Ser Ile Ala Leu Val Gln
            435                 440                 445
Ala Lys Glu Val Thr Arg Tyr Ser Val Ala Leu Ala Trp Leu Glu Pro
450                 455                 460
Asp Arg Pro Asn Gly Val Ile Leu Glu Tyr Gly Val Lys Tyr Tyr Glu
465                 470                 475                 480
Lys Asp Gln Asn Glu Arg Ser Tyr Arg Ile Val Arg Thr Ala Ala Arg
                485                 490                 495
Asn Thr Asp Ile Lys Gly Leu Asn Pro Leu Thr Ser Tyr Val Phe His
            500                 505                 510
Val Arg Ala Arg Thr Ala Ala Gly Tyr Gly Asp Phe Ser Glu Pro Leu
            515                 520                 525
Glu Val Thr Thr Asn Thr Val Pro Ser Arg Ile Ile Gly Asp Gly Ala
            530                 535                 540
Asn Ser Thr Val Leu Leu Val Ser Val Ser Gly Ser Val Val Leu Val
545                 550                 555                 560
Val Ile Leu Ile Ala Ala Phe Val Ile Ser Arg Arg Ser Lys Tyr
                565                 570                 575
Ser Lys Ala Lys Gln Glu Ala Asp Glu Glu Lys His Leu Asn Gln Gly
            580                 585                 590
Val Arg Thr Tyr Val Asp Pro Phe Thr Tyr Glu Asp Pro Asn Gln Ala
            595                 600                 605
Val Arg Glu Phe Ala Lys Glu Ile Asp Ala Ser Cys Ile Lys Ile Glu
            610                 615                 620
Lys Val Ile Gly Val Gly Glu Phe Gly Glu Val Cys Ser Gly Arg Leu
625                 630                 635                 640
Lys Val Pro Gly Lys Arg Glu Ile Cys Val Ala Ile Lys Thr Leu Lys
                645                 650                 655
Ala Gly Tyr Thr Asp Lys Gln Arg Arg Asp Phe Leu Ser Glu Ala Ser
            660                 665                 670
Ile Met Gly Gln Phe Asp His Pro Asn Ile Ile His Leu Glu Gly Val
            675                 680                 685
Val Thr Lys Cys Lys Pro Val Met Ile Ile Thr Glu Tyr Met Glu Asn
            690                 695                 700
Gly Ser Leu Asp Ala Phe Leu Arg Lys Asn Asp Gly Arg Phe Thr Val
705                 710                 715                 720
Ile Gln Leu Val Gly Met Leu Arg Gly Ile Gly Ser Gly Met Lys Tyr
                725                 730                 735
Leu Ser Asp Met Ser Tyr Val His Arg Asp Leu Ala Ala Arg Asn Ile
            740                 745                 750
Leu Val Asn Ser Asn Leu Val Cys Lys Val Ser Asp Phe Gly Met Ser
            755                 760                 765
Arg Val Leu Glu Asp Asp Pro Glu Ala Ala Tyr Thr Thr Arg Gly Gly
            770                 775                 780
Lys Ile Pro Ile Arg Trp Thr Ala Pro Glu Ala Ile Ala Tyr Arg Lys
785                 790                 795                 800
Phe Thr Ser Ala Ser Asp Val Trp Ser Tyr Gly Ile Val Met Trp Glu
                805                 810                 815
Val Met Ser Tyr Gly Glu Arg Pro Tyr Trp Asp Met Ser Asn Gln Asp
            820                 825                 830
```

```
Val Ile Lys Ala Ile Glu Glu Gly Tyr Arg Leu Pro Pro Pro Met Asp
        835                 840                 845

Cys Pro Ile Ala Leu His Gln Leu Met Leu Asp Cys Trp Gln Lys Glu
    850                 855                 860

Arg Ser Asp Arg Pro Lys Phe Gly Gln Ile Val Asn Met Leu Asp Lys
865                 870                 875                 880

Leu Ile Arg Asn Pro Asn Ser Leu Lys Arg Thr Gly Thr Glu Ser Ser
                885                 890                 895

Arg Pro Asn Thr Ala Leu Leu Asp Pro Ser Ser Pro Glu Phe Ser Ala
            900                 905                 910

Val Val Ser Val Gly Asp Trp Leu Gln Ala Ile Lys Met Asp Arg Tyr
        915                 920                 925

Lys Asp Asn Phe Thr Ala Ala Gly Tyr Thr Thr Leu Glu Ala Val Val
    930                 935                 940

His Val Asn Gln Glu Asp Leu Ala Arg Ile Gly Ile Thr Ala Ile Thr
945                 950                 955                 960

His Gln Asn Lys Ile Leu Ser Ser Val Gln Ala Met Arg Thr Gln Met
                965                 970                 975

Gln Gln Met His Gly Arg Met Val Pro Val
            980                 985

<210> SEQ ID NO 5
<211> LENGTH: 4349
<212> TYPE: DNA
<213> ORGANISM: Homo sapiens
<220> FEATURE:
<221> NAME/KEY: CDS
<222> LOCATION: (445)..(3093)

<400> SEQUENCE: 5
tttttgaatc ggttgtggcg gccgcggcga ggaatggcgg tatttgtgag aggagtcggc        60
gtttgaagag gtggaactcc tagggctttt ttgagagtga cggagtctac ctcttgttac       120
ctagactgga gtgcagtggc acgatctcgg ctcactgcaa cctctgcctc ccgggttcaa       180
gcgattctcc tgcctcagcc tcctgagtag ctgggattac aggtgcctgc caccaagccc       240
agctaatttt tgtatttta gtagagatgg ggtttcattg tgttggccag gctggtctcg       300
aactcctgac ctcgtgatcc gcccgccttg gcctcccaaa gtgctaggat tacaagtgtg       360
agccaccgcg tccggccttt caaatggtat tttgattttt cctcttccag tccttaaagc       420
agctgattta gaagaataca aatc atg gct gaa aat agt gta tta aca tcc        471
                         Met Ala Glu Asn Ser Val Leu Thr Ser
                         1               5 act act ggg agg act agc ttg gca gac tct tcc att ttt gat tct aaa        519
Thr Thr Gly Arg Thr Ser Leu Ala Asp Ser Ser Ile Phe Asp Ser Lys
10              15                  20                  25 gtt act gag att tcc aag gaa aac tta ctt att gga tct act tca tat        567
Val Thr Glu Ile Ser Lys Glu Asn Leu Leu Ile Gly Ser Thr Ser Tyr
            30                  35                  40 gta gaa gag atg cct cag att gaa aca aga gtg ata ttg gtt caa gaa        615
Val Glu Glu Met Pro Gln Ile Glu Thr Arg Val Ile Leu Val Gln Glu
        45                  50                  55 gct gga aaa caa gaa gaa ctt ata aaa gcc tta aag gac att aaa gtg        663
Ala Gly Lys Gln Glu Glu Leu Ile Lys Ala Leu Lys Asp Ile Lys Val
    60                  65                  70 ggc ttt gta aag atg gag tca gtg gaa gaa ttt gaa ggt ttg gat tct        711
Gly Phe Val Lys Met Glu Ser Val Glu Glu Phe Glu Gly Leu Asp Ser
75                  80                  85 ccg gaa ttt gaa aat gta ttt gta gtc acg gac ttt cag gat tct gtc        759
Pro Glu Phe Glu Asn Val Phe Val Val Thr Asp Phe Gln Asp Ser Val
```

```
                Pro Glu Phe Glu Asn Val Phe Val Val Thr Asp Phe Gln Asp Ser Val
                90              95                  100                 105 tttaatgacctctacaaggctgattgtagagttattggaccaccagtt              807
Phe Asn Asp Leu Tyr Lys Ala Asp Cys Arg Val Ile Gly Pro Pro Val
                110                 115                 120 gtattaaattgttcacaaaaaggagagcctttgccatttcatgtcgc              855
Val Leu Asn Cys Ser Gln Lys Gly Glu Pro Leu Pro Phe Ser Cys Arg
                125                 130                 135 ccgttgtattgtacaagtatgatgaatctagtactatgctttactgga              903
Pro Leu Tyr Cys Thr Ser Met Met Asn Leu Val Leu Cys Phe Thr Gly
                140                 145                 150 tttaggaaaaaagaagaactagtcaggttggtgacattggtcatcac              951
Phe Arg Lys Lys Glu Glu Leu Val Arg Leu Val Thr Leu Val His His
                155                 160                 165 atgggtggagttattcgaaaagactttaattcaaaagttacacatttg              999
Met Gly Gly Val Ile Arg Lys Asp Phe Asn Ser Lys Val Thr His Leu
170                 175                 180                 185 gtggcaaattgtacacaaggagaaaaattcagggttgctgtgagtcta              1047
Val Ala Asn Cys Thr Gln Gly Glu Lys Phe Arg Val Ala Val Ser Leu
                190                 195                 200 ggtactccaattatgaagccagaatggatttataaagctgggaaagg              1095
Gly Thr Pro Ile Met Lys Pro Glu Trp Ile Tyr Lys Ala Trp Glu Arg
                205                 210                 215 cggaatgaacagggatttctatgcagcagttgatgactttagaaatgaa              1143
Arg Asn Glu Gln Asp Phe Tyr Ala Ala Val Asp Asp Phe Arg Asn Glu
                220                 225                 230 tttaaagttcctccatttcaagattgtattttaagtttcctggattt              1191
Phe Lys Val Pro Pro Phe Gln Asp Cys Ile Leu Ser Phe Leu Gly Phe
235                 240                 245 tcagatgaagagaaaaccaatatggaagaaatgactgaaatgcaagga              1239
Ser Asp Glu Glu Lys Thr Asn Met Glu Glu Met Thr Glu Met Gln Gly
250                 255                 260                 265 ggtaaatatttaccgcttggagatgaaagatgcactcacttagtagtt              1287
Gly Lys Tyr Leu Pro Leu Gly Asp Glu Arg Cys Thr His Leu Val Val
                270                 275                 280 gaagagaatatagtaaaagatcttcccttcgaacctcaaagaaactt              1335
Glu Glu Asn Ile Val Lys Asp Leu Pro Phe Glu Pro Ser Lys Lys Leu
                285                 290                 295 tatgttgtcaagcaagagtggttctggggaagcattcaaatggatgcc              1383
Tyr Val Val Lys Gln Glu Trp Phe Trp Gly Ser Ile Gln Met Asp Ala
                300                 305                 310 cgagctggagaaactatgtatttatatgaaaaggcaaatactcctgag              1431
Arg Ala Gly Glu Thr Met Tyr Leu Tyr Glu Lys Ala Asn Thr Pro Glu
                315                 320                 325 ctcaagaaatcagtgtcaatgctttctctaaataccctaacagcaat              1479
Leu Lys Lys Ser Val Ser Met Leu Ser Leu Asn Thr Pro Asn Ser Asn
330                 335                 340                 345 cgcaaacgacgtcgtttaaaagaaacacttgctcagcttcaagagag              1527
Arg Lys Arg Arg Arg Leu Lys Glu Thr Leu Ala Gln Leu Ser Arg Glu
                350                 355                 360 acagacgtgtcaccatttccacccgtaagcgcccatcagctgagcat              1575
Thr Asp Val Ser Pro Phe Pro Pro Arg Lys Arg Pro Ser Ala Glu His
                365                 370                 375 tccctttccatagggtcactctagatatcaacacaccagagtct              1623
Ser Leu Ser Ile Gly Ser Leu Leu Asp Ile Ser Asn Thr Pro Glu Ser
                380                 385                 390 agcattaactatggagacaccccaaagtctgtactaagtcttctaaa              1671
Ser Ile Asn Tyr Gly Asp Thr Pro Lys Ser Cys Thr Lys Ser Ser Lys
                395                 400                 405 agctccactccagttcctccaagcagtcagcaaggtggcaagttgca              1719
```

-continued

| | | |
|---|---|---|
| Ser Ser Thr Pro Val Pro Ser Lys Gln Ser Ala Arg Trp Gln Val Ala<br>410                       415                       420                       425 | |
| aaa gag ctt tat caa act gaa agt aat tat gtt aat ata ttg gca aca<br>Lys Glu Leu Tyr Gln Thr Glu Ser Asn Tyr Val Asn Ile Leu Ala Thr<br>                     430                             435                       440 | 1767 |
| att att cag tta ttt caa gta cca ttg gaa gag gaa gga caa cgt ggt<br>Ile Ile Gln Leu Phe Gln Val Pro Leu Glu Glu Glu Gly Gln Arg Gly<br>                   445                       450                       455 | 1815 |
| gga cct atc ctt gca cca gag gag att aag act att ttt ggt agc atc<br>Gly Pro Ile Leu Ala Pro Glu Glu Ile Lys Thr Ile Phe Gly Ser Ile<br>        460                       465                       470 | 1863 |
| cca gat atc ttt gat gta cac act aag ata aag gat gat ctt gaa gac<br>Pro Asp Ile Phe Asp Val His Thr Lys Ile Lys Asp Asp Leu Glu Asp<br>     475                       480                       485 | 1911 |
| ctt ata gtt aat tgg gat gag agc aaa agc att ggt gac att ttt ctg<br>Leu Ile Val Asn Trp Asp Glu Ser Lys Ser Ile Gly Asp Ile Phe Leu<br>490                       495                       500                       505 | 1959 |
| aaa tat tca aaa gat ttg gta aaa acc tac cct ccc ttt gta aac ttc<br>Lys Tyr Ser Lys Asp Leu Val Lys Thr Tyr Pro Pro Phe Val Asn Phe<br>                   510                       515                       520 | 2007 |
| ttt gaa atg agc aag gaa aca att att aaa tgt gaa aaa cag aaa cca<br>Phe Glu Met Ser Lys Glu Thr Ile Ile Lys Cys Glu Lys Gln Lys Pro<br>        525                       530                       535 | 2055 |
| aga ttt cat gct ttt ctc aag ata aac caa gca aaa cca gaa tgt gga<br>Arg Phe His Ala Phe Leu Lys Ile Asn Gln Ala Lys Pro Glu Cys Gly<br>     540                       545                       550 | 2103 |
| cgg cag agc ctt gtt gaa ctt ctt atc cga cca gta cag agg tta ccc<br>Arg Gln Ser Leu Val Glu Leu Leu Ile Arg Pro Val Gln Arg Leu Pro<br>555                       560                       565 | 2151 |
| agt gtt gca tta ctt tta aat gat ctt aag aag cat aca gct gat gaa<br>Ser Val Ala Leu Leu Leu Asn Asp Leu Lys Lys His Thr Ala Asp Glu<br>570                       575                       580                       585 | 2199 |
| aat cca gac aaa agc act tta gaa aaa gct att gga tca ctg aag gaa<br>Asn Pro Asp Lys Ser Thr Leu Glu Lys Ala Ile Gly Ser Leu Lys Glu<br>                   590                       595                       600 | 2247 |
| gta atg acg cat att aat gag gat aag aga aaa aca gaa gct caa aag<br>Val Met Thr His Ile Asn Glu Asp Lys Arg Lys Thr Glu Ala Gln Lys<br>        605                       610                       615 | 2295 |
| caa att ttt gat gtt gtt tat gaa gta gat gga tgc cca gct aat ctt<br>Gln Ile Phe Asp Val Val Tyr Glu Val Asp Gly Cys Pro Ala Asn Leu<br>     620                       625                       630 | 2343 |
| tta tct tct cac cga agc tta gta cag cgg gtt gaa aca att tct cta<br>Leu Ser Ser His Arg Ser Leu Val Gln Arg Val Glu Thr Ile Ser Leu<br>635                       640                       645 | 2391 |
| ggt gag cac ccc tgt gac aga gga gaa caa gta act ctc ttc ctc ttc<br>Gly Glu His Pro Cys Asp Arg Gly Glu Gln Val Thr Leu Phe Leu Phe<br>650                       655                       660                       665 | 2439 |
| aat gat tgc cta gag ata gca aga aaa cgg cac aag gtt att ggc act<br>Asn Asp Cys Leu Glu Ile Ala Arg Lys Arg His Lys Val Ile Gly Thr<br>                   670                       675                       680 | 2487 |
| ttt agg agt cct cat ggc caa acc cga ccc cca gct tct ctt aag cat<br>Phe Arg Ser Pro His Gly Gln Thr Arg Pro Pro Ala Ser Leu Lys His<br>        685                       690                       695 | 2535 |
| att cac cta atg cct ctt tct cag att aag aag gta ttg gac ata aga<br>Ile His Leu Met Pro Leu Ser Gln Ile Lys Lys Val Leu Asp Ile Arg<br>     700                       705                       710 | 2583 |
| gag aca gaa gat tgc cat aat gct ttt gcc ttg ctt gtg agg cca cca<br>Glu Thr Glu Asp Cys His Asn Ala Phe Ala Leu Leu Val Arg Pro Pro<br>715                       720                       725 | 2631 |
| aca gag cag gca aat gtg cta ctc agt ttc cag atg aca tca gat gaa | 2679 |

```
Thr Glu Gln Ala Asn Val Leu Leu Ser Phe Gln Met Thr Ser Asp Glu
730                 735                 740                 745 ctt cca aaa gaa aac tgg cta aag atg ctg tgt cga cat gta gct aac      2727
Leu Pro Lys Glu Asn Trp Leu Lys Met Leu Cys Arg His Val Ala Asn
                750                 755                 760 acc att tgt aaa gca gat gct gag aat ctt att tat act gct gat cca      2775
Thr Ile Cys Lys Ala Asp Ala Glu Asn Leu Ile Tyr Thr Ala Asp Pro
            765                 770                 775 gaa tcc ttt gaa gta aat aca aaa gat atg gac agt aca ttg agt aga      2823
Glu Ser Phe Glu Val Asn Thr Lys Asp Met Asp Ser Thr Leu Ser Arg
        780                 785                 790 gca tca aga gca ata aaa aag act tca aaa aag gtt aca aga gca ttc      2871
Ala Ser Arg Ala Ile Lys Lys Thr Ser Lys Lys Val Thr Arg Ala Phe
    795                 800                 805 tct ttc tcc aaa act cca aaa aga gct ctt cga agg gct ctt atg aca      2919
Ser Phe Ser Lys Thr Pro Lys Arg Ala Leu Arg Arg Ala Leu Met Thr
810                 815                 820                 825 tcc cac ggc tca gtg gag gga aga agt cct tcc agc aat gat aag cat      2967
Ser His Gly Ser Val Glu Gly Arg Ser Pro Ser Ser Asn Asp Lys His
                830                 835                 840 gta atg agt cgt ctt tct agc aca tca tca tta gca ggt atc cct tct      3015
Val Met Ser Arg Leu Ser Ser Thr Ser Ser Leu Ala Gly Ile Pro Ser
            845                 850                 855 ccc tcc ctt gtc agc ctt cct tcc ttc ttt gaa agg aga agt cat acg      3063
Pro Ser Leu Val Ser Leu Pro Ser Phe Phe Glu Arg Arg Ser His Thr
        860                 865                 870 tta agt aga tct aca act cat ttg ata tga agcgttacca aaatcttaaa        3113
Leu Ser Arg Ser Thr Thr His Leu Ile
    875                 880 ttatagaaat gtatagacac ctcatactca aataagaaac tgacttaaat ggtacttgta    3173
attagcacgt tggtgaaagc tggaaggaag ataaataaca ctaaactatg ctatttgatt    3233
tttcttcttg aaagagtaag gtttacctgt tacattttca agttaattca tgtaaaaaat    3293
gatagtgatt ttgatgtaat ttatctcttg tttgaatctg tcattcaaag gccaataatt    3353
taagttgcta tcagctgata ttagtagctt tgcaaccctg atagagtaaa taaattttat    3413
gggtgggtgc caaatactgc tgtgaatcta tttgtatagt atccatgaat gaatttatgg    3473
aaatagatat ttgtgcagct caatttatgc agagattaaa tgacatcata atactggatg    3533
aaaacttgca tagaattctg attaaatagt gggtctgttt cacatgtgca gtttgaagta    3593
tttaaataac cactcctttc acagtttatt tccttctcaa gcgttttcaa gatctagcat    3653
gtggatttta aaagatttgc cctcattaac aagaataaca tttaaggag attgtttcaa    3713 aatattttg caaattgaga taaggacaga aagattgaga acattgtat attttgcaaa     3773 aacaagatgt ttgtagctgt ttcagagaga gtacggtata tttatggtaa ttttatccac   3833
tagcaaatct tgatttagtt tgatagtcgt cgtcggaatt ttattttgaa ggataagacc   3893
atgggaaaat tgtggtaaag actgtttgta cccttcatga ataattctg aagttgccat    3953 cagttttact aatcttctgt gaaatgcata gatatgcgca tgttcaactt tttattgtgg   4013
tcttataatt aaatgtaaaa ttgaaaattc atttgctgtt tcaaagtgtg atatctttca   4073
caatagcctt tttatagtca gtaattcaga ataatcaagt tcatatggat aaatgcattt   4133
ttatttccta tttcttagg gagtgctaca atgtttgtc acttaaattt caagtttctg     4193
ttttaatagt taactgacta tagattgttt tctatgccat gtatgtgcca cttctgagag   4253
tagtaaatga ctctttgcta catttttaaaa gcaattgtat tagtaagaac tttgtaaata  4313
aatacctaaa acccaagtgt aaaaaaaaaa aaaaaa                             4349
```

<210> SEQ ID NO 6
<211> LENGTH: 882
<212> TYPE: PRT
<213> ORGANISM: Homo sapiens

<400> SEQUENCE: 6

```
Met Ala Glu Asn Ser Val Leu Thr Ser Thr Gly Arg Thr Ser Leu
1               5                   10                  15

Ala Asp Ser Ser Ile Phe Asp Ser Lys Val Thr Glu Ile Ser Lys Glu
            20                  25                  30

Asn Leu Leu Ile Gly Ser Thr Ser Tyr Val Glu Met Pro Gln Ile
            35                  40                  45

Glu Thr Arg Val Ile Leu Val Gln Glu Ala Gly Lys Gln Glu Glu Leu
50                      55                  60

Ile Lys Ala Leu Lys Asp Ile Lys Val Gly Phe Val Lys Met Glu Ser
65                  70                  75                  80

Val Glu Glu Phe Glu Gly Leu Asp Ser Pro Glu Phe Glu Asn Val Phe
                    85                  90                  95

Val Val Thr Asp Phe Gln Asp Ser Val Phe Asn Asp Leu Tyr Lys Ala
                100                 105                 110

Asp Cys Arg Val Ile Gly Pro Pro Val Leu Asn Cys Ser Gln Lys
            115                 120                 125

Gly Glu Pro Leu Pro Phe Ser Cys Arg Pro Leu Tyr Cys Thr Ser Met
130                 135                 140

Met Asn Leu Val Leu Cys Phe Thr Gly Phe Arg Lys Lys Glu Glu Leu
145                 150                 155                 160

Val Arg Leu Val Thr Leu Val His His Met Gly Gly Val Ile Arg Lys
                165                 170                 175

Asp Phe Asn Ser Lys Val Thr His Leu Val Ala Asn Cys Thr Gln Gly
            180                 185                 190

Glu Lys Phe Arg Val Ala Val Ser Leu Gly Thr Pro Ile Met Lys Pro
        195                 200                 205

Glu Trp Ile Tyr Lys Ala Trp Glu Arg Arg Asn Glu Gln Asp Phe Tyr
210                 215                 220

Ala Ala Val Asp Asp Phe Arg Asn Glu Phe Lys Val Pro Pro Phe Gln
225                 230                 235                 240

Asp Cys Ile Leu Ser Phe Leu Gly Phe Ser Asp Glu Glu Lys Thr Asn
                245                 250                 255

Met Glu Glu Met Thr Glu Met Gln Gly Gly Lys Tyr Leu Pro Leu Gly
            260                 265                 270

Asp Glu Arg Cys Thr His Leu Val Val Glu Glu Asn Ile Val Lys Asp
        275                 280                 285

Leu Pro Phe Glu Pro Ser Lys Lys Leu Tyr Val Val Lys Gln Glu Trp
290                 295                 300

Phe Trp Gly Ser Ile Gln Met Asp Ala Arg Ala Gly Glu Thr Met Tyr
305                 310                 315                 320

Leu Tyr Glu Lys Ala Asn Thr Pro Glu Leu Lys Lys Ser Val Ser Met
                325                 330                 335

Leu Ser Leu Asn Thr Pro Asn Ser Asn Arg Lys Arg Arg Leu Lys
            340                 345                 350

Glu Thr Leu Ala Gln Leu Ser Arg Glu Thr Asp Val Ser Pro Phe Pro
        355                 360                 365

Pro Arg Lys Arg Pro Ser Ala Glu His Ser Leu Ser Ile Gly Ser Leu
    370                 375                 380
```

```
Leu Asp Ile Ser Asn Thr Pro Glu Ser Ser Ile Asn Tyr Gly Asp Thr
385                 390                 395                 400

Pro Lys Ser Cys Thr Lys Ser Ser Lys Ser Ser Thr Pro Val Pro Ser
            405                 410                 415

Lys Gln Ser Ala Arg Trp Gln Val Ala Lys Glu Leu Tyr Gln Thr Glu
                420                 425                 430

Ser Asn Tyr Val Asn Ile Leu Ala Thr Ile Ile Gln Leu Phe Gln Val
            435                 440                 445

Pro Leu Glu Glu Glu Gly Gln Arg Gly Gly Pro Ile Leu Ala Pro Glu
        450                 455                 460

Glu Ile Lys Thr Ile Phe Gly Ser Ile Pro Asp Ile Phe Asp Val His
465                 470                 475                 480

Thr Lys Ile Lys Asp Asp Leu Glu Asp Leu Ile Val Asn Trp Asp Glu
                485                 490                 495

Ser Lys Ser Ile Gly Asp Ile Phe Leu Lys Tyr Ser Lys Asp Leu Val
            500                 505                 510

Lys Thr Tyr Pro Pro Phe Val Asn Phe Phe Glu Met Ser Lys Glu Thr
        515                 520                 525

Ile Ile Lys Cys Glu Lys Gln Lys Pro Arg Phe His Ala Phe Leu Lys
530                 535                 540

Ile Asn Gln Ala Lys Pro Glu Cys Gly Arg Gln Ser Leu Val Glu Leu
545                 550                 555                 560

Leu Ile Arg Pro Val Gln Arg Leu Pro Ser Val Ala Leu Leu Leu Asn
            565                 570                 575

Asp Leu Lys Lys His Thr Ala Asp Glu Asn Pro Asp Lys Ser Thr Leu
        580                 585                 590

Glu Lys Ala Ile Gly Ser Leu Lys Glu Val Met Thr His Ile Asn Glu
            595                 600                 605

Asp Lys Arg Lys Thr Glu Ala Gln Lys Gln Ile Phe Asp Val Val Tyr
        610                 615                 620

Glu Val Asp Gly Cys Pro Ala Asn Leu Leu Ser Ser His Arg Ser Leu
625                 630                 635                 640

Val Gln Arg Val Glu Thr Ile Ser Leu Gly Glu His Pro Cys Asp Arg
            645                 650                 655

Gly Glu Gln Val Thr Leu Phe Leu Phe Asn Asp Cys Leu Glu Ile Ala
        660                 665                 670

Arg Lys Arg His Lys Val Ile Gly Thr Phe Arg Ser Pro His Gly Gln
        675                 680                 685

Thr Arg Pro Pro Ala Ser Leu Lys His Ile His Leu Met Pro Leu Ser
690                 695                 700

Gln Ile Lys Lys Val Leu Asp Ile Arg Glu Thr Glu Asp Cys His Asn
705                 710                 715                 720

Ala Phe Ala Leu Leu Val Arg Pro Pro Thr Glu Gln Ala Asn Val Leu
            725                 730                 735

Leu Ser Phe Gln Met Thr Ser Asp Glu Leu Pro Lys Glu Asn Trp Leu
        740                 745                 750

Lys Met Leu Cys Arg His Val Ala Asn Thr Ile Cys Lys Ala Asp Ala
            755                 760                 765

Glu Asn Leu Ile Tyr Thr Ala Asp Pro Glu Ser Phe Glu Val Asn Thr
        770                 775                 780

Lys Asp Met Asp Ser Thr Leu Ser Arg Ala Ser Arg Ala Ile Lys Lys
785                 790                 795                 800

Thr Ser Lys Lys Val Thr Arg Ala Phe Ser Phe Ser Lys Thr Pro Lys
```

|  | 805 |  |  |  | 810 |  |  |  | 815 |  |  |
|---|---|---|---|---|---|---|---|---|---|---|---|

Arg Ala Leu Arg Arg Ala Leu Met Thr Ser His Gly Ser Val Glu Gly
        820                  825                 830

Arg Ser Pro Ser Ser Asn Asp Lys His Val Met Ser Arg Leu Ser Ser
        835                  840               845

Thr Ser Ser Leu Ala Gly Ile Pro Ser Pro Ser Leu Val Ser Leu Pro
    850                  855               860

Ser Phe Phe Glu Arg Arg Ser His Thr Leu Ser Arg Ser Thr Thr His
865                870               875              880

Leu Ile

<210> SEQ ID NO 7
<211> LENGTH: 1372
<212> TYPE: DNA
<213> ORGANISM: Homo sapiens
<220> FEATURE:
<221> NAME/KEY: CDS
<222> LOCATION: (206)..(397)

<400> SEQUENCE: 7

| | |
|---|---|
| gcacgagggc gcttttgtct ccggtgagtt ttgtggcggg aagcttctgc gctggtgctt | 60 |
| agtaaccgac tttcctccgg actcctgcac gacctgctcc tacagccggc gatccactcc | 120 |
| cggctgttcc cccggagggt ccagaggcct tcagaagga gaaggcagct ctgtttctct | 180 | gcagaggagt agggtccttt cagcc atg aag cat gtg ttg aac ctc tac ctg    232
                                    Met Lys His Val Leu Asn Leu Tyr Leu
                                     1               5 tta ggt gtg gta ctg acc cta ctc tcc atc ttc gtt aga gtg atg gag    280
Leu Gly Val Val Leu Thr Leu Leu Ser Ile Phe Val Arg Val Met Glu
10                 15               20               25 tcc cta gaa ggc tta cta gag agc cca tcg cct ggg acc tcc tgg acc    328
Ser Leu Glu Gly Leu Leu Glu Ser Pro Ser Pro Gly Thr Ser Trp Thr
                30               35               40 acc aga agc caa cta gcc aac aca gag ccc acc aag ggc ctt cca gac    376
Thr Arg Ser Gln Leu Ala Asn Thr Glu Pro Thr Lys Gly Leu Pro Asp
               45               50               55 cat cca tcc aga agc atg tga taagacctcc ttccatactg gccatatttt    427
His Pro Ser Arg Ser Met
          60

| | |
|---|---|
| ggaacactga cctagacatg tccagatggg agtcccattc ctagcagaca agctgagcac | 487 |
| cgttgtaacc agagaactat tactaggcct tgaagaacct gtctaactgg atgctcattg | 547 |
| cctgggcaag gcctgtttag gccggttgcg gtggctcatg cctgtaatcc tagcactttg | 607 |
| ggaggctgag gtgggtggat cacctgaggt caggagttcg agaccagcct cgccaacatg | 667 |
| gcgaaacccc atctctacta aaaatacaaa agttagctgg gtgtggtggc agaggcctgt | 727 |
| aatcccagtt ccttgggagg ctgaggcggg agaattgctt gaacccgggg acggaggttg | 787 |
| cagtgaaccg agatcgcact gctgtaccca gcctgggcca cagtgcaaga ctccatctca | 847 |
| aaaaaaaaaa gaaagaaaaa agcctgttta atgcacaggt gtgagtggat tgcttatggc | 907 |
| tatgagatag gttgatctcg cccttacccc ggggtctggt gtatgctgtg ctttcctcag | 967 |
| cagtatggct ctgacatctc ttagatgtcc caacttcagc tgttgggaga tggtgatatt | 1027 |
| ttcaacccta cttcctaaac atctgtctgg ggttccttta gtcttgaatg tcttatgctc | 1087 |
| aattatttgg tgttgagcct ctcttccaca agagctcctc catgtttgga tagcagttga | 1147 |
| agaggttgtg tgggtgggct gttgggagtg aggatggagt gttcagtgcc catttctcat | 1207 |
| tttacatttt aaagtcgttc ctccaacata gtgtgtattg gtctgaaggg ggtggtggga | 1267 |

```
tgccaaagcc tgctcaagtt atggacattg tggccaccat gtggcttaaa tgattttttc      1327
taactaataa agtggaatat atatttcaaa aaaaaaaaaa aaaaa                      1372

<210> SEQ ID NO 8
<211> LENGTH: 63
<212> TYPE: PRT
<213> ORGANISM: Homo sapiens

<400> SEQUENCE: 8

Met Lys His Val Leu Asn Leu Tyr Leu Leu Gly Val Val Leu Thr Leu
1               5                   10                  15

Leu Ser Ile Phe Val Arg Val Met Glu Ser Leu Glu Gly Leu Leu Glu
            20                  25                  30

Ser Pro Ser Pro Gly Thr Ser Trp Thr Thr Arg Ser Gln Leu Ala Asn
        35                  40                  45

Thr Glu Pro Thr Lys Gly Leu Pro Asp His Pro Ser Arg Ser Met
    50                  55                  60

<210> SEQ ID NO 9
<211> LENGTH: 3516
<212> TYPE: DNA
<213> ORGANISM: Homo sapiens
<220> FEATURE:
<221> NAME/KEY: CDS
<222> LOCATION: (767)..(1990)

<400> SEQUENCE: 9
ggatcctgga gacaactttg ccgtgtgacg cgccggagg actgcagggc ccgcggccga       60
gggctcggcg ccgcctgtga gcgggcccgc gcggccggct ctcccgggca ccaagcttgc      120
tccgcgccac tgcccgccgg cccgcggcga ggacgacctg cccgtctccg ccgccggcgg     180
cccttcctgg cgcgaggcag tgagggcgag gcgctcaggt gcgagcgcgg ggccccgccg     240
cagcgcccgc cgcagcgccg cgccaagccg cgccggctc cgctccgggg ggctccagcg     300
ccttcgcttc cgtctcagcc aagttgcgtg gacccgctct ttcgccacct tccccagccg     360
ccggccgaac cgccgctccc actgacgctg ctttcgcttc acccgaaccg gggctgcggg    420
gcccccgacg cggaaaggat ggggagaagg ctgcagatgc cgaggcgccc cgagacgccc    480
gtgcggcagt gacccgcgac ctccgccccg cccggcgcgc cctcgggcc ccggggccc      540 tcggcgcccc ttccctgccg cgcgggaacc cccgaggccc ggccggcccc ctcccctgc     600 gagccggcgg cagccctccc ggcgggcggg cgggcggagg cccgggcggg cgcgggcgcg    660
ggcgggggcg gggcggggcg gcgcgcccgg agcccggagc ccggccctgc gctcggctcg    720

775
actcggctcg cctcgcggcg ggcgccctcg tcgccagcgg cgcacc atg gac ggg
                                                   Met Asp Gly
                                                   1 ctg ccc ggt cgg gcg ctg ggg gcc gcc tgc ctt ctg ctg ctg gcg gcc      823
Leu Pro Gly Arg Ala Leu Gly Ala Ala Cys Leu Leu Leu Leu Ala Ala
        5                   10                  15 ggc tgg ctg ggg cct gag gcc tgg ggc tca ccc acg ccc ccg ccg acg      871
Gly Trp Leu Gly Pro Glu Ala Trp Gly Ser Pro Thr Pro Pro Pro Thr
20                  25                  30                  35 cct gcc gcg ccg ccg cca ccc ccg cca ccc gga gcc ccg ggt ggc tcg      919
Pro Ala Ala Pro Pro Pro Pro Pro Pro Pro Gly Ala Pro Gly Gly Ser
                40                  45                  50 cag gac acc tgt acg tcg tgc ggc ggc ttc cgg cgg cca gag gag ctc      967
Gln Asp Thr Cys Thr Ser Cys Gly Gly Phe Arg Arg Pro Glu Glu Leu
        55                  60                  65
```

```
ggc cga gtg gac ggc gac ttc ctg gag gcg gtg aag cgg cac atc ttg    1015
Gly Arg Val Asp Gly Asp Phe Leu Glu Ala Val Lys Arg His Ile Leu
        70                  75                  80 agc cgc ctg cag atg cgg ggc cgg ccc aac atc acg cac gcc gtg cct    1063
Ser Arg Leu Gln Met Arg Gly Arg Pro Asn Ile Thr His Ala Val Pro
    85                  90                  95 aag gcc gcc atg gtc acg gcc ctg cgc aag ctg cac gcg ggc aag gtg    1111
Lys Ala Ala Met Val Thr Ala Leu Arg Lys Leu His Ala Gly Lys Val
100                 105                 110                 115 cgc gag gac ggc cgc gtg gag atc ccg cac ctc gac ggc cac gcc agc    1159
Arg Glu Asp Gly Arg Val Glu Ile Pro His Leu Asp Gly His Ala Ser
                120                 125                 130 ccg ggc gcc gac ggc cag gag cgc gtt tcc gaa atc atc agc ttc gcc    1207
Pro Gly Ala Asp Gly Gln Glu Arg Val Ser Glu Ile Ile Ser Phe Ala
            135                 140                 145 gag aca gat ggc ctc gcc tcc tcc cgg gtc cgc cta tac ttc ttc atc    1255
Glu Thr Asp Gly Leu Ala Ser Ser Arg Val Arg Leu Tyr Phe Phe Ile
        150                 155                 160 tcc aac gaa ggc aac cag aac ctg ttt gtg gtc cag gcc agc ctg tgg    1303
Ser Asn Glu Gly Asn Gln Asn Leu Phe Val Val Gln Ala Ser Leu Trp
    165                 170                 175 ctt tac ctg aaa ctc ctg ccc tac gtc ctg gag aag ggc agc cgg cgg    1351
Leu Tyr Leu Lys Leu Leu Pro Tyr Val Leu Glu Lys Gly Ser Arg Arg
180                 185                 190                 195 aag gtg cgg gtc aaa gtg tac ttc cag gag cag ggc cac ggt gac agg    1399
Lys Val Arg Val Lys Val Tyr Phe Gln Glu Gln Gly His Gly Asp Arg
                200                 205                 210 tgg aac atg gtg gag aag agg gtg gac ctc aag cgc agc ggc tgg cat    1447
Trp Asn Met Val Glu Lys Arg Val Asp Leu Lys Arg Ser Gly Trp His
            215                 220                 225 acc ttc cca ctc acg gag gcc atc cag gcc ttg ttt gag cgg ggc gag    1495
Thr Phe Pro Leu Thr Glu Ala Ile Gln Ala Leu Phe Glu Arg Gly Glu
        230                 235                 240 cgg cga ctc aac cta gac gtg cag tgt gac agc tgc cag gag ctg gcc    1543
Arg Arg Leu Asn Leu Asp Val Gln Cys Asp Ser Cys Gln Glu Leu Ala
    245                 250                 255 gtg gtg ccg gtg ttc gtg gac cca ggc gaa gag tcg cac cga ccc ttt    1591
Val Val Pro Val Phe Val Asp Pro Gly Glu Glu Ser His Arg Pro Phe
260                 265                 270                 275 gtg gtg gtg cag gct cgg ctg ggc gac agc agg cac cgc att cgc aag    1639
Val Val Val Gln Ala Arg Leu Gly Asp Ser Arg His Arg Ile Arg Lys
                280                 285                 290 cga ggc ctg gag tgc gat ggc cgg acc aac ctc tgt tgc agg caa cag    1687
Arg Gly Leu Glu Cys Asp Gly Arg Thr Asn Leu Cys Cys Arg Gln Gln
            295                 300                 305 ttc ttc att gac ttc cgc ctc atc ggc tgg aac gac tgg atc ata gca    1735
Phe Phe Ile Asp Phe Arg Leu Ile Gly Trp Asn Asp Trp Ile Ile Ala
        310                 315                 320 ccc acc ggc tac tac ggc aac tac tgt gag ggc agc tgc cca gcc tac    1783
Pro Thr Gly Tyr Tyr Gly Asn Tyr Cys Glu Gly Ser Cys Pro Ala Tyr
    325                 330                 335 ctg gca ggg gtc ccc ggc tct gcc tcc tcc ttc cac acg gct gtg gtg    1831
Leu Ala Gly Val Pro Gly Ser Ala Ser Ser Phe His Thr Ala Val Val
340                 345                 350                 355 aac cag tac cgc atg cgg ggt ctg aac ccc ggc acg gtg aac tcc tgc    1879
Asn Gln Tyr Arg Met Arg Gly Leu Asn Pro Gly Thr Val Asn Ser Cys
                360                 365                 370 tgc att ccc acc aag ctg agc acc atg tcc atg ctg tac ttc gat gat    1927
Cys Ile Pro Thr Lys Leu Ser Thr Met Ser Met Leu Tyr Phe Asp Asp
            375                 380                 385
```

-continued

| | | |
|---|---|---|
| gag tac aac atc gtc aag cgg gac gtg ccc aac atg att gtg gag gag<br>Glu Tyr Asn Ile Val Lys Arg Asp Val Pro Asn Met Ile Val Glu Glu<br>      390                 395                 400 | | 1975 |
| tgc ggc tgc gcc tga cagtgcaagg caggggcacg gtggtggggc acggagggca<br>Cys Gly Cys Ala<br>    405 | | 2030 |
| gtcccgggtg ggcttcttcc agcccccgc gggaacgggg tacacggtgg gctgagtaca | | 2090 |
| gtcattctgt tgggctgtgg agatagtgcc agggtgcggc ctgagatatt tttctacagc | | 2150 |
| ttcatagagc aaccagtcaa aaccagagcg agaaccctca actgacatga aatactttaa | | 2210 |
| aatgcacacg tagccacgca cagccagacg catcctgcca cccacacagc agcctccagg | | 2270 |
| ataccagcaa atggatgcgg tgacaaatgg cagcttagct acaaatgcct gtcagtcgga | | 2330 |
| gagaatgggg tgagcagcca ccattccacc agctggcccg gccacgtctc gaagttgcgc | | 2390 |
| cttcccgagc acacataaaa gcacaaagac agagacgcag agagagagag agagccacgg | | 2450 |
| agaggaaaag cagatgcagg ggtgggagc gcagctcggc ggaggctgcg tgtgccccgt | | 2510 |
| ggcttttacc aggcctgctc tgcctggctc gatgtctgct tcttcccagc ctgggatcct | | 2570 |
| tcgtgcttca aggcctgggg agcctgtcct tccatgccct tgtcgaggga agagacccca | | 2630 |
| gaaaggacac aacccgtcag agacctggga gcaggggcaa tgaccgtttg actgtttgtg | | 2690 |
| gcttgggcct ctgacatgac ttatgtgtgt gtgtgttttt ggggtgggga gggagggaga | | 2750 |
| gaagaggggg ctaaatttga tgctttaact gatctccaac agttgacagg tcatccttgc | | 2810 |
| cagttgtata actgaaaaag gactttctca ccaggtatga cctttaagt gaaaatctga | | 2870 |
| attgttctaa atgaaagaa aaaagttgc aatctgtgcc cttcattggg gacattcctc | | 2930 |
| taggactggt ttggggacgg gtgggaatga cccctaggca aggggatgag accgcaggag | | 2990 |
| gaaatggcgg ggaggtggca ttcttgaact gctgaggatg gggggtgtcc cctcagcgga | | 3050 |
| ggccaaggga ggggagcagc ctagttggtc ttggagagat ggggaaggct ttcagctgat | | 3110 |
| ttgcagaagt tgcccatgtg ggcccaacca tcagggctgg ccgtggacgt ggcccctgcc | | 3170 |
| cactcacctg cccgcctgcc cgcccgcccg catagcactt gcagacctgc ctgaacgcac | | 3230 |
| atgacatagc acttgccgat ctgcgtgtgc ccagaagtgg cccttggccg agcgccgaac | | 3290 |
| tcgctcgccc tctagatgtc caagtgccac gtgaactatg caatttaaag ggttgaccca | | 3350 |
| cactagacga aactggactc gtacgactct ttttatattt tttatacttg aaatgaaatc | | 3410 |
| ctttgcttct tttttaagcg aatgattgct tttaatgttt gcactgattt agttgcatga | | 3470 |
| ttagtcagaa actgccattt gaaaaaaag ttatttttat agcagc | | 3516 |

<210> SEQ ID NO 10
<211> LENGTH: 407
<212> TYPE: PRT
<213> ORGANISM: Homo sapiens

<400> SEQUENCE: 10

Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
            20                  25                  30

Pro Pro Thr Pro Ala Ala Pro Pro Pro Pro Pro Pro Gly Ala Pro
        35                  40                  45

Gly Gly Ser Gln Asp Thr Cys Thr Ser Cys Gly Gly Phe Arg Arg Pro
    50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
              85                  90                  95

Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly
        115                 120                 125

His Ala Ser Pro Gly Ala Asp Gly Gln Glu Arg Val Ser Glu Ile Ile
    130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Val Gln Ala
                165                 170                 175

Ser Leu Trp Leu Tyr Leu Lys Leu Leu Pro Tyr Val Leu Glu Lys Gly
            180                 185                 190

Ser Arg Arg Lys Val Arg Val Lys Val Tyr Phe Gln Glu Gln Gly His
        195                 200                 205

Gly Asp Arg Trp Asn Met Val Glu Lys Arg Val Asp Leu Lys Arg Ser
    210                 215                 220

Gly Trp His Thr Phe Pro Leu Thr Glu Ala Ile Gln Ala Leu Phe Glu
225                 230                 235                 240

Arg Gly Glu Arg Leu Asn Leu Asp Val Gln Cys Asp Ser Cys Gln
                245                 250                 255

Glu Leu Ala Val Val Pro Val Phe Val Asp Pro Gly Glu Glu Ser His
            260                 265                 270

Arg Pro Phe Val Val Val Gln Ala Arg Leu Gly Asp Ser Arg His Arg
        275                 280                 285

Ile Arg Lys Arg Gly Leu Glu Cys Asp Gly Arg Thr Asn Leu Cys Cys
    290                 295                 300

Arg Gln Gln Phe Phe Ile Asp Phe Arg Leu Ile Gly Trp Asn Asp Trp
305                 310                 315                 320

Ile Ile Ala Pro Thr Gly Tyr Tyr Gly Asn Tyr Cys Glu Gly Ser Cys
                325                 330                 335

Pro Ala Tyr Leu Ala Gly Val Pro Gly Ser Ala Ser Ser Phe His Thr
            340                 345                 350

Ala Val Val Asn Gln Tyr Arg Met Arg Gly Leu Asn Pro Gly Thr Val
        355                 360                 365

Asn Ser Cys Cys Ile Pro Thr Lys Leu Ser Thr Met Ser Met Leu Tyr
    370                 375                 380

Phe Asp Asp Glu Tyr Asn Ile Val Lys Arg Asp Val Pro Asn Met Ile
385                 390                 395                 400

Val Glu Glu Cys Gly Cys Ala
                405

<210> SEQ ID NO 11
<211> LENGTH: 2972
<212> TYPE: DNA
<213> ORGANISM: Homo sapiens
<220> FEATURE:
<221> NAME/KEY: CDS
<222> LOCATION: (28)..(2700)

<400> SEQUENCE: 11
tcttcggacc taggctgccc tgccgtc atg tcg caa ggg atc ctt tct ccg cca      54
                              Met Ser Gln Gly Ile Leu Ser Pro Pro
                                1               5 gcg ggc ttg ctg tcc gat gac gat gtc gta gtt tct ccc atg ttt gag      102

-continued

| | | | | | | | | | | | | | | | | |
|---|---|---|---|---|---|---|---|---|---|---|---|---|---|---|---|---|
| | Ala | Gly | Leu | Leu | Ser | Asp | Asp | Val | Val | Ser | Pro | Met | Phe | Glu | | |
| | 10 | | | | 15 | | | | 20 | | | | | 25 | | |
| tcc | aca | gct | gca | gat | ttg | ggg | tct | gtg | gta | cgc | aag | aac | ctg | cta | tca | 150 |
| Ser | Thr | Ala | Ala | Asp | Leu | Gly | Ser | Val | Val | Arg | Lys | Asn | Leu | Leu | Ser | |
| | | | 30 | | | | | 35 | | | | | 40 | | | |
| gac | tgc | tct | gtc | gtc | tct | acc | tcc | cta | gag | gac | aag | cag | cag | gtt | cca | 198 |
| Asp | Cys | Ser | Val | Val | Ser | Thr | Ser | Leu | Glu | Asp | Lys | Gln | Gln | Val | Pro | |
| | | | 45 | | | | | 50 | | | | | 55 | | | |
| tct | gag | gac | agt | atg | gag | aag | gtg | aaa | gta | tac | ttg | agg | gtt | agg | ccc | 246 |
| Ser | Glu | Asp | Ser | Met | Glu | Lys | Val | Lys | Val | Tyr | Leu | Arg | Val | Arg | Pro | |
| | | 60 | | | | 65 | | | | | 70 | | | | | |
| ttg | tta | cct | tca | gag | ttg | gaa | cga | cag | gaa | gat | cag | ggt | tgt | gtc | cgt | 294 |
| Leu | Leu | Pro | Ser | Glu | Leu | Glu | Arg | Gln | Glu | Asp | Gln | Gly | Cys | Val | Arg | |
| | 75 | | | | 80 | | | | | 85 | | | | | | |
| att | gag | aat | gtg | gag | acc | ctt | gtt | cta | caa | gca | ccc | aag | gac | tcg | ttt | 342 |
| Ile | Glu | Asn | Val | Glu | Thr | Leu | Val | Leu | Gln | Ala | Pro | Lys | Asp | Ser | Phe | |
| 90 | | | | 95 | | | | | 100 | | | | | 105 | | |
| gcc | ctg | aag | agc | aat | gaa | cgg | gga | att | ggc | caa | gcc | aca | cac | agg | ttc | 390 |
| Ala | Leu | Lys | Ser | Asn | Glu | Arg | Gly | Ile | Gly | Gln | Ala | Thr | His | Arg | Phe | |
| | | | 110 | | | | | 115 | | | | | 120 | | | |
| acc | ttt | tcc | cag | atc | ttt | ggg | cca | gaa | gtg | gga | cag | gca | tcc | ttc | ttc | 438 |
| Thr | Phe | Ser | Gln | Ile | Phe | Gly | Pro | Glu | Val | Gly | Gln | Ala | Ser | Phe | Phe | |
| | | 125 | | | | | 130 | | | | | 135 | | | | |
| aac | cta | act | gtg | aag | gag | atg | gta | aag | gat | gta | ctc | aaa | ggg | cag | aac | 486 |
| Asn | Leu | Thr | Val | Lys | Glu | Met | Val | Lys | Asp | Val | Leu | Lys | Gly | Gln | Asn | |
| | | 140 | | | | | 145 | | | | | 150 | | | | |
| tgg | ctc | atc | tat | aca | tat | gga | gtc | act | aac | tca | ggg | aaa | acc | cac | acg | 534 |
| Trp | Leu | Ile | Tyr | Thr | Tyr | Gly | Val | Thr | Asn | Ser | Gly | Lys | Thr | His | Thr | |
| | 155 | | | | | 160 | | | | | 165 | | | | | |
| att | caa | ggt | acc | atc | aag | gat | gga | ggg | att | ctc | ccc | cgg | tcc | ctg | gcg | 582 |
| Ile | Gln | Gly | Thr | Ile | Lys | Asp | Gly | Gly | Ile | Leu | Pro | Arg | Ser | Leu | Ala | |
| 170 | | | | | 175 | | | | | 180 | | | | | 185 | |
| ctg | atc | ttc | aat | agc | ctc | caa | ggc | caa | ctt | cat | cca | aca | cct | gat | ctg | 630 |
| Leu | Ile | Phe | Asn | Ser | Leu | Gln | Gly | Gln | Leu | His | Pro | Thr | Pro | Asp | Leu | |
| | | | 190 | | | | | 195 | | | | | 200 | | | |
| aag | ccc | ttg | ctc | tcc | aat | gag | gta | atc | tgg | cta | gac | agc | aag | cag | atc | 678 |
| Lys | Pro | Leu | Leu | Ser | Asn | Glu | Val | Ile | Trp | Leu | Asp | Ser | Lys | Gln | Ile | |
| | | 205 | | | | | 210 | | | | | 215 | | | | |
| cga | cag | gag | gaa | atg | aag | aag | ctg | tcc | ctg | cta | aat | gga | ggc | ctc | caa | 726 |
| Arg | Gln | Glu | Glu | Met | Lys | Lys | Leu | Ser | Leu | Leu | Asn | Gly | Gly | Leu | Gln | |
| | 220 | | | | | 225 | | | | | 230 | | | | | |
| gag | gag | gag | ctg | tcc | act | tcc | ttg | aag | agg | agt | gtc | tac | atc | gaa | agt | 774 |
| Glu | Glu | Glu | Leu | Ser | Thr | Ser | Leu | Lys | Arg | Ser | Val | Tyr | Ile | Glu | Ser | |
| | 235 | | | | | 240 | | | | | 245 | | | | | |
| cgg | ata | ggt | acc | agc | acc | agc | ttc | gac | agt | ggc | att | gct | ggg | ctc | tct | 822 |
| Arg | Ile | Gly | Thr | Ser | Thr | Ser | Phe | Asp | Ser | Gly | Ile | Ala | Gly | Leu | Ser | |
| 250 | | | | | 255 | | | | | 260 | | | | | 265 | |
| tct | atc | agt | cag | tgt | acc | agc | agt | agc | cag | ctg | gat | gaa | aca | agt | cat | 870 |
| Ser | Ile | Ser | Gln | Cys | Thr | Ser | Ser | Ser | Gln | Leu | Asp | Glu | Thr | Ser | His | |
| | | | 270 | | | | | 275 | | | | | 280 | | | |
| cga | tgg | gca | cag | cca | gac | act | gcc | cca | cta | cct | gtc | ccg | gca | aac | att | 918 |
| Arg | Trp | Ala | Gln | Pro | Asp | Thr | Ala | Pro | Leu | Pro | Val | Pro | Ala | Asn | Ile | |
| | | 285 | | | | | 290 | | | | | 295 | | | | |
| cgc | ttc | tcc | atc | tgg | atc | tca | ttc | ttt | gag | atc | tac | aac | gaa | ctg | ctt | 966 |
| Arg | Phe | Ser | Ile | Trp | Ile | Ser | Phe | Phe | Glu | Ile | Tyr | Asn | Glu | Leu | Leu | |
| | | 300 | | | | | 305 | | | | | 310 | | | | |
| tat | gac | cta | tta | gaa | ccg | cct | agc | caa | cag | cgc | aag | agg | cag | act | ttg | 1014 |
| Tyr | Asp | Leu | Leu | Glu | Pro | Pro | Ser | Gln | Gln | Arg | Lys | Arg | Gln | Thr | Leu | |
| | 315 | | | | | 320 | | | | | 325 | | | | | |
| cgg | cta | tgc | gag | gat | caa | aat | ggc | aat | ccc | tat | gtg | aaa | gat | ctc | aac | 1062 |

```
                                                                -continued

Arg Leu Cys Glu Asp Gln Asn Gly Asn Pro Tyr Val Lys Asp Leu Asn
330             335                 340                 345 tgg att cat gtg caa gat gct gag gag gcc tgg aag ctc cta aaa gtg    1110
Trp Ile His Val Gln Asp Ala Glu Glu Ala Trp Lys Leu Leu Lys Val
            350                 355                 360 ggt cgt aag aac cag agc ttt gcc agc acc cac ctc aac cag aac tcc    1158
Gly Arg Lys Asn Gln Ser Phe Ala Ser Thr His Leu Asn Gln Asn Ser
                365                 370                 375 agc cgc agt cac agc atc ttc tca atc agg atc cta cac ctt cag ggg    1206
Ser Arg Ser His Ser Ile Phe Ser Ile Arg Ile Leu His Leu Gln Gly
            380                 385                 390 gaa gga gat ata gtc ccc aag atc agc gag ctg tca ctc tgt gat ctg    1254
Glu Gly Asp Ile Val Pro Lys Ile Ser Glu Leu Ser Leu Cys Asp Leu
395                 400                 405 gct ggc tca gag cgc tgc aaa gat cag aag agt ggt gaa cgg ttg aag    1302
Ala Gly Ser Glu Arg Cys Lys Asp Gln Lys Ser Gly Glu Arg Leu Lys
410                 415                 420                 425 gaa gca gga aac att aac acc tct cta cac acc ctg ggc cgc tgt att    1350
Glu Ala Gly Asn Ile Asn Thr Ser Leu His Thr Leu Gly Arg Cys Ile
                430                 435                 440 gct gcc ctt cgt caa aac cag cag aac cgg tca aag cag aac ctg gtt    1398
Ala Ala Leu Arg Gln Asn Gln Gln Asn Arg Ser Lys Gln Asn Leu Val
            445                 450                 455 ccc ttc cgt gac agc aag ttg act cga gtg ttc caa ggt ttc ttc aca    1446
Pro Phe Arg Asp Ser Lys Leu Thr Arg Val Phe Gln Gly Phe Phe Thr
        460                 465                 470 ggc cga ggc cgt tcc tgc atg att gtc aat gtg aat ccc tgt gca tct    1494
Gly Arg Gly Arg Ser Cys Met Ile Val Asn Val Asn Pro Cys Ala Ser
475                 480                 485 acc tat gat gaa act ctt cat gtg gcc aag ttc tca gcc att gct agc    1542
Thr Tyr Asp Glu Thr Leu His Val Ala Lys Phe Ser Ala Ile Ala Ser
490                 495                 500                 505 cag ctt gtg cat gcc cca cct atg caa ctg gga ttc cca tcc ctg cac    1590
Gln Leu Val His Ala Pro Pro Met Gln Leu Gly Phe Pro Ser Leu His
                510                 515                 520 tcg ttc atc aag gaa cat agt ctt cag gta tcc ccc agc tta gag aaa    1638
Ser Phe Ile Lys Glu His Ser Leu Gln Val Ser Pro Ser Leu Glu Lys
            525                 530                 535 ggg gct aag gca gac aca ggc ctt gat gat gat att gaa aat gaa gct    1686
Gly Ala Lys Ala Asp Thr Gly Leu Asp Asp Asp Ile Glu Asn Glu Ala
        540                 545                 550 gac atc tcc atg tat ggc aaa gag gag ctc cta caa gtt gtg gaa gcc    1734
Asp Ile Ser Met Tyr Gly Lys Glu Glu Leu Leu Gln Val Val Glu Ala
555                 560                 565 atg aag aca ctg ctt ttg aag gaa cga cag gaa aag cta cag ctg gag    1782
Met Lys Thr Leu Leu Leu Lys Glu Arg Gln Glu Lys Leu Gln Leu Glu
570                 575                 580                 585 atg cat ctc cga gat gaa att tgc aat gag atg gta gaa cag atg caa    1830
Met His Leu Arg Asp Glu Ile Cys Asn Glu Met Val Glu Gln Met Gln
                590                 595                 600 cag cgg gaa cag tgg tgc agt gaa cat ttg gac acc caa aag gaa cta    1878
Gln Arg Glu Gln Trp Cys Ser Glu His Leu Asp Thr Gln Lys Glu Leu
            605                 610                 615 ttg gag gaa atg tat gaa gaa aaa cta aat atc ctc aag gag tca ctg    1926
Leu Glu Glu Met Tyr Glu Glu Lys Leu Asn Ile Leu Lys Glu Ser Leu
        620                 625                 630 aca agt ttt tac caa gaa gag att cag gag cgg gat gaa aag att gaa    1974
Thr Ser Phe Tyr Gln Glu Glu Ile Gln Glu Arg Asp Glu Lys Ile Glu
635                 640                 645 gag cta gaa gct ctc ttg cag gaa gcc aga caa cag tca gtg gcc cat    2022
```

| | | | | | | | | | | | | | | | |
|---|---|---|---|---|---|---|---|---|---|---|---|---|---|---|---|
|Glu|Leu|Glu|Ala|Leu|Leu|Gln|Glu|Ala|Arg|Gln|Gln|Ser|Val|Ala|His|
|650| | | | |655| | | | |660| | | | |665|

```
cag caa tca ggg tct gaa ttg gcc cta cgg cgg tca caa agg ttg gca         2070
Gln Gln Ser Gly Ser Glu Leu Ala Leu Arg Arg Ser Gln Arg Leu Ala
            670                 675                 680 gct tct gcc tcc acc cag cag ctt cag gag gtt aaa gct aaa tta cag         2118
Ala Ser Ala Ser Thr Gln Gln Leu Gln Glu Val Lys Ala Lys Leu Gln
        685                 690                 695 cag tgc aaa gca gag cta aac tct acc act gaa gag ttg cat aag tat         2166
Gln Cys Lys Ala Glu Leu Asn Ser Thr Thr Glu Glu Leu His Lys Tyr
    700                 705                 710 cag aaa atg tta gaa cca cca ccc tca gcc aag ccc ttc acc att gat         2214
Gln Lys Met Leu Glu Pro Pro Pro Ser Ala Lys Pro Phe Thr Ile Asp
715                 720                 725 gtg gac aag aag tta gaa gag ggc cag aag aat ata agg ctg ttg cgg         2262
Val Asp Lys Lys Leu Glu Glu Gly Gln Lys Asn Ile Arg Leu Leu Arg
730                 735                 740                 745 aca gag ctt cag aaa ctt ggt gag tct ctc caa tca gca gag aga gct         2310
Thr Glu Leu Gln Lys Leu Gly Glu Ser Leu Gln Ser Ala Glu Arg Ala
            750                 755                 760 tgt tgc cac agc act ggg gca gga aaa ctt cgt caa gcc ttg acc act         2358
Cys Cys His Ser Thr Gly Ala Gly Lys Leu Arg Gln Ala Leu Thr Thr
        765                 770                 775 tgt gat gac atc tta atc aaa cag gac cag act ctg gct gaa ctg cag         2406
Cys Asp Asp Ile Leu Ile Lys Gln Asp Gln Thr Leu Ala Glu Leu Gln
    780                 785                 790 aac aac atg gtg cta gtg aaa ctg gac ctt cgg aag aag gca gca tgt         2454
Asn Asn Met Val Leu Val Lys Leu Asp Leu Arg Lys Lys Ala Ala Cys
795                 800                 805 att gct gag cag tat cat act gtg ttg aaa ctc caa ggc cag gtt tct         2502
Ile Ala Glu Gln Tyr His Thr Val Leu Lys Leu Gln Gly Gln Val Ser
810                 815                 820                 825 gcc aaa aag cgc ctt ggt acc aac cag gaa aat cag caa cca aac caa         2550
Ala Lys Lys Arg Leu Gly Thr Asn Gln Glu Asn Gln Gln Pro Asn Gln
            830                 835                 840 caa cca cca ggg aag aaa cca ttc ctt cga aat tta ctt ccc cga aca         2598
Gln Pro Pro Gly Lys Lys Pro Phe Leu Arg Asn Leu Leu Pro Arg Thr
        845                 850                 855 cca acc tgc caa agc tca aca gac tgc agc cct tat gcc cgg atc cta         2646
Pro Thr Cys Gln Ser Ser Thr Asp Cys Ser Pro Tyr Ala Arg Ile Leu
    860                 865                 870 cgc tca cgg cgt tcc cct tta ctc aaa tct ggg cct ttt ggc aaa aag         2694
Arg Ser Arg Arg Ser Pro Leu Leu Lys Ser Gly Pro Phe Gly Lys Lys
875                 880                 885 tac taa ggctgtgggg aaagagaaga gcagtcatgg ccctgaggtg ggtcagctac          2750
Tyr
890 tctcctgaag aaataggtct cttttatgct ttaccatata tcaggaatta tatccaggat       2810 gcaatactca gacactagct ttttctcac ttttgtatta taaccaccta tgtaatctca        2870 tgttgttgtt ttttttttatt tacttatatg atttctatgc acacaaaaac agttatatta     2930 aagatattat tgttcacatt ttttattgaa aaaaaaaaaa aa                          2972

<210> SEQ ID NO 12
<211> LENGTH: 890
<212> TYPE: PRT
<213> ORGANISM: Homo sapiens

<400> SEQUENCE: 12

Met Ser Gln Gly Ile Leu Ser Pro Pro Ala Gly Leu Leu Ser Asp Asp
```

-continued

```
1               5                   10                  15
Asp Val Val Ser Pro Met Phe Glu Ser Thr Ala Ala Asp Leu Gly
                20                  25                  30

Ser Val Val Arg Lys Asn Leu Leu Ser Asp Cys Ser Val Ser Thr
                35                  40                  45

Ser Leu Glu Asp Lys Gln Gln Val Pro Ser Glu Asp Ser Met Glu Lys
50                  55                  60

Val Lys Val Tyr Leu Arg Val Arg Pro Leu Leu Pro Ser Glu Leu Glu
65                  70                  75                  80

Arg Gln Glu Asp Gln Gly Cys Val Arg Ile Glu Asn Val Glu Thr Leu
                        85                  90                  95

Val Leu Gln Ala Pro Lys Asp Ser Phe Ala Leu Lys Ser Asn Glu Arg
                100                 105                 110

Gly Ile Gly Gln Ala Thr His Arg Phe Thr Phe Ser Gln Ile Phe Gly
                115                 120                 125

Pro Glu Val Gly Gln Ala Ser Phe Phe Asn Leu Thr Val Lys Glu Met
                130                 135                 140

Val Lys Asp Val Leu Lys Gly Gln Asn Trp Leu Ile Tyr Thr Tyr Gly
145                 150                 155                 160

Val Thr Asn Ser Gly Lys Thr His Thr Ile Gln Gly Thr Ile Lys Asp
                165                 170                 175

Gly Gly Ile Leu Pro Arg Ser Leu Ala Leu Ile Phe Asn Ser Leu Gln
                180                 185                 190

Gly Gln Leu His Pro Thr Pro Asp Leu Lys Pro Leu Leu Ser Asn Glu
                195                 200                 205

Val Ile Trp Leu Asp Ser Lys Gln Ile Arg Gln Glu Glu Met Lys Lys
210                 215                 220

Leu Ser Leu Leu Asn Gly Gly Leu Gln Glu Glu Leu Ser Thr Ser
225                 230                 235                 240

Leu Lys Arg Ser Val Tyr Ile Glu Ser Arg Ile Gly Thr Ser Thr Ser
                245                 250                 255

Phe Asp Ser Gly Ile Ala Gly Leu Ser Ser Ile Ser Gln Cys Thr Ser
                260                 265                 270

Ser Ser Gln Leu Asp Glu Thr Ser His Arg Trp Ala Gln Pro Asp Thr
                275                 280                 285

Ala Pro Leu Pro Val Pro Ala Asn Ile Arg Phe Ser Ile Trp Ile Ser
                290                 295                 300

Phe Phe Glu Ile Tyr Asn Glu Leu Leu Tyr Asp Leu Leu Glu Pro Pro
305                 310                 315                 320

Ser Gln Gln Arg Lys Arg Gln Thr Leu Arg Leu Cys Glu Asp Gln Asn
                325                 330                 335

Gly Asn Pro Tyr Val Lys Asp Leu Asn Trp Ile His Val Gln Asp Ala
                340                 345                 350

Glu Glu Ala Trp Lys Leu Leu Lys Val Gly Arg Lys Asn Gln Ser Phe
                355                 360                 365

Ala Ser Thr His Leu Asn Gln Asn Ser Ser Arg Ser His Ser Ile Phe
                370                 375                 380

Ser Ile Arg Ile Leu His Leu Gln Gly Glu Gly Asp Ile Val Pro Lys
385                 390                 395                 400

Ile Ser Glu Leu Ser Leu Cys Asp Leu Ala Gly Ser Glu Arg Cys Lys
                405                 410                 415

Asp Gln Lys Ser Gly Glu Arg Leu Lys Glu Ala Gly Asn Ile Asn Thr
                420                 425                 430
```

-continued

```
Ser Leu His Thr Leu Gly Arg Cys Ile Ala Ala Leu Arg Gln Asn Gln
        435                 440                 445

Gln Asn Arg Ser Lys Gln Asn Leu Val Pro Phe Arg Asp Ser Lys Leu
    450                 455                 460

Thr Arg Val Phe Gln Gly Phe Phe Thr Gly Arg Gly Arg Ser Cys Met
465                 470                 475                 480

Ile Val Asn Val Asn Pro Cys Ala Ser Thr Tyr Asp Glu Thr Leu His
                485                 490                 495

Val Ala Lys Phe Ser Ala Ile Ala Ser Gln Leu Val His Ala Pro Pro
            500                 505                 510

Met Gln Leu Gly Phe Pro Ser Leu His Ser Phe Ile Lys Glu His Ser
        515                 520                 525

Leu Gln Val Ser Pro Ser Leu Glu Lys Gly Ala Lys Ala Asp Thr Gly
    530                 535                 540

Leu Asp Asp Asp Ile Glu Asn Glu Ala Asp Ile Ser Met Tyr Gly Lys
545                 550                 555                 560

Glu Glu Leu Leu Gln Val Val Glu Ala Met Lys Thr Leu Leu Lys
                565                 570                 575

Glu Arg Gln Glu Lys Leu Gln Leu Glu Met His Leu Arg Asp Glu Ile
            580                 585                 590

Cys Asn Glu Met Val Glu Gln Met Gln Gln Arg Glu Gln Trp Cys Ser
        595                 600                 605

Glu His Leu Asp Thr Gln Lys Glu Leu Leu Glu Glu Met Tyr Glu Glu
    610                 615                 620

Lys Leu Asn Ile Leu Lys Glu Ser Leu Thr Ser Phe Tyr Gln Glu Glu
625                 630                 635                 640

Ile Gln Glu Arg Asp Glu Lys Ile Glu Glu Leu Glu Ala Leu Leu Gln
                645                 650                 655

Glu Ala Arg Gln Gln Ser Val Ala His Gln Gln Ser Gly Ser Glu Leu
            660                 665                 670

Ala Leu Arg Arg Ser Gln Arg Leu Ala Ala Ser Ala Ser Thr Gln Gln
        675                 680                 685

Leu Gln Glu Val Lys Ala Lys Leu Gln Gln Cys Lys Ala Glu Leu Asn
    690                 695                 700

Ser Thr Thr Glu Glu Leu His Lys Tyr Gln Lys Met Leu Glu Pro Pro
705                 710                 715                 720

Pro Ser Ala Lys Pro Phe Thr Ile Asp Val Asp Lys Leu Leu Glu Glu
                725                 730                 735

Gly Gln Lys Asn Ile Arg Leu Leu Arg Thr Glu Leu Gln Leu Leu Gly
            740                 745                 750

Glu Ser Leu Gln Ser Ala Glu Arg Ala Cys Cys His Ser Thr Gly Ala
        755                 760                 765

Gly Lys Leu Arg Gln Ala Leu Thr Thr Cys Asp Asp Ile Leu Ile Lys
    770                 775                 780

Gln Asp Gln Thr Leu Ala Glu Leu Gln Asn Asn Met Val Leu Val Lys
785                 790                 795                 800

Leu Asp Leu Arg Lys Ala Ala Cys Ile Ala Glu Gln Tyr His Thr
                805                 810                 815

Val Leu Lys Leu Gln Gly Gln Val Ser Ala Lys Lys Arg Leu Gly Thr
            820                 825                 830

Asn Gln Glu Asn Gln Gln Pro Asn Gln Gln Pro Pro Gly Lys Lys Pro
        835                 840                 845

Phe Leu Arg Asn Leu Leu Pro Arg Thr Pro Thr Cys Gln Ser Ser Thr
    850                 855                 860
```

```
Asp Cys Ser Pro Tyr Ala Arg Ile Leu Arg Ser Arg Ser Pro Leu
865                 870                 875                 880

Leu Lys Ser Gly Pro Phe Gly Lys Lys Tyr
                885                 890

<210> SEQ ID NO 13
<211> LENGTH: 2150
<212> TYPE: DNA
<213> ORGANISM: Homo sapiens
<220> FEATURE:
<221> NAME/KEY: CDS
<222> LOCATION: (105)..(2033)

<400> SEQUENCE: 13
ctcgagccac gaaggcccccg ctgtcctgtc tagcagatac ttgcacggtt tacagaaatt      60
cggtccctgg gtcgtgtcag gaaactggaa aaaaggtcat aagc atg aag cgc agt     116
                                                  Met Lys Arg Ser
                                                    1 tca gtt tcc agc ggt ggt gct ggc cgc ctc tcc atg cag gag tta aga      164
Ser Val Ser Ser Gly Gly Ala Gly Arg Leu Ser Met Gln Glu Leu Arg
  5              10                  15                  20 tcc cag gat gta aat aaa caa ggc ctc tat acc cct caa acc aaa gag      212
Ser Gln Asp Val Asn Lys Gln Gly Leu Tyr Thr Pro Gln Thr Lys Glu
                 25                  30                  35 aaa cca acc ttt gga aag ttg agt ata aac aaa ccg aca tct gaa aga      260
Lys Pro Thr Phe Gly Lys Leu Ser Ile Asn Lys Pro Thr Ser Glu Arg
             40                  45                  50 aaa gtc tcg cta ttt ggc aaa aga act agt gga cat gga tcc cgg aat      308
Lys Val Ser Leu Phe Gly Lys Arg Thr Ser Gly His Gly Ser Arg Asn
         55                  60                  65 agt caa ctt ggt ata ttt tcc agt tct gag aaa atc aag gac ccg aga      356
Ser Gln Leu Gly Ile Phe Ser Ser Ser Glu Lys Ile Lys Asp Pro Arg
 70                  75                  80 cca ctt aat gac aaa gca ttc att cag cag tgt att cga caa ctc tgt      404
Pro Leu Asn Asp Lys Ala Phe Ile Gln Gln Cys Ile Arg Gln Leu Cys
 85                  90                  95                 100 gag ttt ctt aca gaa aat ggt tat gca cat aat gtg tcc atg aaa tct      452
Glu Phe Leu Thr Glu Asn Gly Tyr Ala His Asn Val Ser Met Lys Ser
                105                 110                 115 cta caa gct ccc tct gtt aaa gac ttc ctg aag atc ttc aca ttt ctt      500
Leu Gln Ala Pro Ser Val Lys Asp Phe Leu Lys Ile Phe Thr Phe Leu
            120                 125                 130 tat ggc ttc ctg tgc ccc tca tac gaa ctt cct gac aca aag ttt gaa      548
Tyr Gly Phe Leu Cys Pro Ser Tyr Glu Leu Pro Asp Thr Lys Phe Glu
        135                 140                 145 gaa gag gtt cca aga atc ttt aaa gac ctt ggg tat cct ttt gca cta      596
Glu Glu Val Pro Arg Ile Phe Lys Asp Leu Gly Tyr Pro Phe Ala Leu
    150                 155                 160 tcc aaa agc tcc atg tac aca gtg ggg gct cct cat aca tgg cct cac      644
Ser Lys Ser Ser Met Tyr Thr Val Gly Ala Pro His Thr Trp Pro His
165                 170                 175                 180 att gtg gca gcc tta gtt tgg cta ata gac tgc atc aag ata cat act      692
Ile Val Ala Ala Leu Val Trp Leu Ile Asp Cys Ile Lys Ile His Thr
                185                 190                 195 gcc atg aaa gaa agc tca cct tta ttt gat gat ggg cag cct tgg gga      740
Ala Met Lys Glu Ser Ser Pro Leu Phe Asp Asp Gly Gln Pro Trp Gly
            200                 205                 210 gaa gaa act gaa gat gga att atg cat aat aag ttg ttt ttg gac tac      788
Glu Glu Thr Glu Asp Gly Ile Met His Asn Lys Leu Phe Leu Asp Tyr
        215                 220                 225
```

| | | |
|---|---|---|
| acc ata aaa tgc tat gag agt ttt atg agt ggt gcc gac agc ttt gat<br>Thr Ile Lys Cys Tyr Glu Ser Phe Met Ser Gly Ala Asp Ser Phe Asp<br>230 235 240 | | 836 |
| gag atg aat gca gag ctg cag tca aaa ctg aag gat tta ttt aat gtg<br>Glu Met Asn Ala Glu Leu Gln Ser Lys Leu Lys Asp Leu Phe Asn Val<br>245 250 255 260 | | 884 |
| gat gct ttt aag ctg gaa tca tta gaa gca aaa aac aga gca ttg aat<br>Asp Ala Phe Lys Leu Glu Ser Leu Glu Ala Lys Asn Arg Ala Leu Asn<br>265 270 275 | | 932 |
| gaa cag att gca aga ttg gaa caa gaa aga gaa aaa gaa ccg aat cgt<br>Glu Gln Ile Ala Arg Leu Glu Gln Glu Arg Glu Lys Glu Pro Asn Arg<br>280 285 290 | | 980 |
| cta gag tcg ttg aga aaa ctg aag gct tcc tta caa gga gat gtt caa<br>Leu Glu Ser Leu Arg Lys Leu Lys Ala Ser Leu Gln Gly Asp Val Gln<br>295 300 305 | | 1028 |
| aag tat cag gca tac atg agc aat ttg gag tct cat tca gcc att ctt<br>Lys Tyr Gln Ala Tyr Met Ser Asn Leu Glu Ser His Ser Ala Ile Leu<br>310 315 320 | | 1076 |
| gac cag aaa tta aat ggt ctc aat gag gaa att gct aga gta gaa cta<br>Asp Gln Lys Leu Asn Gly Leu Asn Glu Glu Ile Ala Arg Val Glu Leu<br>325 330 335 340 | | 1124 |
| gaa tgt gaa aca ata aaa cag gag aac act cga cta cag aat atc att<br>Glu Cys Glu Thr Ile Lys Gln Glu Asn Thr Arg Leu Gln Asn Ile Ile<br>345 350 355 | | 1172 |
| gac aac cag aag tac tca gtt gca gac att gag cga ata aat cat gaa<br>Asp Asn Gln Lys Tyr Ser Val Ala Asp Ile Glu Arg Ile Asn His Glu<br>360 365 370 | | 1220 |
| aga aat gaa ttg cag cag act att aat aaa tta acc aag gac ctg gaa<br>Arg Asn Glu Leu Gln Gln Thr Ile Asn Lys Leu Thr Lys Asp Leu Glu<br>375 380 385 | | 1268 |
| gct gaa caa cag aag ttg tgg aat gag gag tta aaa tat gcc aga ggc<br>Ala Glu Gln Gln Lys Leu Trp Asn Glu Glu Leu Lys Tyr Ala Arg Gly<br>390 395 400 | | 1316 |
| aaa gaa gcg att gaa aca caa tta gca gag tat cac aaa ttg gct aga<br>Lys Glu Ala Ile Glu Thr Gln Leu Ala Glu Tyr His Lys Leu Ala Arg<br>405 410 415 420 | | 1364 |
| aaa tta aaa ctt att cct aaa ggt gct gag aat tcc aaa ggt tat gac<br>Lys Leu Lys Leu Ile Pro Lys Gly Ala Glu Asn Ser Lys Gly Tyr Asp<br>425 430 435 | | 1412 |
| ttt gaa att aag ttt aat ccc gag gct ggt gcc aac tgc ctt gtc aaa<br>Phe Glu Ile Lys Phe Asn Pro Glu Ala Gly Ala Asn Cys Leu Val Lys<br>440 445 450 | | 1460 |
| tac agg gct caa gtt tat gta cct ctt aag gaa ctc ctg aat gaa act<br>Tyr Arg Ala Gln Val Tyr Val Pro Leu Lys Glu Leu Leu Asn Glu Thr<br>455 460 465 | | 1508 |
| gaa gaa gaa att aat aaa gcc cta aat aaa aaa atg ggt ttg gag gat<br>Glu Glu Glu Ile Asn Lys Ala Leu Asn Lys Lys Met Gly Leu Glu Asp<br>470 475 480 | | 1556 |
| act tta gaa caa ttg aat gca atg ata aca gaa agc aag aga agt gtg<br>Thr Leu Glu Gln Leu Asn Ala Met Ile Thr Glu Ser Lys Arg Ser Val<br>485 490 495 500 | | 1604 |
| aga act ctg aaa gaa gaa gtt caa aag ctg gat gat ctt tac caa caa<br>Arg Thr Leu Lys Glu Glu Val Gln Lys Leu Asp Asp Leu Tyr Gln Gln<br>505 510 515 | | 1652 |
| aaa att aag gaa gca gag gaa gag gat gaa aaa tgt gcc agt gag ctt<br>Lys Ile Lys Glu Ala Glu Glu Glu Asp Glu Lys Cys Ala Ser Glu Leu<br>520 525 530 | | 1700 |
| gag tcc ttg gag aaa cac aag cac ctg cta gaa agt act gtt aac cag<br>Glu Ser Leu Glu Lys His Lys His Leu Leu Glu Ser Thr Val Asn Gln<br>535 540 545 | | 1748 |

```
ggg ctc agt gaa gct atg aat gaa tta gat gct gtt cag cgg gaa tac    1796
Gly Leu Ser Glu Ala Met Asn Glu Leu Asp Ala Val Gln Arg Glu Tyr
    550                 555                 560 caa cta gtt gtg caa acc acg act gaa gaa aga cga aaa gtg gga aat    1844
Gln Leu Val Val Gln Thr Thr Thr Glu Glu Arg Arg Lys Val Gly Asn
565                 570                 575                 580 aac ttg caa cgt ctg tta gag atg gtt gct aca cat gtt ggg tct gta    1892
Asn Leu Gln Arg Leu Leu Glu Met Val Ala Thr His Val Gly Ser Val
                585                 590                 595 gag aaa cat ctt gag gag cag att gct aaa gtt gat aga gaa tat gaa    1940
Glu Lys His Leu Glu Glu Gln Ile Ala Lys Val Asp Arg Glu Tyr Glu
            600                 605                 610 gaa tgc atg tca gaa gat ctc tcg gaa aat att aaa gag att aga gat    1988
Glu Cys Met Ser Glu Asp Leu Ser Glu Asn Ile Lys Glu Ile Arg Asp
        615                 620                 625 aag tat gag aag aaa gct act cta att aag tct tct gaa gaa tga        2033
Lys Tyr Glu Lys Lys Ala Thr Leu Ile Lys Ser Ser Glu Glu
    630                 635                 640 agataaaatg ttgatcatgt atatatatcc atagtgaata aaattgtctc agtaaaaaaa  2093
aaaaaaaaaa aaaaaaaaaa aaaaaaaaaa aaaaaaaaaa aaaaaaaaaa aaaaaaa     2150

<210> SEQ ID NO 14
<211> LENGTH: 642
<212> TYPE: PRT
<213> ORGANISM: Homo sapiens

<400> SEQUENCE: 14

Met Lys Arg Ser Ser Val Ser Ser Gly Gly Ala Gly Arg Leu Ser Met
1               5                   10                  15

Gln Glu Leu Arg Ser Gln Asp Val Asn Lys Gln Gly Leu Tyr Thr Pro
            20                  25                  30

Gln Thr Lys Glu Lys Pro Thr Phe Gly Lys Leu Ser Ile Asn Lys Pro
        35                  40                  45

Thr Ser Glu Arg Lys Val Ser Leu Phe Gly Lys Arg Thr Ser Gly His
    50                  55                  60

Gly Ser Arg Asn Ser Gln Leu Gly Ile Phe Ser Ser Glu Lys Ile
65                  70                  75                  80

Lys Asp Pro Arg Pro Leu Asn Asp Lys Ala Phe Ile Gln Gln Cys Ile
                85                  90                  95

Arg Gln Leu Cys Glu Phe Leu Thr Glu Asn Gly Tyr Ala His Asn Val
            100                 105                 110

Ser Met Lys Ser Leu Gln Ala Pro Ser Val Lys Asp Phe Leu Lys Ile
        115                 120                 125

Phe Thr Phe Leu Tyr Gly Phe Leu Cys Pro Ser Tyr Glu Leu Pro Asp
    130                 135                 140

Thr Lys Phe Glu Glu Val Pro Arg Ile Phe Lys Asp Leu Gly Tyr
145                 150                 155                 160

Pro Phe Ala Leu Ser Lys Ser Ser Met Tyr Thr Val Gly Ala Pro His
                165                 170                 175

Thr Trp Pro His Ile Val Ala Ala Leu Val Trp Leu Ile Asp Cys Ile
            180                 185                 190

Lys Ile His Thr Ala Met Lys Glu Ser Ser Pro Leu Phe Asp Gly
        195                 200                 205

Gln Pro Trp Gly Glu Glu Thr Glu Asp Gly Ile Met His Asn Lys Leu
    210                 215                 220

Phe Leu Asp Tyr Thr Ile Lys Cys Tyr Glu Ser Phe Met Ser Gly Ala
225                 230                 235                 240
```

```
Asp Ser Phe Asp Glu Met Asn Ala Glu Leu Gln Ser Lys Leu Lys Asp
            245                 250                 255
Leu Phe Asn Val Asp Ala Phe Lys Leu Glu Ser Leu Glu Ala Lys Asn
            260                 265                 270
Arg Ala Leu Asn Glu Gln Ile Ala Arg Leu Gln Glu Arg Glu Lys
            275                 280                 285
Glu Pro Asn Arg Leu Glu Ser Leu Arg Lys Leu Lys Ala Ser Leu Gln
            290                 295                 300
Gly Asp Val Gln Lys Tyr Gln Ala Tyr Met Ser Asn Leu Glu Ser His
305                 310                 315                 320
Ser Ala Ile Leu Asp Gln Lys Leu Asn Gly Leu Asn Glu Glu Ile Ala
            325                 330                 335
Arg Val Glu Leu Glu Cys Glu Thr Ile Lys Gln Glu Asn Thr Arg Leu
            340                 345                 350
Gln Asn Ile Ile Asp Asn Gln Lys Tyr Ser Val Ala Asp Ile Glu Arg
            355                 360                 365
Ile Asn His Glu Arg Asn Glu Leu Gln Gln Thr Ile Asn Lys Leu Thr
            370                 375                 380
Lys Asp Leu Glu Ala Glu Gln Lys Leu Trp Asn Glu Glu Leu Lys
385                 390                 395                 400
Tyr Ala Arg Gly Lys Glu Ala Ile Glu Thr Gln Leu Ala Glu Tyr His
            405                 410                 415
Lys Leu Ala Arg Lys Leu Lys Leu Ile Pro Lys Gly Ala Glu Asn Ser
            420                 425                 430
Lys Gly Tyr Asp Phe Glu Ile Lys Phe Asn Pro Glu Ala Gly Ala Asn
            435                 440                 445
Cys Leu Val Lys Tyr Arg Ala Gln Val Tyr Val Pro Leu Lys Glu Leu
            450                 455                 460
Leu Asn Glu Thr Glu Glu Ile Asn Lys Ala Leu Asn Lys Lys Met
465                 470                 475                 480
Gly Leu Glu Asp Thr Leu Glu Gln Leu Asn Ala Met Ile Thr Glu Ser
            485                 490                 495
Lys Arg Ser Val Arg Thr Leu Lys Glu Val Gln Lys Leu Asp Asp
            500                 505                 510
Leu Tyr Gln Gln Lys Ile Lys Glu Ala Glu Glu Asp Glu Lys Cys
            515                 520                 525
Ala Ser Glu Leu Glu Ser Leu Glu Lys His Lys His Leu Leu Glu Ser
            530                 535                 540
Thr Val Asn Gln Gly Leu Ser Glu Ala Met Asn Glu Leu Asp Ala Val
545                 550                 555                 560
Gln Arg Glu Tyr Gln Leu Val Val Gln Thr Thr Thr Glu Glu Arg Arg
            565                 570                 575
Lys Val Gly Asn Asn Leu Gln Arg Leu Leu Glu Met Val Ala Thr His
            580                 585                 590
Val Gly Ser Val Glu Lys His Leu Glu Glu Gln Ile Ala Lys Val Asp
            595                 600                 605
Arg Glu Tyr Glu Glu Cys Met Ser Glu Asp Leu Ser Glu Asn Ile Lys
            610                 615                 620
Glu Ile Arg Asp Lys Tyr Glu Lys Lys Ala Thr Leu Ile Lys Ser Ser
625                 630                 635                 640
Glu Glu
```

<210> SEQ ID NO 15

```
<211> LENGTH: 2984
<212> TYPE: DNA
<213> ORGANISM: Homo sapiens
<220> FEATURE:
<221> NAME/KEY: CDS
<222> LOCATION: (75)..(2648)

<400> SEQUENCE: 15
ggaaattcaa acgtgtttgc ggaaaggagt ttgggttcca tcttttcatt tccccagcgc      60
agctttctgt agaa atg gaa tcc gag gat tta agt ggc aga gaa ttg aca     110
              Met Glu Ser Glu Asp Leu Ser Gly Arg Glu Leu Thr
                1               5                  10 att gat tcc ata atg aac aaa gtg aga gac att aaa aat aag ttt aaa     158
Ile Asp Ser Ile Met Asn Lys Val Arg Asp Ile Lys Asn Lys Phe Lys
           15                  20                  25 aat gaa gac ctt act gat gaa cta agc ttg aat aaa att tct gct gat     206
Asn Glu Asp Leu Thr Asp Glu Leu Ser Leu Asn Lys Ile Ser Ala Asp
 30                  35                  40 act aca gat aac tcg gga act gtt aac caa att atg atg atg gca aac     254
Thr Thr Asp Asn Ser Gly Thr Val Asn Gln Ile Met Met Met Ala Asn
 45                  50                  55                  60 aac cca gag gac tgg ttg agt ttg ttg ctc aaa cta gag aaa aac agt     302
Asn Pro Glu Asp Trp Leu Ser Leu Leu Leu Lys Leu Glu Lys Asn Ser
                 65                  70                  75 gtt ccg cta agt gat gct ctt tta aat aaa ttg att ggt cgt tac agt     350
Val Pro Leu Ser Asp Ala Leu Leu Asn Lys Leu Ile Gly Arg Tyr Ser
             80                  85                  90 caa gca att gaa gcg ctt ccc cca gat aaa tat ggc caa aat gag agt     398
Gln Ala Ile Glu Ala Leu Pro Pro Asp Lys Tyr Gly Gln Asn Glu Ser
         95                 100                 105 ttt gct aga att caa gtg aga ttt gct gaa tta aaa gct att caa gag     446
Phe Ala Arg Ile Gln Val Arg Phe Ala Glu Leu Lys Ala Ile Gln Glu
    110                 115                 120 cca gat gat gca cgt gac tac ttt caa atg gcc aga gca aac tgc aag     494
Pro Asp Asp Ala Arg Asp Tyr Phe Gln Met Ala Arg Ala Asn Cys Lys
125                 130                 135                 140 aaa ttt gct ttt gtt cat ata tct ttt gca caa ttt gaa ctg tca caa     542
Lys Phe Ala Phe Val His Ile Ser Phe Ala Gln Phe Glu Leu Ser Gln
                145                 150                 155 ggt aat gtc aaa aaa agt aaa caa ctt ctt caa aaa gct gta gaa cgt     590
Gly Asn Val Lys Lys Ser Lys Gln Leu Leu Gln Lys Ala Val Glu Arg
            160                 165                 170 gga gca gta cca cta gaa atg ctg gaa att gcc ctg cgg aat tta aac     638
Gly Ala Val Pro Leu Glu Met Leu Glu Ile Ala Leu Arg Asn Leu Asn
        175                 180                 185 ctc caa aaa aag cag ctg ctt tca gag gag gaa aag aag aat tta tca     686
Leu Gln Lys Lys Gln Leu Leu Ser Glu Glu Glu Lys Lys Asn Leu Ser
    190                 195                 200 gca tct acg gta tta act gcc caa gaa tca ttt tcc ggt tca ctt ggg     734
Ala Ser Thr Val Leu Thr Ala Gln Glu Ser Phe Ser Gly Ser Leu Gly
205                 210                 215                 220 cat tta cag aat agg aac aac agt tgt gat tcc aga gga cag act act     782
His Leu Gln Asn Arg Asn Asn Ser Cys Asp Ser Arg Gly Gln Thr Thr
                225                 230                 235 aaa gcc agg ttt tta tat gga gag aac atg cca cca caa gat gca gaa     830
Lys Ala Arg Phe Leu Tyr Gly Glu Asn Met Pro Pro Gln Asp Ala Glu
            240                 245                 250 ata ggt tac cgg aat tca ttg aga caa act aac aaa act aaa cag tca     878
Ile Gly Tyr Arg Asn Ser Leu Arg Gln Thr Asn Lys Thr Lys Gln Ser
        255                 260                 265 tgc cca ttt gga aga gtc cca gtt aac ctt cta aat agc cca gat tgt     926
```

```
Cys Pro Phe Gly Arg Val Pro Val Asn Leu Leu Asn Ser Pro Asp Cys
        270                 275                 280 gat gtg aag aca gat gat tca gtt gta cct tgt ttt atg aaa aga caa       974
Asp Val Lys Thr Asp Asp Ser Val Val Pro Cys Phe Met Lys Arg Gln
285                 290                 295                 300 acc tct aga tca gaa tgc cga gat ttg gtt gtg cct gga tct aaa cca      1022
Thr Ser Arg Ser Glu Cys Arg Asp Leu Val Val Pro Gly Ser Lys Pro
                305                 310                 315 agt gga aat gat tcc tgt gaa tta aga aat tta aag tct gtt caa aat      1070
Ser Gly Asn Asp Ser Cys Glu Leu Arg Asn Leu Lys Ser Val Gln Asn
                320                 325                 330 agt cat ttc aag gaa cct ctg gtg tca gat gaa aag agt tct gaa ctt      1118
Ser His Phe Lys Glu Pro Leu Val Ser Asp Glu Lys Ser Ser Glu Leu
                335                 340                 345 att att act gat tca ata acc ctg aag aat aaa acg gaa tca agt ctt      1166
Ile Ile Thr Asp Ser Ile Thr Leu Lys Asn Lys Thr Glu Ser Ser Leu
        350                 355                 360 cta gct aaa tta gaa gaa act aaa gag tat caa gaa cca gag gtt cca      1214
Leu Ala Lys Leu Glu Glu Thr Lys Glu Tyr Gln Glu Pro Glu Val Pro
365                 370                 375                 380 gag agt aac cag aaa cag tgg caa tct aag aga aag tca gag tgt att      1262
Glu Ser Asn Gln Lys Gln Trp Gln Ser Lys Arg Lys Ser Glu Cys Ile
                385                 390                 395 aac cag aat cct gct gca tct tca aat cac tgg cag att ccg gag tta      1310
Asn Gln Asn Pro Ala Ala Ser Ser Asn His Trp Gln Ile Pro Glu Leu
                400                 405                 410 gcc cga aaa gtt aat aca gag cag aaa cat acc act ttt gag caa cct      1358
Ala Arg Lys Val Asn Thr Glu Gln Lys His Thr Thr Phe Glu Gln Pro
                415                 420                 425 gtc ttt tca gtt tca aaa cag tca cca cca ata tca aca tct aaa tgg      1406
Val Phe Ser Val Ser Lys Gln Ser Pro Pro Ile Ser Thr Ser Lys Trp
430                 435                 440 ttt gac cca aaa tct att tgt aag aca cca agc agc aat acc ttg gat      1454
Phe Asp Pro Lys Ser Ile Cys Lys Thr Pro Ser Ser Asn Thr Leu Asp
445                 450                 455                 460 gat tac atg agc tgt ttt aga act cca gtt gta aag aat gac ttt cca      1502
Asp Tyr Met Ser Cys Phe Arg Thr Pro Val Val Lys Asn Asp Phe Pro
                465                 470                 475 cct gct tgt cag ttg tca aca cct tat ggc caa cct gcc tgt ttc cag      1550
Pro Ala Cys Gln Leu Ser Thr Pro Tyr Gly Gln Pro Ala Cys Phe Gln
                480                 485                 490 cag caa cag cat caa ata ctt gcc act cca ctt caa aat tta cag gtt      1598
Gln Gln Gln His Gln Ile Leu Ala Thr Pro Leu Gln Asn Leu Gln Val
                495                 500                 505 tta gca tct tct tca gca aat gaa tgc att tcg gtt aaa gga aga att      1646
Leu Ala Ser Ser Ser Ala Asn Glu Cys Ile Ser Val Lys Gly Arg Ile
510                 515                 520 tat tcc att tta aag cag ata gga agt gga ggt tca agc aag gta ttt      1694
Tyr Ser Ile Leu Lys Gln Ile Gly Ser Gly Gly Ser Ser Lys Val Phe
525                 530                 535                 540 cag gtg tta aat gaa aag aaa cag ata tat gct ata aaa tat gtg aac      1742
Gln Val Leu Asn Glu Lys Lys Gln Ile Tyr Ala Ile Lys Tyr Val Asn
                545                 550                 555 tta gaa gaa gca gat aac caa act ctt gat agt tac cgg aac gaa ata      1790
Leu Glu Glu Ala Asp Asn Gln Thr Leu Asp Ser Tyr Arg Asn Glu Ile
                560                 565                 570 gct tat ttg aat aaa cta caa caa cac agt gat aag atc atc cga ctt      1838
Ala Tyr Leu Asn Lys Leu Gln Gln His Ser Asp Lys Ile Ile Arg Leu
                575                 580                 585 tat gat tat gaa atc acg gac cag tac atc tac atg gta atg gag tgt      1886
```

```
                    Tyr Asp Tyr Glu Ile Thr Asp Gln Tyr Ile Tyr Met Val Met Glu Cys
                                590             595                 600 gga aat att gat ctt aat agt tgg ctt aaa aag aaa aaa tcc att gat           1934
Gly Asn Ile Asp Leu Asn Ser Trp Leu Lys Lys Lys Lys Ser Ile Asp
605                 610                 615                 620 cca tgg gaa cgc aag agt tac tgg aaa aat atg tta gag gca gtt cac           1982
Pro Trp Glu Arg Lys Ser Tyr Trp Lys Asn Met Leu Glu Ala Val His
                625                 630                 635 aca atc cat caa cat ggc att gtt cac agt gat ctt aaa cca gct aac           2030
Thr Ile His Gln His Gly Ile Val His Ser Asp Leu Lys Pro Ala Asn
                640                 645                 650 ttt ctg ata gtt gat gga atg cta aag cta att gat ttt ggg att gca           2078
Phe Leu Ile Val Asp Gly Met Leu Lys Leu Ile Asp Phe Gly Ile Ala
            655                 660                 665 aac caa atg caa cca gat aca aca agt gtt gtt aaa gat tct cag gtt           2126
Asn Gln Met Gln Pro Asp Thr Thr Ser Val Val Lys Asp Ser Gln Val
670                 675                 680 ggc aca gtt aat tat atg cca cca gaa gca atc aaa gat atg tct tcc           2174
Gly Thr Val Asn Tyr Met Pro Pro Glu Ala Ile Lys Asp Met Ser Ser
685                 690                 695                 700 tcc aga gag aat ggg aaa tct aag tca aag ata agc ccc aaa agt gat           2222
Ser Arg Glu Asn Gly Lys Ser Lys Ser Lys Ile Ser Pro Lys Ser Asp
                705                 710                 715 gtt tgg tcc tta gga tgt att ttg tac tat atg act tac ggg aaa aca           2270
Val Trp Ser Leu Gly Cys Ile Leu Tyr Tyr Met Thr Tyr Gly Lys Thr
                720                 725                 730 cca ttt cag cag ata att aat cag att tct aaa tta cat gcc ata att           2318
Pro Phe Gln Gln Ile Ile Asn Gln Ile Ser Lys Leu His Ala Ile Ile
            735                 740                 745 gat cct aat cat gaa att gaa ttt ccc gat att cca gag aaa gat ctt           2366
Asp Pro Asn His Glu Ile Glu Phe Pro Asp Ile Pro Glu Lys Asp Leu
        750                 755                 760 caa gat gtg tta aag tgt tgt tta aaa agg gac cca aaa cag agg ata           2414
Gln Asp Val Leu Lys Cys Cys Leu Lys Arg Asp Pro Lys Gln Arg Ile
765                 770                 775                 780 tcc att cct gag ctc ctg gct cat ccc tat gtt caa att caa act cat           2462
Ser Ile Pro Glu Leu Leu Ala His Pro Tyr Val Gln Ile Gln Thr His
                785                 790                 795 cca gtt aac caa atg gcc aag gga acc act gaa gaa atg aaa tat gtt           2510
Pro Val Asn Gln Met Ala Lys Gly Thr Thr Glu Glu Met Lys Tyr Val
                800                 805                 810 ctg ggc caa ctt gtt ggt ctg aat tct cct aac tcc att ttg aaa gct           2558
Leu Gly Gln Leu Val Gly Leu Asn Ser Pro Asn Ser Ile Leu Lys Ala
            815                 820                 825 gct aaa act tta tat gaa cac tat agt ggt ggt gaa agt cat aat tct           2606
Ala Lys Thr Leu Tyr Glu His Tyr Ser Gly Gly Glu Ser His Asn Ser
830                 835                 840 tca tcc tcc aag act ttt gaa aaa aaa agg gga aaa aaa tga                   2648
Ser Ser Ser Lys Thr Phe Glu Lys Lys Arg Gly Lys Lys
845                 850                 855 tttgcagtta ttcgtaatgt caaataccac ctataaaata tattggactg ttatactctt         2708
gaatccctgt ggaaatctac atttgaagac aacatcactc tgaagtgtta tcagcaaaaa         2768
aaattcagta gattatcttt aaaagaaaac tgtaaaaata gcaaccactt atggtactgt         2828
atatattgta gacttgtttt ctctgtttta tgctcttgtg taatctactt gacatcattt         2888
tactcttgga atagtgggtg gatagcaagt atattctaaa aactttgta aataaagttt          2948 tgtggctaaa atgacactaa aaaaaaaaaa aaaaaa                                    2984
```

<210> SEQ ID NO 16
<211> LENGTH: 857
<212> TYPE: PRT
<213> ORGANISM: Homo sapiens

<400> SEQUENCE: 16

```
Met Glu Ser Glu Asp Leu Ser Gly Arg Glu Leu Thr Ile Asp Ser Ile
  1               5                  10                  15

Met Asn Lys Val Arg Asp Ile Lys Asn Lys Phe Lys Asn Glu Asp Leu
                 20                  25                  30

Thr Asp Glu Leu Ser Leu Asn Lys Ile Ser Ala Asp Thr Thr Asp Asn
             35                  40                  45

Ser Gly Thr Val Asn Gln Ile Met Met Met Ala Asn Asn Pro Glu Asp
         50                  55                  60

Trp Leu Ser Leu Leu Lys Leu Glu Lys Asn Ser Val Pro Leu Ser
 65                  70                  75                  80

Asp Ala Leu Leu Asn Lys Leu Ile Gly Arg Tyr Ser Gln Ala Ile Glu
                 85                  90                  95

Ala Leu Pro Pro Asp Lys Tyr Gly Gln Asn Glu Ser Phe Ala Arg Ile
            100                 105                 110

Gln Val Arg Phe Ala Glu Leu Lys Ala Ile Gln Glu Pro Asp Asp Ala
        115                 120                 125

Arg Asp Tyr Phe Gln Met Ala Arg Ala Asn Cys Lys Lys Phe Ala Phe
    130                 135                 140

Val His Ile Ser Phe Ala Gln Phe Glu Leu Ser Gln Gly Asn Val Lys
145                 150                 155                 160

Lys Ser Lys Gln Leu Leu Gln Lys Ala Val Glu Arg Gly Ala Val Pro
                165                 170                 175

Leu Glu Met Leu Glu Ile Ala Leu Arg Asn Leu Asn Leu Gln Lys Lys
            180                 185                 190

Gln Leu Leu Ser Glu Glu Lys Lys Asn Leu Ser Ala Ser Thr Val
        195                 200                 205

Leu Thr Ala Gln Glu Ser Phe Ser Gly Ser Leu Gly His Leu Gln Asn
    210                 215                 220

Arg Asn Asn Ser Cys Asp Ser Arg Gly Gln Thr Thr Lys Ala Arg Phe
225                 230                 235                 240

Leu Tyr Gly Glu Asn Met Pro Pro Gln Asp Ala Glu Ile Gly Tyr Arg
                245                 250                 255

Asn Ser Leu Arg Gln Thr Asn Lys Thr Lys Gln Ser Cys Pro Phe Gly
            260                 265                 270

Arg Val Pro Val Asn Leu Leu Asn Ser Pro Asp Cys Asp Val Lys Thr
        275                 280                 285

Asp Asp Ser Val Val Pro Cys Phe Met Lys Arg Gln Thr Ser Arg Ser
    290                 295                 300

Glu Cys Arg Asp Leu Val Val Pro Gly Ser Lys Pro Ser Gly Asn Asp
305                 310                 315                 320

Ser Cys Glu Leu Arg Asn Leu Lys Ser Val Gln Asn Ser His Phe Lys
                325                 330                 335

Glu Pro Leu Val Ser Asp Glu Lys Ser Ser Glu Leu Ile Ile Thr Asp
            340                 345                 350

Ser Ile Thr Leu Lys Asn Lys Thr Glu Ser Ser Leu Leu Ala Lys Leu
        355                 360                 365

Glu Glu Thr Lys Glu Tyr Gln Glu Pro Glu Val Pro Glu Ser Asn Gln
    370                 375                 380

Lys Gln Trp Gln Ser Lys Arg Lys Ser Glu Cys Ile Asn Gln Asn Pro
```

-continued

```
            385                 390                 395                 400
Ala Ala Ser Ser Asn His Trp Gln Ile Pro Glu Leu Ala Arg Lys Val
                    405                 410                 415
Asn Thr Glu Gln Lys His Thr Thr Phe Glu Gln Pro Val Phe Ser Val
                    420                 425                 430
Ser Lys Gln Ser Pro Pro Ile Ser Thr Ser Lys Trp Phe Asp Pro Lys
                    435                 440                 445
Ser Ile Cys Lys Thr Pro Ser Ser Asn Thr Leu Asp Asp Tyr Met Ser
            450                 455                 460
Cys Phe Arg Thr Pro Val Val Lys Asn Asp Phe Pro Pro Ala Cys Gln
465                 470                 475                 480
Leu Ser Thr Pro Tyr Gly Gln Pro Ala Cys Phe Gln Gln Gln His
                    485                 490                 495
Gln Ile Leu Ala Thr Pro Leu Gln Asn Leu Gln Val Leu Ala Ser Ser
                    500                 505                 510
Ser Ala Asn Glu Cys Ile Ser Val Lys Gly Arg Ile Tyr Ser Ile Leu
            515                 520                 525
Lys Gln Ile Gly Ser Gly Gly Ser Ser Lys Val Phe Gln Val Leu Asn
            530                 535                 540
Glu Lys Lys Gln Ile Tyr Ala Ile Lys Tyr Val Asn Leu Glu Glu Ala
545                 550                 555                 560
Asp Asn Gln Thr Leu Asp Ser Tyr Arg Asn Glu Ile Ala Tyr Leu Asn
                    565                 570                 575
Lys Leu Gln Gln His Ser Asp Lys Ile Ile Arg Leu Tyr Asp Tyr Glu
                    580                 585                 590
Ile Thr Asp Gln Tyr Ile Tyr Met Val Met Glu Cys Gly Asn Ile Asp
                    595                 600                 605
Leu Asn Ser Trp Leu Lys Lys Lys Ser Ile Asp Pro Trp Glu Arg
            610                 615                 620
Lys Ser Tyr Trp Lys Asn Met Leu Glu Ala Val His Thr Ile His Gln
625                 630                 635                 640
His Gly Ile Val His Ser Asp Leu Lys Pro Ala Asn Phe Leu Ile Val
                    645                 650                 655
Asp Gly Met Leu Lys Leu Ile Asp Phe Gly Ile Ala Asn Gln Met Gln
                    660                 665                 670
Pro Asp Thr Thr Ser Val Val Lys Asp Ser Gln Val Gly Thr Val Asn
                    675                 680                 685
Tyr Met Pro Pro Glu Ala Ile Lys Asp Met Ser Ser Ser Arg Glu Asn
            690                 695                 700
Gly Lys Ser Lys Ser Lys Ile Ser Pro Lys Ser Asp Val Trp Ser Leu
705                 710                 715                 720
Gly Cys Ile Leu Tyr Tyr Met Thr Tyr Gly Lys Thr Pro Phe Gln Gln
                    725                 730                 735
Ile Ile Asn Gln Ile Ser Lys Leu His Ala Ile Asp Pro Asn His
                    740                 745                 750
Glu Ile Glu Phe Pro Asp Ile Pro Glu Lys Asp Leu Gln Asp Val Leu
                    755                 760                 765
Lys Cys Cys Leu Lys Arg Asp Pro Lys Gln Arg Ile Ser Ile Pro Glu
            770                 775                 780
Leu Leu Ala His Pro Tyr Val Gln Ile Gln Thr His Pro Val Asn Gln
785                 790                 795                 800
Met Ala Lys Gly Thr Thr Glu Glu Met Lys Tyr Val Leu Gly Gln Leu
                    805                 810                 815
```

```
                          Val Gly Leu Asn Ser Pro Asn Ser Ile Leu Lys Ala Ala Lys Thr Leu
                                          820                 825                 830

Tyr Glu His Tyr Ser Gly Gly Glu Ser His Asn Ser Ser Ser Ser Lys
                                      835                 840                 845

Thr Phe Glu Lys Lys Arg Gly Lys Lys
                                  850                 855

<210> SEQ ID NO 17
<211> LENGTH: 1735
<212> TYPE: DNA
<213> ORGANISM: Homo sapiens
<220> FEATURE:
<221> NAME/KEY: CDS
<222> LOCATION: (242)..(913)

<400> SEQUENCE: 17
gttatcagag gtgagcccgt gctcttcagc ggagaagatc ccctacctgg ccgccggcca        60
ctttctgtgg gccgtggggt cctcaaggag acggcccttg ggctcagggg ctgcgtttcc       120
acacgcgcct ttcccagggc tcccgcgccc gttcctgcct ggccgccggc cgctccaaca       180
gcagcacaag gcgggactca gaaccggcgt tcagggccgc cagcggccgc gaggccctga       240 g atg agg ctc caa aga ccc cga cag gcc ccg gcg ggt ggg agg cgc gcg       289
  Met Arg Leu Gln Arg Pro Arg Gln Ala Pro Ala Gly Gly Arg Arg Ala
   1               5                  10                  15 ccc cgg ggc ggg cgg ggc tcc ccc tac cgg cca gac ccg ggg aga ggc         337
Pro Arg Gly Gly Arg Gly Ser Pro Tyr Arg Pro Asp Pro Gly Arg Gly
             20                  25                  30 gcg cgg agg ctg cga agg ttc cag aag ggc ggg gag ggg gcg ccg cgc         385
Ala Arg Arg Leu Arg Arg Phe Gln Lys Gly Gly Glu Gly Ala Pro Arg
         35                  40                  45 gct gac cct ccc tgg gca ccg ctg ggg acg atg gcg ctg ctc gcc ttg         433
Ala Asp Pro Pro Trp Ala Pro Leu Gly Thr Met Ala Leu Leu Ala Leu
 50                  55                  60 ctg ctg gtc gtg gcc cta ccg cgg gtg tgg aca gac gcc aac ctg act         481
Leu Leu Val Val Ala Leu Pro Arg Val Trp Thr Asp Ala Asn Leu Thr
 65                  70                  75                  80 gcg aga caa cga gat cca gag gac tcc cag cga acg gac gag ggt gac         529
Ala Arg Gln Arg Asp Pro Glu Asp Ser Gln Arg Thr Asp Glu Gly Asp
                 85                  90                  95 aat aga gtg tgg tgt cat gtt tgt gag aga gaa aac act ttc gag tgc         577
Asn Arg Val Trp Cys His Val Cys Glu Arg Glu Asn Thr Phe Glu Cys
            100                 105                 110 cag aac cca agg agg tgc aaa tgg aca gag cca tac tgc gtt ata gcg         625
Gln Asn Pro Arg Arg Cys Lys Trp Thr Glu Pro Tyr Cys Val Ile Ala
        115                 120                 125 gcc gtg aaa ata ttt cca cgt ttt ttc atg gtt gcg aag cag tgc tcc         673
Ala Val Lys Ile Phe Pro Arg Phe Phe Met Val Ala Lys Gln Cys Ser
    130                 135                 140 gct ggt tgt gca gcg atg gag aga ccc aag cca gag gag aag cgg ttt         721
Ala Gly Cys Ala Ala Met Glu Arg Pro Lys Pro Glu Glu Lys Arg Phe
145                 150                 155                 160 ctc ctg gaa gag ccc atg ccc ttc ttt tac ctc aag tgt tgt aaa att         769
Leu Leu Glu Glu Pro Met Pro Phe Phe Tyr Leu Lys Cys Cys Lys Ile
                165                 170                 175 cgc tac tgc aat tta gag ggg cca cct atc aac tca tca gtg ttc aaa         817
Arg Tyr Cys Asn Leu Glu Gly Pro Pro Ile Asn Ser Ser Val Phe Lys
            180                 185                 190 gaa tat gct ggg agc atg ggt gag agc tgt ggt ggg ctg tgg ctg gcc         865
Glu Tyr Ala Gly Ser Met Gly Glu Ser Cys Gly Gly Leu Trp Leu Ala
        195                 200                 205
```

-continued

```
atc ctc ctg ctg ctg gcc tcc att gca gcc ggc ctc agc ctg tct tga       913
Ile Leu Leu Leu Leu Ala Ser Ile Ala Ala Gly Leu Ser Leu Ser
    210                 215                 220 gccacgggac tgccacagac tgagccttcc ggagcatgga ctcgctccag accgttgtca     973
cctgttgcat taaacttgtt ttctgttgat tacctcttgg tttgacttcc cagggtcttg    1033
ggatgggaga gtggggatca ggtgcagttg gctcttaacc ctcaagggtt ctttaactca    1093
cattcagagg aagtccagat ctcctgagta gtgattttgg tgacaagttt ttctctttga    1153
aatcaaacct tgtaactcat ttattgctga tggccactct tttccttgac tcccctctgc    1213
ctctgagggc ttcagtattg atggggaggg aggcctaagt accactcatg agagtatgt     1273
gctgagatgc ttccgacctt tcaggtgacg caggaacact gggggagtct gaatgattgg    1333
ggtgaagaca tccctggagt gaaggactcc tcagcatggg gggcagtggg cacacgtta     1393
gggctgcccc cattccagtg gtggaggcgc tgtggatggc tgcttttcct caacctttcc    1453
taccagattc caggaggcag aagataacta attgtgttga agaaacttag acttcaccca    1513
ccagctggca caggtgcaca gattcataaa ttcccacacg tgtgtgttca acatctgaaa    1573
cttaggccaa gtagagagca tcagggtaaa tggcgttcat ttctctgtta agatgcagcc    1633
atccatgggg agctgagaaa tcagactcaa agttccacca aaaacaaata caaggggact   1693
tcaaaagttc acgaaaaaat tgaattaaaa gataaaaatt aa                      1735
```

<210> SEQ ID NO 18
<211> LENGTH: 223
<212> TYPE: PRT
<213> ORGANISM: Homo sapiens

<400> SEQUENCE: 18

```
Met Arg Leu Gln Arg Pro Arg Gln Ala Pro Ala Gly Gly Arg Arg Ala
1               5                   10                  15

Pro Arg Gly Gly Arg Gly Ser Pro Tyr Arg Pro Asp Pro Gly Arg Gly
            20                  25                  30

Ala Arg Arg Leu Arg Arg Phe Gln Lys Gly Gly Glu Gly Ala Pro Arg
        35                  40                  45

Ala Asp Pro Pro Trp Ala Pro Leu Gly Thr Met Ala Leu Leu Ala Leu
    50                  55                  60

Leu Leu Val Val Ala Leu Pro Arg Val Trp Thr Asp Ala Asn Leu Thr
65                  70                  75                  80

Ala Arg Gln Arg Asp Pro Glu Asp Ser Gln Arg Thr Asp Gly Asp
                85                  90                  95

Asn Arg Val Trp Cys His Val Cys Glu Arg Glu Asn Thr Phe Glu Cys
            100                 105                 110

Gln Asn Pro Arg Arg Cys Lys Trp Thr Glu Pro Tyr Cys Val Ile Ala
        115                 120                 125

Ala Val Lys Ile Phe Pro Arg Phe Phe Met Val Ala Lys Gln Cys Ser
    130                 135                 140

Ala Gly Cys Ala Ala Met Glu Arg Pro Lys Pro Glu Glu Lys Arg Phe
145                 150                 155                 160

Leu Leu Glu Glu Pro Met Pro Phe Phe Tyr Leu Lys Cys Cys Lys Ile
                165                 170                 175

Arg Tyr Cys Asn Leu Glu Gly Pro Pro Ile Asn Ser Ser Val Phe Lys
            180                 185                 190

Glu Tyr Ala Gly Ser Met Gly Glu Ser Cys Gly Gly Leu Trp Leu Ala
        195                 200                 205

Ile Leu Leu Leu Leu Ala Ser Ile Ala Ala Gly Leu Ser Leu Ser
```

```
<210> SEQ ID NO 19
<211> LENGTH: 9
<212> TYPE: PRT
<213> ORGANISM: artificial
<220> FEATURE:
<223> OTHER INFORMATION: An artificially synthesized peptide sequence

<400> SEQUENCE: 19

Ile Tyr Glu Val Met Val Leu Ala Met
1               5

<210> SEQ ID NO 20
<211> LENGTH: 9
<212> TYPE: PRT
<213> ORGANISM: artificial
<220> FEATURE:
<223> OTHER INFORMATION: An artificially synthesized peptide sequence

<400> SEQUENCE: 20

Leu Phe Leu Leu Leu Val Leu Leu Leu
1               5

<210> SEQ ID NO 21
<211> LENGTH: 9
<212> TYPE: PRT
<213> ORGANISM: artificial
<220> FEATURE:
<223> OTHER INFORMATION: An artificially synthesized peptide sequence

<400> SEQUENCE: 21

Val Phe Arg Glu Ala Glu Val Thr Leu
1               5

<210> SEQ ID NO 22
<211> LENGTH: 9
<212> TYPE: PRT
<213> ORGANISM: artificial
<220> FEATURE:
<223> OTHER INFORMATION: An artificially synthesized peptide sequence

<400> SEQUENCE: 22

Leu Tyr Val Glu Val Thr Asn Glu Ala
1               5

<210> SEQ ID NO 23
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 23

Lys Tyr Glu Ala His Val Pro Glu Asn
1               5

<210> SEQ ID NO 24
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 24

Lys Tyr Glu Leu Phe Gly His Ala Val
1               5
```

```
<210> SEQ ID NO 25
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 25

Arg Ser Leu Lys Glu Arg Asn Pro Leu
1               5

<210> SEQ ID NO 26
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 26

Arg Gly Pro Leu Ala Ser Leu Leu Leu
1               5

<210> SEQ ID NO 27
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 27

Lys Gly Gly Phe Ile Leu Pro Val Leu
1               5

<210> SEQ ID NO 28
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 28

Thr Tyr Asn Gly Val Val Ala Tyr Ser
1               5

<210> SEQ ID NO 29
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 29

Leu Phe Ser Thr Asp Asn Asp Asp Phe
1               5

<210> SEQ ID NO 30
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 30

Asp Tyr Leu Asn Glu Trp Gly Ser Arg Phe
1               5                   10

<210> SEQ ID NO 31
```

```
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 31

Thr Tyr Asn Gly Val Val Ala Tyr Ser Ile
1               5                   10

<210> SEQ ID NO 32
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 32

Leu Phe Leu Leu Leu Val Leu Leu Leu Leu
1               5                   10

<210> SEQ ID NO 33
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 33

Asp Phe Glu Ala Lys Asn Gln His Thr Leu
1               5                   10

<210> SEQ ID NO 34
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 34

Lys Tyr Glu Ala His Val Pro Glu Asn Ala
1               5                   10

<210> SEQ ID NO 35
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 35

Lys Tyr Glu Leu Phe Gly His Ala Val Ser
1               5                   10

<210> SEQ ID NO 36
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 36

Arg Asn Asn Ile Tyr Glu Val Met Val Leu
1               5                   10

<210> SEQ ID NO 37
<211> LENGTH: 10
<212> TYPE: PRT
```

```
<213> ORGANISM: Artificial
<220> FEATURE:
<223> OTHER INFORMATION: An artificially synthesized peptide sequence

<400> SEQUENCE: 37

Arg Gly Pro Leu Ala Ser Leu Leu Leu Leu
1               5                   10

<210> SEQ ID NO 38
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 38

Arg Ile Leu Arg Asp Pro Ala Gly Trp Leu
1               5                   10

<210> SEQ ID NO 39
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 39

Cys Asn Gln Ser Pro Val Arg Gln Val Leu
1               5                   10

<210> SEQ ID NO 40
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 40

Val Tyr Ile Glu Ile Lys Phe Thr Leu
1               5

<210> SEQ ID NO 41
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 41

Arg Tyr Ser Val Ala Leu Ala Trp Leu
1               5

<210> SEQ ID NO 42
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 42

Val Tyr Pro Ala Asn Glu Val Thr Leu
1               5

<210> SEQ ID NO 43
<211> LENGTH: 9
<212> TYPE: PRT
<213> ORGANISM: Artificial
<220> FEATURE:
```

-continued

<223> OTHER INFORMATION: An artificially synthesized peptide sequence

<400> SEQUENCE: 43

His Tyr Thr Pro Gln Gln Asn Gly Leu
1               5

<210> SEQ ID NO 44
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 44

Phe Tyr Phe Ala Leu Phe Ser Cys Leu
1               5

<210> SEQ ID NO 45
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 45

Gly Tyr Gly Asp Phe Ser Glu Pro Leu
1               5

<210> SEQ ID NO 46
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 46

Lys Phe Gly Gln Ile Val Asn Met Leu
1               5

<210> SEQ ID NO 47
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 47

Ala Tyr Thr Thr Arg Gly Gly Lys Ile
1               5

<210> SEQ ID NO 48
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 48

Lys Tyr Asn Pro Asn Pro Asp Gln Ser
1               5

<210> SEQ ID NO 49
<211> LENGTH: 9
<212> TYPE: PRT
<213> ORGANISM: Artificial
<220> FEATURE:
<223> OTHER INFORMATION: An artificially synthesized peptide sequence

```
<400> SEQUENCE: 49

Arg Asn Ile Leu Val Asn Ser Asn Leu
1               5

<210> SEQ ID NO 50
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 50

Lys Tyr Leu Ser Asp Met Ser Tyr Val
1               5

<210> SEQ ID NO 51
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 51

Lys Leu Ile Arg Asn Pro Asn Ser Leu
1               5

<210> SEQ ID NO 52
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 52

Arg Tyr Lys Asp Asn Phe Thr Ala Ala
1               5

<210> SEQ ID NO 53
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 53

Lys Ala Ile Glu Glu Gly Tyr Arg Leu
1               5

<210> SEQ ID NO 54
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 54

Lys Tyr Ser Lys Ala Lys Gln Glu Ala
1               5

<210> SEQ ID NO 55
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 55
```

```
Ala Phe Gln Asp Val Gly Ala Cys Ile
1               5

<210> SEQ ID NO 56
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 56

Trp Leu Val Pro Ile Gly Asn Cys Leu
1               5

<210> SEQ ID NO 57
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 57

Arg Pro Pro Ser Ala Pro Leu Asn Leu
1               5

<210> SEQ ID NO 58
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 58

Lys Cys Pro Leu Thr Val Arg Asn Leu
1               5

<210> SEQ ID NO 59
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 59

Ser Tyr Asn Val Val Cys Lys Lys Cys
1               5

<210> SEQ ID NO 60
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 60

Val Tyr Pro Ala Asn Glu Val Thr Leu Leu
1               5                   10

<210> SEQ ID NO 61
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 61

Met Tyr Cys Gly Ala Asp Gly Glu Trp Leu
1               5                   10
```

```
<210> SEQ ID NO 62
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 62

Gly Tyr Thr Asp Lys Gln Arg Arg Asp Phe
1               5                   10

<210> SEQ ID NO 63
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 63

Phe Tyr Phe Ala Leu Phe Ser Cys Leu Phe
1               5                   10

<210> SEQ ID NO 64
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 64

Lys Phe Thr Leu Arg Asp Cys Asn Ser Leu
1               5                   10

<210> SEQ ID NO 65
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 65

Ser Tyr Gly Glu Arg Pro Tyr Trp Asp Met
1               5                   10

<210> SEQ ID NO 66
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 66

Ile Phe Tyr Phe Ala Leu Phe Ser Cys Leu
1               5                   10

<210> SEQ ID NO 67
<211> LENGTH: 10
<212> TYPE: PRT
<213> ORGANISM: Artificial
<220> FEATURE:
<223> OTHER INFORMATION: SYGIVMWEVM

<400> SEQUENCE: 67

Ser Tyr Gly Ile Val Met Trp Glu Val Met
1               5                   10
```

```
<210> SEQ ID NO 68
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 68

Glu Phe Gly Glu Val Cys Ser Gly Arg Leu
1               5                   10

<210> SEQ ID NO 69
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 69

Lys Tyr Asn Pro Asn Pro Asp Gln Ser Val
1               5                   10

<210> SEQ ID NO 70
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 70

Asn Phe Thr Ala Ala Gly Tyr Thr Thr Leu
1               5                   10

<210> SEQ ID NO 71
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 71

Gln Phe Asp His Pro Asn Ile Ile His Leu
1               5                   10

<210> SEQ ID NO 72
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 72

Ala Phe Leu Arg Lys Asn Asp Gly Arg Phe
1               5                   10

<210> SEQ ID NO 73
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 73

Lys Gln Glu Ala Asp Glu Glu Lys His Leu
1               5                   10

<210> SEQ ID NO 74
<211> LENGTH: 10
```

```
<212> TYPE: PRT
<213> ORGANISM: Artificial
<220> FEATURE:
<223> OTHER INFORMATION: An artificially synthesized peptide sequence

<400> SEQUENCE: 74

Arg Gly Ile Gly Ser Gly Met Lys Tyr Leu
1               5                   10

<210> SEQ ID NO 75
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 75

Arg Val Tyr Ile Glu Ile Lys Phe Thr Leu
1               5                   10

<210> SEQ ID NO 76
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 76

Ser Tyr Val Phe His Val Arg Ala Arg Thr
1               5                   10

<210> SEQ ID NO 77
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 77

Glu Trp Leu Val Pro Ile Gly Asn Cys Leu
1               5                   10

<210> SEQ ID NO 78
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 78

Arg Val Tyr Pro Ala Asn Glu Val Thr Leu
1               5                   10

<210> SEQ ID NO 79
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 79

Glu Tyr Met Glu Asn Gly Ser Leu Asp Ala
1               5                   10

<210> SEQ ID NO 80
<211> LENGTH: 9
<212> TYPE: PRT
<213> ORGANISM: Artificial
```

```
<220> FEATURE:
<223> OTHER INFORMATION: An artificially synthesized peptide sequence

<400> SEQUENCE: 80

Thr Tyr Pro Pro Phe Val Asn Phe Phe
1               5

<210> SEQ ID NO 81
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 81

Leu Tyr Cys Thr Ser Met Met Asn Leu
1               5

<210> SEQ ID NO 82
<211> LENGTH: 9
<212> TYPE: PRT
<213> ORGANISM: Artificial
<220> FEATURE:
<223> OTHER INFORMATION: An artificially synthesized peptide seque

<400> SEQUENCE: 82

Leu Tyr Val Val Lys Gln Glu Trp Phe
1               5

<210> SEQ ID NO 83
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 83

Asn Tyr Val Asn Ile Leu Ala Thr Ile
1               5

<210> SEQ ID NO 84
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 84

Ile Tyr Thr Ala Asp Pro Glu Ser Phe
1               5

<210> SEQ ID NO 85
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 85

Leu Tyr Lys Ala Asp Cys Arg Val Ile
1               5

<210> SEQ ID NO 86
<211> LENGTH: 9
<212> TYPE: PRT
<213> ORGANISM: Artificial
<220> FEATURE:
<223> OTHER INFORMATION: An artificially synthesized peptide sequence
```

```
<400> SEQUENCE: 86

Ser Phe Gln Met Thr Ser Asp Glu Leu
1               5

<210> SEQ ID NO 87
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 87

Ile Phe Leu Lys Tyr Ser Lys Asp Leu
1               5

<210> SEQ ID NO 88
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 88

Phe Phe Glu Arg Arg Ser His Thr Leu
1               5

<210> SEQ ID NO 89
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 89

Asp Phe Asn Ser Lys Val Thr His Leu
1               5

<210> SEQ ID NO 90
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 90

Lys Gln Glu Glu Leu Ile Lys Ala Leu
1               5

<210> SEQ ID NO 91
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 91

Arg Gly Glu Gln Val Thr Leu Phe Leu
1               5

<210> SEQ ID NO 92
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 92
```

Arg Leu Pro Ser Val Ala Leu Leu Leu
1               5

<210> SEQ ID NO 93
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 93

Lys Pro Glu Cys Gly Arg Gln Ser Leu
1               5

<210> SEQ ID NO 94
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 94

Ile Phe Gly Ser Ile Pro Asp Ile Phe
1               5

<210> SEQ ID NO 95
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 95

Arg Val Ile Gly Pro Pro Val Val Leu
1               5

<210> SEQ ID NO 96
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 96

Lys Tyr Ser Lys Asp Leu Val Lys Thr
1               5

<210> SEQ ID NO 97
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 97

Asp Phe Tyr Ala Ala Val Asp Asp Phe
1               5

<210> SEQ ID NO 98
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 98

Leu Tyr Glu Lys Ala Asn Thr Pro Glu Leu

-continued

<210> SEQ ID NO 99
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 99

Asn Tyr Val Asn Ile Leu Ala Thr Ile Ile
1               5                   10

<210> SEQ ID NO 100
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 100

Ser Tyr Val Glu Glu Glu Met Pro Gln Ile
1               5                   10

<210> SEQ ID NO 101
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 101

Asp Phe Gln Asp Ser Val Phe Asn Asp Leu
1               5                   10

<210> SEQ ID NO 102
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 102

Ser Phe Phe Glu Arg Arg Ser His Thr Leu
1               5                   10

<210> SEQ ID NO 103
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 103

Ser Phe Ser Lys Thr Pro Lys Arg Ala Leu
1               5                   10

<210> SEQ ID NO 104
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 104

Lys Tyr Leu Pro Leu Gly Asp Glu Arg Cys
1               5                   10

<210> SEQ ID NO 105
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 105

Glu Phe Glu Gly Leu Asp Ser Pro Glu Phe
1               5                   10

<210> SEQ ID NO 106
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 106

Lys Val Pro Pro Phe Gln Asp Cys Ile Leu
1               5                   10

<210> SEQ ID NO 107
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 107

Arg Pro Pro Thr Glu Gln Ala Asn Val Leu
1               5                   10

<210> SEQ ID NO 108
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 108

Lys Tyr Ser Lys Asp Leu Val Lys Thr Tyr
1               5                   10

<210> SEQ ID NO 109
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 109

Val Val Glu Glu Asn Ile Val Lys Asp Leu
1               5                   10

<210> SEQ ID NO 110
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 110

Ile Phe Val Arg Val Met Glu Ser Leu
1               5

<210> SEQ ID NO 111

```
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 111

Arg Val Met Glu Ser Leu Glu Gly Leu
1               5

<210> SEQ ID NO 112
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 112

Leu Tyr Leu Leu Gly Val Val Leu Thr Leu
1               5                   10

<210> SEQ ID NO 113
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 113

Arg Val Met Glu Ser Leu Glu Gly Leu Leu
1               5                   10

<210> SEQ ID NO 114
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 114

Tyr Leu Leu Gly Val Val Leu Thr Leu
1               5

<210> SEQ ID NO 115
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 115

Val Leu Thr Leu Leu Ser Ile Phe Val
1               5

<210> SEQ ID NO 116
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 116

Thr Leu Leu Ser Ile Phe Val Arg Val
1               5

<210> SEQ ID NO 117
<211> LENGTH: 9
<212> TYPE: PRT
```

```
<213> ORGANISM: Artificial
<220> FEATURE:
<223> OTHER INFORMATION: An artificially synthesized peptide sequence

<400> SEQUENCE: 117

Val Leu Asn Leu Tyr Leu Leu Gly Val
1               5

<210> SEQ ID NO 118
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 118

Leu Leu Gly Val Val Leu Thr Leu Leu
1               5

<210> SEQ ID NO 119
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 119

Arg Val Met Glu Ser Leu Glu Gly Leu
1               5

<210> SEQ ID NO 120
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 120

Asn Leu Tyr Leu Leu Gly Val Val Leu
1               5

<210> SEQ ID NO 121
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 121

Tyr Leu Leu Gly Val Val Leu Thr Leu Leu
1               5                   10

<210> SEQ ID NO 122
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 122

Val Val Leu Thr Leu Leu Ser Ile Phe Val
1               5                   10

<210> SEQ ID NO 123
<211> LENGTH: 10
<212> TYPE: PRT
<213> ORGANISM: Artificial
<220> FEATURE:
```

<223> OTHER INFORMATION: An artificially synthesized peptide sequence

<400> SEQUENCE: 123

Gly Leu Leu Glu Ser Pro Ser Pro Gly Thr
1               5                   10

<210> SEQ ID NO 124
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 124

Asn Leu Tyr Leu Leu Gly Val Val Leu Thr
1               5                   10

<210> SEQ ID NO 125
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 125

Val Leu Asn Leu Tyr Leu Leu Gly Val Val
1               5                   10

<210> SEQ ID NO 126
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 126

Thr Leu Leu Ser Ile Phe Val Arg Val Met
1               5                   10

<210> SEQ ID NO 127
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 127

Ser Ile Phe Val Arg Val Met Glu Ser Leu
1               5                   10

<210> SEQ ID NO 128
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 128

Leu Thr Leu Leu Ser Ile Phe Val Arg Val
1               5                   10

<210> SEQ ID NO 129
<211> LENGTH: 9
<212> TYPE: PRT
<213> ORGANISM: Artificial
<220> FEATURE:
<223> OTHER INFORMATION: An artificially synthesized peptide sequence

```
<400> SEQUENCE: 129

Leu Tyr Phe Asp Asp Glu Tyr Asn Ile
1               5

<210> SEQ ID NO 130
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 130

Leu Phe Glu Arg Gly Glu Arg Arg Leu
1               5

<210> SEQ ID NO 131
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 131

Arg Ala Leu Gly Ala Ala Cys Leu Leu
1               5

<210> SEQ ID NO 132
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 132

Glu Tyr Asn Ile Val Lys Arg Asp Val
1               5

<210> SEQ ID NO 133
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 133

Leu Tyr Leu Lys Leu Leu Pro Tyr Val Leu
1               5                   10

<210> SEQ ID NO 134
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 134

Leu Phe Val Val Gln Ala Ser Leu Trp Leu
1               5                   10

<210> SEQ ID NO 135
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 135
```

```
Arg Gln Gln Phe Phe Ile Asp Phe Arg Leu
1               5                   10

<210> SEQ ID NO 136
<211> LENGTH: 10
<212> TYPE: PRT
<213> ORGANISM: Artificial
<220> FEATURE:
<223> OTHER INFORMATION: DFLEAVKRHI

<400> SEQUENCE: 136

Asp Phe Leu Glu Ala Val Lys Arg His Ile
1               5                   10

<210> SEQ ID NO 137
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 137

Arg Ala Leu Gly Ala Ala Cys Leu Leu Leu
1               5                   10

<210> SEQ ID NO 138
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 138

Arg Pro Phe Val Val Val Gln Ala Arg Leu
1               5                   10

<210> SEQ ID NO 139
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 139

Ala Tyr Leu Ala Gly Val Pro Gly Ser Ala
1               5                   10

<210> SEQ ID NO 140
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 140

Ser Leu Trp Leu Tyr Leu Lys Leu Leu
1               5

<210> SEQ ID NO 141
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 141

Leu Leu Leu Leu Ala Ala Gly Trp Leu
1               5
```

```
<210> SEQ ID NO 142
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 142

Asn Leu Phe Val Val Gln Ala Ser Leu
1               5

<210> SEQ ID NO 143
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 143

Asn Met Val Glu Lys Arg Val Asp Leu
1               5

<210> SEQ ID NO 144
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 144

Phe Val Val Gln Ala Ser Leu Trp Leu
1               5

<210> SEQ ID NO 145
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 145

Gln Gln Phe Phe Ile Asp Phe Arg Leu
1               5

<210> SEQ ID NO 146
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 146

Arg Leu Gly Asp Ser Arg His Arg Ile
1               5

<210> SEQ ID NO 147
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 147

Val Gln Ala Ser Leu Trp Leu Tyr Leu
1               5
```

```
<210> SEQ ID NO 148
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 148

Glu Leu Ala Val Val Pro Val Phe Val
1               5

<210> SEQ ID NO 149
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 149

Arg Leu Ile Gly Trp Asn Asp Trp Ile
1               5

<210> SEQ ID NO 150
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 150

Arg Val Ser Glu Ile Ile Ser Phe Ala
1               5

<210> SEQ ID NO 151
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 151

Gly Leu Ala Ser Ser Arg Val Arg Leu
1               5

<210> SEQ ID NO 152
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 152

Ala Leu Gly Ala Ala Cys Leu Leu Leu
1               5

<210> SEQ ID NO 153
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 153

Val Gln Cys Asp Ser Cys Gln Glu Leu
1               5

<210> SEQ ID NO 154
<211> LENGTH: 10
```

```
<212> TYPE: PRT
<213> ORGANISM: Artificial
<220> FEATURE:
<223> OTHER INFORMATION: An artificially synthesized peptide sequence

<400> SEQUENCE: 154

Trp Leu Tyr Leu Lys Leu Leu Pro Tyr Val
1               5                   10

<210> SEQ ID NO 155
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 155

Asn Leu Cys Cys Arg Gln Gln Phe Phe Ile
1               5                   10

<210> SEQ ID NO 156
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 156

Ala Leu Phe Glu Arg Gly Glu Arg Arg Leu
1               5                   10

<210> SEQ ID NO 157
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 157

Met Leu Tyr Phe Asp Asp Glu Tyr Asn Ile
1               5                   10

<210> SEQ ID NO 158
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 158

Cys Leu Leu Leu Leu Ala Ala Gly Trp Leu
1               5                   10

<210> SEQ ID NO 159
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 159

Ala Leu Gly Ala Ala Cys Leu Leu Leu Leu
1               5                   10

<210> SEQ ID NO 160
<211> LENGTH: 10
<212> TYPE: PRT
<213> ORGANISM: Artificial
```

```
<220> FEATURE:
<223> OTHER INFORMATION: An artificially synthesized peptide sequence

<400> SEQUENCE: 160

Arg Leu Ile Gly Trp Asn Asp Trp Ile Ile
1               5                   10

<210> SEQ ID NO 161
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 161

Val Val Gln Ala Ser Leu Trp Leu Tyr Leu
1               5                   10

<210> SEQ ID NO 162
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 162

Gln Glu Leu Ala Val Val Pro Val Phe Val
1               5                   10

<210> SEQ ID NO 163
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 163

Phe Ile Ser Asn Glu Gly Asn Gln Asn Leu
1               5                   10

<210> SEQ ID NO 164
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 164

Arg Gln Gln Phe Phe Ile Asp Phe Arg Leu
1               5                   10

<210> SEQ ID NO 165
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 165

Gly Leu Asn Pro Gly Thr Val Asn Ser Cys
1               5                   10

<210> SEQ ID NO 166
<211> LENGTH: 10
<212> TYPE: PRT
<213> ORGANISM: Artificial
<220> FEATURE:
<223> OTHER INFORMATION: An artificially synthesized peptide sequence
```

```
<400> SEQUENCE: 166

Arg Leu Gln Met Arg Gly Arg Pro Asn Ile
1               5                   10

<210> SEQ ID NO 167
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 167

Arg Val Asp Gly Asp Phe Leu Glu Ala Val
1               5                   10

<210> SEQ ID NO 168
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 168

Ile Tyr Asn Glu Leu Leu Tyr Asp Leu
1               5

<210> SEQ ID NO 169
<211> LENGTH: 9
<212> TYPE: PRT
<213> ORGANISM: Artificial
<220> FEATURE:
<223> OTHER INFORMATION: MYEEKLNIL

<400> SEQUENCE: 169

Met Tyr Glu Glu Lys Leu Asn Ile Leu
1               5

<210> SEQ ID NO 170
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 170

Val Tyr Leu Arg Val Arg Pro Leu Leu
1               5

<210> SEQ ID NO 171
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 171

Lys Phe Ser Ala Ile Ala Ser Gln Leu
1               5

<210> SEQ ID NO 172
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 172
```

```
Ser Phe Phe Glu Ile Tyr Asn Glu Leu
1               5

<210> SEQ ID NO 173
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 173

Ile Phe Asn Ser Leu Gln Gly Gln Leu
1               5

<210> SEQ ID NO 174
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 174

Phe Phe Glu Ile Tyr Asn Glu Leu Leu
1               5

<210> SEQ ID NO 175
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 175

Met Phe Glu Ser Thr Ala Ala Asp Leu
1               5

<210> SEQ ID NO 176
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 176

Ser Phe Asp Ser Gly Ile Ala Gly Leu
1               5

<210> SEQ ID NO 177
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 177

Arg Phe Ser Ile Trp Ile Ser Phe Phe
1               5

<210> SEQ ID NO 178
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 178

Ile Phe Ser Ile Arg Ile Leu His Leu
```

```
<210> SEQ ID NO 179
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 179

Lys Ile Glu Glu Leu Glu Ala Leu Leu
1               5

<210> SEQ ID NO 180
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 180

Lys Leu Asn Ile Leu Lys Glu Ser Leu
1               5

<210> SEQ ID NO 181
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 181

Lys Leu Gln Gln Cys Lys Ala Glu Leu
1               5

<210> SEQ ID NO 182
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 182

Phe Thr Ile Asp Val Asp Lys Lys Leu
1               5

<210> SEQ ID NO 183
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 183

Gln Leu Gln Glu Val Lys Ala Lys Leu
1               5

<210> SEQ ID NO 184
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 184

Ile Tyr Asn Glu Leu Leu Tyr Asp Leu Leu
1               5                   10
```

<210> SEQ ID NO 185
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 185

Arg Ser Leu Ala Leu Ile Phe Asn Ser Leu
1               5                   10

<210> SEQ ID NO 186
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 186

Ser Phe Phe Glu Ile Tyr Asn Glu Leu Leu
1               5                   10

<210> SEQ ID NO 187
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 187

Arg Leu Leu Arg Thr Glu Leu Gln Lys Leu
1               5                   10

<210> SEQ ID NO 188
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 188

Lys Asn Ile Arg Leu Leu Arg Thr Glu Leu
1               5                   10

<210> SEQ ID NO 189
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 189

Arg Gln Glu Glu Met Lys Lys Leu Ser Leu
1               5                   10

<210> SEQ ID NO 190
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 190

Arg Val Arg Pro Leu Leu Pro Ser Glu Leu
1               5                   10

<210> SEQ ID NO 191

```
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 191

Arg Ile Leu Arg Ser Arg Arg Ser Pro Leu
1               5                   10

<210> SEQ ID NO 192
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 192

Arg Ile Glu Asn Val Glu Thr Leu Val Leu
1               5                   10

<210> SEQ ID NO 193
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 193

Lys Asn Gln Ser Phe Ala Ser Thr His Leu
1               5                   10

<210> SEQ ID NO 194
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 194

Lys Val Tyr Leu Arg Val Arg Pro Leu Leu
1               5                   10

<210> SEQ ID NO 195
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 195

Asp Ser Met Glu Lys Val Lys Val Tyr Leu
1               5                   10

<210> SEQ ID NO 196
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 196

Lys Tyr Gln Ala Tyr Met Ser Asn Leu
1               5

<210> SEQ ID NO 197
<211> LENGTH: 9
<212> TYPE: PRT
```

<213> ORGANISM: Artificial
<220> FEATURE:
<223> OTHER INFORMATION: An artificially synthesized peptide sequence

<400> SEQUENCE: 197

Val Tyr Val Pro Leu Lys Glu Leu Leu
1               5

<210> SEQ ID NO 198
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 198

Glu Tyr His Lys Leu Ala Arg Lys Leu
1               5

<210> SEQ ID NO 199
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 199

Ser Tyr Glu Leu Pro Asp Thr Lys Phe
1               5

<210> SEQ ID NO 200
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 200

Lys Tyr Glu Lys Lys Ala Thr Leu Ile
1               5

<210> SEQ ID NO 201
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 201

Lys Tyr Ala Arg Gly Lys Glu Ala Ile
1               5

<210> SEQ ID NO 202
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 202

Asp Phe Leu Lys Ile Phe Thr Phe Leu
1               5

<210> SEQ ID NO 203
<211> LENGTH: 9
<212> TYPE: PRT
<213> ORGANISM: Artificial
<220> FEATURE:

<223> OTHER INFORMATION: An artificially synthesized peptide sequence

<400> SEQUENCE: 203

Gly Phe Leu Cys Pro Ser Tyr Glu Leu
1               5

<210> SEQ ID NO 204
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 204

Leu Phe Asn Val Asp Ala Phe Lys Leu
1               5

<210> SEQ ID NO 205
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 205

Ser Phe Asp Glu Met Asn Ala Glu Leu
1               5

<210> SEQ ID NO 206
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 206

Ile Phe Thr Phe Leu Tyr Gly Phe Leu
1               5

<210> SEQ ID NO 207
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 207

Lys Phe Glu Glu Glu Val Pro Arg Ile
1               5

<210> SEQ ID NO 208
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 208

Arg Ile Asn His Glu Arg Asn Glu Leu
1               5

<210> SEQ ID NO 209
<211> LENGTH: 9
<212> TYPE: PRT
<213> ORGANISM: Artificial
<220> FEATURE:
<223> OTHER INFORMATION: An artificially synthesized peptide sequence

```
<400> SEQUENCE: 209

Ser Phe Met Ser Gly Ala Asp Ser Phe
1               5

<210> SEQ ID NO 210
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 210

Ile Phe Lys Asp Leu Gly Tyr Pro Phe
1               5

<210> SEQ ID NO 211
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 211

Glu Tyr Gln Leu Val Val Gln Thr Thr
1               5

<210> SEQ ID NO 212
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 212

Lys Ala Leu Asn Lys Lys Met Gly Leu
1               5

<210> SEQ ID NO 213
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 213

Glu Val Pro Arg Ile Phe Lys Asp Leu
1               5

<210> SEQ ID NO 214
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 214

Lys Tyr Arg Ala Gln Val Tyr Val Pro Leu
1               5                   10

<210> SEQ ID NO 215
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 215
```

```
Glu Tyr Glu Glu Cys Met Ser Glu Asp Leu
1               5                   10

<210> SEQ ID NO 216
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 216

Lys Tyr Ser Val Ala Asp Ile Glu Arg Ile
1               5                   10

<210> SEQ ID NO 217
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 217

Asp Tyr Thr Ile Lys Cys Tyr Glu Ser Phe
1               5                   10

<210> SEQ ID NO 218
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 218

Lys Phe Glu Glu Glu Val Pro Arg Ile Phe
1               5                   10

<210> SEQ ID NO 219
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 219

Ala Phe Ile Gln Gln Cys Ile Arg Gln Leu
1               5                   10

<210> SEQ ID NO 220
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 220

Arg Ser Gln Asp Val Asn Lys Gln Gly Leu
1               5                   10

<210> SEQ ID NO 221
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 221

Arg Thr Leu Lys Glu Glu Val Gln Lys Leu
1               5                   10
```

```
<210> SEQ ID NO 222
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 222

Arg Gly Lys Glu Ala Ile Glu Thr Gln Leu
1               5                   10

<210> SEQ ID NO 223
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 223

Arg Ala Leu Asn Glu Gln Ile Ala Arg Leu
1               5                   10

<210> SEQ ID NO 224
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 224

Glu Tyr Gln Leu Val Val Gln Thr Thr Thr
1               5                   10

<210> SEQ ID NO 225
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 225

Glu Thr Glu Glu Glu Ile Asn Lys Ala Leu
1               5                   10

<210> SEQ ID NO 226
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 226

Leu Leu Glu Ser Thr Val Asn Gln Gly Leu
1               5                   10

<210> SEQ ID NO 227
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 227

Tyr Met Ser Cys Phe Arg Thr Pro Val
1               5
```

```
<210> SEQ ID NO 228
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 228

Lys Gln Ile Tyr Ala Ile Lys Tyr Val
1               5

<210> SEQ ID NO 229
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 229

Asn Met Leu Glu Ala Val His Thr Ile
1               5

<210> SEQ ID NO 230
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 230

Leu Leu Asn Ser Pro Asp Cys Asp Val
1               5

<210> SEQ ID NO 231
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 231

Ile Leu Ala Thr Pro Leu Gln Asn Leu
1               5

<210> SEQ ID NO 232
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 232

Tyr Val Leu Gly Gln Leu Val Gly Leu
1               5

<210> SEQ ID NO 233
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 233

Ser Leu Gly Cys Ile Leu Tyr Tyr Met
1               5

<210> SEQ ID NO 234
<211> LENGTH: 9
```

```
<212> TYPE: PRT
<213> ORGANISM: Artificial
<220> FEATURE:
<223> OTHER INFORMATION: An artificially synthesized peptide sequence

<400> SEQUENCE: 234

Gln Met Gln Pro Asp Thr Thr Ser Val
1               5

<210> SEQ ID NO 235
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 235

Gly Thr Thr Glu Glu Met Lys Tyr Val
1               5

<210> SEQ ID NO 236
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 236

Leu Ile Val Asp Gly Met Leu Lys Leu
1               5

<210> SEQ ID NO 237
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 237

Ser Leu Leu Ala Lys Leu Glu Glu Thr
1               5

<210> SEQ ID NO 238
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 238

Leu Phe Glu Arg Gly Glu Arg Arg Leu
1               5

<210> SEQ ID NO 239
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 239

Leu Leu Ala His Pro Tyr Val Gln Ile
1               5

<210> SEQ ID NO 240
<211> LENGTH: 9
<212> TYPE: PRT
<213> ORGANISM: Artificial
```

```
<220> FEATURE:
<223> OTHER INFORMATION: An artificially synthesized peptide sequence

<400> SEQUENCE: 240

Lys Leu Ile Gly Arg Tyr Ser Gln Ala
1               5

<210> SEQ ID NO 241
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 241

Asn Leu Asn Leu Gln Lys Lys Gln Leu
1               5

<210> SEQ ID NO 242
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 242

Met Gln Pro Asp Thr Thr Ser Val Val
1               5

<210> SEQ ID NO 243
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 243

Lys Leu Gln Gln His Ser Asp Lys Ile
1               5

<210> SEQ ID NO 244
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 244

Phe Ala Phe Val His Ile Ser Phe Ala
1               5

<210> SEQ ID NO 245
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 245

Cys Glu Leu Arg Asn Leu Lys Ser Val
1               5

<210> SEQ ID NO 246
<211> LENGTH: 9
<212> TYPE: PRT
<213> ORGANISM: Artificial
<220> FEATURE:
<223> OTHER INFORMATION: An artificially synthesized peptide sequence
```

```
<400> SEQUENCE: 246

Ser Ile Leu Lys Ala Ala Lys Thr Leu
1               5

<210> SEQ ID NO 247
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 247

Leu Leu Leu Lys Leu Glu Lys Asn Ser Val
1               5                   10

<210> SEQ ID NO 248
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 248

Asn Leu Leu Asn Ser Pro Asp Cys Asp Val
1               5                   10

<210> SEQ ID NO 249
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 249

Phe Leu Ile Val Asp Gly Met Leu Lys Leu
1               5                   10

<210> SEQ ID NO 250
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 250

Thr Thr Phe Glu Gln Pro Val Phe Ser Val
1               5                   10

<210> SEQ ID NO 251
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 251

Val Leu Asn Glu Lys Lys Gln Ile Tyr Ala
1               5                   10

<210> SEQ ID NO 252
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 252
```

```
Gly Met Leu Lys Leu Ile Asp Phe Gly Ile
1               5                   10

<210> SEQ ID NO 253
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 253

Leu Leu Ser Glu Glu Lys Lys Asn Leu
1               5                   10

<210> SEQ ID NO 254
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 254

Tyr Met Ser Cys Phe Arg Thr Pro Val Val
1               5                   10

<210> SEQ ID NO 255
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 255

Met Met Ala Asn Asn Pro Glu Asp Trp Leu
1               5                   10

<210> SEQ ID NO 256
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 256

Met Val Met Glu Cys Gly Asn Ile Asp Leu
1               5                   10

<210> SEQ ID NO 257
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 257

Tyr Met Pro Pro Glu Ala Ile Lys Asp Met
1               5                   10

<210> SEQ ID NO 258
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 258

Lys Leu Ile Gly Arg Tyr Ser Gln Ala Ile
```

```
<210> SEQ ID NO 259
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 259

Asn Gln Met Gln Pro Asp Thr Thr Ser Val
1               5                   10

<210> SEQ ID NO 260
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 260

Gln Ile Leu Ala Thr Pro Leu Gln Asn Leu
1               5                   10

<210> SEQ ID NO 261
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 261

Leu Ile Val Asp Gly Met Leu Lys Leu Ile
1               5                   10

<210> SEQ ID NO 262
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 262

Asn Leu Asn Leu Gln Lys Lys Gln Leu Leu
1               5                   10

<210> SEQ ID NO 263
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 263

Gln Met Gln Pro Asp Thr Thr Ser Val Val
1               5                   10

<210> SEQ ID NO 264
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 264

Lys Gly Thr Thr Glu Glu Met Lys Tyr Val
1               5                   10
```

<210> SEQ ID NO 265
<211> LENGTH: 10
<212> TYPE: PRT
<213> ORGANISM: Artificial
<220> FEATURE:
<223> OTHER INFORMATION: An artificially synthesized peptide sequenc

<400> SEQUENCE: 265

Leu Thr Ile Asp Ser Ile Met Asn Lys Val
1               5                   10

<210> SEQ ID NO 266
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 266

Lys Leu Gln Gln His Ser Asp Lys Ile Ile
1               5                   10

<210> SEQ ID NO 267
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 267

Lys Ile Phe Pro Arg Phe Phe Met Val
1               5

<210> SEQ ID NO 268
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 268

Gly Leu Trp Leu Ala Ile Leu Leu Leu
1               5

<210> SEQ ID NO 269
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 269

Leu Leu Val Val Ala Leu Pro Arg Val
1               5

<210> SEQ ID NO 270
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 270

Ala Leu Leu Ala Leu Leu Leu Val Val
1               5

<210> SEQ ID NO 271

<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 271

Trp Leu Ala Ile Leu Leu Leu Leu Ala
1               5

<210> SEQ ID NO 272
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 272

Leu Leu Ala Ser Ile Ala Ala Gly Leu
1               5

<210> SEQ ID NO 273
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 273

Leu Leu Leu Leu Ala Ser Ile Ala Ala
1               5

<210> SEQ ID NO 274
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 274

Phe Met Val Ala Lys Gln Cys Ser Ala
1               5

<210> SEQ ID NO 275
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 275

Thr Met Ala Leu Leu Ala Leu Leu Leu
1               5

<210> SEQ ID NO 276
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 276

Met Ala Leu Leu Ala Leu Leu Leu Val
1               5

<210> SEQ ID NO 277
<211> LENGTH: 9
<212> TYPE: PRT

```
<213> ORGANISM: Artificial
<220> FEATURE:
<223> OTHER INFORMATION: An artificially synthesized peptide sequence

<400> SEQUENCE: 277

Ala Ile Leu Leu Leu Leu Ala Ser Ile
1               5

<210> SEQ ID NO 278
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 278

Ala Leu Pro Arg Val Trp Thr Asp Ala
1               5

<210> SEQ ID NO 279
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 279

Ser Met Gly Glu Ser Cys Gly Gly Leu
1               5

<210> SEQ ID NO 280
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 280

Leu Leu Ala Leu Leu Leu Val Val Ala
1               5

<210> SEQ ID NO 281
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 281

Val Val Ala Leu Pro Arg Val Trp Thr
1               5

<210> SEQ ID NO 282
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 282

Arg Val Trp Thr Asp Ala Asn Leu Thr
1               5

<210> SEQ ID NO 283
<211> LENGTH: 9
<212> TYPE: PRT
<213> ORGANISM: Artificial
<220> FEATURE:
```

<223> OTHER INFORMATION: An artificially synthesized peptide sequence

<400> SEQUENCE: 283

Phe Leu Leu Glu Glu Pro Met Pro Phe
1               5

<210> SEQ ID NO 284
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 284

Leu Ala Leu Leu Leu Val Val Ala Leu
1               5

<210> SEQ ID NO 285
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 285

Gly Thr Met Ala Leu Leu Ala Leu Leu
1               5

<210> SEQ ID NO 286
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 286

Leu Leu Leu Val Val Ala Leu Pro Arg Val
1               5                   10

<210> SEQ ID NO 287
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 287

Gly Leu Trp Leu Ala Ile Leu Leu Leu Leu
1               5                   10

<210> SEQ ID NO 288
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 288

Leu Leu Leu Ala Ser Ile Ala Ala Gly Leu
1               5                   10

<210> SEQ ID NO 289
<211> LENGTH: 10
<212> TYPE: PRT
<213> ORGANISM: Artificial
<220> FEATURE:
<223> OTHER INFORMATION: An artificially synthesized peptide sequence

```
<400> SEQUENCE: 289

Thr Met Ala Leu Leu Ala Leu Leu Leu Val
1               5                   10

<210> SEQ ID NO 290
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 290

Leu Leu Ala Leu Leu Leu Val Val Ala Leu
1               5                   10

<210> SEQ ID NO 291
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 291

Phe Leu Leu Glu Glu Pro Met Pro Phe Phe
1               5                   10

<210> SEQ ID NO 292
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 292

Ile Leu Leu Leu Leu Ala Ser Ile Ala Ala
1               5                   10

<210> SEQ ID NO 293
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 293

Lys Ile Phe Pro Arg Phe Phe Met Val Ala
1               5                   10

<210> SEQ ID NO 294
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 294

Ala Leu Leu Ala Leu Leu Leu Val Val Ala
1               5                   10

<210> SEQ ID NO 295
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 295
```

```
Leu Val Val Ala Leu Pro Arg Val Trp Thr
1               5                   10

<210> SEQ ID NO 296
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 296

Met Ala Leu Leu Ala Leu Leu Leu Val Val
1               5                   10

<210> SEQ ID NO 297
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 297

Arg Leu Gln Arg Pro Arg Gln Ala Pro Ala
1               5                   10

<210> SEQ ID NO 298
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 298

Cys Gln Asn Pro Arg Arg Cys Lys Trp Thr
1               5                   10

<210> SEQ ID NO 299
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 299

Arg Val Trp Thr Asp Ala Asn Leu Thr Ala
1               5                   10

<210> SEQ ID NO 300
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 300

Trp Ala Pro Leu Gly Thr Met Ala Leu Leu
1               5                   10

<210> SEQ ID NO 301
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 301

Thr Glu Pro Tyr Cys Val Ile Ala Ala Val
1               5                   10
```

```
<210> SEQ ID NO 302
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 302

Leu Glu Glu Pro Met Pro Phe Phe Tyr Leu
1               5                   10

<210> SEQ ID NO 303
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 303

Leu Glu Gly Pro Pro Ile Asn Ser Ser Val
1               5                   10

<210> SEQ ID NO 304
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 304

Tyr Leu Lys Cys Cys Lys Ile Arg Tyr Cys
1               5                   10

<210> SEQ ID NO 305
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 305

Val Lys Ile Phe Pro Arg Phe Phe Met Val
1               5                   10

<210> SEQ ID NO 306
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 306

Lys Ile Phe Pro Ser Lys Arg Ile Leu
1               5

<210> SEQ ID NO 307
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 307

Arg Gly Ser Val Leu Glu Gly Val Leu
1               5
```

```
<210> SEQ ID NO 308
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 308

Phe Leu Leu Leu Val Leu Leu Leu Leu
1               5

<210> SEQ ID NO 309
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 309

Ile Gly Asn Phe Ile Ile Glu Asn Leu
1               5

<210> SEQ ID NO 310
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 310

Thr Ala Val Ala Val Val Glu Ile Leu
1               5

<210> SEQ ID NO 311
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 311

Asn Gln Ser Pro Val Arg Gln Val Leu
1               5

<210> SEQ ID NO 312
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 312

Lys Gln Asp Thr Tyr Asp Val His Leu
1               5

<210> SEQ ID NO 313
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 313

Asp Tyr Glu Gly Ser Gly Ser Asp Ala
1               5

<210> SEQ ID NO 314
<211> LENGTH: 9
```

```
<212> TYPE: PRT
<213> ORGANISM: Artificial
<220> FEATURE:
<223> OTHER INFORMATION: An artificially synthesized peptide sequence

<400> SEQUENCE: 314

Gly Trp Leu Leu Leu Asn Lys Pro Leu
1               5

<210> SEQ ID NO 315
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 315

Ile Leu Pro Val Leu Gly Ala Val Leu
1               5

<210> SEQ ID NO 316
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 316

Thr Ala Pro Pro Tyr Asp Thr Leu Leu
1               5

<210> SEQ ID NO 317
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 317

Val Val Leu Ser Leu Lys Lys Phe Leu
1               5

<210> SEQ ID NO 318
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 318

Ala Leu Leu Phe Leu Leu Leu Val Leu
1               5

<210> SEQ ID NO 319
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 319

Val Thr Asn Glu Ala Pro Phe Val Leu
1               5

<210> SEQ ID NO 320
<211> LENGTH: 9
<212> TYPE: PRT
<213> ORGANISM: Artificial
```

```
<220> FEATURE:
<223> OTHER INFORMATION: An artificially synthesized peptide sequence

<400> SEQUENCE: 320

Ala Val Leu Ala Leu Leu Phe Leu Leu
1               5

<210> SEQ ID NO 321
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 321

Asp Thr Tyr Asp Val His Leu Ser Leu
1               5

<210> SEQ ID NO 322
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 322

Gly Pro Leu Ala Ser Leu Leu Leu Leu
1               5

<210> SEQ ID NO 323
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 323

Val Leu Asn Ile Thr Asp Lys Asp Leu
1               5

<210> SEQ ID NO 324
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 324

Ala Val Glu Lys Glu Thr Gly Trp Leu
1               5

<210> SEQ ID NO 325
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 325

Asn Asn Ile Tyr Glu Val Met Val Leu
1               5

<210> SEQ ID NO 326
<211> LENGTH: 9
<212> TYPE: PRT
<213> ORGANISM: Artificial
<220> FEATURE:
<223> OTHER INFORMATION: An artificially synthesized peptide sequence
```

<400> SEQUENCE: 326

Leu Leu Leu Leu Gln Val Cys Trp Leu
1               5

<210> SEQ ID NO 327
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 327

Gly Cys Pro Gly Gln Glu Pro Ala Leu
1               5

<210> SEQ ID NO 328
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 328

Glu Tyr Thr Leu Thr Ile Gln Ala Thr
1               5

<210> SEQ ID NO 329
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 329

Glu Thr Val Gln Glu Arg Arg Ser Leu
1               5

<210> SEQ ID NO 330
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 330

Ser Tyr Arg Ile Leu Arg Asp Pro Ala
1               5

<210> SEQ ID NO 331
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 331

Gly Gln Val Thr Ala Val Gly Thr Leu
1               5

<210> SEQ ID NO 332
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 332

```
Gly Ala Val Leu Ala Leu Leu Phe Leu
1               5

<210> SEQ ID NO 333
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 333

Gly Ile Leu Thr Thr Arg Lys Gly Leu
1               5

<210> SEQ ID NO 334
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 334

His Pro Glu Ser Asn Gln Gly Ile Leu
1               5

<210> SEQ ID NO 335
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 335

Val Leu Ala Leu Leu Phe Leu Leu Leu
1               5

<210> SEQ ID NO 336
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 336

Glu Gly Asp Thr Val Val Leu Ser Leu
1               5

<210> SEQ ID NO 337
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 337

Thr Ile Ser Val Ile Ser Ser Gly Leu
1               5

<210> SEQ ID NO 338
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 338

Val Leu Gly Ala Val Leu Ala Leu Leu
```

```
<210> SEQ ID NO 339
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 339

Glu Trp Gly Ser Arg Phe Lys Lys Leu
1               5

<210> SEQ ID NO 340
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 340

Lys Val Val Glu Val Gln Glu Gly Ile
1               5

<210> SEQ ID NO 341
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 341

Thr Tyr Asp Val His Leu Ser Leu Ser
1               5

<210> SEQ ID NO 342
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 342

Phe Tyr Ser Ile Thr Gly Pro Gly Ala
1               5

<210> SEQ ID NO 343
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 343

Ile Tyr Thr Tyr Asn Gly Val Val Ala
1               5

<210> SEQ ID NO 344
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 344

Phe Ile Leu Pro Val Leu Gly Ala Val Leu
1               5                   10
```

<210> SEQ ID NO 345
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 345

Ala Val Leu Ala Leu Leu Phe Leu Leu Leu
1               5                   10

<210> SEQ ID NO 346
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 346

Gly Thr Ile Ser Val Ile Ser Ser Gly Leu
1               5                   10

<210> SEQ ID NO 347
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 347

Asp Tyr Glu Gly Ser Gly Ser Asp Ala Ala
1               5                   10

<210> SEQ ID NO 348
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 348

Thr Val Val Leu Ser Leu Lys Lys Phe Leu
1               5                   10

<210> SEQ ID NO 349
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 349

Phe Ala Val Glu Lys Glu Thr Gly Trp Leu
1               5                   10

<210> SEQ ID NO 350
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 350

Ala Leu Leu Phe Leu Leu Leu Val Leu Leu
1               5                   10

<210> SEQ ID NO 351

```
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 351

Ser Gln Glu Pro Lys Asp Pro His Asp Leu
1               5                   10

<210> SEQ ID NO 352
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 352

Leu Ala Leu Leu Phe Leu Leu Leu Val Leu
1               5                   10

<210> SEQ ID NO 353
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 353

Gly Ala Glu Gln Glu Pro Gly Gln Ala Leu
1               5                   10

<210> SEQ ID NO 354
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 354

Gly Ala Val Leu Ala Leu Leu Phe Leu Leu
1               5                   10

<210> SEQ ID NO 355
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 355

Val Asn Glu Glu Gly Asp Thr Val Val Leu
1               5                   10

<210> SEQ ID NO 356
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 356

Asn Ala Val Gly His Glu Val Gln Arg Leu
1               5                   10

<210> SEQ ID NO 357
<211> LENGTH: 10
<212> TYPE: PRT
```

```
<213> ORGANISM: Artificial
<220> FEATURE:
<223> OTHER INFORMATION: An artificially synthesized peptide sequence

<400> SEQUENCE: 357

Thr Asn Glu Ala Pro Phe Val Leu Lys Leu
1               5                   10

<210> SEQ ID NO 358
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 358

Glu Asn Gln Lys Ile Ser Tyr Arg Ile Leu
1               5                   10

<210> SEQ ID NO 359
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 359

Ser Leu Leu Leu Leu Gln Val Cys Trp Leu
1               5                   10

<210> SEQ ID NO 360
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 360

Gly Leu Glu Ala Arg Pro Glu Val Val Leu
1               5                   10

<210> SEQ ID NO 361
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 361

Glu Val Gln Arg Leu Thr Val Thr Asp Leu
1               5                   10

<210> SEQ ID NO 362
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 362

Gly Leu Pro Arg Gly Pro Leu Ala Ser Leu
1               5                   10

<210> SEQ ID NO 363
<211> LENGTH: 10
<212> TYPE: PRT
<213> ORGANISM: Artificial
<220> FEATURE:
```

<223> OTHER INFORMATION: An artificially synthesized peptide sequence

<400> SEQUENCE: 363

Leu Pro Val Leu Gly Ala Val Leu Ala Leu
1               5                   10

<210> SEQ ID NO 364
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 364

Gln Val Leu Asn Ile Thr Asp Lys Asp Leu
1               5                   10

<210> SEQ ID NO 365
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 365

Ala Val Glu Lys Glu Thr Gly Trp Leu Leu
1               5                   10

<210> SEQ ID NO 366
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 366

Ser Gly Gln Val Thr Ala Val Gly Thr Leu
1               5                   10

<210> SEQ ID NO 367
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 367

Gln Gly Ile Leu Thr Thr Arg Lys Gly Leu
1               5                   10

<210> SEQ ID NO 368
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 368

Ser Pro Pro Thr Thr Gly Thr Gly Thr Leu
1               5                   10

<210> SEQ ID NO 369
<211> LENGTH: 10
<212> TYPE: PRT
<213> ORGANISM: Artificial
<220> FEATURE:
<223> OTHER INFORMATION: An artificially synthesized peptide sequence

```
<400> SEQUENCE: 369

Asn Ser Pro Ala Trp Arg Ala Thr Tyr Leu
1               5                  10

<210> SEQ ID NO 370
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 370

Gly Pro Phe Pro Gln Arg Leu Asn Gln Leu
1               5                  10

<210> SEQ ID NO 371
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 371

Glu Ile Gly Asn Phe Ile Ile Glu Asn Leu
1               5                  10

<210> SEQ ID NO 372
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 372

Thr Thr Ala Val Ala Val Val Glu Ile Leu
1               5                  10

<210> SEQ ID NO 373
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 373

Ile Tyr Thr Tyr Asn Gly Val Val Ala Tyr
1               5                  10

<210> SEQ ID NO 374
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 374

Asp Tyr Asp Tyr Leu Asn Glu Trp Gly Ser
1               5                  10

<210> SEQ ID NO 375
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 375
```

```
Ala Leu Phe Ser Cys Leu Phe Gly Ile
1               5
```

<210> SEQ ID NO 376
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 376

```
Gly Leu Asn Pro Leu Thr Ser Tyr Val
1               5
```

<210> SEQ ID NO 377
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 377

```
Cys Leu Phe Gly Ile Cys Asp Ala Val
1               5
```

<210> SEQ ID NO 378
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 378

```
Gln Met His Gly Arg Met Val Pro Val
1               5
```

<210> SEQ ID NO 379
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 379

```
Lys Leu Asn Thr Glu Ile Arg Asp Val
1               5
```

<210> SEQ ID NO 380
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 380

```
Trp Leu Val Pro Ile Gly Asn Cys Leu
1               5
```

<210> SEQ ID NO 381
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 381

```
Lys Leu Ile Arg Asn Pro Asn Ser Leu
1               5
```

```
<210> SEQ ID NO 382
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 382

Val Val Ile Leu Ile Ala Ala Phe Val
1               5

<210> SEQ ID NO 383
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 383

Val Met Trp Glu Val Met Ser Tyr Gly
1               5

<210> SEQ ID NO 384
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 384

Gly Ile Gly Ser Gly Met Lys Tyr Leu
1               5

<210> SEQ ID NO 385
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 385

Asn Ile Leu Val Asn Ser Asn Leu Val
1               5

<210> SEQ ID NO 386
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 386

Thr Thr Leu Glu Ala Val Val His Val
1               5

<210> SEQ ID NO 387
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 387

Tyr Leu Leu Gly Val Val Leu Thr Leu
1               5
```

```
<210> SEQ ID NO 388
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 388

Leu Tyr Leu Leu Gly Val Val Leu Thr
1               5

<210> SEQ ID NO 389
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 389

Val Met Glu Ser Leu Glu Gly Leu Leu
1               5

<210> SEQ ID NO 390
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 390

Leu Leu Gly Val Val Leu Thr Leu Leu
1               5

<210> SEQ ID NO 391
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 391

Tyr Leu Leu Gly Val Val Leu Thr Leu Leu
1               5                   10

<210> SEQ ID NO 392
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 392

Leu Asn Leu Tyr Leu Leu Gly Val Val Leu
1               5                   10

<210> SEQ ID NO 393
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 393

Leu Ala Asn Thr Glu Pro Thr Lys Gly Leu
1               5                   10

<210> SEQ ID NO 394
<211> LENGTH: 10
```

```
<212> TYPE: PRT
<213> ORGANISM: Artificial
<220> FEATURE:
<223> OTHER INFORMATION: An artificially synthesized peptide sequence

<400> SEQUENCE: 394

Ser Ile Phe Val Arg Val Met Glu Ser Leu
1               5                   10

<210> SEQ ID NO 395
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 395

Leu Tyr Leu Lys Leu Leu Pro Tyr Val
1               5

<210> SEQ ID NO 396
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 396

Ile Ser Asn Glu Gly Asn Gln Asn Leu
1               5

<210> SEQ ID NO 397
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 397

Arg Ser Gly Trp His Thr Phe Pro Leu
1               5

<210> SEQ ID NO 398
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 398

Ala Ser Leu Trp Leu Tyr Leu Lys Leu
1               5

<210> SEQ ID NO 399
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 399

Ala Tyr Leu Ala Gly Val Pro Gly Ser
1               5

<210> SEQ ID NO 400
<211> LENGTH: 9
<212> TYPE: PRT
<213> ORGANISM: Artificial
```

```
<220> FEATURE:
<223> OTHER INFORMATION: An artificially synthesized peptide sequence

<400> SEQUENCE: 400

Asn Met Val Glu Lys Arg Val Asp Leu
1               5

<210> SEQ ID NO 401
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 401

Ala Met Val Thr Ala Leu Arg Lys Leu
1               5

<210> SEQ ID NO 402
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 402

Val Gln Cys Asp Ser Cys Gln Glu Leu
1               5

<210> SEQ ID NO 403
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 403

Asn Ser Cys Cys Ile Pro Thr Lys Leu
1               5

<210> SEQ ID NO 404
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 404

Asn Tyr Cys Glu Gly Ser Cys Pro Ala
1               5

<210> SEQ ID NO 405
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 405

Phe Val Val Gln Ala Ser Leu Trp Leu
1               5

<210> SEQ ID NO 406
<211> LENGTH: 9
<212> TYPE: PRT
<213> ORGANISM: Artificial
<220> FEATURE:
<223> OTHER INFORMATION: An artificially synthesized peptide sequence
```

```
<400> SEQUENCE: 406

Val Asn Gln Tyr Arg Met Arg Gly Leu
1               5

<210> SEQ ID NO 407
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 407

Gln Phe Phe Ile Asp Phe Arg Leu Ile
1               5

<210> SEQ ID NO 408
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 408

Leu Leu Leu Leu Ala Ala Gly Trp Leu
1               5

<210> SEQ ID NO 409
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 409

Gln Gln Phe Phe Ile Asp Phe Arg Leu
1               5

<210> SEQ ID NO 410
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 410

Asn Leu Phe Val Val Gln Ala Ser Leu
1               5

<210> SEQ ID NO 411
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 411

Tyr Tyr Gly Asn Tyr Cys Glu Gly Ser
1               5

<210> SEQ ID NO 412
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 412
```

Gln Asn Leu Phe Val Val Gln Ala Ser Leu
1               5                   10

<210> SEQ ID NO 413
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 413

Asp Val Gln Cys Asp Ser Cys Gln Glu Leu
1               5                   10

<210> SEQ ID NO 414
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 414

Val Val Gln Ala Ser Leu Trp Leu Tyr Leu
1               5                   10

<210> SEQ ID NO 415
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 415

Leu Tyr Phe Asp Asp Glu Tyr Asn Ile Val
1               5                   10

<210> SEQ ID NO 416
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 416

Phe Pro Leu Thr Glu Ala Ile Gln Ala Leu
1               5                   10

<210> SEQ ID NO 417
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 417

Arg Thr Asn Leu Cys Cys Arg Gln Gln Phe
1               5                   10

<210> SEQ ID NO 418
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 418

Ala Ala Met Val Thr Ala Leu Arg Lys Leu

```
<210> SEQ ID NO 419
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 419

Val Asn Ser Cys Cys Ile Pro Thr Lys Leu
1               5                   10

<210> SEQ ID NO 420
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 420

Cys Leu Leu Leu Leu Ala Ala Gly Trp Leu
1               5                   10

<210> SEQ ID NO 421
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 421

Val Val Asn Gln Tyr Arg Met Arg Gly Leu
1               5                   10

<210> SEQ ID NO 422
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 422

Asp Gly Leu Ala Ser Ser Arg Val Arg Leu
1               5                   10

<210> SEQ ID NO 423
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 423

Gly Leu Glu Cys Asp Gly Arg Thr Asn Leu
1               5                   10

<210> SEQ ID NO 424
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 424

Asn Tyr Cys Glu Gly Ser Cys Pro Ala Tyr
1               5                   10
```

```
<210> SEQ ID NO 425
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 425

Ala Ser Leu Trp Leu Tyr Leu Lys Leu Leu
1               5                   10

<210> SEQ ID NO 426
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 426

Trp Asn Met Val Glu Lys Arg Val Asp Leu
1               5                   10

<210> SEQ ID NO 427
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 427

Phe Leu Glu Ala Val Lys Arg His Ile Leu
1               5                   10

<210> SEQ ID NO 428
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 428

Tyr Cys Glu Gly Ser Cys Pro Ala Tyr Leu
1               5                   10

<210> SEQ ID NO 429
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 429

Ala Val Lys Arg His Ile Leu Ser Arg Leu
1               5                   10

<210> SEQ ID NO 430
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 430

Gln Ala Ser Leu Trp Leu Tyr Leu Lys Leu
1               5                   10

<210> SEQ ID NO 431
```

```
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 431

Gly Tyr Tyr Gly Asn Tyr Cys Glu Gly Ser
1               5                   10

<210> SEQ ID NO 432
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 432

Leu Tyr Phe Phe Ile Ser Asn Glu Gly Asn
1               5                   10

<210> SEQ ID NO 433
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 433

Tyr Tyr Gly Asn Tyr Cys Glu Gly Ser Cys
1               5                   10

<210> SEQ ID NO 434
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 434

Ile Leu Leu Leu Leu Ala Ser Ile Ala
1               5

<210> SEQ ID NO 435
<211> LENGTH: 3218
<212> TYPE: DNA
<213> ORGANISM: Homo sapiens
<220> FEATURE:
<221> NAME/KEY: CDS
<222> LOCATION: (47)..(1270)

<400> SEQUENCE: 435
actcggctcg cctcgcggcg ggcgccctcg tcgccagcgg cgcacc atg gac ggg        55

Met Asp Gly
                                                 1 ctg ccc ggt cgg gcg ctg ggg gcc gcc tgc ctt ctg ctg ctg gcg gcc      103
Leu Pro Gly Arg Ala Leu Gly Ala Ala Cys Leu Leu Leu Leu Ala Ala
        5                   10                  15 ggc tgg ctg ggg cct gag gcc tgg ggc tca ccc acg ccc ccg ccg acg      151
Gly Trp Leu Gly Pro Glu Ala Trp Gly Ser Pro Thr Pro Pro Pro Thr
20                  25                  30                  35 cct gcc gcg ccg ccg cca ccc ccg cca ccc gga tcc ccg ggt ggc tcg      199
Pro Ala Ala Pro Pro Pro Pro Pro Pro Gly Ser Pro Gly Gly Ser
40                  45                  50 cag gac acc tgt acg tcg tgc ggc ggc ttc cgg cgg cca gag gag ctc      247
Gln Asp Thr Cys Thr Ser Cys Gly Gly Phe Arg Arg Pro Glu Glu Leu
```

```
                                      55                    60                    65
ggc cga gtg gac ggc gac ttc ctg gag gcg gtg aag cgg cac atc ttg       295
Gly Arg Val Asp Gly Asp Phe Leu Glu Ala Val Lys Arg His Ile Leu
 70                  75                    80 agc cgc ctg cag atg cgg ggc cgg ccc aac atc acg cac gcc gtg cct       343
Ser Arg Leu Gln Met Arg Gly Arg Pro Asn Ile Thr His Ala Val Pro
 85                  90                    95 aag gcc gcc atg gtc acg gcc ctg cgc aag ctg cac gcg ggc aag gtg       391
Lys Ala Ala Met Val Thr Ala Leu Arg Lys Leu His Ala Gly Lys Val
100                 105                   110                 115 cgc gag gac ggc cgc gtg gag atc ccg cac ctc gac ggc cac gcc agc       439
Arg Glu Asp Gly Arg Val Glu Ile Pro His Leu Asp Gly His Ala Ser
120                 125                   130 ccg ggc gcc gac ggc cag gag cgc gtt tcc gaa atc atc agc ttc gcc       487
Pro Gly Ala Asp Gly Gln Glu Arg Val Ser Glu Ile Ile Ser Phe Ala
135                 140                   145 gag aca gat ggc ctc gcc tcc tcc cgg gtc cgc cta tac ttc ttc atc       535
Glu Thr Asp Gly Leu Ala Ser Ser Arg Val Arg Leu Tyr Phe Phe Ile
150                 155                   160 tcc aac gaa ggc aac cag aac ctg ttt gtg gtc cag gcc agc ctg tgg       583
Ser Asn Glu Gly Asn Gln Asn Leu Phe Val Val Gln Ala Ser Leu Trp
165                 170                   175 ctt tac ctg aaa ctc ctg ccc tac gtc ctg gag aag ggc agc cgg cgg       631
Leu Tyr Leu Lys Leu Leu Pro Tyr Val Leu Glu Lys Gly Ser Arg Arg
180                 185                   190                 195 aag gtg cgg gtc aaa gtg tac ttc cag gag cag ggc cac ggt gac agg       679
Lys Val Arg Val Lys Val Tyr Phe Gln Glu Gln Gly His Gly Asp Arg
200                 205                   210 tgg aac atg gtg gag aag agg gtg gac ctc aag cgc agc ggc tgg cat       727
Trp Asn Met Val Glu Lys Arg Val Asp Leu Lys Arg Ser Gly Trp His
215                 220                   225 acc ttc cca ctc acg gag gcc atc cag gcc ttg ttt gag cgg ggc gag       775
Thr Phe Pro Leu Thr Glu Ala Ile Gln Ala Leu Phe Glu Arg Gly Glu
230                 235                   240 cgg cga ctc aac cta gac gtg cag tgt gac agc tgc cag gag ctg gcc       823
Arg Arg Leu Asn Leu Asp Val Gln Cys Asp Ser Cys Gln Glu Leu Ala
245                 250                   255 gtg gtg ccg gtg ttc gtg gac cca ggc gaa gag tcg cac cgg ccc ttt       871
Val Val Pro Val Phe Val Asp Pro Gly Glu Glu Ser His Arg Pro Phe
260                 265                   270                 275 gtg gtg gtg cag gct cgg ctg ggc gac agc agg cac cgc att cgc aag       919
Val Val Val Gln Ala Arg Leu Gly Asp Ser Arg His Arg Ile Arg Lys
280                 285                   290 cga ggc ctg gag tgc gat ggc cgg acc aac ctc tgt tgc agg caa cag       967
Arg Gly Leu Glu Cys Asp Gly Arg Thr Asn Leu Cys Cys Arg Gln Gln
295                 300                   305 ttc ttc att gac ttc cgc ctc atc ggc tgg aac gac tgg atc ata gca      1015
Phe Phe Ile Asp Phe Arg Leu Ile Gly Trp Asn Asp Trp Ile Ile Ala
310                 315                   320 ccc acc ggc tac tac ggg aac tac tgt gag ggc agc tgc cca gcc tac      1063
Pro Thr Gly Tyr Tyr Gly Asn Tyr Cys Glu Gly Ser Cys Pro Ala Tyr
325                 330                   335 ctg gca ggg gtc ccc ggc tct gcc tcc tcc ttc cac acg gct gtg gtg      1111
Leu Ala Gly Val Pro Gly Ser Ala Ser Ser Phe His Thr Ala Val Val
340                 345                   350                 355 aac cag tac cgc atg cgg ggt ctg aac ccc ggc acg gtg aac tcc tgc      1159
Asn Gln Tyr Arg Met Arg Gly Leu Asn Pro Gly Thr Val Asn Ser Cys
360                 365                   370 tgc att ccc acc aag ctg agc acc atg tcc atg ctg tac ttc gat gat      1207
Cys Ile Pro Thr Lys Leu Ser Thr Met Ser Met Leu Tyr Phe Asp Asp
```

```
            375                 380                 385
gag tac aac atc gtc aag cgg gac gtg ccc aac atg att gtg gag gag   1255
Glu Tyr Asn Ile Val Lys Arg Asp Val Pro Asn Met Ile Val Glu Glu
390                 395                 400 tgc ggc tgc gcc tga cagtgcaagg caggggcacg gtggtgggc acggagggca     1310
Cys Gly Cys Ala
405 gtcccgggtg ggcttcttcc agccccgcg ggaacggggg tacacggtgg gctgagtaca   1370 gtcattctgt tgggctgtgg agatagtgcc agggtgcggc ctgagatatt tttctacagc  1430 ttcatagagc aaccagtcaa aaccagagcg agaaccctca actgacatga aatactttaa  1490 aatgcacacg tagccacgca cagccagacg catcctgcca cccacacagc agcctccagg  1550 ataccagcaa atggatgcgg tgacaaatgg cagcttagct acaaatgcct gtcagtcgga  1610 gagaatgggg tgagcagcca ccattcccac cagctggccc ggccactctg aattgcgcct  1670 tccgagcaca cataaaagca caagacaga gacgcagaga gagagagaga gccacggaga  1730 ggaaaagcag atgcaggggt ggggagcgca gctcggcgga ggctgcgtgt gccccgtggc  1790 ttttaccagg cctgctctgc ctggctcgat gtctgcttct tccccagcct gggatccttc   1850 gtgcttcaag gcctggggag cctgtccttc catgcccttg tcgagggaaa gagacccaga  1910 aaggacacaa cccgtcagag acctgggagc aggggcaatg accgtttgac tgtttgtggc  1970 ttgggcctct gacatgactt atgtgtgtgt gtgtttttgg ggtggggagg gagggagaga  2030 agaggggggct aaatttgatg ctttaactga tctccaacag ttgacaggtc atccttgcca  2090 gttgtataac tgaaaaagga cttttctacc aggtatgacc ttttaagtga aaatctgaat  2150 tgttctaaat ggaagaaaa aaagttgcaa tctgtgccct tcattgggga cattcctcta    2210 ggactggttt ggggacgggt gggaatgacc ctaggcaag gggatgagac cgcaggagga   2270 aatggcgggg aggaggcatt cttgaactgc tgaggatggg gggtgtcccc tcagcggagg   2330 ccaagggagg ggagcagcct agttggtctt ggagagatgg ggaaggcttt cagctgattt   2390 gcagaagttg cccatgtggg ccccagccat cagggctggc cgtggacgtg gcccctgccc   2450 actcacctgc ccgcctgccc gcccgcccgc atagcacttg cagacctgcc tgaacgcaca   2510 tgacatagca cttgccgatc tgcgtgtgtc cagaagtggc ccttggccga cgccgaact    2570 cgctcgccct ctagatgtcc aagtgccacg tgaactatgc aatttaaagg ttgacccac    2630 actagacgaa actggactcg tacgactctt tttatatttt ttatacttga aatgaaatcc   2690 tttgcttctt ttttaagcga atgattgctt ttaatgtttg cactgattta gttgcatgat   2750 tagtcagaaa ctgccatttg aaaaaaagtt attttttatag cagcaaaaaa aaaaaaaaa   2810 gaatacagtt aaatgtatta tacataattt tggaaccaaa gaggccaaca gatcagtttt  2870 aattttatta gacggtgagg ccatctgaga tgaggtggac gttctgagca gtcccttgag   2930 tggcctgcca acgtttcagg gtatgaatgg attttgttta ttcggtttga tgtgtctttt    2990 ccatccttac acacccagaa ggtagagtaa aaatgactat gatagaatgc aggtgtgtat  3050 ccttaaatcc tcatctttat gtttatttaa taaagctccc cttagattct gtttcataat   3110 aatttaaaac caaacaattt tcccatagac ttgctgttaa agtattgtac gtttgtgtac  3170 agtttaagaa aataaaagat tgagtgccac gggaaaaaaa aaaaaaaa                3218

<210> SEQ ID NO 436
<211> LENGTH: 407
<212> TYPE: PRT
<213> ORGANISM: Homo sapiens
```

<400> SEQUENCE: 436

```
Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
20                  25                  30

Pro Pro Thr Pro Ala Ala Pro Pro Pro Pro Pro Pro Gly Ser Pro
35                  40                  45

Gly Gly Ser Gln Asp Thr Cys Thr Ser Cys Gly Gly Phe Arg Arg Pro
50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
85                  90                  95

Ala Val Pro Lys Ala Ala Met Val Thr Ala Leu Arg Lys Leu His Ala
100                 105                 110

Gly Lys Val Arg Glu Asp Gly Arg Val Glu Ile Pro His Leu Asp Gly
115                 120                 125

His Ala Ser Pro Gly Ala Asp Gly Gln Glu Arg Val Ser Glu Ile Ile
130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Val Gln Ala
165                 170                 175

Ser Leu Trp Leu Tyr Leu Lys Leu Leu Pro Tyr Val Leu Glu Lys Gly
180                 185                 190

Ser Arg Arg Lys Val Arg Val Lys Val Tyr Phe Gln Glu Gln Gly His
195                 200                 205

Gly Asp Arg Trp Asn Met Val Glu Lys Arg Val Asp Leu Lys Arg Ser
210                 215                 220

Gly Trp His Thr Phe Pro Leu Thr Glu Ala Ile Gln Ala Leu Phe Glu
225                 230                 235                 240

Arg Gly Glu Arg Arg Leu Asn Leu Asp Val Gln Cys Asp Ser Cys Gln
245                 250                 255

Glu Leu Ala Val Val Pro Val Phe Val Asp Pro Gly Glu Glu Ser His
260                 265                 270

Arg Pro Phe Val Val Val Gln Ala Arg Leu Gly Asp Ser Arg His Arg
275                 280                 285

Ile Arg Lys Arg Gly Leu Glu Cys Asp Gly Arg Thr Asn Leu Cys Cys
290                 295                 300

Arg Gln Gln Phe Phe Ile Asp Phe Arg Leu Ile Gly Trp Asn Asp Trp
305                 310                 315                 320

Ile Ile Ala Pro Thr Gly Tyr Tyr Gly Asn Tyr Cys Glu Gly Ser Cys
325                 330                 335

Pro Ala Tyr Leu Ala Gly Val Pro Gly Ser Ala Ser Ser Phe His Thr
340                 345                 350

Ala Val Val Asn Gln Tyr Arg Met Arg Gly Leu Asn Pro Gly Thr Val
355                 360                 365

Asn Ser Cys Cys Ile Pro Thr Lys Leu Ser Thr Met Ser Met Leu Tyr
370                 375                 380

Phe Asp Asp Glu Tyr Asn Ile Val Lys Arg Asp Val Pro Asn Met Ile
385                 390                 395                 400

Val Glu Glu Cys Gly Cys Ala
405
```

PEPTIDE VACCINES FOR CANCERS EXPRESSING TUMOR-ASSOCIATED ANTIGENS

PRIORITY

This application is a divisional of U.S. patent application Ser. No. 12/542,638, filed Aug. 17, 2009, which is a continuation-in-part of PCT/JP2008/000290 (WO 2008/102557) filed Feb. 21, 2008, which claims priority to U.S. Provisional Application Ser. No. 60/902,949, filed Feb. 21, 2007. This application also claims the benefit of Ser. No. 61/089,973 filed Aug. 19, 2008. All of these applications are incorporated herein by reference.

TECHNICAL FIELD

The present application claims the benefit of U.S. Provisional Application No. 60/902,949, filed Feb. 21, 2007, the entire disclosure of which is hereby incorporated herein by reference for all purposes.

The present invention relates to the field of biological science, more specifically to the field of cancer therapy. In particular, the present invention relates to novel immunogenic peptides that serve as extremely effective as cancer vaccines, and drugs for treating and preventing tumors containing such peptides.

BACKGROUND ART

It has been demonstrated that CD8+ cytotoxic T lymphocytes (CTLs) recognize epitope peptides derived from tumor-associated antigens (TAAs) presented on MHC class I molecules, and subsequently lyse the tumor cells. Since the discovery of the MAGE family as the first example of TAAs, many other TAAs have been discovered using immunological approaches (Boon T. (1993) Int J Cancer 54: 177-80.; Boon T. et al., (1996) J Exp Med 183: 725-9.; van der Bruggen P et al., (1991) Science 254: 1643-7.; Brichard V et al., (1993) J Exp Med 178: 489-95.; Kawakami Y et al., (1994) J Exp Med 180: 347-52.). Some of them are now in clinical development as targets of immunotherapy. TAAs discovered to date include MAGE (van der Bruggen P et al., (1991) Science 254: 1643-7.), gp100 (Kawakami Y et al., (1994) J Exp Med 180: 347-52.), SART (Shichijo S et al., (1998) J Exp Med 187:277-88.), and NY-ESO-1 (Chen Y. T. et al., (1997) Proc. Natl. Acd. Sci. USA, 94: 1914-8.). On the other hand, certain gene products demonstrated to be somewhat specifically over-expressed in tumor cells have been shown to be recognized as targets for inducing cellular immune responses. Such gene products include p53 (Umano Y et al., (2001) Br J Cancer, 84:1052-7.), HER2/neu (Tanaka H et al., (2001) Br J Cancer, 84: 94-9.), CEA (Nukaya I et al., (1999) Int. J. Cancer 80, 92-7.) and the like.

Despite significant progress in basic and clinical research concerning TAAs (Rosenberg S A et al., (1998) Nature Med, 4: 321-7.; Mukherji B. et al., (1995) Proc Natl Acad Sci USA, 92: 8078-82.: Hu X et al., (1996) Cancer Res, 56: 2479-83.), only a very limited number of candidate TAAs suitable for treatment of cancers are presently available. TAAs that are abundantly expressed in cancer cells, and whose expression is restricted to cancer cells, would be promising candidates as immunotherapeutic targets.

Both HLA-A24 and HLA-A0201 are common HLA alleles in the Japanese and Caucasian populations (Date Y et al., (1996) Tissue Antigens 47: 93-101.; Kondo A et al., (1995) J Immunol 155: 4307-12.; Kubo R T et al., (1994) J Immunol 152: 3913-24.; Imanishi et al., Proceeding of the eleventh International Histocompatibility Workshop and Conference Oxford University Press, Oxford, 1065 (1992); Williams F et al., (1997) Tissue Antigen 49: 129-33.). Thus, antigenic peptides of cancers presented by these HLA alleles may find particular utility in the treatment of cancers among Japanese and Caucasian patients. Further, it is known that the induction of low-affinity CTL in vitro usually results from exposure to high concentrations of peptides, generating a high level of specific peptide/MHC complexes on antigen-presenting cells (APCs), which will effectively activate these CTL (Alexander-Miller et al., (1996) Proc Natl Acad Sci USA 93: 4102-7.).

Recently, HLA class I-binding peptide sequence can be expected using algorithms (Jounal of Immunological Methods, (1995), Vol. 185, pp. 181-190, J. Immunol., (1994), Vol. 152, pp. 163-175, protein science, (2000), Vol. 9, pp. 1838-1846). However, it is hard to say that the expected epitope peptide can be cut to the size and expressed on the target cell surface with HLA molecule and recognized by CTL. Moreover, the algorithm, for example BIMAS (http://bimas.dcrt.nih.gov/cgi-bin/molbio/ken_parker_comboform) (Parker K C, et al., (1994) J Immunol.; 152(1):163-75.; Kuzushima K, et al., (2001) Blood.; 98(6):1872-81.)) can suggest the HLA molecule-binding peptide, but the suggested peptide is not so rigorous (Bachinsky M M, et. al., Cancer Immun. 2005 Mar. 22; 5:6.). Thus TAA screening still remains a lot of challenges and difficulties.

Recent developments in cDNA microarray technologies have enabled the construction of comprehensive profiles of gene expression in malignant cells as compared to normal cells (Okabe, H. et al., (2001) Cancer Res., 61, 2129-37.; Lin Y M. et al., (2002) Oncogene, 21; 4120-8.; Hasegawa S. et al., (2002) Cancer Res 62:7012-7.). This approach enables a more thorough understanding of the complex nature of cancer cells and the mechanisms of carcinogenesis and facilitates the identification of genes whose expression is deregulated in tumors (Bienz M. et al., (2000) Cell 103, 311-20.). Among the transcripts identified as up-regulated in cancers, CDH3 (GenBank Accession No. NM_001793; SEQ ID Nos. 1, 2), EPHA4 (GenBank Accession No. L36645; SEQ ID Nos. 3, 4), ECT2 (GenBank Accession No. AY376439; SEQ ID Nos. 5, 6), HIG2 (GenBank Accession No. NM_013332; SEQ ID Nos. 7, 8) INHBB (GenBank Accession No. NM_002193; SEQ ID Nos. 9, 435, 10, 436), KIF20A (GenBank Accession No. NM_005733; SEQ ID Nos. 11, 12), KNTC2 (GenBank Accession No. AF017790; SEQ ID Nos. 13, 14), TTK (GenBank Accession No. NM_003318; SEQ ID Nos. 15, 16) and URLC10 (GenBank Accession No. NM_017527; SEQ ID Nos. 17, 18) have been recently discovered. The entire contents of the references are incorporated by reference herein. These genes are of particular interest to the present inventors, being specifically up-regulated in tumor cells of the various cancer tissues of the cases analyzed (see below). Thus, immunogenic peptides derived from CDH3, EPHA4, ECT2, HIG2, INHBB, KIF20A, KNTC2, TTK and URLC10 may find utility in selectively killing tumor cells that express such antigens. The present invention addresses these and other needs.

Since cytotoxic drugs, such as M-VAC, often cause severe adverse reactions, it is clear that thoughtful selection of novel target molecules on the basis of well-characterized mechanisms of action should be very helpful in the development of effective anti-cancer drugs having a minimized risk of side effects. Toward this goal, expression profile analyses were previously performed on various cancers and normal human tissue. Such studies led to the discovery of multiple genes that are specifically over-expressed in cancer (Lin Y M, et al., Oncogene. 2002 Jun. 13; 21:4120-8.; Kitahara O, et al., Cancer Res. 2001 May 1; 61:3544-9.; Suzuki C, et al., Cancer Res. 2003 Nov. 1; 63:7038-41.; Ashida S, Cancer Res. 2004 Sep. 1; 64:5963-72.; Ochi K, et al., Int J Oncol. 2004 March; 24(3):647-55.; Kaneta Y, et al., Int J Oncol. 2003 September; 23:681-91.; Obama K, Hepatology. 2005 June; 41:1339-48.; Kato T, et al., Cancer Res. 2005 Jul. 1; 65:5638-46.; Kitahara O, et al., Neoplasia. 2002 July-August; 4:295-303.; Saito-Hisaminato A et al., DNA Res 2002, 9: 35-45.). Examples of such genes identified as over-expressed in various cancers include, but are not limited to, CDH3, EPHA4, ECT2, HIG2, INHBB, KIF20A, KNTC2, TTK and URLC10. CDH3 has been previously identified as over-expressed in bladder cancer, cervical cancer, cholangiocellular carcinoma, colorectal cancer, endometriosis, gastric cancer, diffuse-type gastric cancer, non-small cell lung cancer (NSCLC), pancreatic cancer, soft tissue tumor and testicular tumor. EPHA4 has been identified in bladder cancer, cervical cancer, cholangiocellular carcinoma, endometriosis, diffuse-type gastric cancer, ovarian cancer, pancreatic cancer, prostate cancer and soft tissue tumor. ECT2 has been identified in bladder cancer, breast cancer, cervical cancer, cholangiocellular carcinoma, chronic myeloid leukemia (CML), colorectal cancer, esophageal cancer, NSCLC, lymphoma, prostate cancer, renal carcinoma and small cell lung cancer (SCLC). HIG2 has been identified in renal carcinoma and SCLC. INHBB has been identified in cholangiocellular carcinoma, esophageal cancer, NSCLC, renal carcinoma, SCLC and soft tissue tumor. KIF20A has been identified in bladder cancer, breast cancer, cholangiocellular carcinoma, esophageal cancer, NSCLC, pancreatic cancer, prostate cancer, renal carcinoma and SCLC. KNTC2 has been identified in bladder cancer, breast cancer, cervical cancer, cholangiocellular carcinoma, CML, colorectal cancer, esophageal cancer, NSCLC, lymphoma, osteosarcoma, ovarian cancer, pancreatic cancer, prostate cancer, renal carcinoma, SCLC and soft tissue tumor. TTK has been identified in bladder cancer, breast cancer, cervical cancer, cholangiocellular carcinoma, CML, colorectal cancer, esophageal cancer, liver cancer, NSCLC, lymphoma, osteosarcoma, prostate cancer, SCLC and soft tissue tumor. URLC10 has been identified in bladder cancer, cervical cancer, cholangiocellular carcinoma, esophageal cancer, gastric cancer, NSCLC, osteosarcoma, pancreatic cancer and SCLC.

SUMMARY OF THE INVENTION

The present invention is based in part on the discovery of the applicable targets of immunotherapy. Because TAAs have often no immunogenicity, the discovery of appropriate targets is of extreme importance. As noted above, CDH3, EPHA4, ECT2, HIG2, INHBB, KIF20A, KNTC2, TTK and URLC10 have been identified as up-regulated in various cancers. More particularly, these genes were identified using gene expression profiling with a genome-wide cDNA microarray. As discussed above, expression of CDH3, EPHA4, ECT2, HIG2, INHBB, KIF20A, KNTC2, TTK and URLC10 has been shown to be specifically up-regulated in various tumor cells, from pancreatic cancer cells to renal cell carcinomas. As described in Table 1, CDH3 expression is validly elevated in 26 out of 34 bladder cancer, 17 out of 19 cervical cancer, all of 19 cholangiocellular carcinoma, 30 out of 34 colorectal cancer, 20 out of 21 endometriosis, 13 out of 20 gastric cancer, 7 out of 8 diffuse-type gastric cancer, 36 out of 37 NSCLC, all of 16 pancreatic cancer, all of 21 soft tissue tumor and all of 10 testicular tumor.

Table 1 further demonstrates that:

EPHA4 expression is validly elevated in 14 out of 34 bladder cancer, 8 out of 14 cervical cancer, 10 out of 25 cholangiocellular carcinoma, 5 out of 15 endometriosis, 5 out of 8 diffuse-type gastric cancer, all of 5 ovarian cancer, all 14 pancreatic cancer, 20 out of 51 prostate cancer and 14 out of 23 soft tissue tumor.

ECT2 expression is validly elevated in 17 out of 19 bladder cancer, 5 out of 12 breast cancer, all of 14 cervical cancer, all of 13 cholangiocellular carcinoma, all of 5 CML, 7 out of 8 colorectal cancer, 12 out of 16 esophageal cancer, 6 out of 16 NSCLC, 8 out of 10 lymphoma, 1 out of 1 pancreatic cancer, 10 out of 13 prostate cancer, 3 out of 6 renal carcinoma and 12 out of 13 SCLC cancer.

HIG2 expression is validly elevated in 19 out of 20 renal cancer and 7 out of 9 soft tissue tumor.

INHBB expression is validly elevated in 10 out of 21 cholangiocellular carcinoma, all of 12 esophageal cancer, 10 out of 13 NSCLC, 22 out of 24 renal carcinoma, 8 out of 14 SCLC cancer and 45 out of 49 soft tissue tumor.

KIF20A expression is validly elevated in all of 31 bladder cancer, 38 out of 61 breast cancer, 10 out of 11 cholangiocellular carcinoma, 7 out of 19 esophageal cancer, 21 out of 22 NSCLC, all of 6 ovarian cancer, 17 out of 36 prostate cancer, 6 out of 11 renal cancer and all of 15 SCLC.

KNTC2 expression is validly elevated in 30 out of 32 bladder cancer, 47 out of 56 breast cancer, all of 10 cervical cancer, 16 out of 22 cholangiocellular carcinoma, 17 out of 37 CML, 3 out of 10 colorectal cancer, 11 out of 46 esophagus cancer, 15 out of 19 NSCLC, 7 out of 8 lymphoma, 20 out of 24 osteosarcoma, 3 out of 5 ovarian cancer, all of 2 pancreatic cancer, 15 out of 37 prostate cancer, 14 out of 19 renal carcinoma, all of 15 SCLC and 40 out of 59 soft tissue tumor.

TTK expression is validly elevated in all of 27 bladder cancer, 25 out of 30 breast cancer, 15 out of 16 cervical cancer, all of 10 cholangiocellular carcinoma, 5 out of 7 CML, 6 out of 10 colorectal cancer, 24 out of 44 esophageal cancer, 8 out of 15 liver cancer, all of 12 NSCLC, all of 6 lymphoma, 13 out of 16 osteoblastoma, 12 out of 17 prostate cancer, all of 15 SCLC and 16 out of 33 soft tissue tumor.

URLC10 expression is validly elevated in all of 29 bladder cancer, 15 out of 16 cervical cancer, all of 7 cholangiocellular carcinoma, 7 out of 19 esophageal cancer, all of 3 gastric cancer, 24 out of 27 NSCLC, 15 out of 19 osteosarcoma, 4 out of 5 pancreatic cancer, 33 out of 43 soft tissue tumor.

The present invention is based, at least in part, on the identification of specific epitope peptides of the gene products of these genes (CDH3, EPHA4, ECT2, HIG2, INHBB, KIF20A, KNTC2, TTK and URLC10) which possess the ability to induce cytotoxic T lymphocytes (CTLs) specific to the corresponding molecules. As discussed in detail below, Peripheral Blood Mononuclear Cells (PBMC) of healthy donor were stimulated using HLA-A*2402 or HLA-A*0201 binding candidate peptides derived from CDH3, EPHA4, ECT2, HIG2, INHBB, KIF20A, KNTC2, TTK or URLC10. CTL clones and/or lines were then established with specific cytotoxicity against the HLA-A24 or HLA-A2 (HLA-A02) positive target cells pulsed with each of the candidate peptides. These results demonstrate that these peptides are HLA-A24 or HLA-A2 (HLA-A02) restricted epitope peptides that can induce potent and specific immune responses against cells expressing CDH3, EPHA4, ECT2, HIG2, INHBB, KIF20A, KNTC2, TTK or URLC10.

Accordingly, the present invention provides methods for treating or preventing a disease associated with the over-expression of CDH3, EPHA4, ECT2, HIG2, INHBB, KIF20A, KNTC2, TTK or URLC10, e.g. cancer. Such methods involve the step of administering to a subject in need thereof a CDH3, EPHA4, ECT2, HIG2, INHBB, KIF20A, KNTC2, TTK and/or URLC10 polypeptides of the invention. Administration of such peptide(s) results in the induction of anti-tumor immunity. Thus, the present invention provides methods for inducing anti-tumor immunity in a subject, such methods involving the step of administering to the subject the CDH3, EPHA4, ECT2, HIG2, INHBB, KIF20A, KNTC2, TTK and/or URLC10 polypeptides, as well as pharmaceutical compositions for treating or preventing a disease associated with the over-expression of CDH3, EPHA4, ECT2, HIG2, INHBB, KIF20A, KNTC2, TTK and/or URLC10, e.g. cancer, that include the CDH3, EPHA4, ECT2, HIG2, INHBB, KIF20A, KNTC2, TTK and URLC10 polypeptides. Examples of such cancers include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The present invention further provides methods for preventing post-surgery recurrence of the disease mentioned above.

Regarding the specific aims and objectives recited above, it will be understood by those skilled in the art that one or more aspects of this invention can meet certain objectives, while one or more other aspects can meet certain other objectives. Each objective may not apply equally, in all its respects, to every aspect of this invention. As such, the objects herein can be viewed in the alternative with respect to any one aspect of this invention.

Additional objects and features of the invention will become more fully apparent when the following detailed description is read in conjunction with the accompanying figures and examples. However, it is to be understood that both the foregoing summary of the invention and the following detailed description are of preferred embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF DRAWINGS

Various aspects and applications of the present invention will become apparent to the skilled artisan upon consideration of the brief description of the figures and the detailed description of the present invention and its preferred embodiments which follows:

FIG. 1 depicts the results of the screening of epitope peptides, which, in turn, demonstrate that CDH3-A24-10-332 (SEQ ID NO: 34), CDH3-A24-10-470 (SEQ ID NO: 358), CDH3-A24-9-513 (SEQ ID NO: 19), CDH3-A24-9-406 (SEQ ID NO: 22), CDH3-A24-10-807 (SEQ ID NO: 30) and CDH3-A24-10-655 (SEQ ID NO: 344) show potent IFN-gamma production. "a" depicts the example of negative peptides which could not be detected CTL-inducing ability despite possible binding activity with HLA-A*2402. "b" depicts the CTL-inducing ability of CDH3-A24-10-332 (SEQ ID NO: 34). CDH3-A24-10-332 (SEQ ID NO: 34) demonstrated potent IFN-gamma production as compared to the control by IFN-gamma ELISPOT assay, and CTL line that was established from the positive well #4 shown in boxed wells, demonstrated the specific response against the target cells pulsed with the epitope peptide. "c" depicts the CTL-inducing ability of CDH3-A24-10-470 (SEQ ID NO: 358). CDH3-A24-10-470 (SEQ ID NO: 358) demonstrated potent IFN-gamma production as compared to the control by IFN-gamma ELISPOT assay, and CTL line that was established from the positive well #4 shown in boxed wells, demonstrated the specific response against the target cells pulsed with the epitope peptide. "d" depicts the CTL-inducing ability of CDH3-A24-9-513 (SEQ ID NO: 19). CDH3-A24-9-513 (SEQ ID NO: 19) demonstrated potent IFN-gamma production as compared to the control by IFN-gamma ELISPOT assay. The well #6 shown in boxed wells in left panel demonstrated the specific response against the target cells pulsed with the epitope peptide. Moreover, CTL line that was established from the positive well #5 shown in boxed wells in middle panel, demonstrated the specific response against the target cells pulsed with the epitope peptide. "e" depicts the CTL-inducing ability of CDH3-A24-9-406 (SEQ ID NO: 22). CDH3-A24-9-406 (SEQ ID NO: 22) demonstrated potent IFN-gamma production as compared to the control by IFN-gamma ELISPOT assay, and CTL line that was established from the positive well #2 shown in boxed wells, demonstrated the specific response against the target cells pulsed with the epitope peptide.

FIG. 1-2

FIG. 1 depicts the results of the screening of epitope peptides, which, in turn, demonstrate that CDH3-A24-10-332 (SEQ ID NO: 34), CDH3-A24-10-470 (SEQ ID NO: 358), CDH3-A24-9-513 (SEQ ID NO: 19), CDH3-A24-9-406 (SEQ ID NO: 22), CDH3-A24-10-807 (SEQ ID NO: 30) and CDH3-A24-10-655 (SEQ ID NO: 344) show potent IFN-gamma production. "f" depicts the CTL-inducing ability of CDH3-A24-10-807 (SEQ ID NO: 30). CDH3-A24-10-807 (SEQ ID NO: 30) demonstrated potent IFN-gamma production as compared to the control by IFN-gamma ELISPOT assay, and CTL line and the clone were established from the positive well #5 shown in boxed wells. The established CTL clone raised against the peptide demonstrated the specific CTL activity against COS7 transfected both full length of CDH3 gene and HLA-A24 molecule (lower right graph). On the other hand, COS7 transfected full length of CDH3 but not HLA-A24 and COS7 transfected HLA-A24 but not full length of CDH3 were prepared for the negative control. The CTL clone showed high specific CTL activity against COS7 that transfected both CDH3 and HLA-A24. "g" depicts the CTL-inducing ability of CDH3-A24-10-655 (SEQ ID NO: 344). CDH3-A24-10-655 (SEQ ID NO: 344) demonstrated potent IFN-gamma production as compared to the control by IFN-gamma ELISPOT assay, and CTL line and the clone were established from the positive well #1 shown in boxed wells. The established CTL clone raised against the peptide demonstrated the specific CTL activity against COS7 transfected both full length of CDH3 gene and HLA-A24 molecule (lower right graph). On the other hand, COS7 transfected full length of CDH3 but not HLA-A24 and COS7 transfected HLA-A24 but not full length of CDH3 were prepared for the negative control. The CTL clone showed high specific CTL activity against COS7 that transfected both CDH3 and HLA-A24.

FIG. 2

Figure 2:
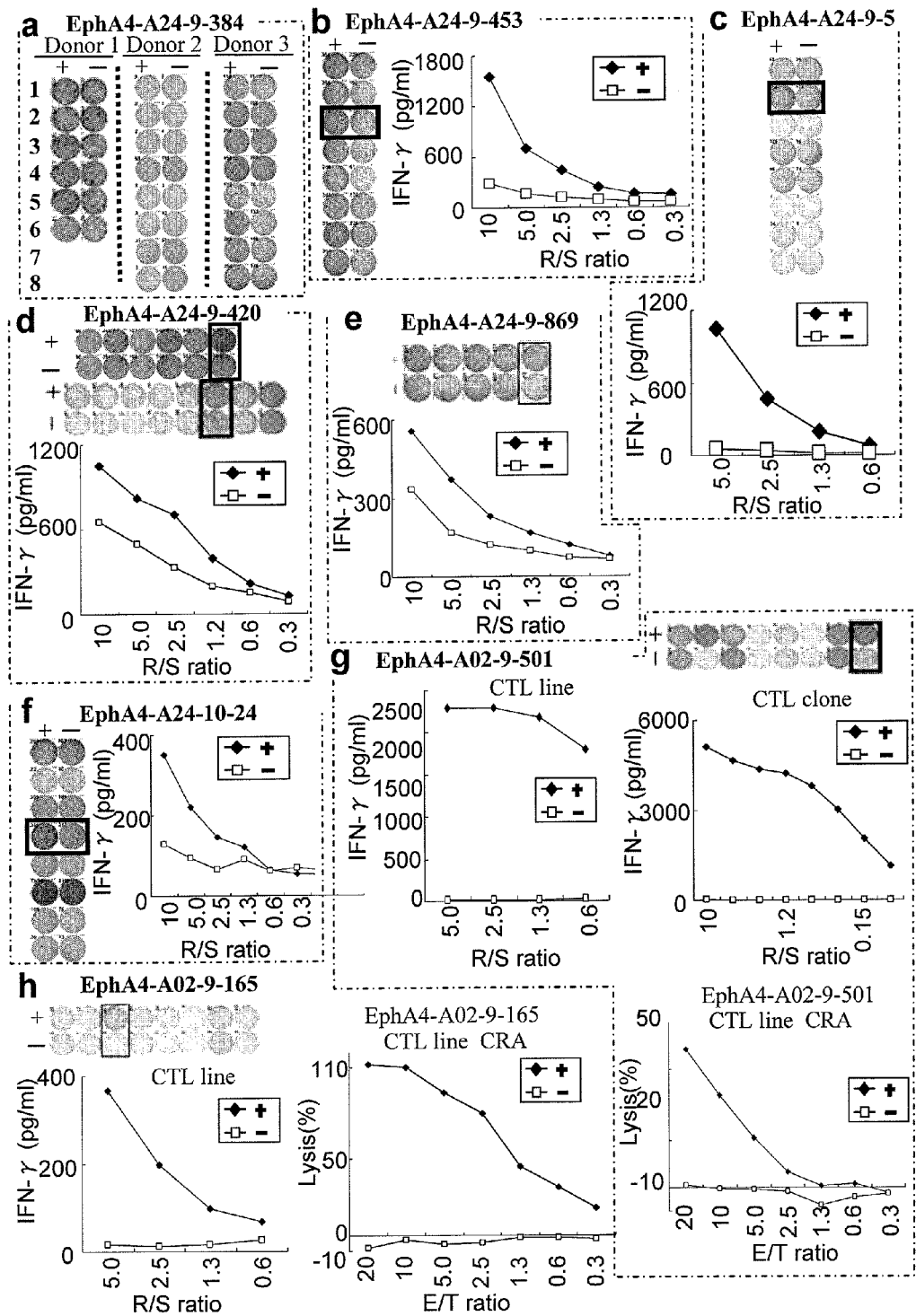

FIG. 2 depicts the results of the screening of epitope peptides, which, in turn, demonstrate that Epha4-A24-9-453 (SEQ ID NO: 41), Epha4-A24-9-5 (SEQ ID NO: 44), Epha4-A24-9-420 (SEQ ID NO: 48), Epha4-A24-9-869 (SEQ ID NO: 46), Epha4-A24-10-24 (SEQ ID NO: 78) Epha4-A02-9-501 (SEQ ID NO: 376) and Epha4-A02-9-165 (SEQ ID NO: 379) show potent IFN-gamma production. "a" depicts the example of negative peptides which could not be detected CTL-inducing ability despite possible binding activity with HLA. "b" depicts the CTL-inducing ability of Epha4-A24-9-453 (SEQ ID NO: 41). Epha4-A24-9-453 (SEQ ID NO: 41) demonstrated potent IFN-gamma production as compared to the control by IFN-gamma ELISPOT assay, and CTL line that was established from the positive well #3 shown in boxed wells, demonstrated the specific response against the target cells pulsed with the epitope peptide. "c" depicts the CTL-inducing ability of Epha4-A24-9-5 (SEQ ID NO: 44). Epha4-A24-9-5 (SEQ ID NO: 44) demonstrated potent IFN-gamma production as compared to the control by IFN-gamma ELISPOT assay, and CTL line, that was established from the positive well #2 shown in boxed wells, demonstrated the specific response against the target cells pulsed with the epitope peptide. "d" depicts the CTL-inducing ability of Epha4-A24-9-420 (SEQ ID NO: 48). Epha4-A24-9-420 (SEQ ID NO: 48) demonstrated potent IFN-gamma production as compared to the control by IFN-gamma ELISPOT assay. The well #6 shown in boxed wells in upper panel demonstrated the specific response against the target cells pulsed with the epitope peptide. Moreover CTL line that was established from the positive well #6 shown in boxed wells in middle panel, demonstrated the specific response against the target cells pulsed with the epitope peptide. "e" depicts the CTL-inducing ability of Epha4-A24-9-869 (SEQ ID NO: 46). Epha4-A24-9-869 (SEQ ID NO: 46) demonstrated potent IFN-gamma production as compared to the control by IFN-gamma ELISPOT assay, and CTL line that was established from the positive well #5 shown in boxed wells, demonstrated the specific response against the target cells pulsed with the epitope peptide. "f" depicts the CTL-inducing ability of Epha4-A24-10-24 (SEQ ID NO: 78). Epha4-A24-10-24 (SEQ ID NO: 78) demonstrated potent IFN-gamma production as compared to the control by IFN-gamma ELISPOT assay, and CTL line that was established from the positive well #4 shown in boxed wells, demonstrated the specific response against the target cells pulsed with the epitope peptide. "g" depicts the CTL-inducing ability of Epha4-A02-9-501 (SEQ ID NO: 376). Epha4-A02-9-501 (SEQ ID NO: 376) demonstrated potent IFN-gamma production as compared to the control by IFN-gamma ELISPOT assay, and CTL line and clone was established from the positive well #8 shown in boxed wells. Cytotoxic activity of the established CTL line against the target cells pulsed with the peptide was measured by Cr-release assay (CRA) (lower graph), and the CTL line had very potent specific cytotoxic activity against the target cells pulsed with the peptides. "h" depicts the CTL-inducing ability of Epha4-A02-9-165 (SEQ ID NO: 379). Epha4-A02-9-165 (SEQ ID NO: 379) demonstrated potent IFN-gamma production as compared to the control by IFN-gamma ELISPOT assay, and CTL line was established from the positive well #3 shown in boxed wells. Cytotoxic activity of the established CTL line against target cells pulsed with peptide was measured by Cr-release assay (CRA) (right graph), and the CTL line had very potent specific cytotoxic activity against the target cells pulsed with the peptides.

FIG. 3

Figure 3:
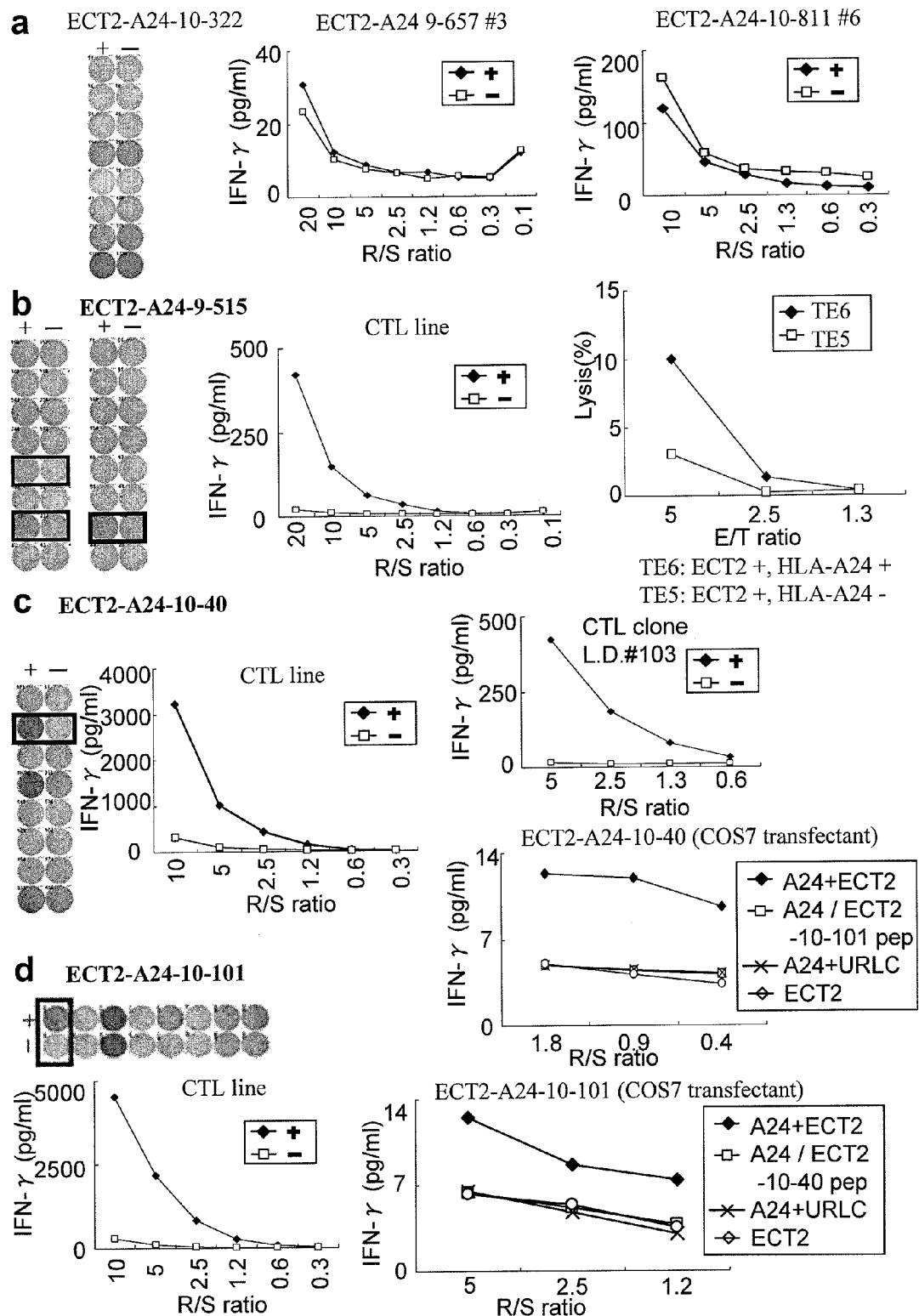

FIG. 3 depicts the results of the screening of epitope peptides, which, in turn, demonstrate that ECT2-A24-9-515 (SEQ ID NO: 80), ECT2-A24-10-40 (SEQ ID NO: 100) and ECT2-A24-10-101 (SEQ ID NO: 101) show potent IFN-gamma production. "a" depicts the example of negative peptides which could not be detected CTL-inducing ability despite possible binding activity with HLA. "b" depicts the CTL-inducing ability of ECT2-A24-9-515 (SEQ ID NO: 80). ECT2-A24-9-515 (SEQ ID NO: 80) demonstrated potent IFN-gamma production as compared to the control by IFN-gamma ELISPOT assay. The well #5 and #7 shown in boxed wells in left panel demonstrated the specific response against the target cells pulsed with the epitope peptide. Moreover, CTL line that was established from the positive well #7 shown in boxed wells in second panel, demonstrated the specific response against the target cells pulsed with the epitope peptide. Cytotoxic activity of the CTL line against cancer cell line, TE6 endogenously expressing ECT2 and HLA-A24 was measured by Cr-release assay (CRA), and the CTL clone had very potent cytotoxic activity against TE6. On the other hand, the effector cells did not demonstrate the cytotoxic activity of the CTL line against cancer cell line, TE5 expressing only ECT2 was not detected. "c" depicts the CTL-inducing ability of ECT2-A24-10-40 (SEQ ID NO: 100). ECT2-A24-10-40 (SEQ ID NO: 100) demonstrated potent IFN-gamma production as compared to the control by IFN-gamma ELISPOT assay, and CTL line and the clone were established from the positive well #2 shown in boxed wells. The established CTL clone raised against the peptide demonstrated specific CTL activity against COS7 transfected both full length of ECT2 gene and HLA-A24 molecule. On the other hand, COS7 transfected full length of ECT2 but not HLA-A24, COS7 transfected HLA-A24 and URLC10 gene as a substitute for full length of ECT2 and COS7 transfected HLA-A24 and pulsed with ECT2-10-101 were prepared for the negative control. The CTL clone showed high specific CTL activity against COS7 that transfected both ECT2 and HLA-A24. "d" depicts the CTL-inducing ability of ECT2-A24-10-101 (SEQ ID NO: 101). ECT2-A24-10-101 (SEQ ID NO: 101) demonstrated potent IFN-gamma production as compared to the control by IFN-gamma ELISPOT assay, and CTL line were established from the positive well #1 shown in boxed wells. The established CTL line raised against the peptide demonstrated specific CTL activity against COS7 transfected both full length of ECT2 gene and HLA-A24 molecule. COS7 transfected full length of ECT2 but not HLA-A24, COS7 transfected HLA-A24 and URLC10 gene as substitute for full length of ECT2 and COS7 transfected HLA-A24 and pulsed with ECT2-10-40 were prepared for the negative control. The CTL clone showed high specific CTL activity against COS7 that transfected both ECT2 and HLA-A24.

FIG. 4-1

Figure 4:
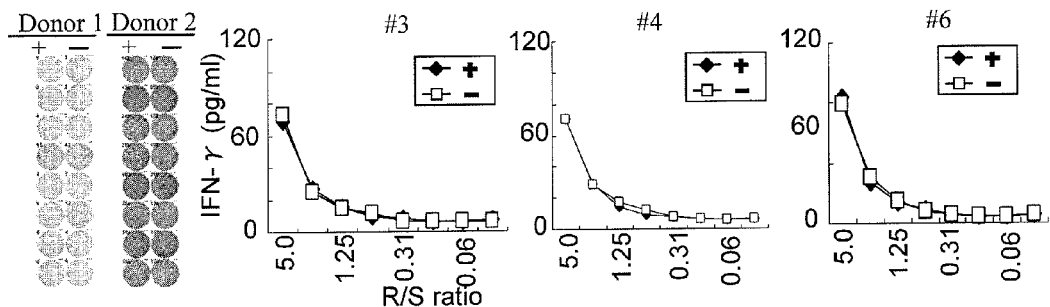
Figure 4:
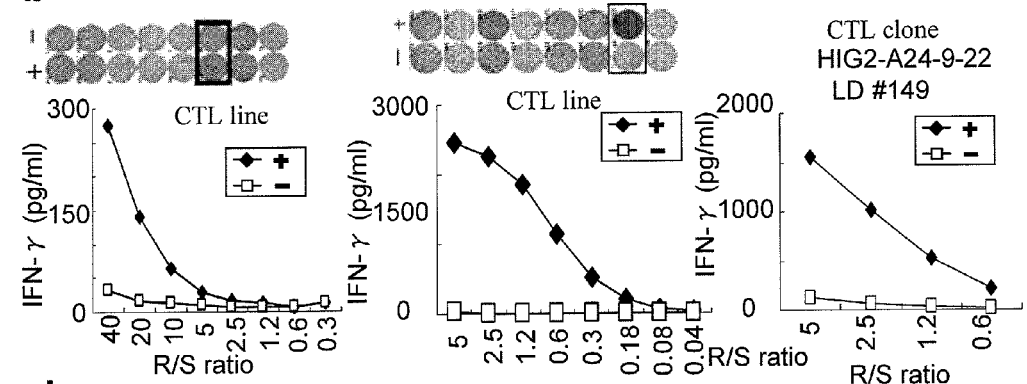
Figure 4:
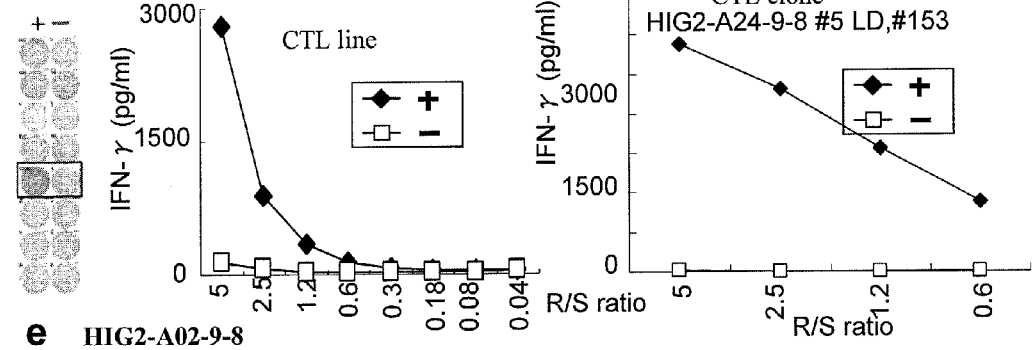
Figure 4:
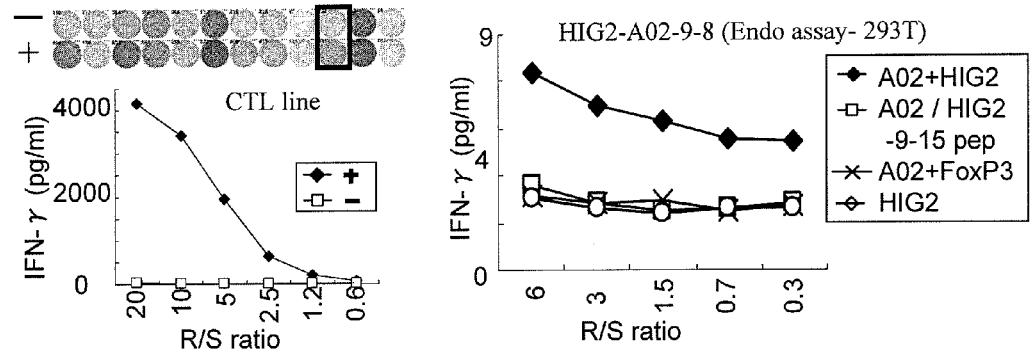
Figure 4:
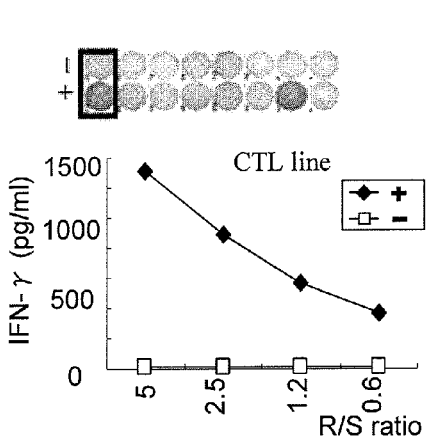
Figure 4:
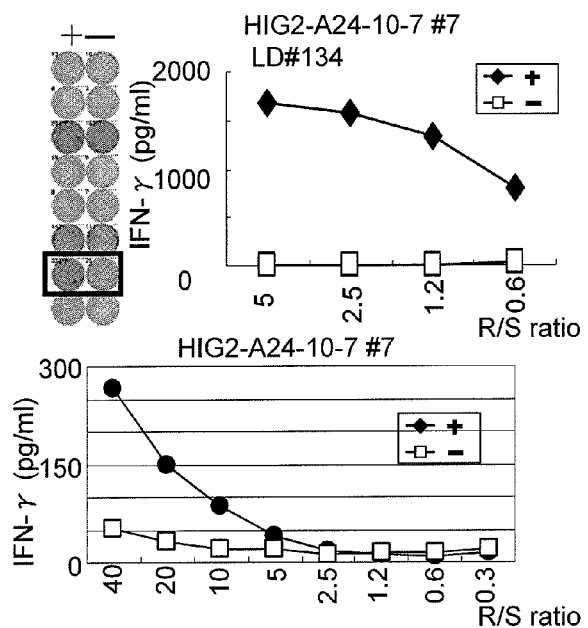
Figure 4:
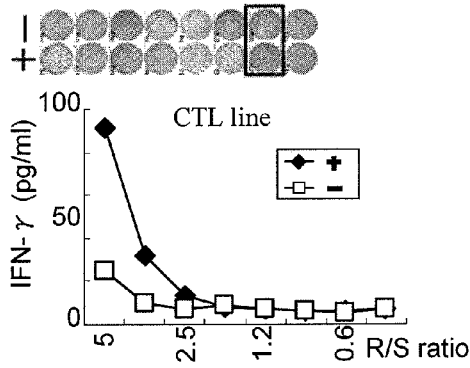
Figure 4:
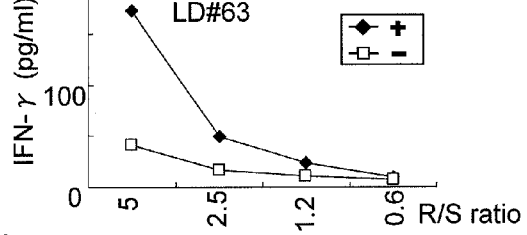
Figure 4:
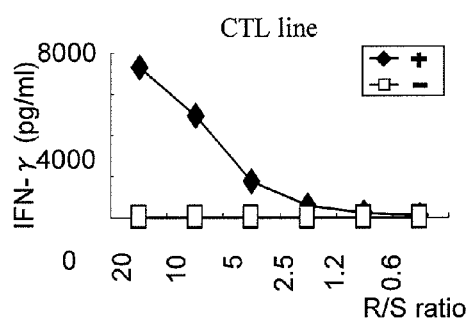
Figure 4:
Figure 4:
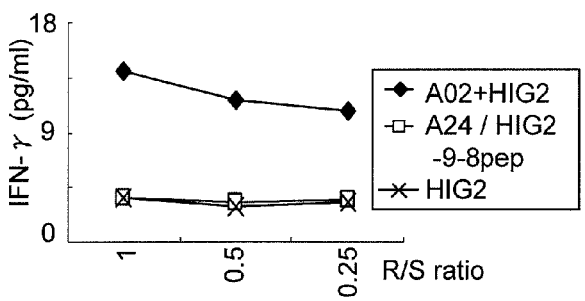
Figure 4:
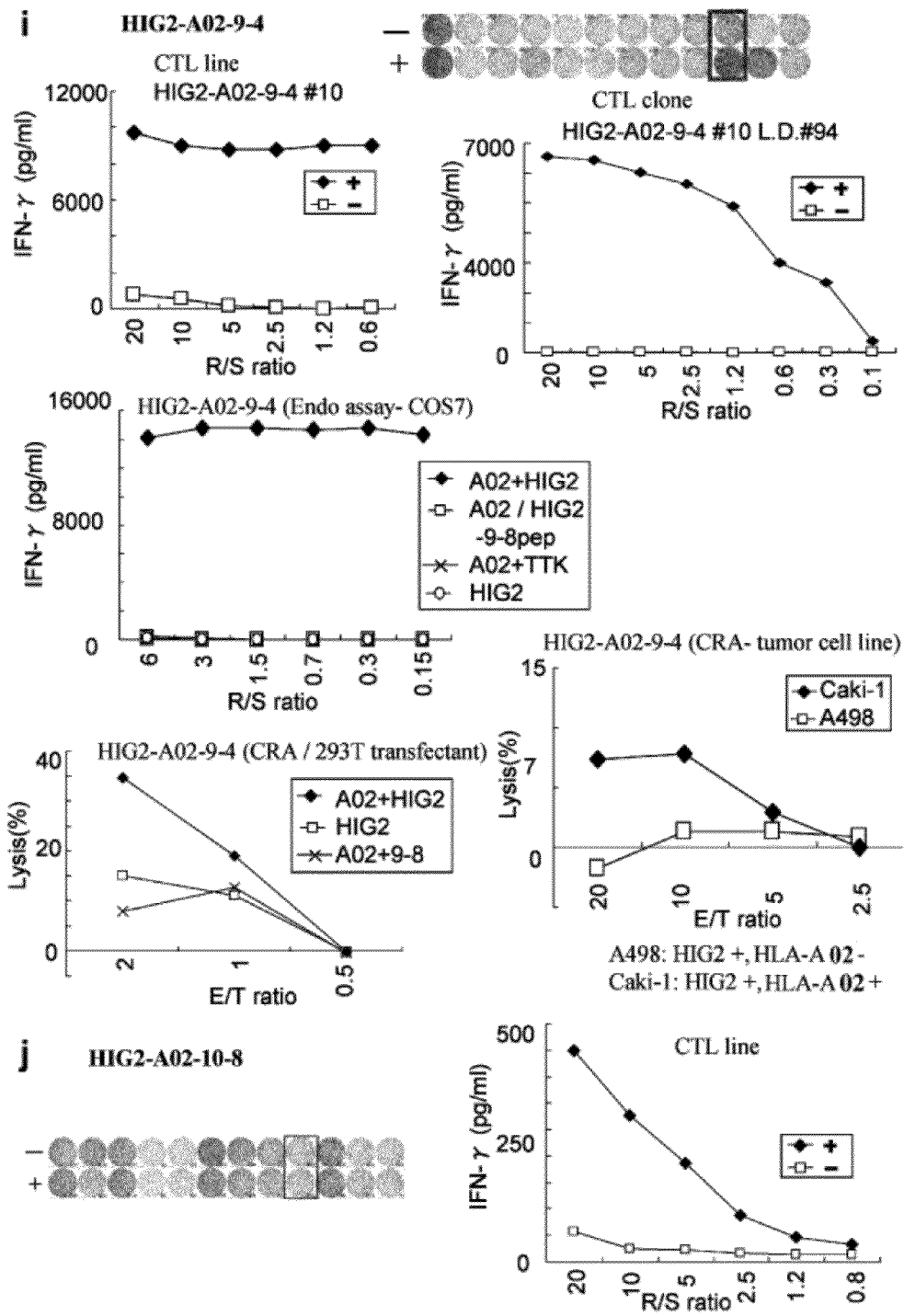

FIG. 4 depicts the results of the screening of epitope peptides, which, in turn, demonstrate that HIG2-A24-9-19 (SEQ ID NO: 110), HIG2-A24-9-22 (SEQ ID NO: 111), HIG2-A24-9-8 (SEQ ID NO: 387), HIG2-A24-10-7 (SEQ ID NO: 112), HIG2-A24-10-18 (SEQ ID NO: 394), HIG2-A02-9-15 (SEQ ID NO: 116), HIG2-A02-9-4 (SEQ ID NO: 117) and HIG2-A02-10-8 (SEQ ID NO: 121) show potent IFN-gamma production. "a" depicts the example of negative peptides which could not be detected CTL-inducing ability despite possible binding activity with HLA. "b" depicts the CTL-inducing ability of HIG2-A24-9-19 (SEQ ID NO: 110). HIG2-A24-9-19 (SEQ ID NO: 110) demonstrated potent IFN-gamma production as compared to the control by IFN-gamma ELISPOT assay, and CTL line, that was established from the positive well #6 shown in boxed wells, demonstrated the specific response against the target cells pulsed with the epitope peptide. "c" depicts the CTL-inducing ability of HIG2-A24-9-22 (SEQ ID NO: 111). HIG2-A24-9-22 (SEQ ID NO: 111) demonstrated potent IFN-gamma production as compared to the control by IFN-gamma ELISPOT assay, and CTL line and clone, that was established from the positive well #7 shown in boxed wells, demonstrated the specific response against the target cells pulsed with the epitope peptide. "d" depicts the CTL-inducing ability of HIG2-A24-9-8 (SEQ ID NO: 387). HIG2-A24-9-8 (SEQ ID NO: 387) demonstrated potent IFN-gamma production as compared to the control by IFN-gamma ELISPOT assay, and CTL line and clone, that were established from the positive well #5 shown in boxed wells, demonstrated the specific response against the target cells pulsed with the epitope peptide. "e" depicts the CTL-inducing ability of HIG2-A02-9-8 (SEQ ID NO: 114). HIG2-A02-9-8 (SEQ ID NO: 114) demonstrated potent IFN-gamma production as compared to the control by IFN-gamma ELISPOT assay, and CTL line was established from the positive well #10 shown in boxed wells. The established CTL line raised against the peptide demonstrate specific CTL activity against 293T transfected both full length of HIG2 gene and HLA-A02 molecule. 293T transfected full length of HIG2 but not HLA-A02, 293Ts transfected HLA-A02 and FoxP3 gene as substitute for full length of HIG2 and 293Ts transfected HLA-A02 and pulsed with HIG2-9-15 were prepared for the negative control. The CTL line showed high specific CTL activity against 293T that transfected both HIG2 and HLA-A02.

FIG. 4-2

FIG. 4 depicts the results of the screening of epitope peptides, which, in turn, demonstrate that HIG2-A24-9-19 (SEQ ID NO: 110), HIG2-A24-9-22 (SEQ ID NO: 111), HIG2-A24-9-8 (SEQ ID NO: 387), HIG2-A24-10-7 (SEQ ID NO: 112), HIG2-A24-10-18 (SEQ ID NO: 394), HIG2-A02-9-15 (SEQ ID NO: 116), HIG2-A02-9-4 (SEQ ID NO: 117) and HIG2-A02-10-8 (SEQ ID NO: 121) show potent IFN-gamma production. "f" depicts the CTL-inducing ability of HIG2-A24-10-7 (SEQ ID NO: 112). HIG2-A24-10-7 (SEQ ID NO: 112) demonstrated potent IFN-gamma production as compared to the control by IFN-gamma ELISPOT assay, and CTL lines or clone, that were established from the positive well #1 and #7 shown in boxed wells, demonstrated the specific response against the target cells pulsed with the epitope peptide. "g" depicts the CTL-inducing ability of HIG2-A24-10-18 (SEQ ID NO: 394). HIG2-A24-10-18 (SEQ ID NO: 394) demonstrated potent IFN-gamma production as compared to the control by IFN-gamma ELISPOT assay, and CTL line and clone, that were established from the positive well #7 shown in boxed wells, demonstrated the specific response against the target cells pulsed with the epitope peptide. "h" depicts the CTL-inducing ability of HIG2-A02-9-15 (SEQ ID NO: 116). HIG2-A02-9-15 (SEQ ID NO: 116) demonstrated potent IFN-gamma production as compared to the control by IFN-gamma ELISPOT assay, and CTL line was established from the positive well #10 shown in boxed wells. The established CTL line raised against the peptide demonstrated specific CTL activity against COS7 transfected both full length of HIG2 gene and HLA-A02 molecule. COS7 transfected full length of HIG2 but not HLA-A02 and COS7s transfected HLA-A02 and pulsed with HIG2-9-8 peptide were prepared for the negative control. The CTL line showed high specific CTL activity against COS7 that transfected both HIG2 and HLA-A02.

FIG. 4-3

FIG. 4 depicts the results of the screening of epitope peptides, which, in turn, demonstrate that HIG2-A24-9-19 (SEQ ID NO: 110), HIG2-A24-9-22 (SEQ ID NO: 111), HIG2-A24-9-8 (SEQ ID NO: 387), HIG2-A24-10-7 (SEQ ID NO: 112), HIG2-A24-10-18 (SEQ ID NO: 394), HIG2-A02-9-15 (SEQ ID NO: 116), HIG2-A02-9-4 (SEQ ID NO: 117) and HIG2-A02-10-8 (SEQ ID NO: 121) show potent IFN-gamma production. "i" depicts the CTL-inducing ability of HIG2-A02-9-4 (SEQ ID NO: 117). HIG2-A02-9-4 (SEQ ID NO: 117) demonstrated potent IFN-gamma production as compared to the control by IFN-gamma ELISPOT assay, and CTL line and clone were established from the positive well #10 shown in boxed wells. The established CTL line raised against the peptide demonstrated specific CTL activity against COS7 transfected both full length of HIG2 gene and HLA-A02 molecule (middle graph). Also, COS7 transfected full length of HIG2 but not HLA-A02, COS7s transfected HLA-A02 and TTK gene as substitute for full length of HIG2 and COS7s transfected HLA-A02 and pulsed with HIG2-9-8 were prepared for the negative control. Cytotoxic activity of the CTL clone against 293T, transfected both full length of HIG2 gene and HLA-A02 molecule, and cancer cell line, Caki-1 endogenously expressing HIG2 and HLA-A02 was measured by Cr-release assay (CRA) (lower graphs), and the CTL clone had very potent cytotoxic activity against the transfectant with both of HIG2 gene and HLA-A02, and Caki-1. On the other hand, the effector cells did not demonstrate the cytotoxic activity of the CTL line against 293T, transfected only HIG2 or only HLA-A02, and cancer cell line, A498 expressing only HIG2 was not detected. "j" depicts the CTL-inducing ability of HIG2-A02-10-8 (SEQ ID NO: 121). HIG2-A02-10-8 (SEQ ID NO: 121) demonstrated potent IFN-gamma production as compared to the control by IFN-gamma ELISPOT assay, and CTL line, that was established from the positive well #9 shown in boxed wells, demonstrated the specific response against the target cells pulsed with the epitope peptide.

FIG. 5-1

Figure 5:
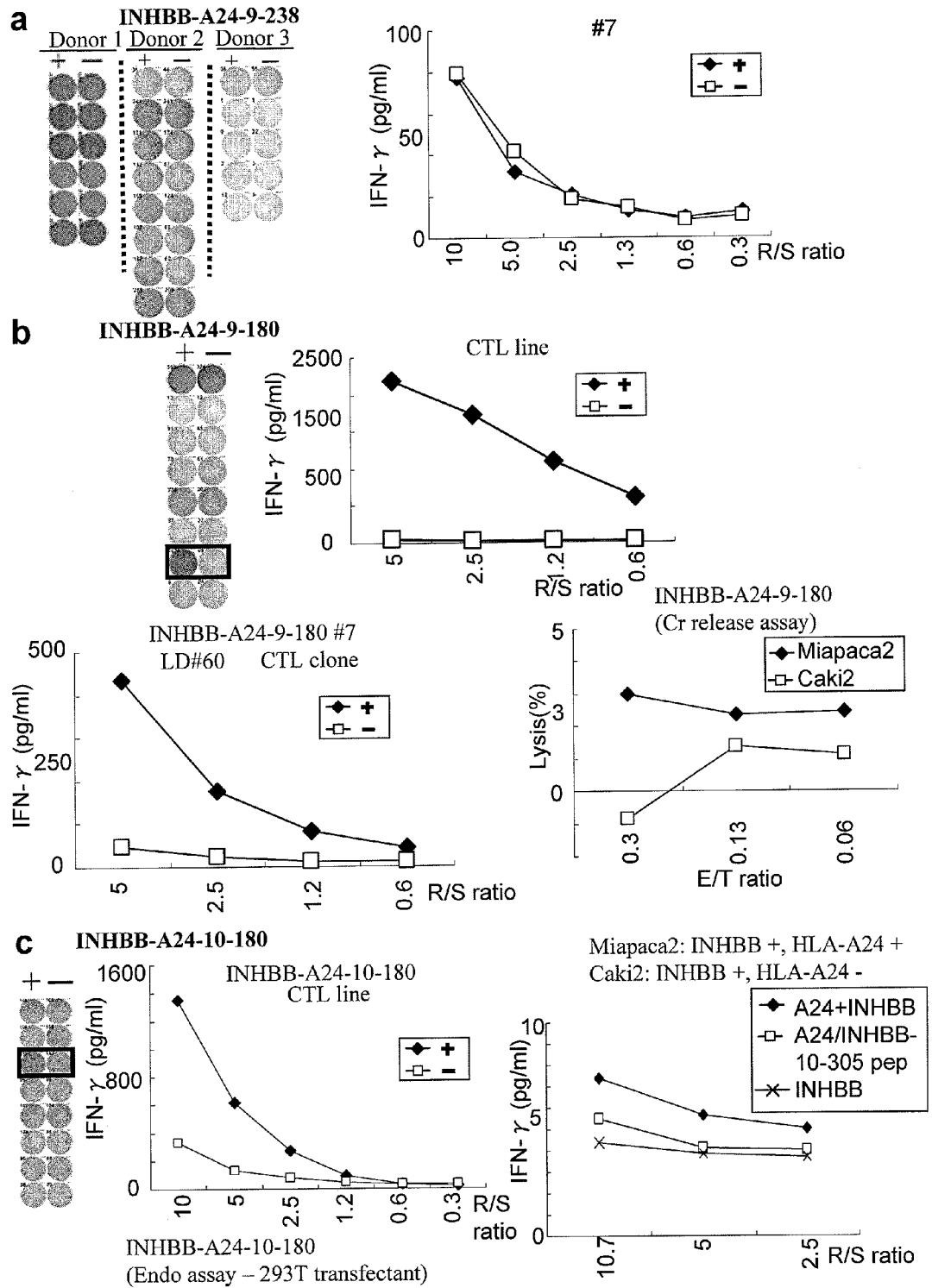
Figure 5:
Figure 5:
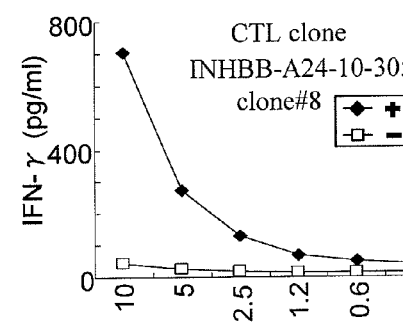
Figure 5:
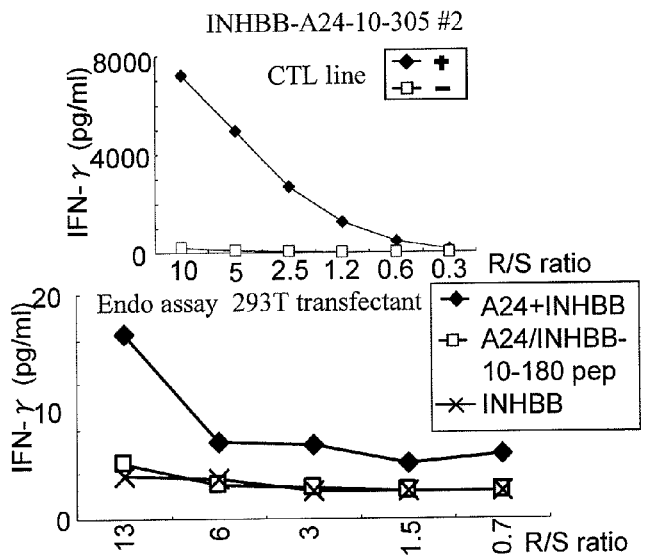
Figure 5:
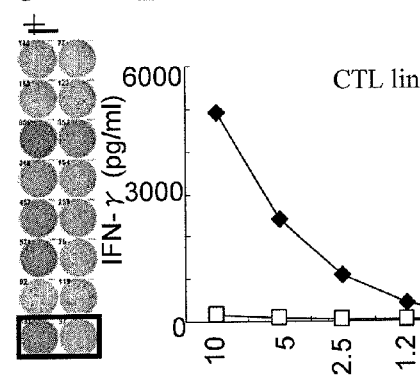
Figure 5:
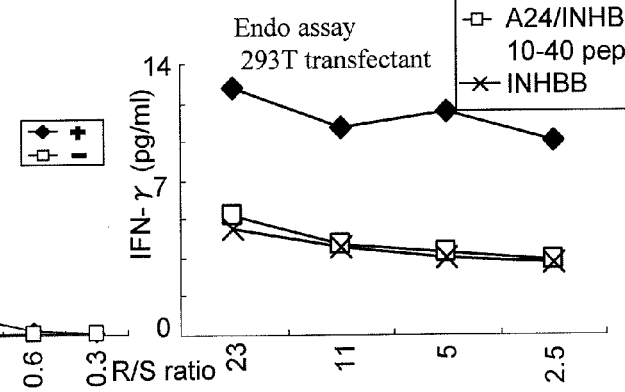
Figure 5:
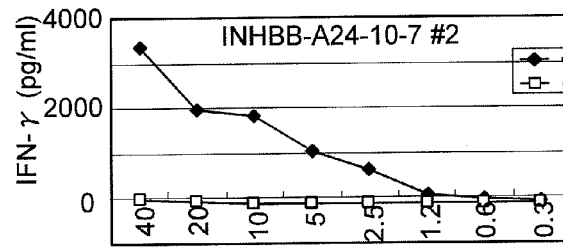
Figure 5:
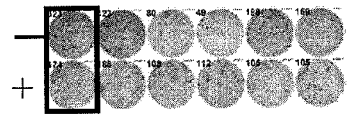
Figure 5:
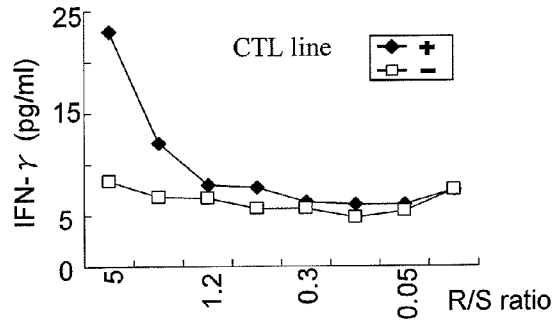

FIG. 5 depicts the results of the screening of epitope peptides, which, in turn, demonstrate that INHBB-A24-9-180 (SEQ ID NO: 395), INHBB-A24-10-180 (SEQ ID NO: 133), INHBB-A24-10-305 (SEQ ID NO: 135), INHBB-A24-10-7 (SEQ ID NO: 137) and INHBB-A24-10-212 (SEQ ID NO: 426) show potent IFN-gamma production. "a" depicts the example of negative peptides which could not be detected CTL-inducing ability despite possible binding activity with HLA. "b" depicts the CTL-inducing ability of INHBB-A24-9-180 (SEQ ID NO: 395). INHBB-A24-9-180 (SEQ ID NO: 395) demonstrated potent IFN-gamma production as compared to the control by IFN-gamma ELISPOT assay, and CTL line and clone was established from the positive well #7 shown in boxed wells. Cytotoxic activity of the established CTL clone against tumor cells, Miapaca2 expressing both of INHBB and HLA-A02 was measured by Cr-release assay (CRA), and the effector cells showed high specific cytotoxic activity against Miapaca2. On the other hand, it did not show significant specific cytotoxic activity against Caki-1 expressing INHBB but not HLA-A02. "c" depicts the CTL-inducing ability of INHBB-A24-10-180 (SEQ ID NO: 133). INHBB-A24-10-180 (SEQ ID NO: 133) demonstrated potent IFN-gamma production as compared to the control by IFN-gamma ELISPOT assay, and CTL line was established from the positive well #3 shown in boxed wells. The established CTL line raised against the peptide demonstrated high specific CTL activity against 293T transfected both of full length of INHBB gene and HLA-A24 molecule. Also, 293T transfected full length of INHBB but not HLA-A24 and 293Ts transfected HLA-A24 and pulsed with INHBB-10-305 peptide were prepared for the negative control.

FIG. 5-2

FIG. 5 depicts the results of the screening of epitope peptides, which, in turn, demonstrate that INHBB-A24-9-180 (SEQ ID NO: 395), INHBB-A24-10-180 (SEQ ID NO: 133), INHBB-A24-10-305 (SEQ ID NO: 135), INHBB-A24-10-7 (SEQ ID NO: 137) and INHBB-A24-10-212 (SEQ ID NO: 426) show potent IFN-gamma production. "d" depicts the CTL-inducing ability of INHBB-A24-10-305 (SEQ ID NO: 135). INHBB-A24-10-305 (SEQ ID NO: 135) demonstrated potent IFN-gamma production as compared to the control by IFN-gamma ELISPOT assay, and CTL line and clone were established from the positive well #2 shown in boxed wells. The established CTL clone raised against the peptide demonstrated high specific CTL activity against 293T transfected both full length of INHBB gene and HLA-A24 molecule. Also, 293T transfected full length of INHBB but HLA-A24 and 293Ts transfected HLA-A24 and pulsed with INHBB-10-180 peptide were prepared for the negative control. "e" depicts the CTL-inducing ability of INHBB-A24-10-7 (SEQ ID NO: 137)). INHBB-A24-10-7 (SEQ ID NO: 137) demonstrated potent IFN-gamma production as compared to the control by IFN-gamma ELISPOT assay, and CTL lines were established from the positive well #8 shown in boxed wells in upper panel and #2 shown in boxed wells in lower panel. The CTL line from #8 well demonstrated specific CTL activity against 293T transfected both full length of INHBB gene and HLA-A24 molecule. Also, 293T transfected full length of INHBB but not HLA-A24 and 293Ts transfected HLA-A24 and pulsed with INHBB-10-40 peptide were prepared for the negative control. "f" depicts the CTL-inducing ability of INHBB-A24-10-212 (SEQ ID NO: 426). INHBB-A24-10-212 (SEQ ID NO: 426) demonstrated potent IFN-gamma production as compared to the control by IFN-gamma ELISPOT assay, and CTL line, that was established from the positive well #1 shown in boxed wells, demonstrated the specific response against the target cells pulsed with the epitope peptide.

FIG. 6-1

Figure 6:
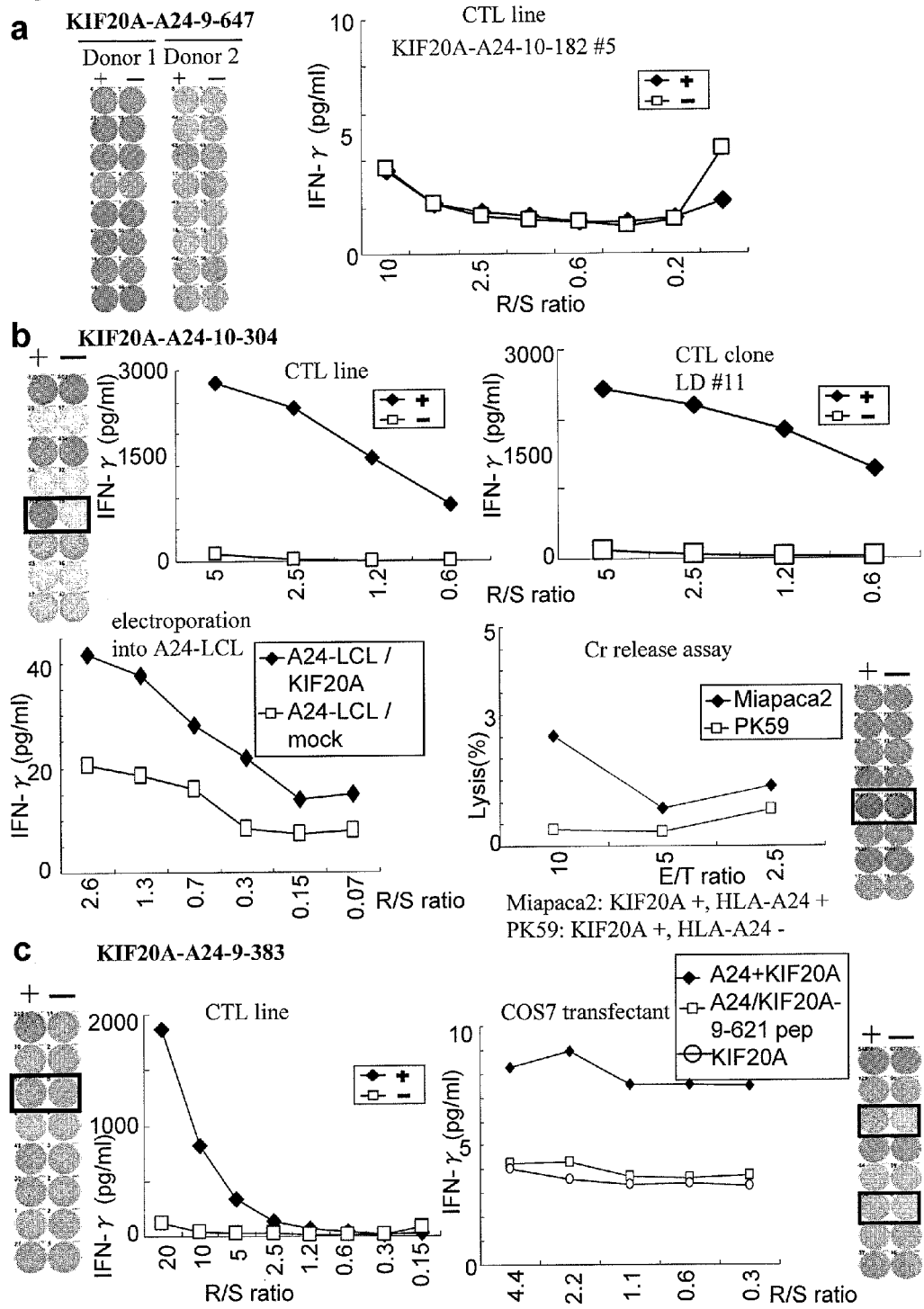
Figure 6:
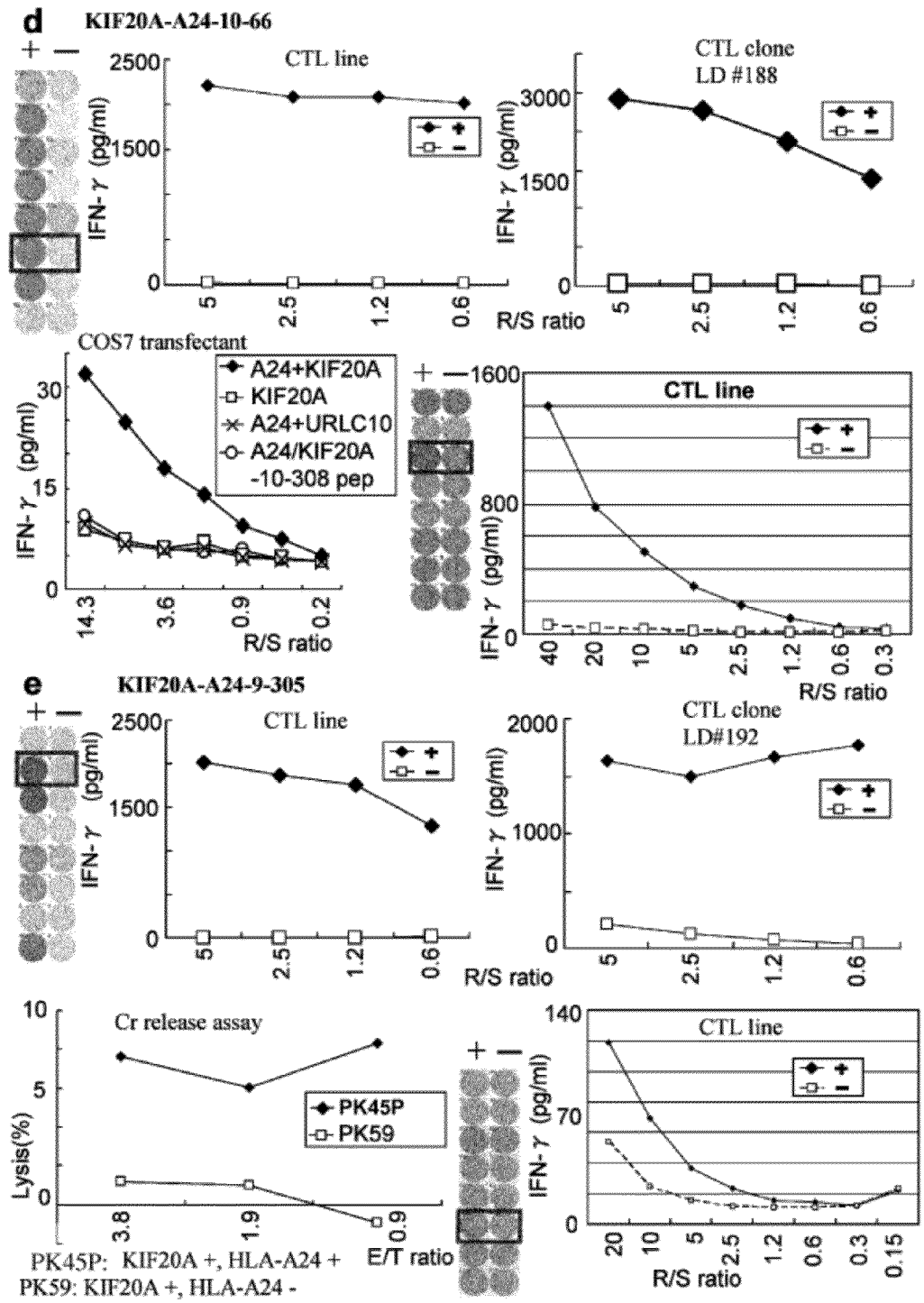

FIG. 6 depicts the results of the screening of epitope peptides, which, in turn, demonstrate that KIF20A-A24-10-304 (SEQ ID NO: 186), KIF20A-A24-9-383 (SEQ ID NO: 178), KIF20A-A24-10-66 (SEQ ID NO: 194) and KIF20A-A24-9-305 (SEQ ID NO: 174) show potent IFN-gamma production. "a" depicts the example of negative peptides which could not be detected CTL-inducing ability despite possible binding activity with HLA. "b" depicts the CTL-inducing ability of KIF20A-A24-10-304 (SEQ ID NO: 186). KIF20A-A24-10-304 (SEQ ID NO: 186) demonstrated potent IFN-gamma production as compared to the control by IFN-gamma ELISPOT assay. The well #5 shown in boxed wells in lower right panel demonstrated the specific response against the target cells pulsed with the epitope peptide. Moreover, CTL line and clone, that were established from the positive well #5 shown in boxed wells in upper left panel, also demonstrated the specific response against the target cells pulsed with the epitope peptide. The established CTL clone raised against the peptide demonstrated specific CTL activity against 24-LCL transfected full length of KIF20A gene. Also, A24-LCL transfected mock vector was prepared for the negative control. Cytotoxic activity of the CTL clone against tumor cells, Miapaca2 expressing both of KIF20A and HLA-A24 was measured by Cr-release assay (CRA), and the CTL clone had very potent specific cytotoxic activity against Miapaca2 (lower right graph). On the other hand, it did not show significant specific cytotoxic activity against PK59 expressing KIF20A but not HLA-A24. "c" depicts the CTL-inducing ability of KIF20A-A24-9-383 (SEQ ID NO: 178). KIF20A-A24-9-383 (SEQ ID NO: 178) demonstrated potent IFN-gamma production as compared to the control by IFN-gamma ELISPOT assay. The well #3 and 4 shown in boxed wells in right panel demonstrated the specific response against the target cells pulsed with the epitope peptide. Moreover, CTL line, that was established from the positive well #3 shown in boxed wells in left panel, also demonstrated the specific response against the target cells pulsed with the epitope peptide. The established CTL line demonstrated high specific CTL activity against COS7 transfected both full length of KIF20A gene and HLA-A24 molecule. Also, COS7 transfected full length of KIF20A but not HLA-A24 and COS7s transfected HLA-A24 and pulsed with KIF20A-9-621 peptide were prepared for the negative control.

FIG. 6-2

FIG. 6 depicts the results of the screening of epitope peptides, which, in turn, demonstrate that KIF20A-A24-10-304 (SEQ ID NO: 186), KIF20A-A24-9-383 (SEQ ID NO: 178), KIF20A-A24-10-66 (SEQ ID NO: 194) and KIF20A-A24-9-305 (SEQ ID NO: 174) show potent IFN-gamma production. "d" depicts the CTL-inducing ability of KIF20A-A24-10-66 (SEQ ID NO: 194). KIF20A-A24-10-66 (SEQ ID NO: 194) demonstrated potent IFN-gamma production as compared to the control by IFN-gamma ELISPOT assay, and CTL lines, that were established from the positive well #6 shown in boxed wells in upper left panel and #3 shown in boxed wells in lower middle panel demonstrated the specific response against the target cells pulsed with the epitope peptide. Moreover, CTL clone selected from CTL line from #6 well by limiting dilution demonstrated specific CTL activity against the target cells. The established CTL clone showed specific CTL activity against COS7 transfected both full length of KIF20A gene and HLA-A24 molecule. Also, COS7 transfected full length of KIF20A but not HLA-A24, COS7s transfected HLA-A24 and URLC10 gene as substitute for full length of KIF20A and COS7 transfected HLA-A24 and pulsed with KIF20A-10-308 peptide were prepared for the negative control. "e" depicts the CTL-inducing ability of KIF20A-A24-9-305 (SEQ ID NO: 174). KIF20A-A24-9-305 (SEQ ID NO: 174) demonstrated potent IFN-gamma production as compared to the control by IFN-gamma ELISPOT assay, and CTL lines, that were established from the positive well #2 shown in boxed wells in upper left panel and #6 shown in boxed wells in lower middle panel, demonstrated the specific response against the target cells pulsed with the epitope peptide. Moreover, CTL clone selected from CTL line from #2 well by limiting dilution demonstrated specific CTL activity against the target cells. Cytotoxic activity of the CTL clone against tumor cells, PK45P expressing both of KIF20A and HLA-A24 was measured by Cr-release assay (CRA), and the CTL clone had very potent cytotoxic activity against PK45P. On the other hand, it did not show significant specific cytotoxic activity against PK59 expressing KIF20A but not HLA-A24.

FIG. 7-1

Figure 7:
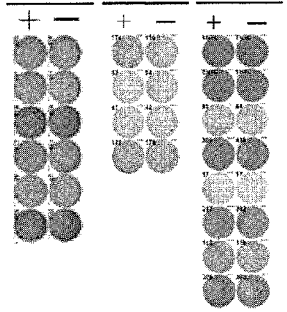
Figure 7:
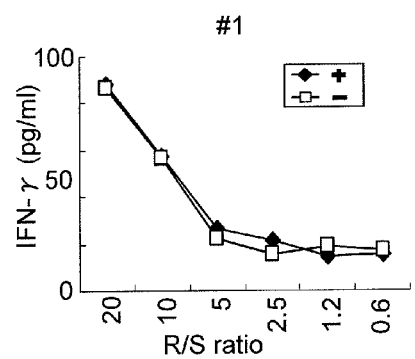
Figure 7:
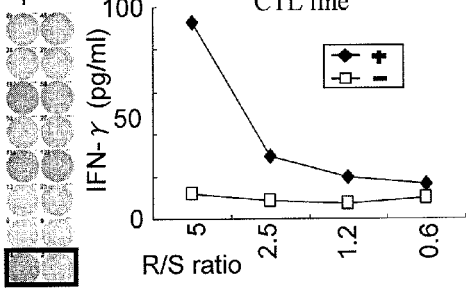
Figure 7:
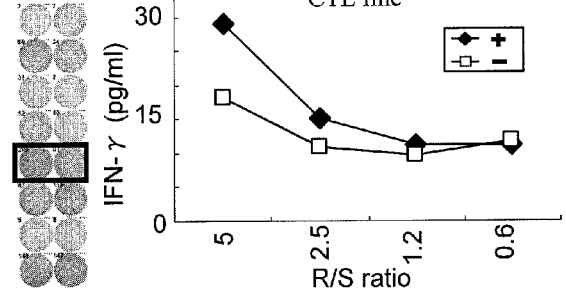
Figure 7:
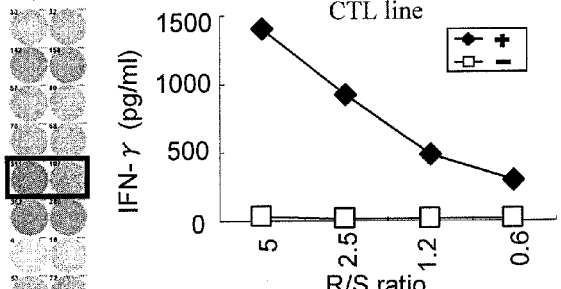
Figure 7:
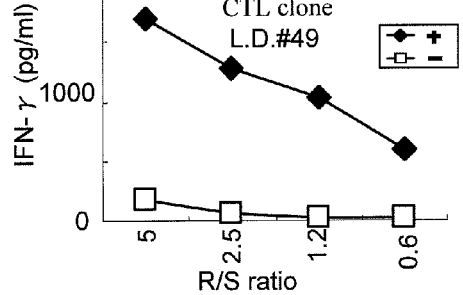
Figure 7:
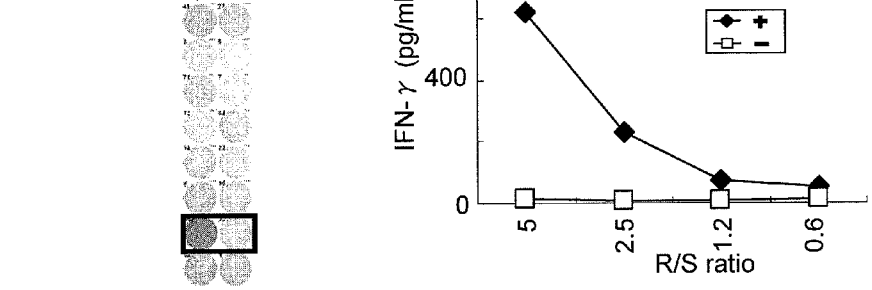
Figure 7:
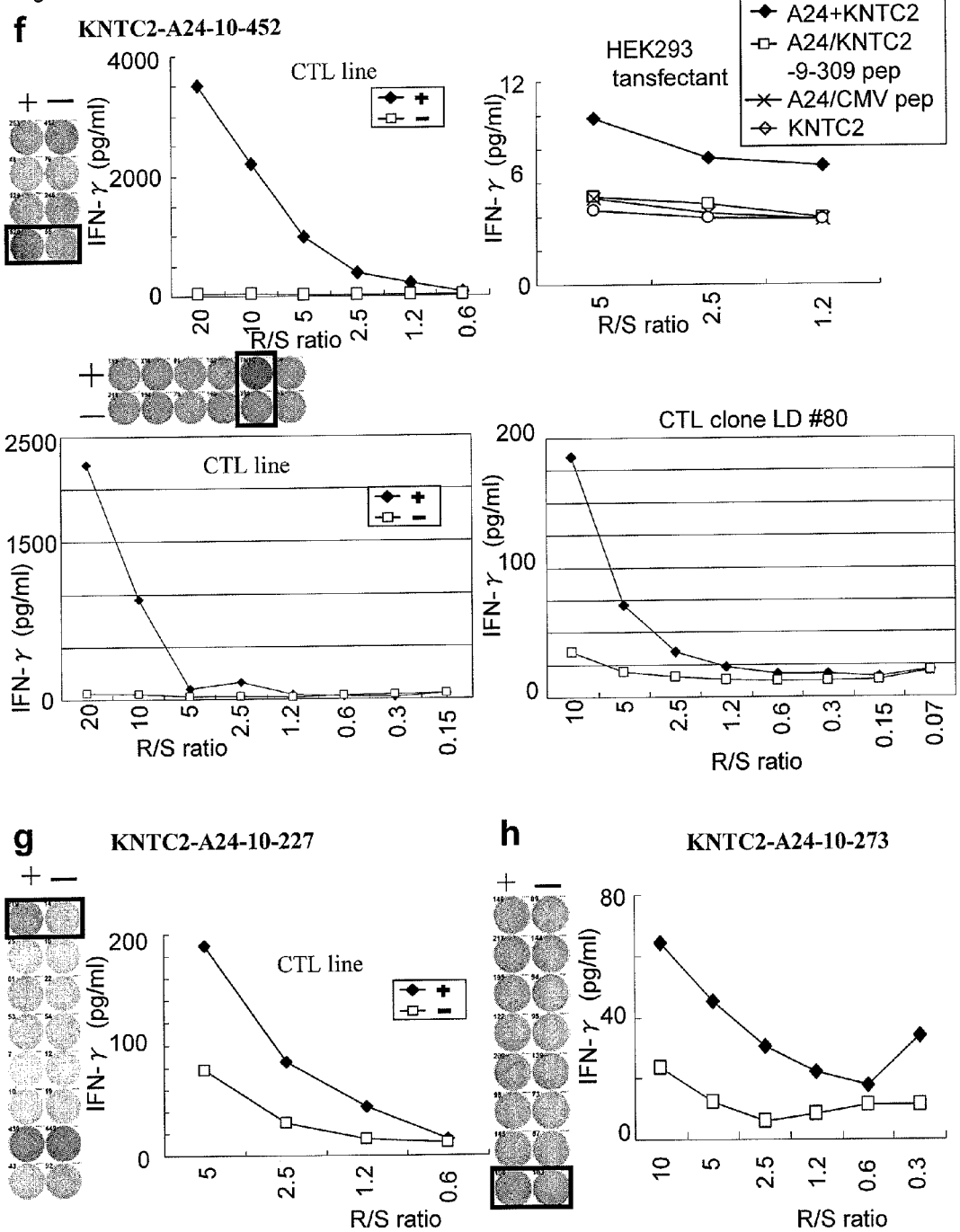

FIG. 7 depicts the results of the screening of epitope peptides, which, in turn, demonstrate that KNTC2-A24-9-309 (SEQ ID NO: 196), KNTC2-A24-9-124 (SEQ ID NO: 202), KNTC2-A24-9-154 (SEQ ID NO: 210) KNTC2-A24-9-150 (SEQ ID NO: 213), KNTC2-A24-10-452 (SEQ ID NO: 214), KNTC2-A24-10-227 (SEQ ID NO: 217) and KNTC2-A24-10-273 (SEQ ID NO: 223) show potent IFN-gamma production. "a" depicts the example of negative peptides which could not be detected CTL-inducing ability despite possible binding activity with HLA. "b" depicts the CTL-inducing ability of KNTC2-A24-9-309 (SEQ ID NO: 196). KNTC2-A24-9-309 (SEQ ID NO: 196) demonstrated potent IFN-gamma production as compared to the control by IFN-gamma ELISPOT assay, and CTL line, that was established from the positive well #8 shown in boxed wells, demonstrated the specific response against the target cells pulsed with the epitope peptide. "c" depicts the CTL-inducing ability of KNTC2-A24-9-124 (SEQ ID NO: 202). KNTC2-A24-9-124 (SEQ ID NO: 202) demonstrated potent IFN-gamma production as compared to the control by IFN-gamma ELISPOT assay, and CTL line, that was established from the positive well #5 shown in boxed wells, demonstrated the specific response against the target cells pulsed with the epitope peptide. "d" depicts the CTL-inducing ability of KNTC2-A24-9-154 (SEQ ID NO: 210). KNTC2-A24-9-154 (SEQ ID NO: 210) demonstrated potent IFN-gamma production as compared to the control by IFN-gamma ELISPOT assay, and CTL line and clone, that were established from the positive well #5 shown in boxed wells demonstrated the specific response against the target cells pulsed with the epitope peptide. "e" depicts the CTL-inducing ability of KNTC2-A24-9-150 (SEQ ID NO: 213). KNTC2-A24-9-150 (SEQ ID NO: 213) demonstrated potent IFN-gamma production as compared to the control by IFN-gamma ELISPOT assay, and CTL line, that was established from the positive well #7 shown in boxed wells, demonstrated the specific response against the target cells pulsed with the epitope peptide.

FIG. 7-2

FIG. 7 depicts the results of the screening of epitope peptides, which, in turn, demonstrate that KNTC2-A24-9-309 (SEQ ID NO: 196), KNTC2-A24-9-124 (SEQ ID NO: 202), KNTC2-A24-9-154 (SEQ ID NO: 210) KNTC2-A24-9-150 (SEQ ID NO: 213), KNTC2-A24-10-452 (SEQ ID NO: 214), KNTC2-A24-10-227 (SEQ ID NO: 217) and KNTC2-A24-10-273 (SEQ ID NO: 223) show potent IFN-gamma production. "f" depicts the CTL-inducing ability of KNTC2-A24-10-452 (SEQ ID NO: 214). KNTC2-A24-10-452 (SEQ ID NO: 214) demonstrated potent IFN-gamma production as compared to the control by IFN-gamma ELISPOT assay, and CTL lines and clone, that were established from the positive well #4 shown in boxed wells in upper left panel and #5 shown in boxed wells in middle panel, demonstrated the specific response against the target cells pulsed with the epitope peptide. Moreover, CTL clone selected from CTL line from #5 well by limiting dilution demonstrated specific CTL activity against the target cells. The established CTL line from #4 well showed specific CTL activity against HEK293 transfected both full length of KNTC2 gene and HLA-A24 molecule. Also, HEK293 transfected full length of KNTC2 but not HLA-A24, HEK293 transfected HLA-A24 but full length of KNTC2 and HEK293 transfected HLA-A24 pulsed with KNTC-9-309 peptide were prepared for the negative control. "g" depicts the CTL-inducing ability of KNTC2-A24-10-227 (SEQ ID NO: 217). KNTC2-A24-10-227 (SEQ ID NO: 217) demonstrated potent IFN-gamma production as compared to the control by IFN-gamma ELISPOT assay, and CTL line, that was established from the positive well #1 shown in boxed well s, demonstrated the specific response against the target cells pulsed with the epitope peptide. "h" depicts the CTL-inducing ability of KNTC2-A24-10-273 (SEQ ID NO: 223). KNTC2-A24-10-273 (SEQ ID NO: 223) demonstrated potent IFN-gamma production as compared to the control by IFN-gamma ELISPOT assay, and CTL line, that was established from the positive well #8 shown in boxed wells, demonstrated the specific response against the target cells pulsed with the epitope peptide.

FIG. 8-1

Figure 8:
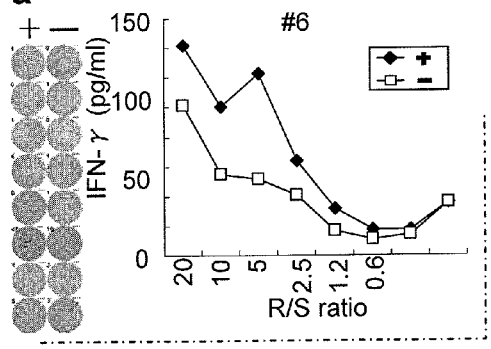
Figure 8:
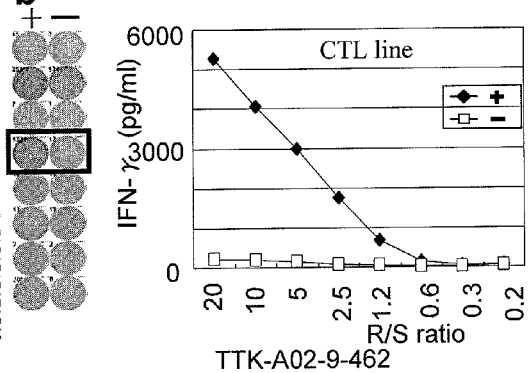
Figure 8:
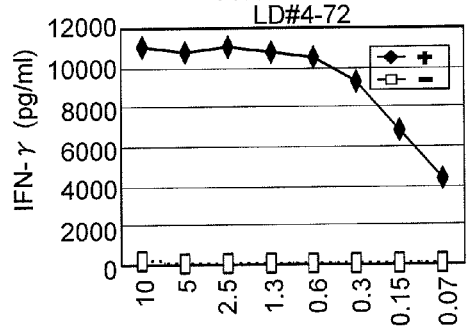
Figure 8:
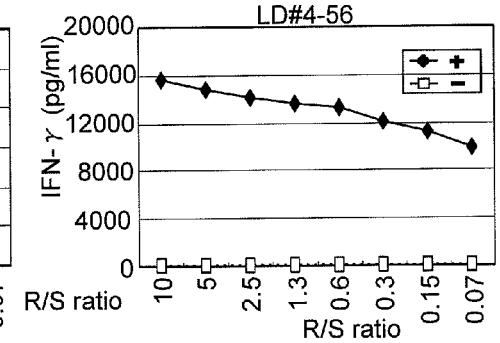
Figure 8:
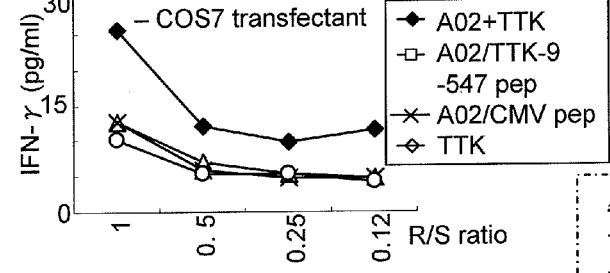
Figure 8:
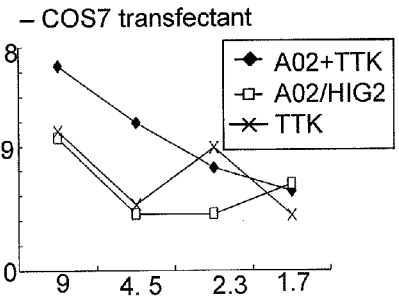
Figure 8:
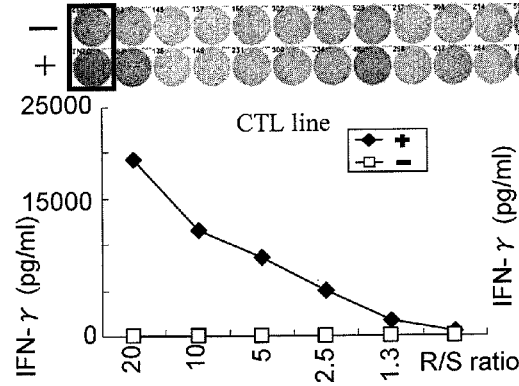
Figure 8:
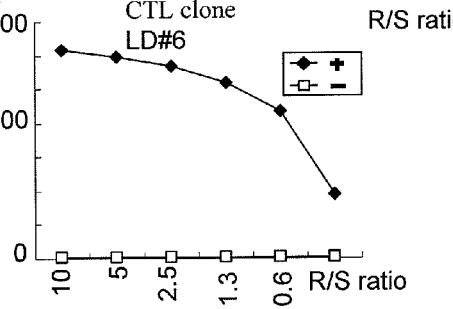
Figure 8:
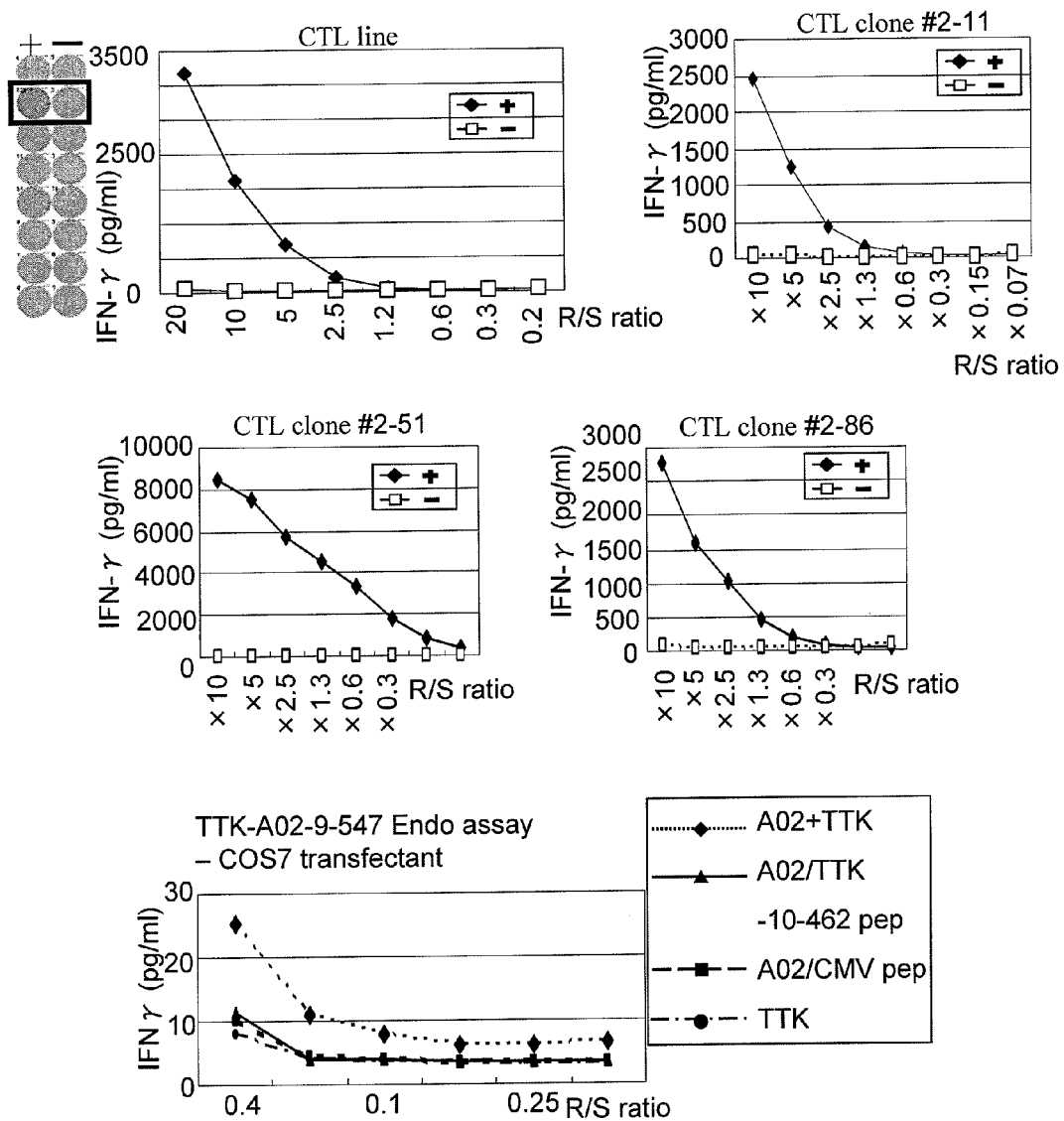
Figure 8:
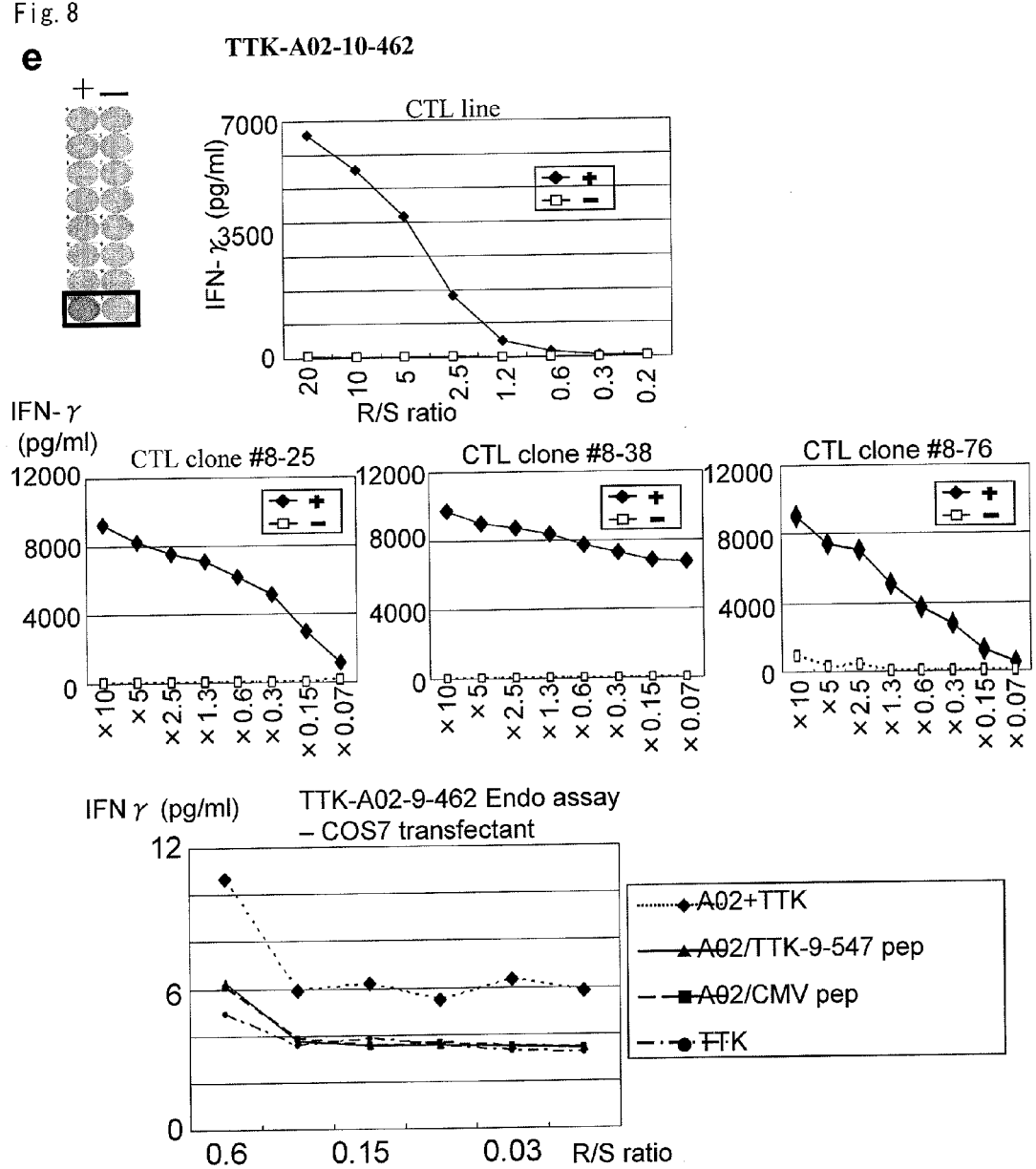

FIG. 8 depicts the results of the screening of epitope peptides, which, in turn, demonstrate that TTK-A02-9-462 (SEQ ID NO: 227), TTK-A02-9-719 (SEQ ID NO: 233), TTK-A02-9-547 (SEQ ID NO: 228) and TTK-A02-10-462 (SEQ ID NO: 254), show potent IFN-gamma production. "a" depicts the example of negative peptides which could not be detected CTL-inducing ability despite possible binding activity with HLA. "b" depicts the CTL-inducing ability of TTK-A02-9-462 (SEQ ID NO: 227). TTK-A02-9-462 (SEQ ID NO: 227) demonstrated potent IFN-gamma production as compared to the control by IFN-gamma ELISPOT assay, and CTL line and two clones, that were established from the positive well #4 shown in boxed wells, demonstrated the specific response against the target cells pulsed with the epitope peptide. The established CTL clone showed high specific CTL activity against COS7 transfected both full length of TTK gene and HLA-A02 molecule. Also, COS7 transfected full length of TTK but not HLA-A02, COS7s transfected HLA-A02 but not full length of TTK and COS7s transfected HLA-A02 pulsed with TTK-9-547 peptide were prepared for the negative control. "c" depicts the CTL-inducing ability of TTK-A02-9-719 (SEQ ID NO: 233). TTK-A02-9-719 (SEQ ID NO: 233) demonstrated potent IFN-gamma production as compared to the control by IFN-gamma ELISPOT assay, and CTL line and clones were established from the positive well #1 shown in boxed wells. The established CTL line showed high specific CTL activity against COS7 transfected both full length of TTK gene and HLA-A02 molecule. Also, COS7 transfected full length of TTK but not HLA-A02 and COS7s transfected HLA-A02 and HIG2 gene as substitute for full length of TTK were prepared for the negative control.

FIG. 8-2

FIG. 8 depicts the results of the screening of epitope peptides, which, in turn, demonstrate that TTK-A02-9-462 (SEQ ID NO: 227), TTK-A02-9-719 (SEQ ID NO: 233), TTK-A02-9-547 (SEQ ID NO: 228) and TTK-A02-10-462 (SEQ ID NO: 254), show potent IFN-gamma production. "d" depicts the CTL-inducing ability of TTK-A02-9-547 (SEQ ID NO: 228). TTK-A02-9-547 (SEQ ID NO: 228) demonstrated potent IFN-gamma production as compared to the control by IFN-gamma ELISPOT assay, and CTL line and clones were established from the positive well #2 shown in boxed wells. The established CTL line showed specific CTL activity against COS7 transfected both full length of TTK gene and HLA-A02 molecule. Also, COS7 transfected full length of TTK but not HLA-A02, COS7s transfected HLA-A02 but not full length of TTK and COS7s transfected HLA-A02 and pulsed with TTK-10-462 were prepared for the negative control.

FIG. 8-3

FIG. 8 depicts the results of the screening of epitope peptides, which, in turn, demonstrate that TTK-A02-9-462 (SEQ ID NO: 227), TTK-A02-9-719 (SEQ ID NO: 233), TTK-A02-9-547 (SEQ ID NO: 228) and TTK-A02-10-462 (SEQ ID NO: 254), show potent IFN-gamma production. "e" depicts the CTL-inducing ability of TTK-A02-10-462 (SEQ ID NO: 254). TTK-A02-10-462 (SEQ ID NO: 254) demonstrated potent IFN-gamma production as compared to the control by IFN-gamma ELISPOT assay, and CTL line and three clones were established from the positive well #8 shown in boxed wells. The established CTL clone showed specific CTL activity against COS7 transfected both full length of TTK gene and HLA-A02 molecule. Also, COS7 transfected full length of TTK but not HLA-A02, COS7s transfected HLA-A02 but not full length of TTK and COS7s transfected HLA-A02 and pulsed with TTK-9-547 peptide were prepared for the negative control.

FIG. 9-1

Figure 9:
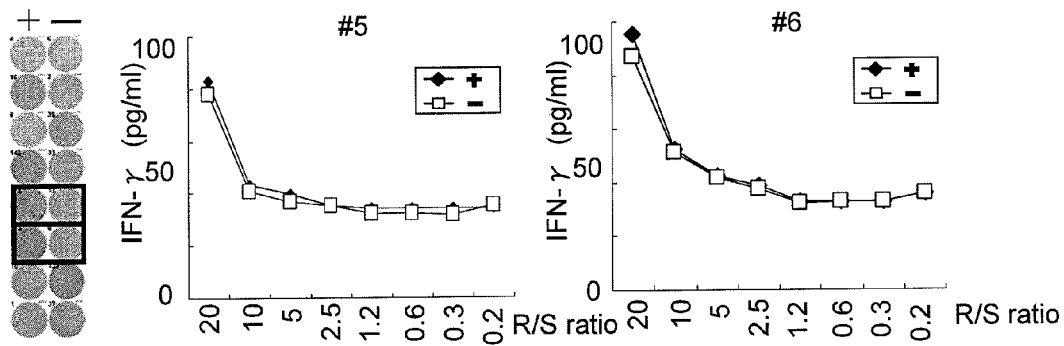
Figure 9:
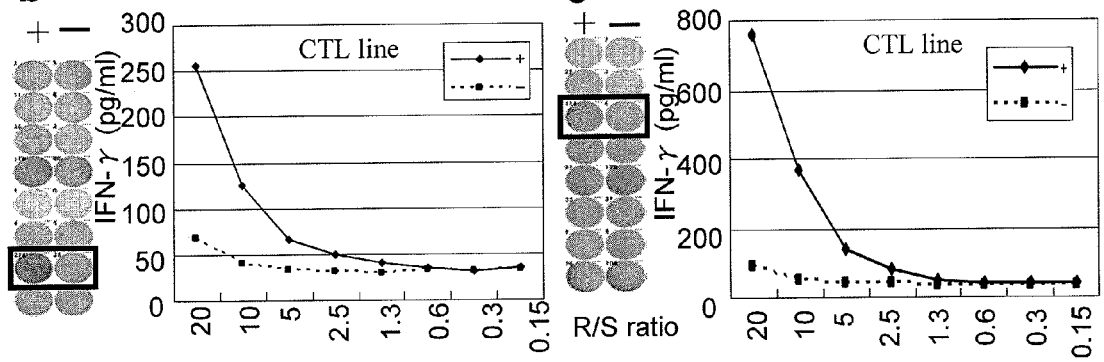
Figure 9:
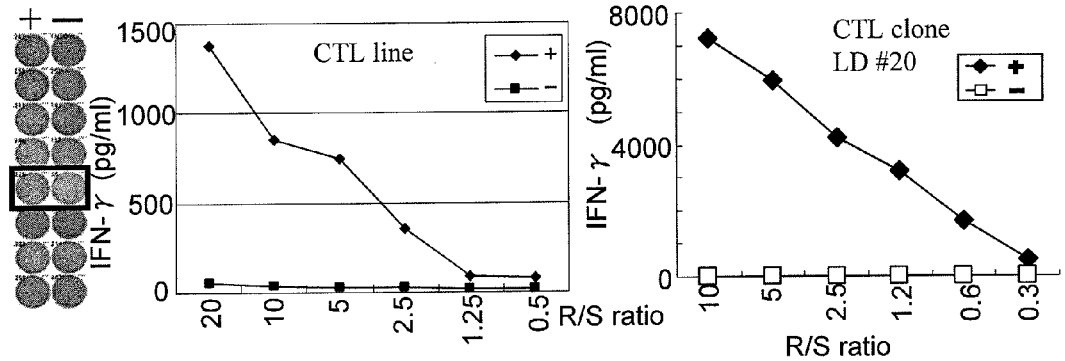
Figure 9:
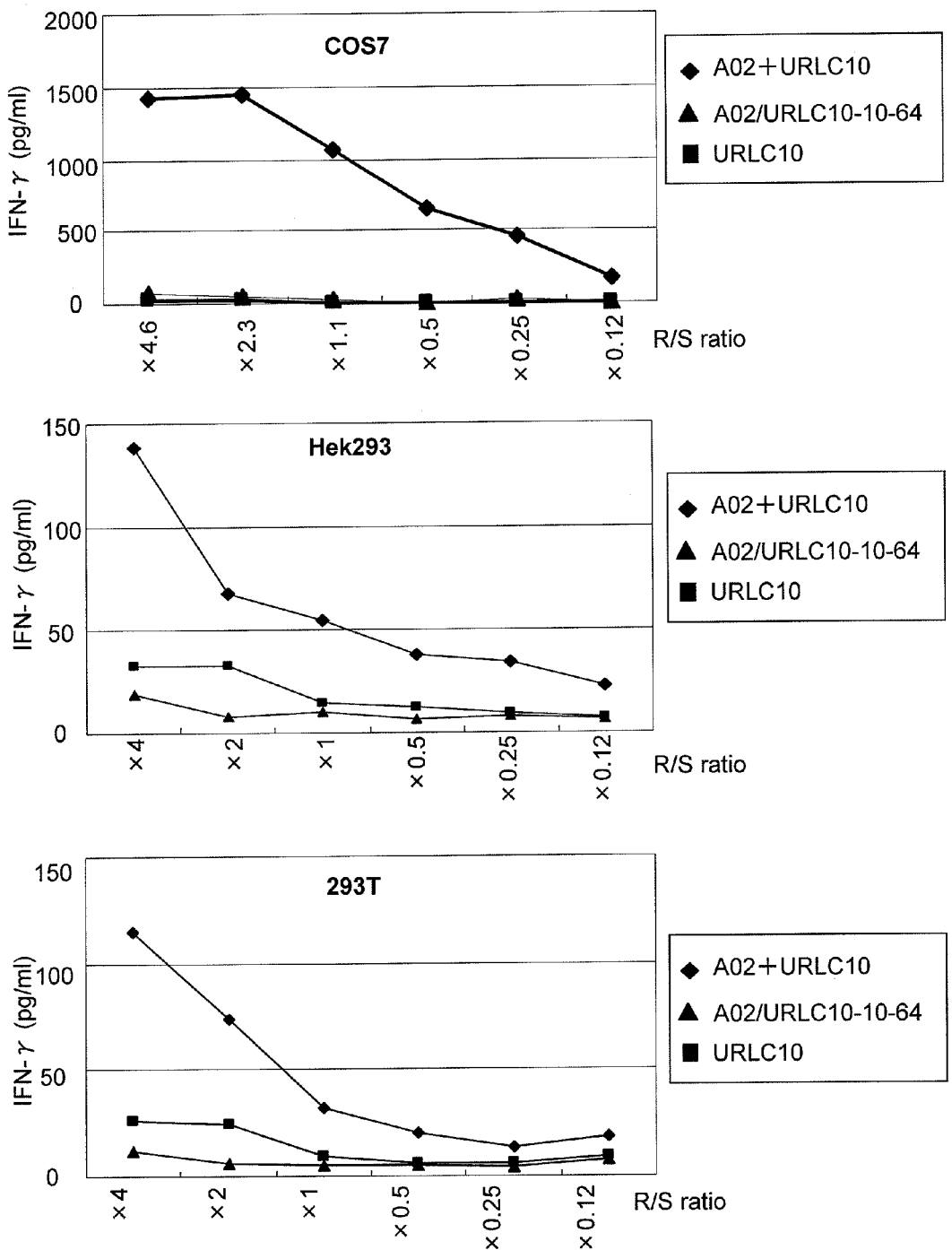

FIG. 9 depicts the results of the screening of epitope peptides, which, in turn, demonstrate that URLC10-A02-9-206 (SEQ ID NO: 271), URLC10-A02-9-212 (SEQ ID NO: 272) and URLC10-A02-10-211 (SEQ ID NO: 288) show potent IFN-gamma production. "a" depicts the example of negative peptides which could not be detected CTL-inducing ability despite possible binding activity with HLA. "b" depicts the CTL-inducing ability of URLC10-A02-9-206 (SEQ ID NO: 271). URLC10-A02-9-206 (SEQ ID NO: 271) demonstrated potent IFN-gamma production as compared to the control by IFN-gamma ELISPOT assay, and CTL line, that was established from the positive well #7 shown in boxed wells, demonstrated the specific response against the target cells pulsed with the epitope peptide. "c" depicts the CTL-inducing ability of URLC10-A02-9-212 (SEQ ID NO: 272). URLC10-A02-9-212 (SEQ ID NO: 272) demonstrated potent IFN-gamma production as compared to the control by IFN-gamma ELISPOT assay, and CTL line, that was established from the positive well #3 shown in boxed wells, demonstrated the specific response against the target cells pulsed with the epitope peptide. "d" depicts the CTL-inducing ability of URLC10-A02-10-211 (SEQ ID NO: 288). URLC10-A02-10-211 (SEQ ID NO: 288) demonstrated potent IFN-gamma production as compared to the control by IFN-gamma ELISPOT assay, and CTL line and clones, were established from the positive well #5 shown in boxed wells.

FIG. 9-2

FIG. 9 depicts the results of the screening of epitope peptides, which, in turn, demonstrate that URLC10-A02-9-206 (SEQ ID NO: 271), URLC10-A02-9-212 (SEQ ID NO: 272) and URLC10-A02-10-211 (SEQ ID NO: 288) show potent IFN-gamma production. "Continuation of d" The established CTL clone showed high specific CTL activity against COS7, Hek293 and 293T which were transfected both full length of URLC10 gene and HLA-A02 molecule. Also, COS7, Hek293 or 293T which were transfected full length of URLC10 but not HLA-A02 and COS7s, Hek293s or 293Ts, which were transfected HLA-A02 and pulsed with URLC10-10-64, were prepared for the negative control.

In this drawings, "+" means the peptide pulsed target, "−" means the no peptide pulsed target, "R" means Responder, "S" means Stimulator, "E" means Effector, and "T" means Target.

FIG. 10

Figure 10:
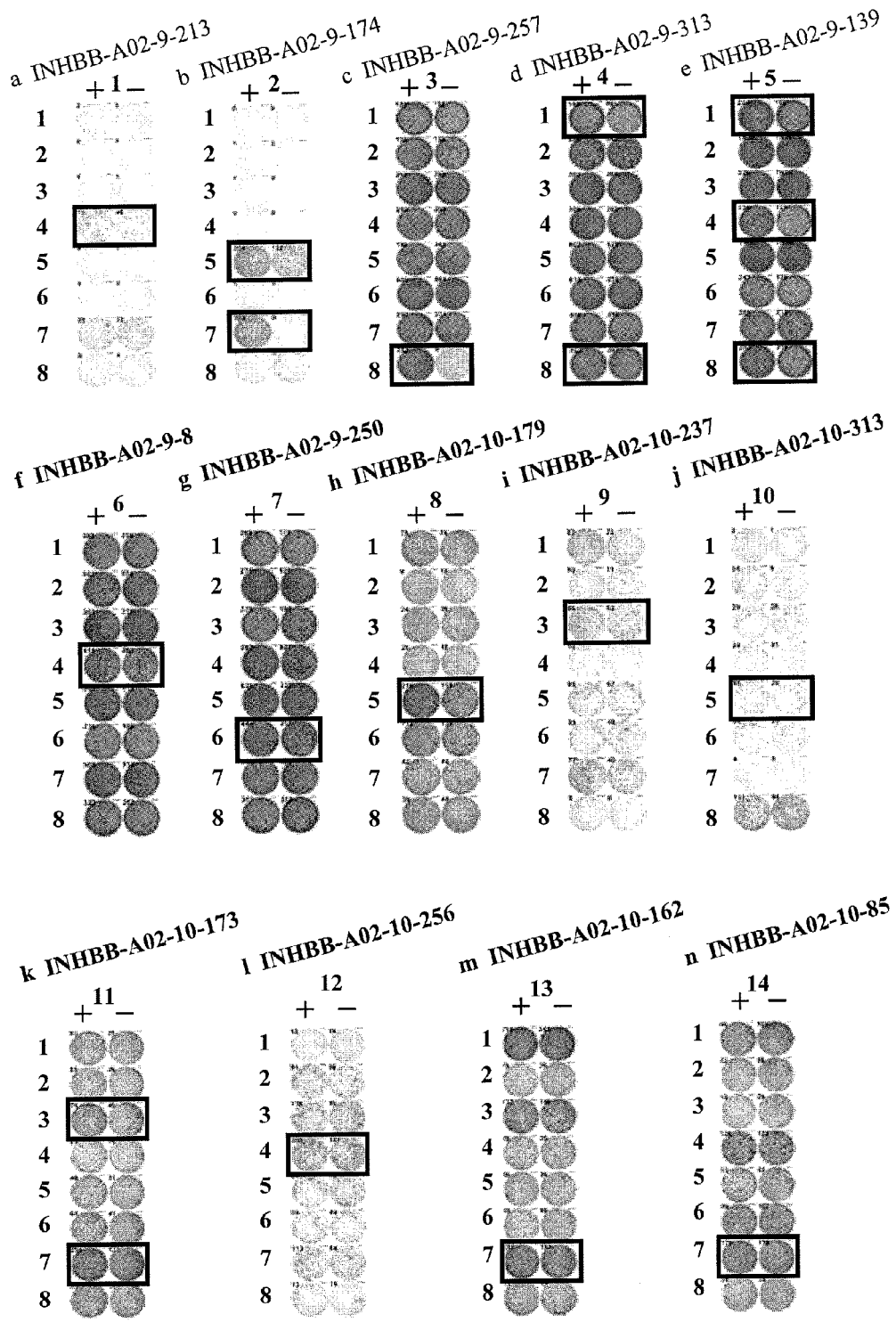

FIG. 10 includes a series of photographs, (a)-(n), depicting the results of IFN-gamma ELISPOT assay on CTLs that were induced with peptides derived from INHBB. The CTLs in well #4 stimulated with INHBB-A02-9-213 (SEQ ID NO: 143) (a), well #5 and #7 stimulated with INHBB-A02-9-174 (SEQ ID NO: 147) (b), well #8 stimulated with INHBB-A02-9-257 (SEQ ID NO: 148) (c), well #1 and #8 stimulated with INHBB-A02-9-313 (SEQ ID NO: 149) (d), well #1, #4 and #8 stimulated with INHBB-A02-9-139 (SEQ ID NO: 150) (e), well #4 stimulated with INHBB-A02-9-8 (SEQ ID NO: 152) (f), well #6 stimulated with INHBB-A02-9-250 (SEQ ID NO: 153) (g), well #5 stimulated with INHBB-A02-10-179 (SEQ ID NO: 154) (h), well #3 stimulated with INHBB-A02-10-237 (SEQ ID NO: 156) (i), well #5 stimulated with INHBB-A02-10-313 (SEQ ID NO: 160) (j), well #3 and #7 stimulated with INHBB-A02-10-173 (SEQ ID NO: 161) (k), well #4 stimulated with INHBB-A02-10-256 (SEQ ID NO: 162) (l), well #7 stimulated with INHBB-A02-10-162 (SEQ ID NO: 163) (m) and well #7 stimulated with INHBB-A02-10-85 (SEQ ID NO: 166) (n) showed potent IFN-gamma production as compared with the control respectively. In the figures, "+" indicates that the target cells in the well were pulsed with the appropriate peptide, and "−" indicates that the target cells had not been pulsed with any peptides.

FIG. 11

Figure 11:
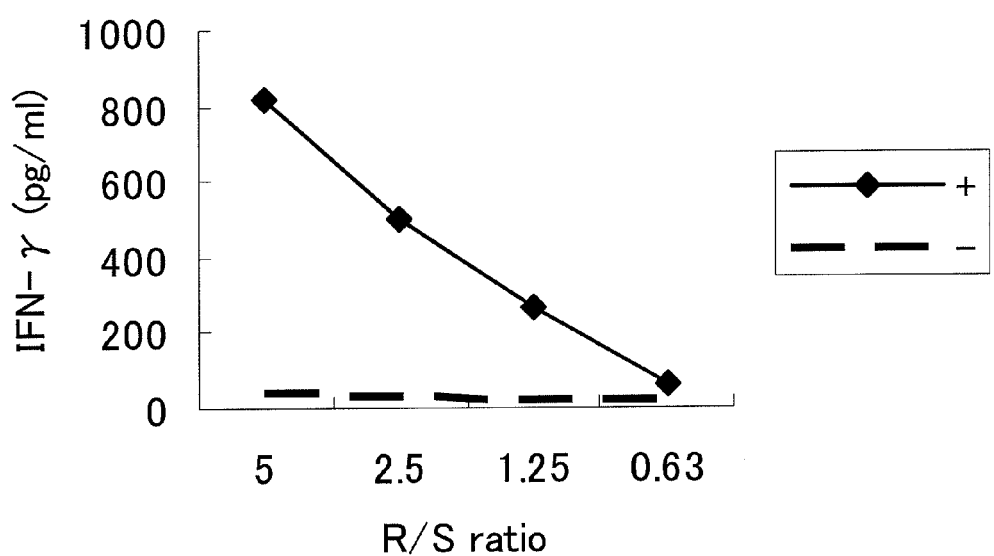

FIG. 11 depicts a line graph showing the results of establishment of CTL lines stimulated with INHBB-A02-9-174 (SEQ ID NO: 147) with IFN-gamma ELISA assay. The depicted results demonstrate that CTL line established by stimulation with the peptide showed potent IFN-gamma production as compared with the control. In the figures, "+" indicates that the target cells were pulsed with the appropriate peptide and "−" indicates that the target cells had not been pulsed with any peptides.

DETAILED DESCRIPTION OF THE INVENTION

The words "a", "an", and "the" as used herein mean "at least one" unless otherwise specifically indicated.

Unless otherwise defined, all technical and scientific terms used herein have the same meaning as commonly understood by one of ordinary skill in the art to which this invention belongs.

The present invention is based in part on the discovery of applicable targets of immunotherapy. Identification of new TAAs, particularly those that induce potent and specific anti-tumor immune responses, warrants further development of the clinical application of the peptide vaccination strategy in various types of cancer (Boon T et al., (1996) J Exp Med 183: 725-9.; van der Bruggen P et al., (1991) Science 254: 1643-7.; Brichard V et al., (1993) J Exp Med 178: 489-95.; Kawakami Y et al., (1994) J Exp Med 180: 347-52.; Shichijo S et al., (1998) J Exp Med 187:277-88.; Chen Y T et al., (1997) Proc. Natl. Acd. Sci. USA, 94: 1914-8.; Harris C C, (1996) J Natl Cancer Inst 88:1442-55.; Butterfield L H et al., (1999) Cancer Res 59:3134-42.; Vissers J L et al., (1999) Cancer Res 59: 5554-9.; van der Burg S H et al., (1996) J. Immunol 156:3308-14.; Tanaka F et al., (1997) Cancer Res 57:4465-8.; Fujie T et al., (1999) Int J Cancer 80:169-72.; Kikuchi M et al., (1999) Int J Cancer 81: 459-66.; Oiso M et al., (1999) Int J Cancer 81:387-94.). Because TAAs have often no immunogenicity, discovery of fitting targets is extremely important issue.

As noted above,

CDH3 (GenBank Accession No. NM_001793; SEQ ID Nos. 1, 2),

EPHA4 (GenBank Accession No. L36645; SEQ ID Nos. 3, 4),

ECT2 (GenBank Accession No. AY376439; SEQ ID Nos. 5, 6),

HIG2 (GenBank Accession No. NM_013332; SEQ ID Nos. 7, 8)

INHBB (GenBank Accession No. NM_002193; SEQ ID Nos. 9, 435, 10, 436),

KIF20A (GenBank Accession No. NM_005733; SEQ ID Nos. 11, 12),

KNTC2 (GenBank Accession No. AF017790; SEQ ID Nos. 13, 14),

TTK (GenBank Accession No. NM_003318; SEQ ID Nos. 15, 16) and

URLC10 (GenBank Accession No. NM_017527; SEQ ID Nos. 17, 18) were previously identified as over-expressed in various cancers using cDNA microarray technologies.

In the present invention, peptides derived from CDH3, EPHA4, ECT2, HIG2, INHBB, KIF20A, KNTC2, TTK or URLC10 are shown to be TAA epitopes restricted by HLA-A24 and HLA-A2 (HLA-A02), an HLA allele commonly found in the Japanese and Caucasian populations. Specifically, using their binding affinities to HLA-A24 or HLA-A2 (HLA-A02), candidates of HLA-A24 or HLA-A2 (HLA-A02) binding peptides derived from CDH3, EPHA4, ECT2, HIG2, INHBB, KIF20A, KNTC2, TTK or URLC10 were identified. After the in vitro stimulation of T-cells by dendritic cells (DCs) loaded with these peptides, CTLs were successfully established using the following peptides.

CDH3-A24-9-513 (SEQ ID NO: 19),
CDH3-A24-9-406 (SEQ ID NO: 22),
CDH3-A24-10-807 (SEQ ID NO: 30),
CDH3-A24-10-332 (SEQ ID NO: 34),
CDH3-A24-10-655 (SEQ ID NO: 344),
CDH3-A24-10-470 (SEQ ID NO: 358),
EphA4-A24-9-453 (SEQ ID NO: 41),
EphA4-A24-9-5 (SEQ ID NO: 44),
EphA4-A24-9-869 (SEQ ID NO: 46),
EphA4-A24-9-420 (SEQ ID NO: 48),
EphA4-A24-10-24 (SEQ ID NO: 78),
EphA4-A02-9-501 (SEQ ID NO: 376),
EphA4-A02-9-165 (SEQ ID NO: 379),
ECT2-A24-9-515 (SEQ ID NO: 80),
ECT2-A24-10-40 (SEQ ID NO: 100),
ECT2-A24-10-101 (SEQ ID NO: 101),
HIG2-A24-9-19 (SEQ ID NO: 110),
HIG2-A24-9-22 (SEQ ID NO: 111),
HIG2-A24-9-8 (SEQ ID NO: 387),
HIG2-A24-10-7 (SEQ ID NO: 112),
HIG2-A24-10-18 (SEQ ID NO: 394),
HIG2-A02-9-8 (SEQ ID NO: 114),
HIG2-A02-9-15 (SEQ ID NO: 116),
HIG2-A02-9-4 (SEQ ID NO: 117),
HIG2-A02-10-8 (SEQ ID NO: 121),
INHBB-A24-9-180 (SEQ ID NO: 395),
INHBB-A24-10-180 (SEQ ID NO: 133),
INHBB-A24-10-305 (SEQ ID NO: 135),
INHBB-A24-10-7 (SEQ ID NO: 137),
INHBB-A24-10-212 (SEQ ID NO: 426),
INHBB-A02-9-213 (SEQ ID NO: 143),
INHBB-A02-9-174 (SEQ ID NO: 147),
INHBB-A02-9-257 (SEQ ID NO: 148),
INHBB-A02-9-313 (SEQ ID NO: 149),
INHBB-A02-9-139 (SEQ ID NO: 150),
INHBB-A02-9-8 (SEQ ID NO: 152),
INHBB-A02-9-250 (SEQ ID NO: 153),
INHBB-A02-10-179 (SEQ ID NO: 154),
INHBB-A02-10-237 (SEQ ID NO: 156),
INHBB-A02-10-313 (SEQ ID NO: 160),
INHBB-A02-10-173 (SEQ ID NO: 161),
INHBB-A02-10-256 (SEQ ID NO: 162),
INHBB-A02-10-162 (SEQ ID NO: 163)
INHBB-A02-10-85 (SEQ ID NO: 166).
KIF20A-A24-9-305 (SEQ ID NO: 174),
KIF20A-A24-9-383 (SEQ ID NO: 178),
KIF20A-A24-10-304 (SEQ ID NO: 186),
KIF20A-A24-10-66 (SEQ ID NO: 194),
KNTC2-A24-9-309 (SEQ ID NO: 196),
KNTC2-A24-9-124 (SEQ ID NO: 202),
KNTC2-A24-9-154 (SEQ ID NO: 210),
KNTC2-A24-9-150 (SEQ ID NO: 213),
KNTC2-A24-10-452 (SEQ ID NO: 214),
KNTC2-A24-10-227 (SEQ ID NO: 217),
KNTC2-A24-10-273 (SEQ ID NO: 223),
TTK-A02-9-462 (SEQ ID NO: 227),
TTK-A02-9-547 (SEQ ID NO: 228),
TTK-A02-9-719 (SEQ ID NO: 233),
TTK-A02-10-462 (SEQ ID NO: 254),
URLC-A02-9-206 (SEQ ID NO: 271),
URLC-A02-9-212 (SEQ ID NO: 272) and
URLC-A02-10-211 (SEQ ID NO: 288)

These peptides are epitope peptides of each TAA restricted by HLA-A24 or HLA-A2 (HLA-A02). Since these antigens are over-expressed in most cancers and are associated with tumor cell proliferation, they find utility as immunotherapeutic targets against cancers. Exemplary cancers include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Accordingly, the present invention further provides methods of treating or preventing a disease associated with the over-expression of CDH3, EPHA4, ECT2, HIG2, INHBB, KIF20A, KNTC2, TTK and/or URLC10, e.g. cancers in a subject, such methods including the steps of administering to the subject an immunogenic peptide of less than about 40 amino acids, often less than about 20 amino acids, usually less than about 15 amino acids and having the amino acid sequence of SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288.

Alternatively, the immunogenic peptide may have an amino acid sequence as set forth in SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 in which 1, 2, or several (e.g., up to 5) amino acids are substituted, deleted or added, provided the resulting variant peptide retains the immunogenic activity (i.e., the ability to induce CTLs specific to cells expressing CDH3, EPHA4, ECT2, HIG2, INHBB, KIF20A, KNTC2, TTK and/or URLC10, e.g. cancers).

The number of residues to be substituted, deleted, or added is generally 5 amino acids or less, preferably 4 amino acids or less, more preferably 3 amino acids or less, even more preferably one or two amino acids. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. Furthermore the present invention provides methods for preventing post-surgery recurrence of these diseases mentioned above.

Variant peptides (i.e., peptides having an amino acid sequence modified by substituting, deleting, or adding one, two or several amino acid residues to an original amino acid sequence) are known to retain the original biological activity (Mark D F et al., (1984) Proc Natl Acad Sci USA 81: 5662-6.; Zoller M J and Smith M, (1982) Nucleic Acids Res 10:6487-500.; Dalbadie-McFarland G et al., (1982) Proc Natl Acad Sci USA 79: 6409-13.). In the context of the present invention, it is preferable that the amino acid modification results in conservation of the properties of the original amino acid side-chain (a process known as conservative amino acid substitution). Examples of properties of amino acid side chains include hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

In preferred embodiments, the immunogenic peptide is a nonapeptide (9-mer) or a decapeptide (10-mer).

The present invention further provides a method of inducing anti-tumor immunity for a disease associated with the over-expression of CDH3, EPHA4, ECT2, HIG2, INHBB, KIF20A, KNTC2, TTK and/or URLC10, e.g. cancers, in a subject, such a method including the steps of administering an immunogenic peptide of the present invention, namely one having the amino acid sequence of SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288, or a variant thereof (i.e., including 1, 2, or several (e.g., up to 5) amino acid substitutions, deletions, or additions) to the subject in need thereof. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

In the context of the present invention, the subject is preferably a mammal Exemplary mammals include, but are not limited to, e.g., a human, non-human primate, mouse, rat, dog, cat, horse, or cow.

In the present invention, the peptide can be administered to a subject via an in vivo or ex vivo protocol. Furthermore, the present invention also provides use of nonapeptide or decapeptide selected from peptides having the amino acid sequence of SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 (and variants thereof) for manufacturing an immunogenic composition for treating or preventing a disease associated with the over-expression of CDH3, EPHA4, ECT2, HIG2, INHBB, KIF20A, KNTC2, TTK and/or URLC10, e.g. cancers. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Homology analyses of the following peptides demonstrate that they do not have significant homology with the peptides derived from any known human gene products.

CDH3-A24-9-513 (SEQ ID NO: 19),
CDH3-A24-9-406 (SEQ ID NO: 22),
CDH3-A24-10-807 (SEQ ID NO: 30),
CDH3-A24-10-332 (SEQ ID NO: 34),
CDH3-A24-10-655 (SEQ ID NO: 344),
CDH3-A24-10-470 (SEQ ID NO: 358),
EphA4-A24-9-453 (SEQ ID NO: 41),
EphA4-A24-9-5 (SEQ ID NO: 44),
EphA4-A24-9-869 (SEQ ID NO: 46),
EphA4-A24-9-420 (SEQ ID NO: 48),
EphA4-A24-10-24 (SEQ ID NO: 78),
EphA4-A02-9-501 (SEQ ID NO: 376),
EphA4-A02-9-165 (SEQ ID NO: 379),
ECT2-A24-9-515 (SEQ ID NO: 80),
ECT2-A24-10-40 (SEQ ID NO: 100),
ECT2-A24-10-101 (SEQ ID NO: 101),
HIG2-A24-9-19 (SEQ ID NO: 110),
HIG2-A24-9-22 (SEQ ID NO: 111),
HIG2-A24-9-8 (SEQ ID NO: 387),
HIG2-A24-10-7 (SEQ ID NO: 112),
HIG2-A24-10-18 (SEQ ID NO: 394),
HIG2-A02-9-8 (SEQ ID NO: 114),
HIG2-A02-9-15 (SEQ ID NO: 116),
HIG2-A02-9-4 (SEQ ID NO: 117),
HIG2-A02-10-8 (SEQ ID NO: 121),
INHBB-A24-9-180 (SEQ ID NO: 395),
INHBB-A24-10-180 (SEQ ID NO: 133),
INHBB-A24-10-305 (SEQ ID NO: 135),
INHBB-A24-10-7 (SEQ ID NO: 137),
INHBB-A24-10-212 (SEQ ID NO: 426),
INHBB-A02-9-213 (SEQ ID NO: 143),
INHBB-A02-9-174 (SEQ ID NO: 147),
INHBB-A02-9-257 (SEQ ID NO: 148),
INHBB-A02-9-313 (SEQ ID NO: 149),
INHBB-A02-9-139 (SEQ ID NO: 150),
INHBB-A02-9-8 (SEQ ID NO: 152),
INHBB-A02-9-250 (SEQ ID NO: 153),
INHBB-A02-10-179 (SEQ ID NO: 154),
INHBB-A02-10-237 (SEQ ID NO: 156),
INHBB-A02-10-313 (SEQ ID NO: 160),
INHBB-A02-10-173 (SEQ ID NO: 161),
INHBB-A02-10-256 (SEQ ID NO: 162),
INHBB-A02-10-162 (SEQ ID NO: 163)
INHBB-A02-10-85 (SEQ ID NO: 166).
KIF20A-A24-9-305 (SEQ ID NO: 174),
KIF20A-A24-9-383 (SEQ ID NO: 178),
KIF20A-A24-10-304 (SEQ ID NO: 186),
KIF20A-A24-10-66 (SEQ ID NO: 194),
KNTC2-A24-9-309 (SEQ ID NO: 196),
KNTC2-A24-9-124 (SEQ ID NO: 202),
KNTC2-A24-9-154 (SEQ ID NO: 210),
KNTC2-A24-9-150 (SEQ ID NO: 213),
KNTC2-A24-10-452 (SEQ ID NO: 214),
KNTC2-A24-10-227 (SEQ ID NO: 217),
KNTC2-A24-10-273 (SEQ ID NO: 223),
TTK-A02-9-462 (SEQ ID NO: 227),
TTK-A02-9-547 (SEQ ID NO: 228),
TTK-A02-9-719 (SEQ ID NO: 233),
TTK-A02-10-462 (SEQ ID NO: 254),
URLC-A02-9-206 (SEQ ID NO: 271),
URLC-A02-9-212 (SEQ ID NO: 272) and
URLC-A02-10-211 (SEQ ID NO: 288)

Accordingly, the possibility of unknown or undesirable immune responses with immunotherapy against these molecules is significantly reduced.

Regarding HLA antigens, the data presented here demonstrate that the uses of A-24 type or A-2 type antigens (which are said to be highly expressed among the Japanese) are favorable for obtaining effective results. The uses of subtypes such as A-2402 and A-0201 are even more preferable. Typically, in the clinic, the type of HLA antigen of the patient requiring treatment is investigated in advance, which, in turn, enables the selection of appropriate peptides having high levels of binding affinity to the patient antigen, or having cytotoxic T cell (CTL) inducibility by antigen presentation. Furthermore, in order to obtain peptides having high binding affinity and CTL inducibility, substitution, deletion, or addition of 1, 2, or several (e.g., up to 5) amino acids may be performed based on the amino acid sequence of the naturally occurring CDH3, EPHA4, ECT2, HIG2, INHBB, KIF20A, KNTC2, TTK and URLC10 partial peptide. Herein, the term "several" means refers to 5 or less, more preferably 3 or less. Furthermore, in addition to peptides that are naturally displayed, since the regularity of the sequences of peptides displayed by binding to HLA antigens is already known (Kubo R T, et al., (1994) J. Immunol., 152, 3913-24.; Rammensee H G, et al., (1995) Immunogenetics. 41:178-228.; Kondo A, et al., (1995) J. Immunol. 155:4307-12.), modifications based on such regularity can be performed on the immunogenic peptides of the invention. For example, peptides possessing high HLA-24 binding affinity in which the second amino acid from the N terminus substituted with phenylalanine, tyrosine, methionine, or tryptophan may be favorably used. Likewise, peptides whose C-terminal amino acid is substituted with phenylalanine, leucine, isoleucine, tryptophan, or methionine may also be used favorably. On the other hand, peptides possessing high HLA-A2 (HLA-A02) binding affinity in which the second amino acid from the N terminus substituted with leucine or methionine, and peptides whose C-terminal amino acid is substituted with valine or leucine may be used favorably. The substitution is performed not only at the terminus amino acids but also at the position of potential TCR recognition of peptides. Several studies have demonstrated that amino acid substitutions in a peptide can be equal to or better than the original, for example CAP1, $p53_{(264-222)}$, Her-2/neu$_{(369-377)}$ or gp100$_{(209-217)}$ (Zaremba et al. Cancer Res. 57, 4570-4577, 1997, T. K. Hoffmann et al. J Immunol. (2002) Feb. 1; 168(3):1338-47., S. O. Dionne et al. Cancer Immunol immunother. (2003) 52: 199-206 and S. O. Dionne et al. Cancer Immunology, Immunotherapy (2004) 53, 307-314). Furthermore, 1 to 2 amino acids may be added to the N terminus and/or C terminus of the peptide.

However, when the peptide sequence is identical to a portion of the amino acid sequence of an endogenous or exogenous protein having a different function, side effects such as autoimmune disorders or allergic symptoms against specific substances may be induced. Therefore, it is preferable to avoid the situation wherein the immunogenic sequence matches the amino acid sequence of a known protein. This situation may be avoided by performing a homology search using available databases. If homology searches confirm that peptides in which 1, 2 or several different amino acids do not exist in nature, then the danger that modifications of the above-mentioned amino acid sequence that, for example, increase the binding affinity with HLA antigens, and/or increase the CTL inducibility can be avoided.

Although peptides having high binding affinity to the HLA antigens as described above are expected to be highly effective as cancer vaccines, the candidate peptides, which are selected according to the presence of high binding affinity as an indicator, must be examined for the actual presence of CTL inducibility. CTL inducibility may be routinely confirmed by inducing antigen-presenting cells carrying human MHC antigens (for example, B-lymphocytes, macrophages, and dendritic cells), or more specifically dendritic cells derived from human peripheral blood mononuclear leukocytes, and, after stimulation with the peptide of interest, mixing with CD8-positive cells and measuring the cytotoxic activity against the target cells. As the reaction system, transgenic animals produced to express a human HLA antigen (for example, those described in BenMohamed L, et al., (2000) Hum. Immunol.; 61(8):764-79 Related Articles, Books, Linkout.) may be used. For example, the target cells can be radio-labeled with $^{51}$Cr and such, and cytotoxic activity can be calculated from radioactivity released from the target cells. Alternatively, it can be examined by measuring IFN-gamma produced and released by CTL in the presence of antigen-presenting cells that carry immobilized peptides, and visualizing the inhibition zone on the media using anti-IFN-gamma monoclonal antibodies.

As a result of examining the CTL inducibility of peptides as described above, it was discovered that those peptides having high binding affinity to an HLA antigen did not necessarily have high inducibility. However, nonapeptides or decapeptides selected from the group of peptides having the amino acid sequences indicated by the following peptides showed particularly high CTL inducibility.

CDH3-A24-9-513 (SEQ ID NO: 19),
CDH3-A24-9-406 (SEQ ID NO: 22),
CDH3-A24-10-807 (SEQ ID NO: 30),
CDH3-A24-10-332 (SEQ ID NO: 34),
CDH3-A24-10-655 (SEQ ID NO: 344),
CDH3-A24-10-470 (SEQ ID NO: 358),
EphA4-A24-9-453 (SEQ ID NO: 41),
EphA4-A24-9-5 (SEQ ID NO: 44),
EphA4-A24-9-869 (SEQ ID NO: 46),
EphA4-A24-9-420 (SEQ ID NO: 48),
EphA4-A24-10-24 (SEQ ID NO: 78),
EphA4-A02-9-501 (SEQ ID NO: 376),
EphA4-A02-9-165 (SEQ ID NO: 379),
ECT2-A24-9-515 (SEQ ID NO: 80),
ECT2-A24-10-40 (SEQ ID NO: 100),
ECT2-A24-10-101 (SEQ ID NO: 101),
HIG2-A24-9-19 (SEQ ID NO: 110),
HIG2-A24-9-22 (SEQ ID NO: 111),
HIG2-A24-9-8 (SEQ ID NO: 387),
HIG2-A24-10-7 (SEQ ID NO: 112),
HIG2-A24-10-18 (SEQ ID NO: 394),
HIG2-A02-9-8 (SEQ ID NO: 114),
HIG2-A02-9-15 (SEQ ID NO: 116),
HIG2-A02-9-4 (SEQ ID NO: 117),
HIG2-A02-10-8 (SEQ ID NO: 121),
INHBB-A24-9-180 (SEQ ID NO: 395),
INHBB-A24-10-180 (SEQ ID NO: 133),
INHBB-A24-10-305 (SEQ ID NO: 135),
INHBB-A24-10-7 (SEQ ID NO: 137),
INHBB-A24-10-212 (SEQ ID NO: 426),
INHBB-A02-9-213 (SEQ ID NO: 143),
INHBB-A02-9-174 (SEQ ID NO: 147),
INHBB-A02-9-257 (SEQ ID NO: 148),
INHBB-A02-9-313 (SEQ ID NO: 149),
INHBB-A02-9-139 (SEQ ID NO: 150),
INHBB-A02-9-8 (SEQ ID NO: 152),
INHBB-A02-9-250 (SEQ ID NO: 153),
INHBB-A02-10-179 (SEQ ID NO: 154),
INHBB-A02-10-237 (SEQ ID NO: 156),
INHBB-A02-10-313 (SEQ ID NO: 160),
INHBB-A02-10-173 (SEQ ID NO: 161),
INHBB-A02-10-256 (SEQ ID NO: 162),
INHBB-A02-10-162 (SEQ ID NO: 163)
INHBB-A02-10-85 (SEQ ID NO: 166).
KIF20A-A24-9-305 (SEQ ID NO: 174),
KIF20A-A24-9-383 (SEQ ID NO: 178),
KIF20A-A24-10-304 (SEQ ID NO: 186),
KIF20A-A24-10-66 (SEQ ID NO: 194),
KNTC2-A24-9-309 (SEQ ID NO: 196),

KNTC2-A24-9-124 (SEQ ID NO: 202),
KNTC2-A24-9-154 (SEQ ID NO: 210),
KNTC2-A24-9-150 (SEQ ID NO: 213),
KNTC2-A24-10-452 (SEQ ID NO: 214),
KNTC2-A24-10-227 (SEQ ID NO: 217),
KNTC2-A24-10-273 (SEQ ID NO: 223),
TTK-A02-9-462 (SEQ ID NO: 227),
TTK-A02-9-547 (SEQ ID NO: 228),
TTK-A02-9-719 (SEQ ID NO: 233),
TTK-A02-10-462 (SEQ ID NO: 254),
URLC-A02-9-206 (SEQ ID NO: 271),
URLC-A02-9-212 (SEQ ID NO: 272) and
URLC-A02-10-211 (SEQ ID NO: 288)

As noted above, the present invention provides peptides having cytotoxic T cell inducibility, namely those having the amino acid sequence of SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 or a variant thereof (i.e., those in which 1, 2, or several amino acids are substituted, deleted, or added).

It is preferable that the amino acid sequences composed of 9 or 10 amino acids indicated in SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 or a variant thereof do not match an amino acid sequence associated with another endogenous protein.

In particular, amino acid substitution to leucine or methionine at the second amino acid from the N terminus, amino acid substitution to valine or leucine at the C-terminal amino acid, and amino acid addition of 1 to 2 amino acids at the N terminus and/or C terminus are examples of preferred variants.

One of skill in the art will recognize that in addition to amino acid substitutions and additions, immunologically active fragments of the peptides may also be used in the methods of the invention. Methods for determining active fragments are well known in the art. CTL clones obtained by stimulation by these modified peptides can recognize the original peptides and cause damage for cells expressing the original peptides.

Peptides of the present invention can be prepared using well known techniques. For example, the peptides can be prepared synthetically, using either recombinant DNA technology or chemical synthesis. Peptides of the present invention may be synthesized individually or as longer polypeptides composed of two or more peptides. The peptides of the present invention are preferably isolated, i.e., substantially free of other naturally occurring host cell proteins and fragments thereof.

The peptides of the present invention may contain modifications, such as glycosylation, side chain oxidation, or phosphorylation; so long as the modifications do not destroy the biological activity of the peptides as described herein, namely the ability to binding to an HLA antigen and induce CTL. Other modifications include incorporation of D-amino acids or other amino acid mimetics that can be used, for example, to increase the serum half life of the peptides.

Moreover, this invention may contain a method of screening for a peptide which 1, 2, or several amino acids are substituted, wherein said peptide comprises an amino acid sequence selected from the group consisting of SEQ ID NO: 19, 22, 30, 34, 344, 358, 41, 44, 46, 48, 78, 80, 100, 101, 110, 111, 387, 112, 394, 395, 133, 135, 137, 426, 174, 178, 186, 194, 196, 202, 210, 213, 214, 217 or 223, said method comprising the steps of:

(a) conforming no significant sequence homology to the entire sequence of 1, 2 or several amino acids substitute;

(b) measuring the CTL inducibility of the candidate substitute peptide; and (c) selecting the peptide which CTL inducibility is same to or higher than the original peptide.

Alternatively, this invention may contain a method of screening for a peptide which 1, 2, or several amino acids are substituted, wherein said peptide comprises an amino acid sequence selected from the group consisting of SEQ ID NO: 376, 379, 114, 116, 117, 121, 143, 147, 148, 149, 150, 152, 153, 154, 156, 160, 161, 162, 163, 166, 227, 228, 233, 254, 271, 272 or 288, said method comprising the steps of:

(a) conforming no significant sequence homology to the entire sequence of 1, 2 or several amino acids substitute;

(b) measuring the CTL inducibility of the candidate substitute peptide; and (c) selecting the peptide which CTL inducibility is same to or higher than the original peptide.

For example, in preferred embodiments, the present invention provides a method of identifying for a peptide having an ability to induce CTL against cells expressing at least one tumor-associated antigen, wherein the tumor-associated antigen is antigen selected from the group consisting of CDH3, EPHA4, ECT2, HIG2, INHBB, KIF20A, KNTC2, TTK and URLC10, said method comprising the steps of:

(i) providing or generating at least one candidate sequence which consists of an amino acid sequence modified by substituting, deleting, or adding one, two or several amino acid residues to an original amino acid sequence, wherein the original amino acid sequence is selected from the group consisting of SEQ ID NO: 19, 22, 30, 34, 344, 358, 41, 44, 46, 48, 78, 80, 100, 101, 110, 111, 387, 112, 394, 395, 133, 135, 137, 426, 174, 178, 186, 194, 196, 202, 210, 213, 214, 217 or 223;

(ii) selecting the candidate sequence that does not have substantial significant homology with the peptides derived from any known human gene products other than said tumor-associated antigens;

(iii) contacting a peptide consisting of the candidate sequence selected in step (ii) with antigen presenting cells;

(iv) contacting the antigen presenting cells of step (iii) with T-cells to evaluate the ability of the peptide to stimulate the T-cells; and (v) identifying the peptide of which CTL inducibility is same to or higher than a peptide consisting of the original amino acid sequence.

Alternatively, in preferred embodiments, the present invention provides a method of identifying for a peptide having an ability to induce CTL against cells expressing at least one tumor-associated antigen, wherein the tumor-associated antigen is antigen selected from the group consisting of CDH3, EPHA4, ECT2, HIG2, INHBB, KIF20A, KNTC2, TTK and URLC10, said method comprising the steps of:

(i) providing or generating at least one candidate sequence which consists of an amino acid sequence modified by substituting, deleting, or adding one, two or several amino acid residues to an original amino acid sequence, wherein the original amino acid sequence is selected from the group consisting of SEQ ID NO: 376, 379, 114, 116, 117, 121, 143, 147, 148, 149, 150, 152, 153, 154, 156, 160, 161, 162, 163, 166, 227, 228, 233, 254, 271, 272 or 288;

(ii) selecting the candidate sequence that does not have substantial significant homology with the peptides derived from any known human gene products other than said tumor-associated antigens;

(iii) contacting a peptide consisting of the candidate sequence selected in step (ii) with antigen presenting cells;

(iv) contacting the antigen presenting cells of step (iii) with T-cells to evaluate the ability of the peptide to stimulate the T-cells; and (v) identifying the peptide of which CTL inducibility is same to or higher than a peptide consisting of the original amino acid sequence.

Preferably, the amino acid is substituted for a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids. In the present invention, substantial significant homology is, for example, more than 90%, preferably 95%, more preferably 99% or 100% identity with a known human gene product to be compared.

The peptides of this invention can be prepared as a combination, which includes two or more of peptides of the invention, for use as a vaccine for a disease associated with the over-expression of CDH3, EPHA4, ECT2, HIG2, INHBB, KIF20A, KNTC2, TTK and/or URLC10, e.g. cancers, such a vaccine inducing CTL in vivo. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. The peptides may be in a cocktail or may be conjugated to each other using standard techniques. For example, the peptides can be expressed as a single polypeptide sequence. The peptides in the combination may be the same or different.

By administering the peptides of this invention, the peptides are presented at a high density on the HLA antigens of antigen-presenting cells, which, in turn, induces CTLs that specifically react toward the complex formed between the displayed peptide and the HLA antigen. Alternatively, antigen-presenting cells having immobilized the peptides of this invention on their cell surface, obtained by removing dendritic cells from the subjects, may be stimulated by the peptides of this invention. Re-administration of these cells to the respective subjects induces CTL, and, as a result, aggressiveness towards the target cells can be increased.

More specifically, the present invention provides drugs for treating and/or preventing proliferation, metastasis, and such of a disease associated with the over-expression of CDH3, EPHA4, ECT2, HIG2, INHBB, KIF20A, KNTC2, TTK and/or URLC10, e.g. cancers, which include one or more of peptides of the present invention, or a polynucleotide encoding the peptides. The peptides or polynucleotides of the present invention find particular utility in the treatment of a disease associating CDH3, EPHA4, ECT2, HIG2, INHBB, KIF20A, KNTC2, TTK and/or URLC10, e.g. cancers. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The peptides of this invention can be administered to a subject directly, as a pharmaceutical composition that has been formulated by conventional formulation methods. In such cases, in addition to the peptides of this invention, carriers, excipients, and such that are ordinarily used for drugs can be included as appropriate, without particular limitations. The immunogenic compositions of this invention may be used for treatment and prevention of a disease associated with the over-expression of CDH3, EPHA4, ECT2, HIG2, INHBB, KIF20A, KNTC2, TTK and/or URLC10, e.g. cancers. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The immunogenic compositions for treatment and/or prevention of a disease associated with the over-expression of CDH3, EPHA4, ECT2, HIG2, INHBB, KIF20A, KNTC2, TTK and/or URLC10, e.g. cancers, which include as the active ingredient one or more peptides of the present invention, can further include an adjuvant so that cellular immunity will be established effectively. Alternatively, they may be administered with other active ingredients, such as anti-cancer agents.

The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. Suitable formulations include granules. Suitable adjuvants are described in the literature (Johnson A G. (1994) Clin. Microbiol. Rev., 7:277-89.).

Exemplary adjuvants include, but are not limited to, aluminum phosphate, aluminum hydroxide, and alum. Furthermore, liposome formulations, granular formulations in which the drug is bound to few-mc m diameter beads, and formulations in which a lipid is bound to the peptide may be conveniently used. The method of administration may be oral, intradermal, subcutaneous, intravenous injection, or such, and may include systemic administration or local administration to the vicinity of the targeted tumor.

The dose of the peptide(s) of this invention can be adjusted appropriately according to the disease to be treated, age of the patient, weight, method of administration, and such. Though the dosage is ordinarily 0.001 mg to 1000 mg, preferably 0.01 mg to 100 mg, more preferably 0.1 mg to 10 mg, preferably administered once in a few days to few months, one skilled in the art can readily select the appropriate dose and method of administration, as, the selection and optimization of these parameters is well within routine skill.

The present invention further provides intracellular vesicles called exosomes, which present complexes formed between the peptides of this invention and HLA antigens on their surface. Exosomes can be prepared, for example, by using the methods described in detail in Published Japanese Translation of International Publication Nos. Hei 11-510507 and 2000-512161, and are preferably prepared using antigen-presenting cells obtained from subjects who are targets of treatment and/or prevention. The exosomes of this invention can be inoculated as cancer vaccines, similarly to the peptides of this invention.

The type of HLA antigens used must match that of the subject requiring treatment and/or prevention. For example, in the Japanese population, HLA-A24 or HLA-A2 (HLA-A02), particularly HLA-A2402 or HLA-A0201, is often appropriate.

In some embodiments, the vaccine compositions of the present invention include a component which primes cytotoxic T lymphocytes. Lipids have been identified as agents capable of priming CTL in vivo against viral antigens. For example, palmitic acid residues can be attached to the epsilon- and alpha-amino groups of a lysine residue and then linked to an immunogenic peptide of the invention. The lipidated peptide can then be administered either directly, in a micelle or particle, incorporated into a liposome, or emulsified in an adjuvant. As another example of a lipid priming of CTL responses, E. coli lipoproteins, such as tripalmitoyl-S-glycerylcysteinlyseryl-serine (P3CSS), can be used to prime CTL when covalently attached to an appropriate peptide (see, e.g., Deres K, et al., (1989) Nature 342:561-4.).

The immunogenic compositions of the present invention may also include nucleic acids encoding one or more of the immunogenic peptides disclosed here. See, e.g., Wolff J A et al., (1990) Science 247:1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

The immunogenic peptides of the invention can also be expressed by viral or bacterial vectors. Examples of suitable expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another suitable vector is BCG (Bacille Calmette Guerin). BCG vectors are described in Stover C K, et al., (1991) Nature 351:456-60. A wide variety of other vectors useful for therapeutic administration or immunization e.g., adeno and adeno-associated virus vectors, retroviral vectors, *Salmonella typhi* vectors, detoxified anthrax toxin vectors, and the like, are known in the art. See, e.g., Shata M T, et al., (2000) Mol. Med. Today 6:66-71; Shedlock D J and Weiner D B., et al., (2000) J. Leukoc. Biol. 68:793-806; and Hipp J D, et al., (2000) In Vivo 14:571-85.

The present invention also provides methods of inducing antigen-presenting cells using one or more peptides of this invention. The antigen-presenting cells can be induced by inducing dendritic cells from the peripheral blood monocytes and then contacting (stimulating) them with one or more peptides of this invention in vitro, ex vivo or in vivo. When peptides of the present invention are administered to the subjects, antigen-presenting cells that have the peptides of this invention immobilized to them are induced in the body of the subject. Alternatively, after immobilizing the peptides of this invention to the antigen-presenting cells, the cells can be administered to the subject as a vaccine. For example, the ex vivo administration may include the steps of:

a: collecting antigen-presenting cells from a subject, and b: contacting the antigen-presenting cells of step a with a peptide of the present invention.

Alternatively, according to the present invention, use of the peptides of this invention for manufacturing a pharmaceutical composition inducing antigen-presenting cells is provided. Further, the present invention also provides the peptide of the present invention for inducing antigen-presenting cells. The antigen-presenting cells obtained by step b can be administered to the subject as a vaccine.

This invention also provides a method for inducing antigen-presenting cells having a high level of cytotoxic T cell inducibility, in which the method includes the step of transferring genes composed of polynucleotide(s) encoding one or more peptides of this invention to antigen-presenting cells in vitro. The introduced genes may be in the form of DNAs or RNAs. For the method of introduction, without particular limitations, various methods conventionally performed in this field, such as lipofection, electroporation, and calcium phosphate method may be suitably used. More specifically, transfection may be performed as described in Reeves M E, et al., (1996) Cancer Res., 56:5672-7.; Butterfield L H, et al., (1998) J. Immunol., 161:5607-13.; Boczkowski D, et al., (1996) J. Exp. Med., 184:465-72.; Published Japanese Translation of International Publication No. 2000-509281. By transferring the gene into antigen-presenting cells, the gene undergoes transcription, translation, and such in the cell, and then the obtained protein is processed by MHC Class I or Class II, and proceeds through a presentation pathway to present partial peptides.

The present invention further provides methods for inducing CTL using one or more peptides of this invention. When the peptides of this invention are administered to a subject, CTL are induced in the body of the subject, and the strength of the immune system targeting the cells expressing CDH3, EPHA4, ECT2, HIG2, INHBB, KIF20A, KNTC2, TTK and/or URLC10, e.g. cancer cells in the tumor tissues is thereby enhanced.

The cancers contemplated include, but are not limited to bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. Alternatively, the peptides of the present invention may be used in the context of an ex vivo therapeutic method, in which subject-derived antigen-presenting cells and CD8-positive cells or peripheral blood mononuclear leukocytes are contacted (stimulated) with one or more peptides of this invention in vitro, and, after inducing CTL, the cells are returned to the subject. For example, the method may include the steps of:

a: collecting antigen-presenting cells from a subject, b: contacting the antigen-presenting cells of step a with a peptide of the present invention, c: mixing the antigen-presenting cells of step b with $CD^{8+}$ T cells and co-culturing so as to induce cytotoxic T-cells, and d: collecting $CD^{8+}$ T cells from the co-culture of step c.

Alternatively, according to the present invention, use of the peptides of this invention for manufacturing a pharmaceutical composition inducing CTLs is provided. Further, the present invention also provides the peptide of the present invention for inducing CTLs. The $CD^{8+}$ T cells having cytotoxic activity obtained by step d can be administered to the subject as a vaccine.

The present invention further provides isolated cytotoxic T cells induced using the peptides of this invention. The cytotoxic T cells, induced by stimulation with an antigen-presenting cell presenting one or more peptides of this invention, are preferably derived from subjects who are the target of treatment and/or prevention, and can be administered alone or in combination with other drugs, including one or more peptides of this invention or exosomes having anti-tumor activity. The obtained cytotoxic T cells act specifically against target cells presenting the peptides of this invention, or preferably the same peptide(s) used for induction. The target cells may be cells that express CDH3, EPHA4, ECT2, HIG2, INHBB, KIF20A, KNTC2, TTK and/or URLC10 endogenously, or cells that are transfected with CDH3, EPHA4, ECT2, HIG2, INHBB, KIF20A, KNTC2, TTK and/or URLC10 genes. Cells that present the peptides of this invention on the cell surface, due to stimulation with these peptides, can also become targets of attack.

The present invention also provides antigen-presenting cells presenting complexes formed between HLA antigens and one or more peptides of this invention. The antigen-presenting cells, obtained through contact with the peptides of this invention or the nucleotides encoding such peptides, are preferably derived from subjects who are the target of treatment and/or prevention, and can be administered as vaccines, alone or in combination with other drugs, including the peptides, exosomes, or cytotoxic T cells of the present invention.

The present invention also provides a composition composed of nucleic acids encoding polypeptides that are capable of forming a subunit of a T cell receptor (TCR), and methods of using the same. The TCR subunits have the ability to form TCRs that confer specificity to T cells for tumor cells presenting CDH3, EPHA4, ECT2, HIG2, INHBB, KIF20A, KNTC2, TTK or URLC10. By using the known method in the art, the nucleic acids of alpha- and beta-chain as the TCR subunits of the CTL induced with one or more peptides of this invention may be identified (WO2007/032255 and Morgan et al., J Immunol, 171, 3288 (2003)). The derivative TCRs preferably bind target cells displaying the CDH3, EPHA4, ECT2, HIG2, INHBB, KIF20A, KNTC2, TTK or URLC10 peptide with high avidity, and optionally mediate efficient killing of target cells presenting the CDH3, EPHA4, ECT2, HIG2, INHBB, KIF20A, KNTC2, TTK or URLC10 peptide in vivo and in vitro.

The nucleic acids encoding the TCR subunits can be incorporated into suitable vectors e.g. retroviral vectors. These vectors are well known in the art. The nucleic acids or the vectors containing them usefully can be transferred into a T cell, which T cell is preferably from a patient. Advantageously, the invention provides an off-the-shelf composition allowing rapid modification of a patient's own T cells (or those of another mammal) to rapidly and easily produce modified T cells having excellent cancer cell killing properties.

Also, the present invention provides CTLs which are prepared by transduction with the nucleic acids encoding the TCR subunits polypeptides binding with CDH3, EPHA4, ECT2, HIG2, INHBB, KIF20A, KNTC2, TTK or URLC10 peptide e.g. SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 in the context of HLA-A24 or HLA-A2 (HLA-A02). The transduced CTLs are capable of homing to cancer cells in vivo, and expanded by well known culturing method in vitro (e.g., Kawakami et al., J Immunol., 142, 3452-3461 (1989)). The T cells of the invention can be used to form an immunogenic composition useful in treating or preventing cancer in a patient in need of therapy or protection (WO2006/031221).

In the context of the present invention, the term "vaccine" (also referred to as an immunogenic composition) refers to a substance that induces anti-tumor immunity or suppresses cancers upon inoculation into animals. According to the present invention, polypeptides having the amino acid sequence of SEQ ID NO: 19, 22, 30, 34, 344, 358, 41, 44, 46, 48, 78, 80, 100, 101, 110, 111, 387, 112, 394, 395, 133, 135, 137, 426, 174, 178, 186, 194, 196, 202, 210, 213, 214, 217 or 223 were suggested to be HLA-A24 restricted epitope peptides and those of SEQ ID NO: 376, 379, 114, 116, 117, 121, 143, 147, 148, 149, 150, 152, 153, 154, 156, 160, 161, 162, 163, 166, 227, 228, 233, 254, 271, 272 or 288 were suggested to be HLA-A2 (HLA-A02) restricted epitope peptides that may induce potent and specific immune response against cells expressing CDH3, EPHA4, ECT2, HIG2, INHBB, KIF20A, KNTC2, TTK and/or URLC10, e.g. cancer cells expressing CDH3, EPHA4, ECT2, HIG2, INHBB, KIF20A, KNTC2, TTK and/or URLC10. The cancers contemplated include, but are not limited to bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Thus, the present invention also encompasses a method of inducing anti-tumor immunity using polypeptides having the amino acid sequence of SEQ ID NO: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 or a variant thereof (i.e., including 1, 2, or several (e.g., up to 5) amino acid substitutions, deletions, or additions). In general, anti-tumor immunity includes immune responses such as follows:

an induction of cytotoxic lymphocytes against tumors containing cells expressing CDH3, EPHA4, ECT2, HIG2, INHBB, KIF20A, KNTC2, TTK and/or URLC10, an induction of antibodies that recognize tumors containing cells expressing CDH3, EPHA4, ECT2, HIG2, INHBB, KIF20A, KNTC2, TTK and/or URLC10, and an induction of anti-tumor cytokine production.

Therefore, when a certain peptide induces any one of these immune responses upon inoculation into an animal, the peptide is decided to have anti-tumor immunity inducing effect. The induction of the anti-tumor immunity by a peptide can be detected by observing in vivo or in vitro the response of the immune system in the host against the peptide.

For example, a method for detecting the induction of cytotoxic T lymphocytes is well known. A foreign substance that enters the living body is presented to T cells and B cells by the action of antigen-presenting cells (APCs). T cells that respond to the antigen presented by APC in antigen specific manner differentiate into cytotoxic T cells (also referred to as cytotoxic T lymphocytes or CTLs) due to stimulation by the antigen, and then proliferate; this process is referred to herein as "activation" of T cells. Therefore, CTL induction by a certain peptide can be evaluated by presenting the peptide to a T cell by APC, and detecting the induction of CTL. Furthermore, APCs have the effect of activating CD4+ T cells, CD8+ T cells, macrophages, eosinophils and NK cells. Since CD4+ T cells are also important in anti-tumor immunity, the antitumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, it is well known to evaluate the degree of tumor cell damage using 3H-thymidine uptake activity or LDH (lactose dehydrogenase)-release as the indicator. Furthermore, it can be also examined by measuring IFN-gamma produced and released by CTL in the presence of antigen-presenting cells that carry immobilized peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against cells expressed CDH3, EPHA4, ECT2, HIG2, INHBB, KIF20A, KNTC2, TTK and/or URLC10 are useful as vaccines against diseases associating CDH3, EPHA4, ECT2, HIG2, INHBB, KIF20A, KNTC2, TTK and/or URLC10, e.g. cancers. Furthermore, APC that have acquired the ability to induce CTL against a disease associated with the over-expression of CDH3, EPHA4, ECT2, HIG2, INHBB, KIF20A, KNTC2, TTK and/or URLC10, e.g. cancers, by contacting with the polypeptides are useful as vaccines against the disease. Furthermore, CTL that have acquired cytotoxicity due to presentation of the polypeptide antigens by APC can be also used as vaccines against a disease associating CDH3, EPHA4, ECT2, HIG2, INHBB, KIF20A, KNTC2, TTK and/or URLC10, e.g. cancers. Such therapeutic methods for a disease associating CDH3, EPHA4, ECT2, HIG2, INHBB, KIF20A, KNTC2, TTK and/or URLC10, e.g. cancers, using anti-tumor immunity due to APC and CTL, are referred to as cellular immunotherapy. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Generally, when using a polypeptide for cellular immunotherapy, efficiency of the CTL-induction can be increased by combining a plurality of polypeptides having different structures and contacting them with DC. Therefore, when stimulating DC with protein fragments, it is advantageous to use a mixture of multiple types of fragments.

The induction of anti-tumor immunity by a polypeptide can be further confirmed by observing the induction of antibody production against tumors. For example, when antibodies against a polypeptide are induced in a laboratory animal immunized with the polypeptide, and when growth, proliferation and/or metastasis of tumor cells is suppressed by those antibodies, the polypeptide is determined to induce anti-tumor immunity.

Anti-tumor immunity can be induced by administering a vaccine of this invention, and the induction of anti-tumor immunity enables treatment and prevention of a disease associated with the over-expression of CDH3, EPHA4, ECT2, HIG2, INHBB, KIF20A, KNTC2, TTK and/or URLC10, e.g. cancers. Therapy against or prevention of the onset of a disease associated with the over-expression of CDH3, EPHA4, ECT2, HIG2, INHBB, KIF20A, KNTC2, TTK and/or URLC10, e.g. cancers, may include inhibition of the growth of cells expressing CDH3, EPHA4, ECT2, HIG2, INHBB, KIF20A, KNTC2, TTK and/or URLC10, e.g. cancer cells, involution of these cells and suppression of occurrence of these cells, e.g. cancer cells. Decrease in mortality of individuals having a disease associating CDH3, EPHA4, ECT2, HIG2, INHBB, KIF20A, KNTC2, TTK and/or URLC10, e.g. cancers, decrease of the disease markers in the blood, alleviation of detectable symptoms accompanying the disease and such are also included in the therapy or prevention of the disease, e.g. cancers. Such therapeutic and preventive effects are preferably statistically significant, for example, observed at a significance level of 5% or less, wherein the therapeutic or preventive effect of a vaccine against a disease associating CDH3, EPHA4, ECT2, HIG2, INHBB, KIF20A, KNTC2, TTK and/or URLC10, e.g. cancers, is compared to a control without vaccine administration. For example, Student's t-test, the Mann-Whitney U-test or ANOVA may be used for determining statistical significance.

In that the present invention provides a method for treating, or preventing a disease associated with the over-expression of CDH3, EPHA4, ECT2, HIG2, INHBB, KIF20A, KNTC2, TTK and/or URLC10, e.g. cancers, the therapeutic compounds or compositions may be administered prophylactically or therapeutically to subjects suffering from or at risk of (or susceptible to) developing the disease. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In the context of cancer treatment, the term "efficacious" refers to a treatment that leads to a decrease in size, prevalence or metastatic potential of cancer in a subject. When a treatment is applied prophylactically, "efficacious" means that the treatment retards or prevents occurrence of cancer or alleviates a clinical symptom of cancer. The assessment of cancer can be made using standard clinical protocols. Furthermore, the efficaciousness of a treatment may be determined in association with any known method for diagnosing or treating cancer. For example, cancer can be diagnosed histopathologically or by identifying symptomatic anomalies.

The above-mentioned peptide, having immunological activity, or a polynucleotide or vector encoding such a peptide, may be combined with an adjuvant. An adjuvant refers to a compound that enhances the immune response against the peptide when administered together (or successively) with the peptide having immunological activity. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using APC or CTL as the vaccine of this invention, a disease associated with the over-expression of CDH3, EPHA4, ECT2, HIG2, INHBB, KIF20A, KNTC2, TTK and/or URLC10, e.g. cancers, can be treated or prevented, for example, by the ex vivo method. More specifically, PBMCs of the subject receiving treatment or prevention are collected, contacted ex vivo with a peptide of the present invention. Following the induction of APC or CTL, the cells may be administered to the subject. APC can be also induced by introducing a vector encoding the peptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of diseases in other individuals.

Aspects of the present invention are described in the following examples, which are presented only to illustrate the present invention and to assist one of ordinary skill in making and using the same. The examples are not intended in any way to otherwise limit the scope of the invention.

Although methods and materials similar or equivalent to those described herein can be used in the practice or testing of the present invention, suitable methods and materials are described below.

EXAMPLES

Hereinafter, the present invention is exemplified, but not restricted, by the following Examples. However, materials, methods and such described herein only illustrate aspects of the invention and in no way are intended to limit the scope of the present invention. As such, materials, methods and such similar or equivalent to those described therein may be used in the practice or testing of the present invention.

Example 1

Materials and Methods

Cell Lines

A24-LCL cells (HLA-A24), human B-lymphoblastoid cell line, was established by transforming with Epstain-barr virus. T2 cell, COS7, A498, Caki-2 and HEK 293 were purchased from ATCC. Caki-1 and MIAPaca-2 were purchased from JCRB. PK-45P, PK-59, TE-5 and TE-6 were purchased from TKG. 293 T was purchased from GenHunter.

Candidate Selection of Peptide Derived from CDH3, EPHA4, ECT2, HIG2, INHBB, KIF20A, KNTC2, TTK and URLC10

9-mer and 10-mer peptides derived from CDH3, EPHA4, ECT2, HIG2, INHBB, KIF20A, KNTC2, TTK or URLC10 that bind to HLA-A*2402 or HLA-A*0201 molecule were predicted using the binding prediction software "BIMAS" (http://bimas.dcrt.nih.gov/cgi-bin/molbio/ken_parker_comboform) (Parker K C, et al., (1994) J Immunol.; 152(1):163-75.; Kuzushima K, et al., (2001) Blood.; 98(6):1872-81.). These peptides were synthesized by Sigma (Sapporo, Japan) according to the standard solid phase synthesis method and purified by reversed phase HPLC. The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce CTL responses against peptides presented on HLA. DCs were generated in vitro as described elsewhere (Nukaya I et al., (1999) Int. J. Cancer 80, 92-7., Tsai V et al., (1997) J. Immunol. 158:1796-802.). Briefly, peripheral blood mononuclear cells (PBMCs) isolated from a normal volunteer (HLA-A*2402 and/or HLA-A*0201) by Ficoll-Paque (Pharmacia) solution were separated by adherence to a plastic tissue culture flask (Becton Dickinson) so as to enrich them for the monocyte fraction. The monocyte-enriched population was cultured in the presence of 1000 U/ml of GM-CSF (Genzyme) and 1000 U/ml of IL-4 (Genzyme) in AIM-V (Invitrogen) containing 2% heat-inactivated autologous serum (AS). After 7 days in the culture, the cytokine-generated DCs were pulsed with 20 micro g/ml of the synthesized peptides in the presence of 3 micro g/ml of beta 2-microglobulin for 4 hrs at 20 degrees C. in AIM-V. These peptide-pulsed DCs were then inactivated by MMC (30 micro g/ml for 30 mins) and mixed at a 1:20 ratio with autologous $CD8^+$ T cells, obtained by positive selection with Dynabeads M-450 CD8 (Dynal) and DETACHa BEAD™ (Dynal). These cultures were set up in 48-well plates (Corning); each well contained $1.5 \times 10^4$ peptide-pulsed DCs, $3 \times 10^5$ $CD8^+$ T cells and 10 ng/ml of IL-7 (Genzyme) in 0.5 ml of AIM-V/2% AS. Three days later, these cultures were supplemented with IL-2 (CHIRON) to a final concentration of 20 IU/ml. On day 7 and 14, the T cells were further restimulated with the autologous peptide-pulsed DCs. The DCs were prepared each time by the same way described above. CTL was tested against peptide-pulsed A24-LCL cells or T2 cells after the 3rd round of peptide stimulation on day 21.

CTL Expansion Procedure

CTLs were expanded in culture using the method similar to that described by Riddell S R, et al., (Walter E A et al., (1995) N Engl J Med 333:1038-44.; Riddel S R, et al., (1996) Nature Med. 2:216-23.). A total $5 \times 10^4$ of CTLs were resuspended in 25 ml of AIM-V/5% AS with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS containing 30 IU/ml of IL-2 on days 5, 8 and 11.

Establishment of CTL Clones

The dilutions were made to have 0.3, 1, and 3 CTLs/well in 96 round-bottomed micro titer plate (Nalge Nunc International). CTLs were cultured with $7 \times 10^4$ cells/well of 2 kinds of human B-lymphoblastoid cell lines, 30 ng/ml of anti-CD3 antibody, and 125 U/ml of IL-2 in total of 150 micro l/well of AIM-V containing 5% AS. 50 micro l/well of IL-2 was added to the medium 10 days later so that IL-2 became 125 U/ml in the final concentration. CTL activity of CTLs was tested on the 14th day, and CTL clones were expanded using the same method above.

Specific CTL Activity

To examine the specific CTL activity, IFN-gamma ELISPOT assay and IFN-gamma ELISA assay were performed.

Briefly, peptide-pulsed A24-LCL or T2 cell ($1\times10^4$/well) was prepared as stimulator cells. Cultured Cells in 48 wells or CTL clones after limiting dilution were used as responder cells. IFN-gamma ELISPOT assay and ELISA assay were performed under manufacture procedure.

Establishment of the Cells Forcibly Expressing Either or Both of the Target Gene and HLA-A02 or HLA-A24

The cDNA encoding an open reading frame of target genes or HLA-A02 or HLA-A24 was amplified by PCR. The PCR-amplified product was cloned into pcDNA3.1 myc-His vector (Invitrogen). The plasmids were transfected into the target cells, HLA-A02 and HLA-A24-null normal human cell line COST or 293T using lipofectamine (Invitrogen) according to the manufacturer's recommended procedures. Alternatively, the plasmid contained the target genes were transfected into A24-LCL by electroporation using GenePulserII (Biorad). Briefly, $2.5\times10^6$ A24-LCL cells were pulsed with 10 mcg plasmid at 140V and 1000 micro F. After 2 days from transfection, the transfected cells were treated with Cell dissociation solution and used as the target cells for CTL activity assay.

Cytotoxicity Assay

Cytotoxic activity was evaluated by a four-hour $^{51}$Cr release assay. The target cells were pulsed with a 20 micro g/mL concentration of peptide overnight. The target cells were labeled with 100 micro Ci of $Na_2{}^{51}CrO_4$ at 37 degrees C. for one hour, and then washed three times with RPMI1640. The target cells ($1\times10^4$/100 micro L) and 100 micro L of effector cells at various numbers with a total volume of 200 micro L were placed into a round-bottomed 96-well microtiter plate (Corning), and cultured at 37 degrees C. in a $CO_2$ incubator for four hours. After culturing, 100 micro L of the supernatant was collected from each well, and measured the radioactivity using a gamma counter. Spontaneous release was the radioactivity from the target cells with medium in the absence of effector cells, and maximum release was the radioactivity from the target cells with 1 M HCl.

The Percentage of specific cytotoxicity was determined by calculating as following formula:

% Specific lysis=[(experimental release−spontaneous release)/(maximum release−spontaneous release)]×100.

RESULTS

Enhanced CDH3, EPHA4, ECT2, HIG2, INHBB, KIF20A, KNTC2, TTK and URLC10 Expression in Cancers The global gene expression profile data obtained from various cancers using cDNA-microarray revealed that the expression of the following genes was elevated.

CDH3 (GenBank Accession No. NM_001793; SEQ ID Nos. 1, 2),

EPHA4 (GenBank Accession No. L36645; SEQ ID Nos. 3, 4),

ECT2 (GenBank Accession No. AY376439; SEQ ID Nos. 5, 6),

HIG2 (GenBank Accession No. NM_013332; SEQ ID Nos. 7, 8),

INHBB (GenBank Accession No. NM_002193; SEQ ID Nos. 9, 435, 10, 436),

KIF20A (GenBank Accession No. NM_005733; SEQ ID Nos. 11, 12),

KNTC2 (GenBank Accession No. AF017790; SEQ ID Nos. 13, 14),

TTK (GenBank Accession No. NM_003318; SEQ ID Nos. 15, 16) and

URLC10 (GenBank Accession No. NM_017527; SEQ ID Nos. 17, 18)

CDH3 expression was validly elevated in the following cancers in comparison with corresponding normal tissue.
  26 out of 34 bladder cancer,
  17 out of 19 cervical cancer,
  19 out of 19 cholangiocellular carcinoma,
  30 out of 34 colorectal cancer,
  20 out of 21 endometriosis,
  13 out of 20 gastric cancer,
  7 out of 8 diffuse-type gastric cancer,
  36 out of 37 NSCLC,
  16 out of 16 pancreatic cancer,
  21 out of 21 soft tissue tumor and
  10 out of 10 testicular tumor EPHA4 expression was validly elevated in the following cancers in comparison with corresponding normal tissue.
  14 out of 34 bladder cancer,
  8 out of 14 cervical cancer,
  10 out of 25 cholangiocellular carcinoma,
  5 out of 15 endometriosis,
  5 out of 8 diffuse-type gastric cancer,
  5 out of 5 ovarian cancer,
  14 out of 14 pancreatic cancer,
  20 out of 51 prostate cancer and
  14 out of 23 soft tissue tumor ECT2 expression was validly elevated in the following cancers in comparing with corresponding normal tissue.
  17 out of 19 bladder cancer,
  5 out of 12 breast cancer,
  14 out of 14 cervical cancer,
  13 out of 13 cholangiocellular carcinoma,
  5 out of 5 CML,
  7 out of 8 colorectal cancer,
  12 out of 16 esophageal cancer,
  6 out of 16 NSCLC,
  8 out of 10 lymphoma,
  1 out of 1 pancreatic cancer,
  10 out of 13 prostate cancer,
  3 out of 6 renal carcinoma and
  12 out of 13 SCLC cancer HIG2 expression was validly elevated in 19 out of 20 renal cancer and 7 out of 9 soft tissue tumor in comparing with corresponding normal tissue.

INHBB expression was validly elevated in the following cancers in comparing with corresponding normal tissue.
  10 out of 21 cholangiocellular carcinoma,
  12 out of 12 esophageal cancer,
  10 out of 13 NSCLC,
  22 out of 24 renal carcinoma,
  8 out of 14 SCLC cancer and
  45 out of 49 soft tissue tumor KIF20A expression was validly elevated in the following cancers in comparing with corresponding normal tissue.
  31 out of 31 bladder cancer,
  38 out of 61 breast cancer,
  10 out of 11 cholangiocellular carcinoma,
  7 out of 19 esophageal cancer,
  21 out of 22 NSCLC,
  6 out of 6 ovarian cancer,
  17 out of 36 prostate cancer,
  6 out of 11 renal carcinoma and
  15 out of 15 SCLC KNTC2 expression was validly elevated in the following cancers in comparing with corresponding normal tissue.
30 out of 32 bladder cancer,
47 out of 56 breast cancer,
10 out of 10 cervical cancer,
16 out of 22 cholangiocellular carcinoma,
17 out of 37 CML,
3 out of 10 colorectal cancer,
11 out of 46 esophagus cancer,
15 out of 19 NSCLC,
7 out of 8 lymphoma,
20 out of 24 osteosarcoma,
3 out of 5 ovarian cancer,
2 out of 2 pancreatic cancer,
15 out of 37 prostate cancer,
14 out of 19 renal carcinoma,
15 out of 15 SCLC and
40 out of 59 soft tissue tumor TTK expression was validly elevated in the following cancers in comparing with corresponding normal tissue.
27 out of 27 bladder cancer,
25 out of 30 breast cancer,
15 out of 16 cervical cancer,
10 out of 10 cholangiocellular carcinoma,
5 out of 7 CML,
6 out of 10 colorectal cancer,
24 out of 44 esophageal cancer,
8 out of 15 liver cancer,
12 out of 12 NSCLC,
6 out of 6 lymphoma,
13 out of 16 osteoblastoma,
12 out of 17 prostate cancer,
15 out of 15 SCLC and
16 out of 33 soft tissue tumor URLC10 expression was validly elevated in the following cancers in comparing with corresponding normal tissue
29 out of 29 bladder cancer,
15 out of 16 cervical cancer,
7 out of 7 cholangiocellular carcinoma,
7 out of 19 esophageal cancer,
3 out of 3 gastric cancer, 24 out of 27 NSCLC,
15 out of 19 osteosarcoma,
4 out of 5 pancreatic cancer,
33 out of 43 soft tissue tumor.

TABLE 1

Ratio of cases observed up-regulation of CDH3, EPHA4, ECT2, HIG2, INHBB, KIF20A, KNTC2, TTK or URLC10 in cancerous tissue as compared to normal corresponding tissue

| | CDH3 | EPHA4 | ECT2 | HIG2 | INHBB |
|---|---|---|---|---|---|
| Bladder cancer | 26/34 | 14/34 | 17/19 | — | — |
| Breast cancer | — | — | 5/12 | — | — |
| Cervical cancer | 17/19 | 8/14 | 14/14 | — | — |
| Cholangiocellularcarcinoma | 19/19 | 10/25 | 13/13 | — | 10/21 |
| CML | — | — | 5/5 | — | — |
| Colectal cancer | 30/34 | — | 7/8 | — | — |
| Endometriosis | 20/21 | 5/15 | — | — | — |
| Esophageal cancer | — | — | 12/16 | — | 12/12 |
| Gastric camcer | 13/20 | — | — | — | — |
| Diffuse-type Gastric cancer | 7/8 | 5/8 | — | — | — |
| Liver cancer | — | — | — | — | — |
| non-small cell lung cancer | 36/37 | — | 6/16 | — | 10/13 |
| Lymphoma | — | — | 8/10 | — | — |
| Osteosarcoma | — | — | — | — | — |
| Ovarian cancer | — | 5/5 | — | — | — |
| Pancreatic cancer | 16/16 | 14/14 | 1/1 | — | — |
| Prostate cancer | — | 20/51 | 10/13 | — | — |
| Renal carcinoma | — | — | 3/6 | 19/20 | 22/24 |

TABLE 1-continued

Ratio of cases observed up-regulation of CDH3, EPHA4, ECT2, HIG2, INHBB, KIF20A, KNTC2, TTK or URLC10 in cancerous tissue as compared to normal corresponding tissue

| | | | | | |
|---|---|---|---|---|---|
| Small cell lung cancer | — | — | 12/13 | — | 8/14 |
| Soft tissue tumor | 21/21 | 14/23 | — | 7/9 | 45/49 |
| Testicular tumor | 10/10 | — | — | — | — |

| | KIF20A | KNTC2 | TTK | URLC10 |
|---|---|---|---|---|
| Bladder cancer | 31/31 | 30/32 | 27/27 | 29/29 |
| Breast cancer | 38/61 | 47/56 | 25/30 | — |
| Cervical cancer | — | 10/10 | 15/16 | 15/16 |
| Cholangiocellularcarcinoma | 10/11 | 16/22 | 10/10 | 7/7 |
| CML | — | 17/37 | 5/7 | — |
| Colectal cancer | — | 3/10 | 6/10 | — |
| Endometriosis | — | — | — | — |
| Esophageal cancer | 7/19 | 11/46 | 24/44 | 7/19 |
| Gastric camcer | — | — | — | 3/3 |
| Diffuse-type Gastric cancer | — | — | — | — |
| Liver cancer | — | — | 8/15 | — |
| non-small cell lung cancer | 21/22 | 15/19 | 12/12 | 24/27 |
| Lymphoma | — | 7/8 | 6/6 | — |
| Osteosarcoma | — | 20/24 | 13/16 | 15/19 |
| Ovarian cancer | — | 3/5 | — | — |
| Pancreatic cancer | 6/6 | 2/2 | — | 4/5 |
| Prostate cancer | 17/36 | 15/37 | 12/17 | — |
| Renal carcinoma | 6/11 | 14/19 | — | — |
| Small cell lung cancer | 15/15 | 15/15 | 15/15 | — |
| Soft tissue tumor | — | 40/59 | 16/33 | 33/43 |
| Testicular tumor | — | — | — | — |

Prediction of HLA-A24 or HLA-A2 (HLA-A02) Binding Peptides Derived from CDH3, EPHA4, ECT2, HIG2, INHBB, KIF20A, KNTC2, TTK or URLC10

Table 2 sets forth the HLA-A*2402 binding peptides for CDH3 in order of binding affinity. Table 2A sets forth 9-mer peptides derived from CDH3 and Table 2B sets forth 10-mer peptides derived from CDH3.

Table 3 sets forth the HLA-A*2402 and HLA-A*0201 binding peptides for EPHA4 in order of binding affinity. Table 3A sets forth the HLA-A*2402 binding 9-mer peptides derived from EPHA4, Table 3B shows the HLA-A*2402 binding 10-mer peptides derived from EPHA4 and Table 3C sets forth the HLA-A*0201 binding 9-mer peptides derived from EPHA4.

Table 4 sets forth the HLA-A*2402 binding peptides for ECT2 in order of binding affinity. Table 4A sets forth 9-mer peptides derived from ECT2 and Table 4B shows 10-mer peptides derived from ECT2.

Table 5 sets forth the HLA-A*2402 and HLA-A*0201 binding peptides for HIG2, Table 5A sets forth the HLA-A*2402 binding 9-mer peptides derived from HIG2, Table 5B sets forth the HLA-A*2402 binding 10-mer peptides derived from HIG2, Table 5C sets forth the HLA-A*0201 binding 9-mer peptides derived from HIG2, and Table 5D sets forth HLA-A*0201 binding 10-mer peptides derived from HIG2.

Table 6 sets forth the HLA-A*2402 and HLA-A*0201 binding peptides for INHBB, Table 6A shows the HLA-A*2402 binding 9-mer peptides derived from INHBB, Table 6B sets forth the HLA-A*2402 binding 10-mer peptides derived from INHBB, Table 6C sets forth the HLA-A*0201 binding 9-mer peptides derived from INHBB, and Table 6D sets forth HLA-A*0201 binding 10-mer peptides derived from INHBB.

Table 7 sets forth the HLA-A*2402 binding peptides for KIF20A in order of binding affinity. Table 7A sets forth 9-mer peptides derived from KIF20A and Table 7B sets forth 10-mer peptides derived from KIF20A.

Table 8 sets forth the HLA-A*2402 binding peptides for KNTC2 in order of binding affinity. Table 8A sets forth 9-mer peptides derived from KNTC2 and Table 8B sets forth 10-mer peptides derived from KNTC2.

Table 9 sets forth the HLA-A*0201 binding peptides for TTK in order of binding affinity. Table 9A sets forth 9-mer peptides derived from TTK and Table 9B sets forth 10-mer peptides derived from TTK.

Table 10 sets forth the HLA-A*0201 binding peptides for URLC10 in order of binding affinity. Table 10A sets forth 9-mer peptides derived from URLC10 and Table 10B sets forth 10-mer peptides derived from URLC10.

EXPLANATION AND DEFINITION ABOUT THE TERMS IN TABLES

Start position indicates the number of amino acid from N-terminal.

Binding score is derived from "BIMAS" described in Materials and Methods.

Positive donor number indicates the number of doner whoes CD8+-T-cells can be induced to the specific CTL by the ex vivo stimulation with antigen-presenting cells. This is shown as (positive donor number/whole donor number).

Positive well number indicates the number of wells where specific IFN-gamma production can be detected by IFN-gamma ELISPOT assay. 4 to 8 wells can be prepared from one donor. This is shown as (positive wells number/the number of whole wells tested by IFN-gamma ELISPOT assay).

Positive CTL line indicates the number of CTL line established from positive wells. The generation of CTL line is determined by ELISA. This is shown as (established CTL line number/the number of positive wells tested by IFN-gamma ELISPOT assay).

No positive donor is not defined by no detectable positive wells, but by no established CTL line.

The peptides showed by bold character in tables possesses the stimulation activity of the T cells.

No data at positive donor number, positive well number and positive CTL line indicating "–" means that the peptides can't be synthesized for any reason.

TABLE 2A

HLA-A*2402 binding 9-mer peptides derived from CDH3

| Strat position | Amino acid sequence | Binding Score | Positive donor number | Positive well number | Positive CTL line | SEQ ID NO. |
|---|---|---|---|---|---|---|
| 513 | IYEVMVLAM | 37.5 | 1/3 | | | 19 |
| 667 | LFLLLVLLL | 36 | – | – | – | 20 |
| 30 | VFREAEVTL | 24 | 0/3 | 1/22 | 0/1 | 21 |
| 406 | LYVEVTNEA | 16.632 | 1/3 | | | 22 |
| 332 | KYEAHVPEN | 16.5 | 0/3 | 1/22 | 0/1 | 23 |
| 180 | KYELFGHAV | 15 | 0/3 | 1/22 | 0/1 | 24 |
| 85 | RSLKERNPL | 14.4 | 0/3 | 1/22 | 0/1 | 25 |
| 5 | RGPLASLLL | 12 | 0/3 | 2/22 | 0/2 | 26 |
| 652 | KGGFILPVL | 11.2 | 0/3 | 0/22 | – | 27 |
| 248 | TYNGVVAYS | 10.5 | 0/3 | 2/22 | 0/2 | 28 |
| 65 | LFSTDNDDF | 10 | 0/3 | 0/22 | – | 29 |
| 94 | KIFPSKRIL | 9.6 | 0/1 | 0/8 | – | 306 |
| 221 | RGSVLEGVL | 9.6 | 0/1 | 0/8 | – | 307 |
| 668 | FLLLVLLLL | 8.4 | – | – | – | 308 |
| 754 | IGNFIIENL | 8.4 | – | – | – | 309 |
| 311 | TAVAVVEIL | 8.4 | 0/1 | 0/8 | – | 310 |
| 557 | NQSPVRQVL | 8.064 | 0/1 | 0/8 | – | 311 |
| 611 | KQDTYDVHL | 8 | 0/1 | 0/8 | – | 312 |
| 781 | DYEGSGSDA | 7.5 | 0/1 | 0/8 | – | 313 |
| 165 | GWLLLNKPL | 7.2 | 0/1 | 0/8 | – | 314 |
| 656 | ILPVLGAVL | 7.2 | 0/1 | 0/8 | – | 315 |
| 770 | TAPPYDTLL | 7.2 | 0/1 | 0/8 | – | 316 |
| 602 | VVLSLKKFL | 7.2 | 0/1 | 0/8 | – | 317 |
| 665 | ALLFLLLVL | 7.2 | – | – | – | 318 |
| 410 | VTNEAPFVL | 7.2 | 0/1 | 0/8 | – | 319 |

TABLE 2A-continued

HLA-A*2402 binding 9-mer peptides derived from CDH3

| Strat position | Amino acid sequence | Binding Score | Positive donor number | Positive well number | Positive CTL line | SEQ ID NO. |
|---|---|---|---|---|---|---|
| 662 | AVLALLFLL | 7.2 | — | — | — | 320 |
| 613 | DTYDVHLSL | 6.72 | 0/1 | 0/8 | — | 321 |
| 6 | GPLASLLLL | 6 | 0/1 | 0/8 | — | 322 |
| 564 | VLNITDKDL | 6 | 0/1 | 0/8 | — | 323 |
| 159 | AVEKETGWL | 6 | 0/1 | 0/8 | — | 324 |
| 511 | NNIYEVMVL | 6 | 0/1 | 0/8 | — | 325 |
| 11 | LLLLQVCWL | 6 | — | — | — | 326 |
| 57 | GCPGQEPAL | 6 | 0/1 | 0/8 | — | 327 |
| 293 | EYTLTIQAT | 6 | 0/1 | 0/8 | — | 328 |
| 79 | ETVQERRSL | 6 | 0/1 | 0/8 | — | 329 |
| 475 | SYRILRDPA | 6 | 0/1 | 0/8 | — | 330 |
| 493 | GQVTAVGTL | 6 | 0/1 | 0/8 | — | 331 |
| 661 | GAVLALLFL | 6 | 0/1 | 0/8 | — | 332 |
| 388 | GILTTRKGL | 6 | 0/1 | 0/8 | — | 333 |
| 382 | HPESNQGIL | 6 | 0/1 | 0/8 | — | 334 |
| 663 | VLALLFLLL | 5.76 | — | — | — | 335 |
| 598 | EGDTVVLSL | 5.6 | 0/1 | 0/8 | — | 336 |
| 278 | TISVISSGL | 5.6 | 0/1 | 2/8 | 0/2 | 337 |
| 659 | VLGAVLALL | 5.6 | 0/1 | 0/8 | — | 338 |
| 811 | EWGSRFKKL | 5.28 | 0/1 | 0/8 | — | 339 |
| 445 | KVVEVQEGI | 5.04 | 0/1 | 0/8 | — | 340 |
| 614 | TYDVHLSLS | 5 | 0/1 | 0/8 | — | 341 |
| 142 | FYSITGPGA | 5 | 0/1 | 0/8 | — | 342 |
| 246 | IYTYNGVVA | 5 | 0/1 | 0/8 | — | 343 |

TABLE 2B

HLA-A*2402 binding 10-mer peptides derived from CDH3

| strat position | sequence | Binding Score | positive donor number | positive well number | positive CTL line | SEQ ID NO |
|---|---|---|---|---|---|---|
| 807 | DYLNeWGSRF | 150 | 1/3 | | | 30 |
| 248 | TYNGvVAYSI | 105 | 0/3 | 4/22 | 0/4 | 31 |
| 667 | LFLLIVLLLL | 42 | — | — | — | 32 |
| 397 | DFEAkNQHTL | 30 | 0/3 | 2/22 | 0/2 | 33 |
| 332 | KYEAhVPENA | 21 | 1/3 | | | 34 |
| 180 | KYELFGHAVS | 15 | 0/3 | 2/22 | 0/2 | 35 |
| 510 | RNNIYEVMVL | 12 | 0/3 | 4/22 | 0/4 | 36 |
| 5 | RGPLASLLLL | 12 | 0/3 | 1/22 | 0/1 | 37 |

TABLE 2B-continued

HLA-A*2402 binding 10-mer peptides derived from CDH3

| start position | sequence | Binding Score | positive donor number | positive well number | positive CTL line | SEQ ID NO |
|---|---|---|---|---|---|---|
| 477 | RILRDPAGWL | 12 | 0/3 | 1/22 | 0/1 | 38 |
| 556 | CNQSPVRQVL | 10.08 | 0/3 | 2/22 | 0/2 | 39 |
| 655 | FILPvLGAVL | 8.64 | 1/3 | | | 344 |
| 662 | AVLAILFLLL | 8.64 | — | — | — | 345 |
| 277 | GTISvISSGL | 8.4 | 0/3 | 0/20 | — | 346 |
| 781 | DYEGsGSDAA | 7.5 | 0/3 | 0/20 | — | 347 |
| 601 | TVVLsLKKFL | 7.2 | 0/3 | 3/20 | 0/3 | 348 |
| 158 | FAVEkETGWL | 7.2 | 0/3 | 0/20 | — | 349 |
| 665 | ALLFILLVLL | 7.2 | — | — | — | 350 |
| 259 | SQEPkDPHDL | 7.2 | 0/3 | 0/20 | — | 351 |
| 664 | LALLILLLVL | 7.2 | — | — | — | 352 |
| 42 | GAEQePGQAL | 7.2 | 0/3 | 1/20 | 0/1 | 353 |
| 661 | GAVLaLLFLL | 7.2 | — | — | — | 354 |
| 595 | VNEEgDTVVL | 7.2 | 0/2 | 0/12 | — | 355 |
| 340 | NAVGhEVQRL | 7.2 | 0/2 | 0/12 | — | 356 |
| 411 | TNEApFVLKL | 6.6 | 0/2 | 0/12 | — | 357 |
| 470 | ENQKiSYRIL | 6 | 1/2 | | | 358 |
| 10 | SLLL1QVCWL | 6 | 0/2 | 1/12 | 0/1 | 359 |
| 721 | GLEArPEVVL | 6 | 0/2 | 2/12 | 0/2 | 360 |
| 345 | EVQR1TVTDL | 6 | 0/2 | 4/12 | 0/4 | 361 |
| 2 | GLPRgPLASL | 6 | 0/2 | 3/12 | 0/3 | 362 |
| 657 | LPVLgAVLAL | 6 | — | — | — | 363 |
| 563 | QVLNiTDKDL | 6 | 0/2 | 1/12 | 0/1 | 364 |
| 159 | AVEKeTGWLL | 6 | 0/2 | 2/12 | 0/2 | 365 |
| 492 | SGQVtAVGTL | 6 | 0/2 | — | — | 366 |
| 387 | QGILtTRKGL | 6 | 0/2 | — | — | 367 |
| 525 | SPPTtGTGTL | 6 | 0/2 | 2/12 | 0/2 | 368 |
| 358 | NSPAwRATYL | 6 | 0/2 | 2/12 | 0/2 | 369 |
| 122 | GPFPqRLNQL | 5.76 | 0/2 | 3/12 | 0/3 | 370 |
| 753 | EIGNfIIENL | 5.6 | 0/2 | 1/12 | 0/1 | 371 |
| 310 | TTAVaVVEIL | 5.6 | — | — | — | 372 |
| 246 | IYTYnGVVAY | 5 | 0/2 | 2/12 | 0/2 | 373 |
| 805 | DYDYINEWGS | 5 | 0/2 | 0/12 | — | 374 |

TABLE 3A

HLA-A*2402 binding 9-mer peptides derived from EPHA4

| strat position | sequence | Binding Score | positive donor number | positive well number | positive CTL line | SEQ ID NO |
|---|---|---|---|---|---|---|
| 97 | VYIEIKFTL | 504 | 0/2 | 1/16 | 0/1 | 40 |
| 453 | RYSVALAWL | 400 | 2/3 | | | 41 |
| 25 | VYPANEVTL | 300 | 0/3 | 0/22 | — | 42 |
| 384 | HYTPQQNGL | 288 | 0/3 | 1/22 | 0/1 | 43 |
| 5 | FYFALFSCL | 288 | 1/2 | | | 44 |
| 519 | GYGDFSEPL | 240 | 0/3 | 3/22 | 0/3 | 45 |
| 869 | KFGQIVNML | 67.2 | 1/3 | | | 46 |
| 777 | AYTTRGGKI | 55 | 0/3 | 1/22 | 0/1 | 47 |
| 420 | KYNPNPDQS | 18 | 1/3 | | | 48 |
| 749 | RNILVNSNL | 16.8 | 0/3 | 1/22 | 0/1 | 49 |
| 734 | KYLSDMSYV | 15 | 0/3 | 0/22 | — | 50 |
| 879 | KLIRNPNSL | 14.4 | 0/3 | 0/22 | — | 51 |
| 926 | RYKDNFTAA | 14.4 | 0/3 | 0/22 | — | 52 |
| 834 | KAIEEGYRL | 14.4 | 0/3 | 0/22 | — | 53 |
| 574 | KYSKAKQEA | 13.2 | 0/3 | 0/22 | — | 54 |
| 184 | AFQDVGACI | 12.6 | 0/3 | 1/22 | 0/1 | 55 |
| 252 | WLVPIGNCL | 12.096 | 0/3 | 0/22 | — | 56 |
| 326 | RPPSAPLNL | 12 | 0/3 | 0/22 | — | 57 |
| 203 | KCPLTVRNL | 12 | 0/3 | 0/22 | — | 58 |
| 360 | SYNVVCKKC | 11.55 | 0/3 | 0/22 | — | 59 |

TABLE 3B

HLA-A*2402 binding 10-mer peptides derived from EPHA4

| strat position | sequence | Binding Score | positive donor number | positive well number | positive CTL line | SEQ ID NO |
|---|---|---|---|---|---|---|
| 25 | VYPANEVTLL | 300 | 0/3 | 0/22 | — | 60 |
| 244 | MYCGADGEWL | 200 | 0/3 | 1/22 | 0/1 | 61 |
| 657 | GYTDKQRRDF | 120 | 0/3 | 1/22 | 0/1 | 62 |
| 5 | FYFAIFSCLF | 100 | — | — | — | 63 |
| 102 | KFTLRDCNSL | 48 | 0/3 | 1/22 | 0/1 | 64 |
| 818 | SYGERPYWDM | 30 | 0/3 | 2/22 | 0/2 | 65 |
| 4 | IFYFALFSCL | 28.8 | — | — | — | 66 |
| 808 | SYGIVMWEVM | 25 | — | — | — | 67 |
| 630 | EFGEVCSGRL | 24 | 0/3 | 0/22 | — | 68 |
| 420 | KYNPNPDQSV | 21.6 | 0/3 | 0/22 | — | 69 |
| 930 | NFTAAGYTTL | 20 | 0/2 | 0/16 | — | 70 |
| 675 | QFDHPNIIHL | 20 | 0/3 | 0/22 | — | 71 |
| 708 | AFLRKNDGRF | 15 | 0/3 | 0/22 | — | 72 |
| 579 | KQEADEEKHL | 12 | 0/3 | 1/22 | 0/1 | 73 |
| 727 | RGIGSGMKYL | 12 | 0/3 | 0/22 | — | 74 |
| 96 | RVYIEIKFTL | 11.2 | 0/2 | 1/16 | 0/1 | 75 |
| 507 | SYVFHVRART | 10.5 | 0/3 | 1/22 | 0/1 | 76 |
| 251 | EWLVPIGNCL | 10.08 | 0/3 | 0/22 | — | 77 |
| 24 | RVYPANEVTL | 9.6 | 1/3 | | | 78 |
| 699 | EYMENGSLDA | 9 | 0/3 | 0/22 | — | 79 |

TABLE 3C

HLA-A*0201 binding 9-mer peptides derived from EPHA4

| strat position | sequence | Binding Score | positive donor number | positive well number | positive CTL line | SEQ ID NO |
|---|---|---|---|---|---|---|
| 8 | ALFSCLFGI | 514.942 | — | — | — | 375 |
| 501 | GLNPLTSYV | 382.536 | 1/1 | | | 376 |
| 12 | CLFGICDAV | 126.098 | 0/1 | 1/5 | 0/1 | 377 |
| 977 | QMHGRMVPV | 115.534 | 0/1 | 1/5 | 0/1 | 378 |
| 165 | KLNTEIRDV | 111.979 | 1/1 | | | 379 |
| 252 | WLVPIGNCL | 98.267 | 0/1 | 1/5 | 0/1 | 380 |
| 879 | KLIRNPNSL | 74.768 | 0/1 | 1/5 | 0/1 | 381 |
| 559 | VVILIAAFV | 56.902 | — | — | — | 382 |
| 812 | VMWEVMSYG | 39.386 | 0/1 | 0/5 | — | 383 |
| 728 | GIGSGMKYL | 37.157 | 0/1 | 0/5 | — | 384 |
| 750 | NILVNSNLV | 35.385 | 0/1 | 1/5 | 0/1 | 385 |
| 937 | TTLEAVVHV | 33.705 | 0/1 | 1/5 | 0/1 | 386 |

TABLE 4A

HLA-A*2402 binding 9-mer peptides derived from ECT2

| strat position | sequence | Binding Score | positive donor number | positive well number | positive CTL line | SEQ ID NO |
|---|---|---|---|---|---|---|
| 515 | TYPPFVNFF | 216 | 1/1 | | | 80 |
| 140 | LYCTSMMNL | 200 | 0/1 | 0/8 | — | 81 |
| 298 | LYVVKQEWF | 150 | 0/1 | 0/8 | — | 82 |
| 435 | NYVNILATI | 105 | 0/1 | 0/8 | — | 83 |
| 773 | IYTADPESF | 100 | 0/1 | 0/8 | — | 84 |
| 110 | LYKADCRVI | 50 | 0/1 | 0/8 | — | 85 |
| 739 | SFQMTSDEL | 33 | 0/1 | 0/8 | — | 86 |
| 504 | IFLKYSKDL | 30 | 0/1 | 0/8 | — | 87 |
| 867 | FFERRSHTL | 30 | 0/1 | 0/8 | — | 88 |
| 178 | DFNSKVTHL | 30 | 0/1 | 0/8 | — | 89 |
| 61 | KQEELIKAL | 17.28 | 0/1 | 0/8 | — | 90 |
| 657 | RGEQVTLFL | 16.8 | 0/1 | 2/8 | 0/2 | 91 |
| 568 | RLPSVALLL | 16.8 | 0/1 | 0/8 | — | 92 |
| 550 | KPECGRQSL | 14.4 | 0/1 | 0/8 | — | 93 |
| 470 | IFGSIPDIF | 14 | 0/1 | 0/8 | — | 94 |
| 116 | RVIGPPVVL | 12 | 0/1 | 0/8 | — | 95 |
| 507 | KYSKDLVKT | 11 | 0/1 | 0/8 | — | 96 |
| 223 | DFYAAVDDF | 10 | 0/1 | 0/8 | — | 97 |

TABLE 4B

HLA-A*2402 binding 10-mer peptides derived from ECT2

| strat position | sequence | Binding Score | positive donor number | positive well number | positive CTL line | SEQ ID NO |
|---|---|---|---|---|---|---|
| 322 | LYEKaNTPEL | 330 | 0/1 | 0/8 | — | 98 |
| 435 | NYVNiLATII | 90 | 0/1 | 0/8 | — | 99 |
| 40 | SYVEeEMPQI | 90 | 1/1 | | | 100 |
| 101 | DFQDsVFNDL | 72.576 | 1/1 | | | 101 |
| 866 | SFFErRSHTL | 24 | 0/1 | 0/8 | — | 102 |
| 811 | SFSKtPKRAL | 20 | 0/1 | 1/8 | 0/1 | 103 |
| 268 | KYLPIGDERC | 18 | 0/1 | 0/8 | — | 104 |
| 84 | EFEGIDSPEF | 16.5 | 0/1 | 1/8 | 0/1 | 105 |
| 236 | KVPPfQDCIL | 14.4 | 0/1 | 0/8 | — | 106 |
| 728 | RPPTeQANVL | 14.4 | 0/1 | 0/8 | — | 107 |
| 507 | KYSKdLVKTY | 12 | 0/1 | 0/8 | — | 108 |
| 281 | VVEEnIVKDL | 10.08 | 0/1 | 0/8 | — | 109 |

TABLE 5A

HLA-A*2402 binding 9-mer peptides derived from HIG2

| strat position | sequence | Binding Score | positive donor number | positive well number | positive CTL line | SEQ ID NO |
|---|---|---|---|---|---|---|
| 19 | IFVRVMESL | 42 | 1/3 | | | 110 |
| 22 | RVMESLEGL | 14.4 | 1/3 | | | 111 |
| 8 | YLLGVVLTL | 8.4 | 1/3 | | | 387 |
| 7 | LYLLGVVLT | 7.5 | 0/2 | 3/15 | 0/3 | 388 |
| 23 | VMESLEGLL | 7.2 | 0/2 | 0/16 | — | 389 |
| 9 | LLGVVLTLL | 5.6 | — | — | — | 390 |

TABLE 5B

Table 5B HLA-A*2402 binding 10-mer peptides derived from HIG2

| strat position | sequence | Binding Score | positive donor number | positive well number | positive CTL line | SEQ ID NO |
|---|---|---|---|---|---|---|
| 7 | LYLLGVVLTL | 420 | 1/3 | | | 112 |
| 22 | RVMESLEGLL | 17.28 | 0/3 | 4/24 | 0/4 | 113 |
| 8 | YLLGVVLTLL | 8.4 | — | — | — | 391 |
| 5 | LNLYLLGVVL | 7.2 | 0/2 | 0/12 | — | 392 |
| 46 | LANTEPTKGL | 6 | 0/2 | 0/14 | — | 393 |
| 18 | SIFVRVMESL | 5.6 | 1/2 | | | 394 |

TABLE 5C

HLA-A*0201 binding 9-mer peptides derived from HIG2

| strat position | sequence | Binding Score | positive donor number | positive well number | positive CTL line | SEQ ID NO |
|---|---|---|---|---|---|---|
| 8 | YLLGVVLTL | 836.253 | 1/1 | | | 114 |
| 13 | VLTLLSIFV | 650.311 | 0/1 | 0/12 | — | 115 |
| 15 | TLLSIFVRV | 488.951 | 1/1 | | | 116 |

TABLE 5C-continued

HLA-A*0201 binding 9-mer peptides derived from HIG2

| strat position | sequence | Binding Score | positive donor number | positive well number | positive CTL line | SEQ ID NO |
|---|---|---|---|---|---|---|
| 4 | VLNLYLLGV | 271.948 | 1/1 | | | 117 |
| 9 | LLGVVLTLL | 83.527 | 0/1 | 0/12 | — | 118 |
| 22 | RVMESLEGL | 31.957 | 0/1 | 0/12 | — | 119 |
| 6 | NLYLLGVVL | 28.027 | 0/1 | 0/12 | — | 120 |

TABLE 5D

HLA-A*0201 binding 10-mer peptides derived from HIG2

| strat position | sequence | Binding Score | positive donor number | positive well number | positive CTL line | SEQ ID NO |
|---|---|---|---|---|---|---|
| 8 | YLLGvVLTLL | 836.253 | 1/1 | | | 121 |
| 12 | VVLTlLSIFV | 210.538 | — | — | — | 122 |
| 29 | GLLEsPSPGT | 113.047 | 0/1 | 0/12 | — | 123 |
| 6 | NLYLlGVVLT | 54.847 | — | — | — | 124 |
| 4 | VLNLyLLGVV | 14.495 | 0/1 | 0/12 | — | 125 |
| 15 | TLLSiFVRVM | 13.174 | 0/1 | 0/12 | — | 126 |
| 18 | SIFVrVMESL | 12.248 | 0/1 | 0/12 | — | 127 |
| 14 | LTLLsIFVRV | 11.545 | — | — | — | 128 |

TABLE 6A

HLA-A*2402 binding 9-mer peptides from INHBB

| strat position | sequence | Binding Score | positive donor number | positive well number | positive CTL line | SEQ ID NO |
|---|---|---|---|---|---|---|
| 383 | LYFDDEYNI | 60 | 0/3 | 0/20 | — | 129 |
| 238 | LFERGERRL | 30 | 0/3 | 1/19 | 0/1 | 130 |
| 7 | RALGAACLL | 12 | 0/3 | 0/21 | — | 131 |
| 388 | EYNIVKRDV | 10.5 | 0/3 | 0/18 | — | 132 |
| 180 | LYLKLLPYV | 9 | 1/2 | | — | 395 |
| 163 | ISNEGNQNL | 8.64 | 0/1 | 0/8 | — | 396 |
| 223 | RSGWHTFPL | 8 | 0/1 | 0/6 | — | 397 |
| 176 | ASLWLYLKL | 7.92 | 0/1 | 0/7 | — | 398 |
| 338 | AYLAGVPGS | 7.5 | 0/1 | 1/7 | 0/1 | 399 |
| 213 | NMVEKRVDL | 7.2 | 0/1 | 0/8 | — | 400 |
| 102 | AMVTALRKL | 6.6 | 0/1 | 0/8 | — | 401 |
| 250 | VQCDSCQEL | 6.336 | 0/1 | 0/8 | — | 402 |
| 369 | NSCCIPTKL | 6.16 | 0/1 | 0/8 | — | 403 |
| 330 | NYCEGSCPA | 6 | 0/1 | 0/7 | — | 404 |
| 172 | FVVQASLWL | 6 | 0/1 | 0/8 | — | 405 |
| 355 | VNQYRMRGL | 6 | 0/1 | 0/8 | — | 406 |

TABLE 6A-continued

HLA-A*2402 binding 9-mer peptides from INHBB

| strat position | sequence | Binding Score | positive donor number | positive well number | positive CTL line | SEQ ID NO |
|---|---|---|---|---|---|---|
| 307 | QFFIDFRLI | 6 | 0/1 | 0/7 | — | 407 |
| 14 | LLLLAAGWL | 6 | — | — | — | 408 |
| 306 | QQFFIDFRL | 5.6 | 0/1 | 0/6 | — | 409 |
| 170 | NLFVVQASL | 5.6 | 0/1 | 0/7 | — | 410 |
| 327 | YYGNYCEGS | 5 | 0/1 | 1/8 | 0/1 | 411 |

TABLE 6B

HLA-A*2402 binding 10-mer peptides derived from INHBB

| strat position | sequence | Binding Score | positive donor number | positive well number | positive CTL line | SEQ ID NO |
|---|---|---|---|---|---|---|
| 180 | LYLKLLPYVL | 360 | 1/3 | | | 133 |
| 171 | LFVVQASLWL | 30 | — | — | — | 134 |
| 305 | RQQFFIDFRL | 16.8 | 1/3 | | | 135 |
| 73 | DFLEAVKRHI | 12.6 | 0/3 | 4/20 | 0/4 | 136 |
| 7 | RALGAACLLL | 12 | 1/3 | | | 137 |
| 273 | RPFVVVQARL | 11.2 | 0/3 | 1/20 | 0/1 | 138 |
| 338 | AYLAGVPGSA | 10 | 0/3 | 2/20 | 0/2 | 139 |
| 169 | QNLFvVQASL | 8.4 | 0/1 | 1/6 | 0/1 | 412 |
| 249 | DVQCdSCQEL | 7.92 | 0/1 | 4/6 | 0/4 | 413 |
| 383 | LYFDdEYNIV | 7.2 | 0/1 | 0/6 | — | 415 |
| 229 | FPLTeAIQAL | 7.2 | 0/1 | 1/6 | 0/1 | 416 |
| 299 | RTNLcCRQQF | 7.2 | 0/1 | 5/6 | 0/5 | 417 |
| 101 | AAMVtALRKL | 6.6 | 0/1 | 2/6 | 0/2 | 418 |
| 368 | VNSCcIPTKL | 6.16 | 0/1 | 2/6 | 0/2 | 419 |
| 13 | CLLL1AAGWL | 6 | — | — | — | 420 |
| 354 | VVNQyRMRGL | 6 | 0/1 | 0/6 | — | 421 |
| 150 | DGLAsSRVRL | 6 | 0/1 | 2/6 | 0/2 | 422 |
| 293 | GLECdGRTNL | 6 | 0/1 | 0/6 | | 423 |
| 330 | NYCEgSCPAY | 6 | 0/1 | 1/6 | 0/1 | 424 |
| 176 | ASLW1YLKLL | 6 | 0/1 | 1/6 | 0/1 | 425 |
| 212 | WNMVeKRVDL | 6 | 1/1 | | | 426 |
| 74 | FLEAvKRHIL | 6 | 0/1 | 2/6 | 0/2 | 427 |
| 331 | YCEGsCPAYL | 6 | 0/1 | 1/6 | 0/1 | 428 |
| 77 | AVKRhILSRL | 5.6 | 0/1 | 1/6 | 0/1 | 429 |
| 175 | QASLwLYLKL | 5.28 | 0/1 | 2/6 | 0/2 | 430 |
| 326 | GYYGnYCEGS | 5 | 0/1 | 1/6 | 0/1 | 431 |

TABLE 6B-continued

HLA-A*2402 binding 10-mer peptides derived from INHBB

| strat position | sequence | Binding Score | positive donor number | positive well number | positive CTL line | SEQ ID NO |
|---|---|---|---|---|---|---|
| 159 | LYFFiSNEGN | 5 | 0/1 | 4/6 | 0/4 | 432 |
| 327 | YYGNyCEGSC | 5 | 0/1 | 1/6 | 0/1 | 433 |

TABLE 6C

HLA-A*0201 binding 9-mer peptides derived from INHBB

| strat position | sequence | Binding Score | positive donor number | positive well number | positive CTL line | SEQ ID NO |
|---|---|---|---|---|---|---|
| 177 | SLWLYLKLL | 407.808 | 0/1 | 0/8 | | 140 |
| 14 | LLLLAAGWL | 96.074 | — | — | — | 141 |
| 170 | NLFVVQASL | 79.041 | 0/1 | 0/8 | | 142 |
| 213 | NMVEKRVDL | 63.256 | 0/1 | 0/8 | | 143 |
| 172 | FVVQASLWL | 47.291 | 0/1 | 0/8 | | 144 |
| 306 | QQFFIDFRL | 46.48 | 0/1 | 0/8 | | 145 |
| 281 | RLGDSRHRI | 42.774 | 0/1 | 0/8 | | 146 |
| 174 | VQASLWLYL | 34.427 | 0/1 | 0/8 | | 147 |
| 257 | ELAVVPVFV | 28.69 | 0/1 | 1/8 | 0/1 | 148 |
| 313 | RLIGWNDWI | 28.116 | 0/1 | 1/8 | 0/1 | 149 |
| 139 | RVSEIISFA | 22.546 | 0/1 | 3/8 | 0/3 | 150 |
| 151 | GLASSRVRL | 21.362 | 0/1 | 0/8 | | 151 |
| 8 | ALGAACLLL | 21.362 | 0/1 | 1/8 | 0/1 | 152 |
| 250 | VQCDSCQEL | 15.096 | 0/1 | 1/8 | 0/1 | 153 |

TABLE 6D

HLA-A*0201 binding 10-mer peptides derived from INHBB

| strat position | sequence | Binding Score | positive donor number | positive well number | positive CTL line | SEQ ID NO |
|---|---|---|---|---|---|---|
| 179 | WLYLKLLPYV | 12951.1 | 0/1 | 1/8 | 0/1 | 154 |
| 301 | NLCCRQQFFI | 332.806 | 0/1 | 0/8 | | 155 |
| 237 | ALFERGERRL | 64.814 | 0/1 | 0/8 | | 156 |
| 382 | MLYFDDEYNI | 56.754 | 0/1 | 0/8 | | 157 |
| 13 | CLLLLAAGWL | 56.514 | — | — | — | 158 |
| 8 | ALGAACLLLL | 49.134 | — | — | — | 159 |
| 313 | RLIGWNDWII | 32.081 | 0/1 | 0/8 | | 160 |
| 173 | VVQASLWLYL | 29.711 | 0/1 | 2/8 | 0/2 | 161 |
| 256 | QELAVVPVFV | 27.521 | 0/1 | 0/8 | | 162 |
| 162 | FISNEGNQNL | 13.512 | 0/1 | 1/8 | 0/1 | 163 |

TABLE 6D-continued

HLA-A*0201 binding 10-mer peptides derived from INHBB

| strat position | sequence | Binding Score | positive donor number | positive well number | positive CTL line | SEQ ID NO |
|---|---|---|---|---|---|---|
| 305 | RQQFFIDFRL | 12.562 | 0/1 | 0/8 | | 164 |
| 362 | GLNPGTVNSC | 11.426 | 0/1 | 0/7 | | 165 |
| 85 | RLQMRGRPNI | 10.433 | 0/1 | 1/8 | 0/1 | 166 |
| 69 | RVDGDFLEAV | 10.425 | 0/1 | 0/8 | | 167 |

TABLE 7A

HLA-A*2402 binding 9-mer peptides derived from KIF20A

| strat position | sequence | Binding Score | positive donor number | positive well number | positive CTL line | SEQ ID NO |
|---|---|---|---|---|---|---|
| 308 | IYNELLYDL | 432 | 0/2 | 0/14 | — | 168 |
| 621 | MYEEKLNIL | 432 | 0/2 | 0/14 | — | 169 |
| 67 | VYLRVRPLL | 420 | 0/2 | 0/14 | — | 170 |
| 499 | KFSAIASQL | 56 | 0/2 | 0/14 | — | 171 |
| 304 | SFFEIYNEL | 44.352 | 0/2 | 0/14 | — | 172 |
| 187 | IFNSLQGQL | 36 | 0/2 | 0/14 | — | 173 |
| 305 | FFEIYNELL | 30 | 1/2 | | | 174 |
| 23 | MFESTAADL | 30 | 0/2 | 0/14 | — | 175 |
| 256 | SEDSUIAGL | 20 | 0/2 | 0/14 | — | 176 |
| 298 | RFSIWISFF | 20 | — | — | — | 177 |
| 383 | IFSIRILHL | 20 | 1/2 | | | 178 |
| 647 | KIEELEALL | 17.28 | 0/2 | 0/14 | — | 179 |
| 625 | KLNILKESL | 14.4 | 0/2 | 0/14 | — | 180 |
| 695 | KLQQCKAEL | 13.2 | 0/2 | 0/14 | — | 181 |
| 726 | FTIDVDKKL | 11.088 | 0/2 | 0/14 | — | 182 |
| 688 | QLQEVKAKL | 11.088 | 0/2 | 0/14 | — | 183 |

TABLE 7B

HLA-A*2402 binding 10-mer peptides derived from KIF20A

| strat position | sequence | Binding Score | positive donor number | positive well number | positive CTL line | SEQ ID NO |
|---|---|---|---|---|---|---|
| 308 | IYNE1LYDLL | 432 | 0/2 | 0/14 | — | 184 |
| 182 | RSLA1IFNSL | 24.192 | 0/2 | 1/14 | 0/1 | 185 |
| 304 | SFFEiYNELL | 24 | 1/2 | | | 186 |
| 742 | RLLRtELQKL | 15.84 | 0/2 | 0/14 | — | 187 |
| 739 | KNIR1LRTEL | 15.84 | 0/2 | 0/14 | — | 188 |
| 218 | RQEEmKKLSL | 14.4 | 0/2 | 2/14 | 0/2 | 189 |

TABLE 7B-continued

HLA-A*2402 binding 10-mer peptides derived from KIF20A

| strat position | sequence | Binding Score | positive donor number | positive well number | positive CTL line | SEQ ID NO |
|---|---|---|---|---|---|---|
| 70 | RVRP1LPSEL | 12.672 | 0/2 | 0/14 | — | 190 |
| 871 | RILRsRRSPL | 12 | 0/2 | 0/14 | — | 191 |
| 89 | RIENvETLVL | 12 | 0/2 | 1/14 | 0/1 | 192 |
| 364 | KNQSfASTHL | 12 | 0/2 | 0/14 | — | 193 |
| 66 | KVYLrVRPLL | 11.2 | 1/2 | | | 194 |
| 60 | DSMEkVKVYL | 10.08 | 0/2 | 0/14 | — | 195 |

TABLE 8A

HLA-A*2402 binding 9-mer peptides derived from KNTC2

| strat position | sequence | Binding Score | positive donor number | positive well number | positive CTL line | SEQ ID NO |
|---|---|---|---|---|---|---|
| 309 | KYQAYMSNL | 600 | 1/3 | | | 196 |
| 457 | VYVPLKELL | 432 | 0/3 | 0/18 | — | 197 |
| 414 | EYHKLARKL | 264 | 0/3 | 0/18 | — | 198 |
| 139 | SYELPDTKF | 165 | 0/3 | 0/18 | — | 199 |
| 629 | KYEKKATLI | 150 | 0/3 | 0/18 | — | 200 |
| 400 | KYARGKEAI | 100 | 0/3 | 1/18 | 0/1 | 201 |
| 124 | DFLKIFTFL | 50.4 | 1/3 | | | 202 |
| 134 | GFLCPSYEL | 33 | 0/3 | 0/18 | — | 203 |
| 257 | LFNVDAFKL | 33 | 0/3 | 0/18 | — | 204 |
| 242 | SFDEMNAEL | 26.4 | 0/3 | 0/18 | — | 205 |
| 128 | IFTFLYGFL | 24 | 0/3 | 0/18 | — | 206 |
| 146 | KFEEEVPRI | 18 | 0/3 | 1/18 | 0/1 | 207 |
| 368 | RINHERNEL | 15.84 | 0/3 | 1/18 | 0/1 | 208 |
| 235 | SFMSGADSF | 15 | 0/3 | 0/18 | — | 209 |
| 154 | IFKDLGYPF | 14.4 | 1/3 | | | 210 |
| 563 | EYQLVVQTT | 12.6 | 0/3 | 0/18 | — | 211 |
| 474 | KALNKKMGL | 12 | 0/3 | 1/18 | 0/1 | 212 |
| 150 | EVPRIFKDL | 10.08 | 1/3 | | | 213 |

TABLE 8B

HLA-A*2402 binding 10-mer peptides derived from KNTC2

| strat position | sequence | Binding Score | positive donor number | positive well number | positive CTL line | SEQ ID NO |
|---|---|---|---|---|---|---|
| 452 | KYRAQVYVPL | 560 | 2/3 | | | 214 |
| 610 | EYEECMSEDL | 360 | 0/3 | 1/18 | 0/1 | 215 |

TABLE 8B-continued

HLA-A*2402 binding 10-mer peptides derived from KNTC2

| strat position | sequence | Binding Score | positive donor number | positive well number | positive CTL line | SEQ ID NO |
|---|---|---|---|---|---|---|
| 360 | KYSVADIERI | 100 | 0/3 | 0/18 | — | 216 |
| 227 | DYTIKCYESF | 100 | 1/3 | | | 217 |
| 146 | KFEEVPRIF | 50.4 | 0/3 | 0/18 | — | 218 |
| 90 | AFIQQCIRQL | 30 | 0/3 | 0/18 | — | 219 |
| 20 | RSQDVNKQGL | 17.28 | 0/3 | 1/18 | 0/1 | 220 |
| 501 | RTLKEEVQKL | 15.84 | 0/3 | 0/18 | — | 221 |
| 403 | RGKEAIETQL | 13.44 | 0/3 | 1/18 | 0/1 | 222 |
| 273 | RALNEQIARL | 12 | 1/3 | | | 223 |
| 563 | EYQLVVQTTT | 10.5 | 0/3 | 3/22 | 0/3 | 224 |
| 467 | ETEEEINKAL | 10.08 | 0/3 | 1/22 | 0/1 | 225 |
| 541 | LLESTVNQGL | 10.08 | 0/3 | 1/22 | 0/1 | 226 |

TABLE 9A

HLA-A*0201 binding 9-mer peptides derived from TTK

| strat position | sequence | Binding Score | positive donor number | positive well number | positive CTL line | SEQ ID NO |
|---|---|---|---|---|---|---|
| 462 | YMSCFRTPV | 878.055 | 1/1 | | | 227 |
| 547 | KQIYAIKYV | 312.218 | 1/1 | | | 228 |
| 630 | NMLEAVHTI | 262.897 | 0/1 | 1/8 | 0/1 | 229 |
| 278 | LLNSPDCDV | 118.238 | 0/1 | 1/8 | 0/1 | 230 |
| 498 | ILATPLQNL | 83.527 | 0/1 | 0/8 | — | 231 |
| 811 | YVLGQLVGL | 73.172 | 0/1 | 0/8 | — | 232 |
| 719 | SLGCILYYM | 62.845 | 1/2 | | | 233 |
| 670 | QMQPDTTSV | 50.232 | 0/1 | 0/8 | — | 234 |
| 804 | GTTEEMKYV | 50.102 | 0/1 | 0/8 | — | 235 |
| 654 | LIVDGMLKL | 47.088 | 0/1 | 1/8 | 0/1 | 236 |
| 363 | SLLAKLEET | 31.074 | 0/1 | 0/8 | — | 237 |
| 790 | YVQIQTHPV | 27.995 | 0/1 | 0/8 | — | 238 |
| 785 | LLAHPYVQI | 26.604 | 0/1 | 0/8 | — | 239 |
| 86 | KLIGRYSQA | 26.082 | 0/1 | 0/8 | — | 240 |
| 186 | NLNLQKKQL | 21.362 | 0/1 | 0/8 | — | 241 |
| 671 | MQPDTTSVV | 20.152 | 0/1 | 0/8 | — | 242 |
| 577 | KLQQHSDKI | 17.892 | 0/1 | 0/8 | — | 243 |
| 142 | FAFVHISFA | 14.856 | 0/1 | 0/8 | — | 244 |
| 322 | CELRNLKSV | 11.509 | 0/1 | 0/8 | — | 245 |
| 824 | SILKAAKTL | 10.868 | 0/1 | 0/8 | — | 246 |

TABLE 9B

HLA-A*0201 binding 10-mer peptides derived from TTK

| strat position | sequence | Binding Score | positive donor number | positive well number | positive CTL line | SEQ ID NO |
|---|---|---|---|---|---|---|
| 68 | LLLKLEKNSV | 437.482 | 0/1 | 0/8 | — | 247 |
| 277 | NLLNSPDCDV | 257.342 | 0/1 | 0/8 | — | 248 |
| 653 | FLIVDGMLKL | 226.014 | 0/1 | 0/8 | — | 249 |
| 423 | TTFEQPVFSV | 195.487 | 0/1 | 0/8 | — | 250 |
| 542 | VLNEKKQIYA | 190.448 | 0/1 | 0/8 | — | 251 |
| 658 | GMLKLIDFGI | 161.697 | 0/1 | 0/8 | — | 252 |
| 194 | LLSEEEKKNL | 148.896 | 0/1 | 0/8 | — | 253 |
| 462 | YMSCFRTPVV | 94.738 | 1/1 | | | 254 |
| 57 | MMANNPEDWL | 70.685 | 0/1 | 0/8 | — | 255 |
| 600 | MVMECGNIDL | 48.205 | 0/1 | 0/8 | — | 256 |
| 689 | YMPPEAIKDM | 37.961 | 0/1 | 0/8 | — | 257 |
| 86 | KLIGRYSQAI | 36.515 | 0/1 | 0/8 | — | 258 |
| 669 | NQMQPDTTSV | 26.092 | 0/1 | 1/8 | 0/1 | 259 |
| 497 | QILATPLQNL | 24.997 | 0/1 | 0/8 | — | 260 |
| 654 | LIVDGMLKLI | 22.997 | 0/1 | 0/8 | — | 261 |
| 186 | NLNLQKKQLL | 21.362 | 0/1 | 1/8 | 0/1 | 262 |
| 670 | QMQPDTTSVV | 20.595 | 0/1 | 0/8 | — | 263 |
| 803 | KGTTEEMKYV | 20.102 | 0/1 | 0/8 | — | 264 |
| 11 | LTIDSIMNKV | 15.486 | 0/1 | 0/8 | — | 265 |
| 577 | KLQQHSDKII | 14.971 | 0/1 | 0/8 | — | 266 |

TABLE 10A

HLA-A*0201 binding 9-mer peptides derived from URLC10

| strat position | sequence | Binding Score | positive donor number | positive well number | positive CTL line | SEQ ID NO |
|---|---|---|---|---|---|---|
| 131 | KIFPRFFMV | 1364.78 | 0/1 | 0/8 | — | 267 |
| 204 | GLWLAILLL | 407.808 | 0/1 | 0/8 | — | 268 |
| 65 | LLVVALPRV | 271.948 | 0/1 | 0/8 | — | 269 |
| 60 | ALLALLLVV | 242.674 | — | — | — | 270 |
| 206 | WLAILLLLA | 52.561 | 1/1 | | | 271 |
| 212 | LLASIAAGL | 36.316 | 1/1 | | | 272 |
| 210 | LLLLASIAA | 31.249 | 0/1 | 0/8 | — | 273 |
| 137 | FMVAKQCSA | 16.505 | 0/1 | 2/8 | 0/2 | 274 |
| 58 | TMALLALLL | 15.428 | 0/1 | 2/8 | 0/2 | 275 |
| 59 | MALLALLLV | 13.975 | 0/1 | 2/8 | 0/2 | 276 |
| 209 | ILLLASIA | 12.812 | 0/1 | 0/8 | — | 434 |
| 208 | AILLLASI | 12.208 | — | — | — | 277 |

TABLE 10A-continued

HLA-A*0201 binding 9-mer peptides derived from URLC10

| strat position | sequence | Binding Score | positive donor number | positive well number | positive CTL line | SEQ ID NO |
|---|---|---|---|---|---|---|
| 69 | ALPRVWTDA | 8.446 | 0/1 | 0/8 | — | 278 |
| 197 | SMGESCGGL | 8.223 | 0/1 | 0/8 | — | 279 |
| 61 | LLALLLVVA | 7.964 | — | — | — | 280 |
| 67 | VVALPRVWT | 6.097 | 0/1 | 0/8 | — | 281 |
| 72 | RVWTDANLT | 5.412 | 0/1 | 0/8 | — | 282 |
| 160 | FLLEEPMPF | 5.2 | 0/1 | 1/8 | 0/1 | 283 |
| 62 | LALLLVVAL | 4.292 | 0/1 | 0/8 | — | 284 |
| 57 | GTMALLALL | 2.525 | 0/1 | 1/8 | 0/1 | 285 |

TABLE 10B

HLA-A*0201 binding 10-mer peptides derived from URLC10

| strat position | sequence | Binding Score | positive donor number | positive well number | positive CTL line | SEQ ID NO |
|---|---|---|---|---|---|---|
| 64 | LLLVVALPRV | 1006.21 | 0/1 | 0/8 | — | 286 |
| 204 | GLWLAILLLL | 407.808 | 0/1 | 1/8 | 0/1 | 287 |
| 211 | LLLASIAAGL | 134.369 | 1/1 | | | 288 |
| 258 | TMALLALLLV | 115.534 | — | — | — | 289 |
| 61 | LLALLLVVAL | 83.527 | — | — | — | 290 |
| 160 | FLLEEPMPFF | 65.782 | 0/1 | 0/8 | — | 291 |
| 209 | ILLLLASIAA | 31.249 | 0/1 | 0/8 | — | 292 |
| 131 | KIFPRFFMVA | 26.186 | 0/1 | 0/8 | — | 293 |
| 60 | ALLALLLVVA | 17.334 | — | — | — | 294 |
| 66 | LVVALPRVWT | 6.097 | 0/1 | 0/8 | — | 295 |
| 59 | MALLALLLVV | 5.73 | — | — | — | 296 |
| 2 | RLQRPRQAPA | 4.968 | 0/1 | 1/8 | 0/1 | 297 |
| 112 | CQNPRRCKWT | 4.156 | 0/1 | 0/8 | — | 298 |
| 72 | RVWTDANLTA | 3.608 | 0/1 | 0/8 | — | 299 |
| 53 | WAPLGTMALL | 3.139 | 0/1 | 0/8 | — | 300 |
| 121 | TEPYCVIAAV | 3.111 | 0/1 | 0/8 | — | 301 |
| 162 | LEEPMPFFYL | 2.739 | 0/1 | 1/8 | 0/1 | 302 |
| 181 | LEGPPINSSV | 2.299 | 0/1 | 2/8 | 0/2 | 303 |
| 170 | YLKCCKIRYC | 2.024 | 0/1 | 0/8 | — | 304 |
| 130 | VKIFPRFFMV | 1.81 | 0/1 | 0/8 | — | 305 |

Figure 1:
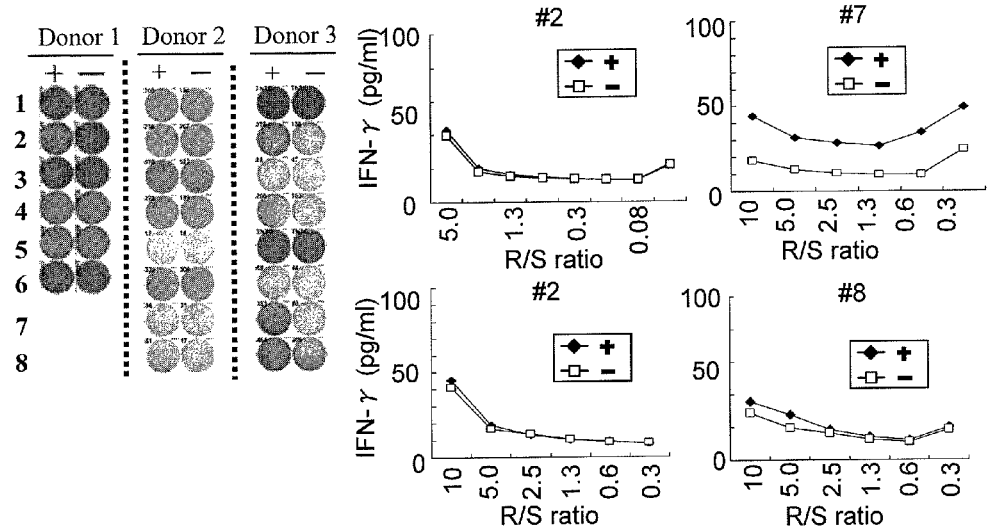
FIG. 1-1
Figure 1:
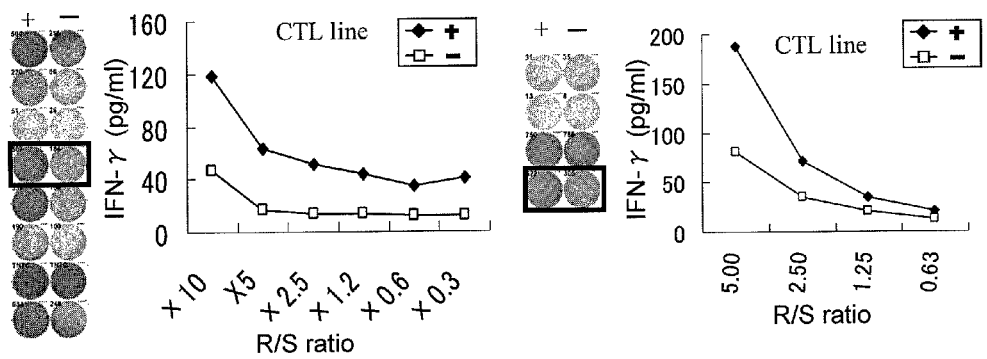
Figure 1:
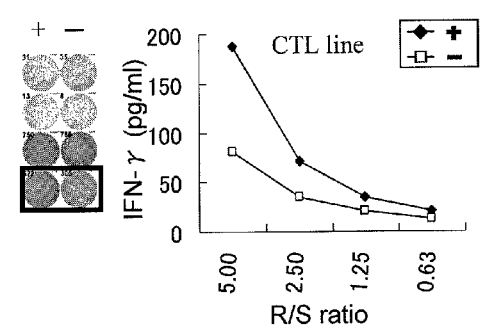
Figure 1:
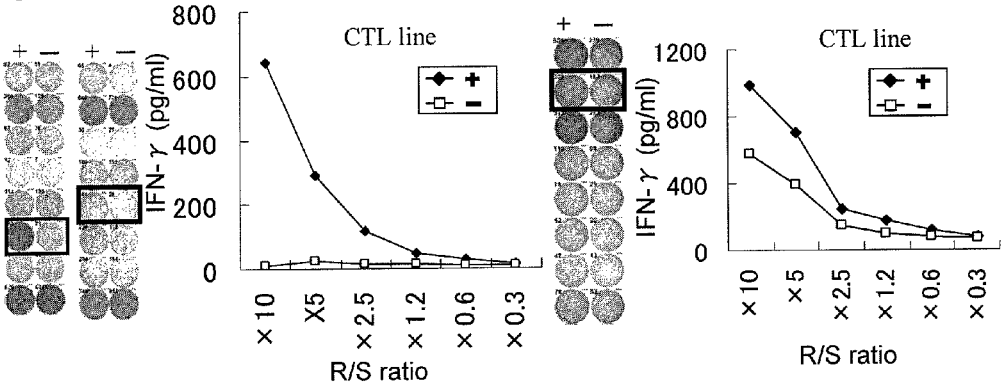
Figure 1:
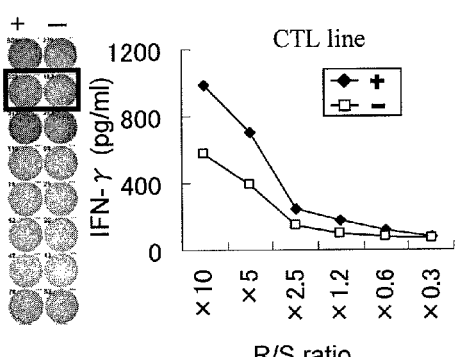
Figure 1:
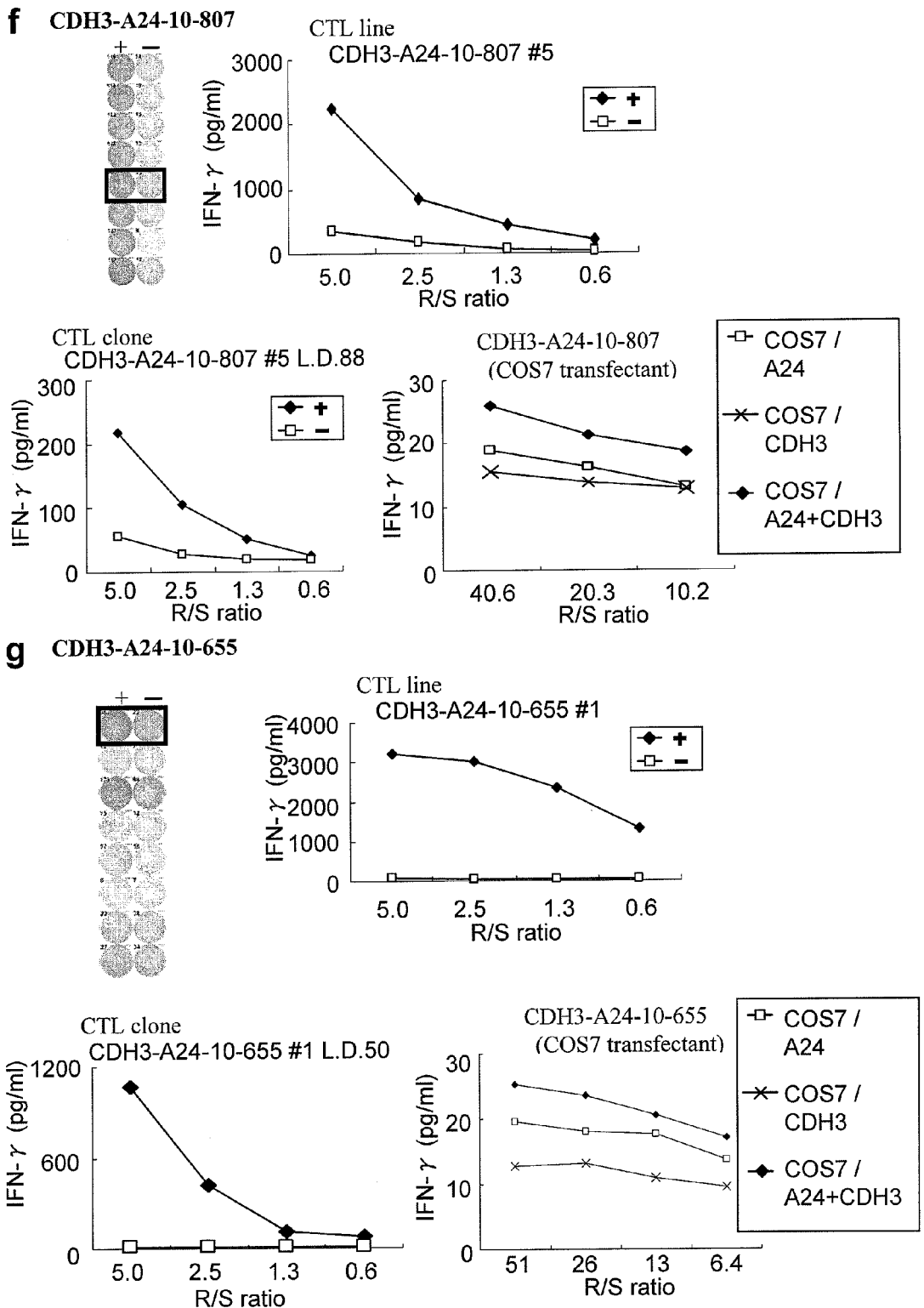

Stimulation of the T Cells Using the Predicted Peptides from CDH3 Restricted with HLA-A*2402 and Establishment for CTL Lines Stimulated with CDH3 Derived Peptides CTLs for those peptides derived from CDH3 were generated according to the protocols set forth in "Materials and Methods" section above. Resulting that CTLs having detectable specific CTL activity, as determined by IFN-gamma ELISPOT assay, are shown in FIG. 1. In particular, CDH3-A24-9-513 (SEQ ID NO: 19), CDH3-A24-9-406 (SEQ ID NO: 22), CDH3-A24-10-807 (SEQ ID NO: 30), CDH3-A24-10-332 (SEQ ID NO: 34), CDH3-A24-10-655 (SEQ ID NO: 344) and CDH3-A24-10-470 (SEQ ID NO: 358) demonstrated potent IFN-gamma production as compared to the control by IFN-gamma ELISPOT assay, and the cells in the positive well number #5 stimulated with SEQ ID NO: 19, #2 with SEQ ID NO: 22, #5 with SEQ ID NO: 30, #4 with SEQ ID NO: 34, #1 with SEQ ID NO: 344 and #4 with SEQ ID NO: 358 were expanded and CTL lines were established. Those CTL lines having higher specific CTL activities against the peptide-pulsed target as compared to the activities against target without peptide pulse were determined by ELISA. Results are shown in FIG. 1. While, other peptides shown in table 2 could not establish the CTL lines despite possible binding activity with HLA-A*2402. For example, the typical negative peptide (CDH3-A24-10-248) were shown in FIG. 1a. In this invention, the peptides which could establish CTL line were selected as potent CTL stimulation peptide.

Establishment for CTL Clones Stimulated with CDH3 Derived Peptides

Furthermore, the limiting dilution from these CTL lines was performed according to the protocols set forth in the "Materials and Methods" section above. The establishment of CTL clones from CDH3-A24-10-807 (SEQ ID NO: 30) #5 and CDH3-A24-10-655 (SEQ ID NO: 344) #1 CTL line are shown in FIGS. 1f and g. CTL clones had potent and specific CTL activities against the peptide-pulsed target as compared to the activities against target without peptide pulse.

Specific CTL Activity Against the Target Cells Expressing CDH3 and HLA-A*2402

The established CTL line raised against these peptides were examined for their ability to recognize the target cells expressing CDH3 and HLA-A*2402. Specific CTL activity against COS7 transfected with both full length CDH3 gene and the HLA-A*2402 molecule, which serves as a specific model for the target cells endogenously express CDH3 and HLA-A*2402, was tested using as effector cells the CTL lines raised by CDH3-A24-10-807 (SEQ ID NO: 30) and CDH3-A24-10-655 (SEQ ID NO: 344). COS7 transfected with full length CDH3 but not HLA-A*2402 and COS7 transfected with HLA-A*2402 but not full length CDH3 were prepared as controls. The CTL clones demonstrated the highest specific CTL activity against COS7 that was transfected with both CDH3 and HLA-A2402 (FIGS. 1f and g).

These results clearly demonstrate that CDH3-A24-10-807 (SEQ ID NO: 30) and CDH3-A24-10-655 (SEQ ID NO: 344) are naturally expressed on the target cell surface with HLA-A2402 molecule and recognize CTL. Furthermore, these peptides are epitope peptides, which may serve as cancer vaccines targeting CDH3 expressed tumors.

Stimulation of the T Cells Using the Predicted Peptides from EPHA4 Restricted with HLA-A*2402 or HLA-A*0201, and Establishment for CTL Lines Stimulated with EPHA4 Derived Peptides CTLs for those peptides derived from EphA4 were generated by IFN-gamma ELISPOT assay. Resulting that CTLs having detectable specific CTL activity, as determined by IFN-gamma ELISPOT assay, are shown in FIG. 2. In particular, EphA4-A24-9-453 (SEQ ID NO: 41), EphA4-A24-9-5 (SEQ ID NO: 44), EphA4-A24-9-869 (SEQ ID NO: 46), EphA4-A24-9-420 (SEQ ID NO: 48), EphA4-A24-10-24 (SEQ ID NO: 78), EphA4-A02-9-501 (SEQ ID NO: 376) and EphA4-A02-9-165 (SEQ ID NO: 379) demonstrated potent IFN-gamma production by IFN-gamma ELISPOT assay, and the cells in the positive well number #3 stimulated with EphA4-A24-9-453 (SEQ ID NO: 41), #2 with EphA4-A24-9-5 (SEQ ID NO: 44), #5 with EphA4-A24-9-869 (SEQ ID NO: 46), #6 with EphA4-A24-9-420 (SEQ ID NO: 48), #4 with EphA4-A24-10-24 (SEQ ID NO: 78), #8 with EphA4-A02-9-501 (SEQ ID NO: 376) and #3 with EphA4-A02-9-165 (SEQ ID NO: 379) were expanded and CTL lines were established. Those CTL lines having higher specific CTL activities against the peptide-pulsed target as compared to the activities against target without peptide pulse were determined by ELISA. Especially, CTL lines stimulated with EphA4-A02-9-501 (SEQ ID NO: 376) and EphA4-A02-9-165 (SEQ ID NO: 379) were tested by $^{51}$Cr-release assay according to the protocols set forth in the "Materials and Methods" section above. Results are shown in FIG. 2a-h. While, other peptides shown in table 3 could not establish the CTL lines despite possible binding activity with HLA-A*2402 or HLA-A*0201. For example, the typical negative peptide (EphA4-A24-9-384) were shown in FIG. 2a. In this invention, the peptides which could establish CTL line were selected as potent CTL stimulation peptides.

Stimulation of the T Cells Using the Predicted Peptides from ECT2 Restricted with HLA-A*2402, and Establishment for CTL Lines Stimulated with ECT2 Derived Peptides CTLs for those peptides derived from ECT2 were generated according to the protocols set forth in the "Materials and Methods" section above. Resulting CTLs having detectable specific CTL activity as determined by an IFN-gamma ELISPOT assay are shown in FIG. 3. In particular, ECT2-A24-9-515 (SEQ ID NO: 80), ECT2-A24-10-40 (SEQ ID NO: 100) and ECT2-A24-10-101 (SEQ ID NO: 101) showed potent IFN-gamma production, and the cells in the positive well number #7 stimulated with ECT2-A24-9-515 (SEQ ID NO: 80), #2 with ECT2-A24-10-40 (SEQ ID NO: 100) and #1 with ECT2-A24-10-101 (SEQ ID NO: 101) were expanded and CTL lines were established. Those CTL lines having higher specific CTL activities against the peptide-pulsed target as compared to the activities against target without peptide pulse were determined by ELISA. Results are shown in FIG. 3a-d. While, other peptides shown in table 4 could not establish the CTL lines despite possible binding activity with HLA-A*2402. For example, the typical negative peptide (ECT2-A24-10-322, ECT2-A24-9-657 and ECT2-A24-10-811) were shown in FIG. 3a. In this invention, the peptides which could establish CTL line were selected as potent CTL stimulation peptide.

Establishment for CTL Clones Stimulated with ECT2 Derived Peptides

Furthermore, the limiting dilution from these CTL lines was performed according to the protocols set forth in the "Materials and Methods" section above. The establishment of CTL clones from ECT2-A24-10-40 (SEQ ID NO: 100) #2 CTL line are shown in FIG. 3c. CTL clones had potent and specific CTL activities against the peptide-pulsed target as compared to the activities against target without peptide pulse.

Specific CTL Activity Against the Target Cells Expressing ECT2 and HLA-A*2402

The established CTL line raised against these peptides were examined for their ability to recognize the target cells expressing ECT2 and HLA-A*2402. Specific CTL activity against COS7 transfected with both full length ECT2 gene and the HLA-A*2402 molecule, which serves as a specific model for the target cells endogenously express ECT2 and HLA-A*2402, was tested using as effector cells the CTL clone raised by ECT2-A24-10-40 (SEQ ID NO: 100) and the CTL line raised by ECT2-A24-10-101 (SEQ ID NO: 101). COS7 transfected with full length ECT2 but not HLA-A*2402 and COS7 transfected with HLA-A*2402 but not full length ECT2 (replaced other gene e.g. URLC10 or INHBB) were prepared as controls. The CTL line demonstrated the highest specific CTL activity against COST that was transfected with both ECT2 and HLA-A2402 (FIGS. 3c and d).

These results clearly demonstrate that ECT2-A24-10-40 (SEQ ID NO: 100) and ECT2-A24-10-101 (SEQ ID NO: 101) are naturally expressed on the target cell surface with HLA-A2402 molecule and recognize CTL. Furthermore, these peptides are epitope peptides, which may serve as cancer vaccines targeting ECT2 expressed tumors.

Cytotoxic Activity Against Cancer Cell Line Endogenously Expressing HLA-A*2402 and ECT2

Furthermore, Cytotoxic activity was examined by cytotoxicity assay according to the protocols set forth in the "Materials and Methods" section above. As a result, as shown in FIG. 3b, CTL clone stimulated with ECT2-A24-9-515 (SEQ ID NO: 80) showed remarkably high cytotoxic effect towards HLA-A24-positive and ECT-positive cancer cell lines TE6, compared to that towards HLA-A24-negative and ECT-positive cancer cell lines TE5.

Stimulation of the T Cells Using the Predicted Peptides from HIG2 Restricted with HLA-A*2402 or HLA-A*0201, and Establishment for CTL Lines Stimulated with HIG2 Derived Peptides CTLs for those peptides derived from HIG2 were generated according to the protocols set forth in the "Materials and Methods" section above. Resulting CTLs having detectable specific CTL activity as determined by an IFN-gamma ELISPOT assay are shown in FIG. 4. In particular, HIG2-A24-9-19 (SEQ ID NO: 110), HIG2-A24-9-22 (SEQ ID NO: 111), HIG2-A24-9-8 (SEQ ID NO: 387), HIG2-A24-10-7 (SEQ ID NO: 112), HIG2-A24-10-18 (SEQ ID NO: 394), HIG2-A02-9-8 (SEQ ID NO: 114), HIG2-A02-9-15 (SEQ ID NO: 116), HIG2-A02-9-4 (SEQ ID NO: 117) and HIG2-A02-10-8 (SEQ ID NO: 121) demonstrated potent IFN-gamma production by IFN-gamma ELISPOT assay, and the cells in the positive well number #6 stimulated with HIG2-A24-9-19 (SEQ ID NO: 110), #7 with HIG2-A24-9-22 (SEQ ID NO: 111), #5 with HIG2-A24-9-8 (SEQ ID NO: 387), #1 with HIG2-A24-10-7 (SEQ ID NO: 112), #7 with HIG2-A24-10-18 (SEQ ID NO: 394), #10 with HIG2-A02-9-8 (SEQ ID NO: 114), #10 with HIG2-A02-9-15 (SEQ ID NO: 116), #10 with HIG2-A02-9-4 (SEQ ID NO: 117) and #9 with HIG2-A02-10-8 (SEQ ID NO: 121) were expanded and CTL lines were established. Those CTL lines having higher specific CTL activities against the peptide-pulsed target as compared to the activities against target without peptide pulse were determined by ELISA. Results are shown in FIG. 4a-j. While, other peptides shown in table 5 could not establish the CTL lines despite possible binding activity with HLA-A*2402. For example, the typical negative peptide (HIG2-A24-9-7) were shown in FIG. 4a. In this invention, the peptides which could establish CTL line were selected as potent CTL stimulation peptide.

Establishment for CTL Clones Stimulated with HIG2 Derived Peptides

Furthermore, the limiting dilution from these CTL lines was performed according to the protocols set forth in the "Materials and Methods" section above. The establishment of CTL clones from HIG2-A24-9-22 (SEQ ID NO: 111) #7 CTL line, HIG2-A24-9-8 (SEQ ID NO: 387) #5 CTL line, HIG2-A24-10-7 (SEQ ID NO: 112) #1 CTL line, HIG2-A24-10-18 (SEQ ID NO: 394) #7 CTL line and HIG2-A02-9-4 (SEQ ID NO: 117) #10 CTL line are shown in FIGS. 4c, e, f, g and i. CTL clones had potent and specific CTL activities against the peptide-pulsed target as compared to the activities against target without peptide pulse.

Specific CTL Activity Against the Target Cells Expressing HIG2 and HLA-A*0201

The established CTL line raised against these peptides were examined for their ability to recognize the target cells expressing HIG2 and HLA-A*0201. Specific CTL activity against 293T or COS7 transfected with both full length HIG2 gene and the HLA-A*0201 molecule, which serves as a specific model for the target cells endogenously express HIG2 and HLA-A*0201, was tested using as effector cells the CTL lines raised by HIG2-A02-9-8 (SEQ ID NO: 114), HIG2-A02-9-15 (SEQ ID NO: 116) and the CTL clone raised by HIG2-A02-9-4 (SEQ ID NO: 117). 293T or COS7 transfected with full length ECT2 but not HLA-A*0201 and 293T or COS7 transfected with HLA-A*0201 but not full length ECT2 (or replaced other gene e.g. FoxP3 or TTK) were prepared as controls. The CTL line demonstrated the highest specific CTL activity against 293T or COS7 that was transfected with both ECT2 and HLA-A*0201 (FIGS. 4e, h and i).

These results clearly demonstrate that HIG2-A02-9-8 (SEQ ID NO: 114), HIG2-A02-9-15 (SEQ ID NO: 116) and HIG2-A02-9-4 (SEQ ID NO: 117) are naturally expressed on the target cell surface with HLA-A2402 or HLA-A0201 molecule and recognize CTL. Furthermore, these peptides are epitope peptides, which may serve as cancer vaccines targeting HIG2 expressed tumors.

Cytotoxic Activity Against Cancer Cell Line Endogenously Expressing HLA-A*0201 and HIG2

Furthermore, Cytotoxic activity was examined by cytotoxicity assay according to the protocols set forth in the "Materials and Methods" section above. As a result, as shown in FIG. 4i, CTL clone stimulated with HIG2-A02-9-4 (SEQ ID NO: 117) showed remarkably high cytotoxic effect towards HLA-A02-positive and HIG2-positive cancer cell lines CAki-1, compared to that towards HLA-A02-negative and HIG2-positive cancer cell lines A498.

Stimulation of the T Cells Using the Predicted Peptides from INHBB Restricted with HLA-A*2402 or HLA-A*0201, and Establishment for CTL Lines Stimulated with INHBB Derived Peptides CTLs for those peptides derived from INHBB were generated according to the protocols set forth in the "Materials and Methods" section above. Resulting CTLs having detectable specific CTL activity as determined by an IFN-gamma ELISPOT assay are shown in FIG. 5. In particular, INHBB-A24-9-180 (SEQ ID NO: 395), INHBB-A24-10-180 (SEQ ID NO: 133), INHBB-A24-10-305 (SEQ ID NO: 135), INHBB-A24-10-7 (SEQ ID NO: 137) and INHBB-A24-10-212 (SEQ ID NO: 426) demonstrated potent IFN-gamma production by IFN-gamma ELISPOT assay, and the cells in the positive well number #7 stimulated with INHBB-A24-9-180 (SEQ ID NO: 395), #3 with INHBB-A24-10-180 (SEQ ID NO: 133), #2 with INHBB-A24-10-305 (SEQ ID NO: 135), #8 and #2 with INHBB-A24-10-7 (SEQ ID NO: 137) and #1 with INHBB-A24-10-212 (SEQ ID NO: 426) were expanded and CTL lines were established. Those CTL lines having higher specific CTL activities against the peptide-pulsed target as compared to the activities against target without peptide pulse were determined by ELISA. Results are shown in FIG. 5b-e. While, other peptides shown in table 6 could not establish the CTL lines despite possible binding activity with HLA-A*2402 and HLA*0201. For example, the typical negative peptide (INHBB-A24-9-238) were shown in FIG. 5a. In this invention, the peptides which could establish CTL line were selected as potent CTL stimulation peptide.

Establishment for CTL Clones Stimulated with INHBB Derived Peptides

Furthermore, the limiting dilution from these CTL lines was performed according to the protocols set forth in the "Materials and Methods" section above. The establishment of CTL clones from INHBB-A24-9-180 (SEQ ID NO: 395) #7 CTL line, and INHBB-A24-10-305 (SEQ ID NO: 135) #2 CTL line are shown in FIGS. 5b and d. CTL clones had potent and specific CTL activities against the peptide-pulsed target as compared to the activities against target without peptide pulse.

Specific CTL Activity Against the Target Cells Expressing INHBB and HLA-A*2402

The established CTL line raised against these peptides were examined for their ability to recognize the target cells expressing INHBB and HLA-A*2402. Specific CTL activity against 293T transfected with both full length INHBB gene and the HLA-A*2402 molecule, which serves as a specific model for the target cells endogenously express INHBB and HLA-A*2402, was tested using as effector cells the CTL lines raised by INHBB-A24-10-180 (SEQ ID NO: 133) and INHBB-A24-10-7 (SEQ ID NO: 137) and the CTL clone raised by INHBB-A24-10-305 (SEQ ID NO: 135), 293T transfected with full length INHBB but not HLA-A*2402 and 293T transfected with HLA-A*2402 but not full length INHBB were prepared as controls. The CTL line demonstrating the highest specific CTL activity against 293T was that transfected with both INHBB and HLA-A*2402 (FIGS. 5c, d and e).

These results clearly demonstrate that INHBB-A24-10-305 (SEQ ID NO: 135), INHBB-A24-10-180 (SEQ ID NO: 133) and INHBB-A24-10-7 (SEQ ID NO: 137) are naturally expressed on the target cell surface with HLA-A2402 molecule and recognize CTL. Furthermore, these peptides are epitope peptides, which may serve as cancer vaccines targeting INHBB expressed tumors.

Cytotoxic Activity Against Cancer Cell Line Endogenously Expressing HLA-A*2402 and INHBB Furthermore, Cytotoxic activity was examined by cytotoxicity assay according to the protocols set forth in the "Materials and Methods" section above. As a result, as shown in FIG. 5b, CTL clone stimulated with INHBB-A24-9-180 (SEQ ID NO: 395) showed remarkably high cytotoxic effect towards HLA-A24-positive and INHBB-positive cancer cell lines MIAPaca2, compared to that towards HLA-A24-negative and INHBB-positive cancer cell lines CAki-2.

Stimulation of the T Cells Using the Predicted Peptides from KIF20A Restricted with HLA-A*2402, and Establishment for CTL Lines Stimulated with KIF20A Derived Peptides CTLs for those peptides derived from KIF20A were generated according to the protocols set forth in the "Materials and Methods" section above. Resulting CTLs having detectable specific CTL activity as determined by an IFN-gamma ELISPOT assay are shown in FIG. 6. In particular, KIF20A-A24-9-305 (SEQ ID NO: 174), KIF20A-A24-9-383 (SEQ ID NO: 178), KIF20A-A24-10-304 (SEQ ID NO: 186) and KIF20A-A24-10-66 (SEQ ID NO: 194) demonstrated potent IFN-gamma production by IFN-gamma ELISPOT assay, and the cells in the positive well number #2 stimulated with KIF20A-A24-9-305 (SEQ ID NO: 174), #3 with KIF20A-A24-9-383 (SEQ ID NO: 178), #5 with KIF20A-A24-10-304 (SEQ ID NO: 186) and #6 with KIF20A-A24-10-66 (SEQ ID NO: 194) were expanded and CTL lines were established. Those CTL lines having higher specific CTL activities against the peptide-pulsed target as compared to the activities against target without peptide pulse were determined by ELISA. Results are shown in FIG. 6a-e. While, other peptides shown in table 7 could not establish the CTL lines despite possible binding activity with HLA-A*2402. For example, the typical negative peptide (KIF20A-A24-9-647 and KIF20A-A24-10-182) were shown in FIG. 6a. In this invention, the peptides which could establish CTL line were selected as potent CTL stimulation peptide.

Establishment for CTL Clones Stimulated with KIF20A Derived Peptides

Furthermore, the limiting dilution from these CTL lines was performed according to the protocols set forth in the "Materials and Methods" section above. The establishment of CTL clones from KIF20A-A24-9-305 (SEQ ID NO: 174) #2 CTL line, KIF20A-A24-10-304 (SEQ ID NO: 186) #5 CTL line and KIF20A-A24-10-66 (SEQ ID NO: 194) #6 CTL line are shown in FIGS. 6b, d and e. CTL clones had potent and specific CTL activities against the peptide-pulsed target as compared to the activities against target without peptide pulse.

Specific CTL Activity Against the Target Cells Expressing KIF20A and HLA-A*2402

The established CTL line raised against these peptides were examined for their ability to recognize the target cells expressing KIF20A and HLA-A*2402. Specific CTL activity against COS7 transfected with both full length KIF20A gene and the HLA-A*2402 molecule and A24-LCL transfected by electropolation with full length KIF20A gene, which serve as a specific model for the target cells endogenously express KIF20A and HLA-A*2402, was tested using as effector cells the CTL lines raised by KIF20A-A24-9-383 (SEQ ID NO: 178) and KIF20A-A24-10-304 (SEQ ID NO: 186) and the CTL clone raised by KIF20A-A24-10-66 (SEQ ID NO: 194). COS7 transfected with full length KIF20A but not HLA-A*2402 and COS7 transfected with HLA-A*2402 but not full length KIF20A (or replaced full length URLC10 gene), COS7 transfected with HLA-A*2402 and pulsed with KIF20A-10-308, and A24-LCL transfected with mock vector were prepared as controls. The CTL line demonstrated the highest specific CTL activity against COS7 that was transfected with both KIF20A and HLA-A*2402 (FIGS. 6b, c and d). Alternatively, the CTL line stimulated with KIF20A-A24-10-304 (SEQ ID NO: 186) demonstrated against A24-LCL transfected with KIF20A.

These results clearly demonstrate that KIF20A-A24-9-383 (SEQ ID NO: 178), KIF20A-A24-10-304 (SEQ ID NO: 186) and KIF20A-A24-10-66 (SEQ ID NO: 194) is naturally expressed on the target cell surface with HLA-A2402 molecule and recognize CTL. Furthermore, these peptides are epitope peptides, which may serve as cancer vaccines targeting KIF20A expressed tumors.

Cytotoxic Activity Against Cancer Cell Line Endogenously Expressing HLA-A*2402 and KIF20A Furthermore, Cytotoxic activity was examined by cytotoxicity assay according to the protocols set forth in the "Materials and Methods" section above. As a result, as shown in FIGS. 6b and e, CTL clone stimulated with KIF20A-A24-9-305 (SEQ ID NO: 174) or KIF20A-A24-10-304 (SEQ ID NO: 186) showed remarkably high cytotoxic effect towards HLA-A24-positive and KIF20A-positive cancer cell lines PK45P or MIAPaca2 respectively, compared to that towards HLA-A24-negative and KIF20A-positive cancer cell lines PK59.

Stimulation of the T Cells Using the Predicted Peptides from KNTC2 Restricted with HLA-A*2402, and Establishment for CTL Lines Stimulated with KNTC2 Derived Peptides CTLs for those peptides derived from KNTC2 were generated according to the protocols set forth in the "Materials and Methods" section above. Resulting CTLs having detectable specific CTL activity as determined by an IFN-gamma ELISPOT assay are shown in FIG. 7. In particular, KNTC2-

A24-9-309 (SEQ ID NO: 196), KNTC2-A24-9-124 (SEQ ID NO: 202), KNTC2-A24-9-154 (SEQ ID NO: 210), KNTC2-A24-9-150 (SEQ ID NO: 213), KNTC2-A24-10-452 (SEQ ID NO: 214), KNTC2-A24-10-227 (SEQ ID NO: 217) and KNTC2-A24-10-273 (SEQ ID NO: 223) demonstrated potent IFN-gamma production by IFN-gamma ELISPOT assay, and the cells in the positive well number #8 stimulated with KNTC2-A24-9-309 (SEQ ID NO: 196), #5 with KNTC2-A24-9-124 (SEQ ID NO: 202), #5 with KNTC2-A24-9-154 (SEQ ID NO: 210), #7 with KNTC2-A24-9-150 (SEQ ID NO: 213), #4 and #5 with KNTC2-A24-10-452 (SEQ ID NO: 214), #1 with KNTC2-A24-10-227 (SEQ ID NO: 217) and #8 with KNTC2-A24-10-273 (SEQ ID NO: 223) were expanded and CTL lines were established. Those CTL lines having higher specific CTL activities against the peptide-pulsed target as compared to the activities against target without peptide pulse were determined by ELISA. Results are shown in FIG. 7a-h. While, other peptides shown in table 8 could not establish the CTL lines despite possible binding activity with HLA-A*2402. For example, the typical negative peptide (KNTC2-A24-10-610) were shown in FIG. 7a. In this invention, the peptides which could establish CTL line were selected as potent CTL stimulation peptide.

Establishment for CTL Clones Stimulated with KNTC2 Derived Peptides

Furthermore, the limiting dilution from these CTL lines was performed according to the protocols set forth in the "Materials and Methods" section above. The establishment of CTL clones from KNTC2-A24-9-154 (SEQ ID NO: 210) #5 CTL line and KNTC2-A24-10-452 (SEQ ID NO: 214) #5 CTL line are shown in FIGS. 7d and f. CTL clones had potent and specific CTL activities against the peptide-pulsed target as compared to the activities against target without peptide pulse.

Specific CTL Activity Against the Target Cells Expressing KNTC2 and HLA-A*2402

The established CTL line raised against these peptides were examined for their ability to recognize the target cells expressing KNTC2 and HLA-A*2402. Specific CTL activity against HEK293 transfected with both full length KNTC2 gene and the HLA-A*2402 molecule which serves as a specific model for the target cells endogenously express KNTC2 and HLA-A*2402, was tested using as effector cells the CTL clones raised by KNTC2-A24-10-452 (SEQ ID NO: 214). HEK293 transfected with full length KNTC2 but not HLA-A*2402, HEK293 transfected with HLA-A*2402 but not full length KNTC2 and HEK293 transfected with HLA-A*2402 and pulsed with KNTC2-9-309 were prepared as controls. The CTL line demonstrating the highest specific CTL activity against HEK293 was that transfected with both KNTC2 and HLA-A*2402 (FIG. 7f).

These results clearly demonstrate that KNTC2-A24-10-452 (SEQ ID NO: 214) is naturally expressed on the target cell surface with HLA-A2402 molecule and recognize CTL. Furthermore, these peptides are epitope peptides, which may serve as cancer vaccines targeting KNTC2 expressed tumors.

Stimulation of the T Cells Using the Predicted Peptides from TTK Restricted with HLA-A*0201, and Establishment for CTL Lines Stimulated with TTK Derived Peptides CTLs for those peptides derived from TTK were generated according to the protocols set forth in the "Materials and Methods" section above. Resulting CTLs having detectable specific CTL activity as determined by an IFN-gamma ELISPOT assay are shown in FIG. 8. As depicted in FIG. 8b-d, TTK-A2-9-462 (SEQ ID NO: 227), TTK-A2-9-547 (SEQ ID NO: 228), TTK-A2-9-719 (SEQ ID NO: 233) and TTK-A2-10-462 (SEQ ID NO: 254) demonstrated potent IFN-gamma production by IFN-gamma ELISPOT assay, and the cells in the positive well number #4 stimulated with TTK-A2-9-462 (SEQ ID NO: 227), #2 with TTK-A2-9-547 (SEQ ID NO: 228), #1 with TTK-A2-9-719 (SEQ ID NO: 233) and #8 with TTK-A2-10-462 (SEQ ID NO: 254) were expanded. Those CTL lines having higher specific CTL activities against the peptide-pulsed target as compared to the activities against target without peptide pulse were determined by ELISA. While, other peptides shown in table 9 could not establish the CTL lines despite possible binding activity with HLA-A*0201. For example, the typical negative peptide (TTK-A2-9-278) were shown in FIG. 8a. In this invention, the peptides which could establish CTL line were selected as potent CTL stimulation peptide.

Establishment for CTL Clones Stimulated with TTK Derived Peptides

Furthermore, the limiting dilution from these CTL lines was performed according to the protocols set forth in the "Materials and Methods" section above. The establishment of CTL clones from TTK-A2-9-462 (SEQ ID NO: 227) #4 CTL line, TTK-A2-9-547 (SEQ ID NO: 228) #2 CTL line, TTK-A2-9-719 (SEQ ID NO: 233) #1 CTL line and TTK-A2-10-462 (SEQ ID NO: 254) #8 CTL line were shown in FIGS. 8b, c, d and e. CTL clones had potent and specific CTL activities against the peptide-pulsed target as compared to the activities against target without peptide pulse.

Specific CTL Activity Against the Target Cells Expressing TTK and HLA-A*0201

The established CTL clone raised against these peptides were examined for their ability to recognize the target cells endogenously expressing TTK and HLA-A*0201. Specific CTL activity against COS7 transfected with both the full length TTK gene and the HLA-A*0201 molecule, which is a specific model for the target cells endogenously express TTK and HLA-A*0201, was tested using as effector cells the CTL clones raised by TTK-A2-9-462 (SEQ ID NO: 227), TTK-A02-9-547 (SEQ ID NO: 228), TTK-A2-9-719 (SEQ ID NO: 233) and TTK-A2-10-462 (SEQ ID NO: 254). COS7 transfected with full length TTK but HLA-A*0201, COS7 transfected HLA-A*0201 but not full length of TTK (or replaced full length HIG2 gene) and COS7 transfected with HLA-A*0201 and pulsed with different target epitope peptide, were prepared as controls. The CTL Clone had the highest specific CTL activity against COST that was transfected with both TTK and HLA-A*0201 (FIGS. 8b, c, d and e).

These results clearly demonstrate that TTK-A2-9-462 (SEQ ID NO: 227), TTK-A02-9-547 (SEQ ID NO: 228), TTK-A2-9-719 (SEQ ID NO: 233) and TTK-A02-10-462 (SEQ ID NO: 254) are naturally expressed on the target cell surface with HLA-A2 (HLA-A02) molecule and recognize CTL. Furthermore, these peptides are epitope peptides, which may serve as cancer vaccines targeting TTK expressed tumors.

Stimulation of the T Cells Using the Predicted Peptides from URLC10 Restricted with HLA-A*0201, and Establishment for CTL Lines Stimulated with URLC10 Derived Peptides CTLs for those peptides derived from URLC10 were generated according to the protocols set forth in the "Materials and Methods" section above. Resulting CTLs having detectable specific CTL activity as determined by IFN-gamma ELISPOT assay are shown in FIG. 9. As shown in FIG. 9b-d, URLC-A2-9-206 (SEQ ID NO: 271), URLC-A2-9-212 (SEQ ID NO: 272) and URLC-A2-10-211 (SEQ ID NO: 288) demonstrated potent IFN-gamma production by IFN-gamma ELISPOT assay, and the cells in the positive well number #7 stimulated with URLC-A2-9-206 (SEQ ID NO: 271), #3 with URLC-A2-9-212 (SEQ ID NO: 272) and #5 with URLC-A2-

10-211 (SEQ ID NO: 288) were expanded. Those CTL lines having higher specific CTL activities against the peptide-pulsed target as compared to the activities against target without peptide pulse were determined by ELISA. While, other peptides shown in table 10 could not establish the CTL lines despite possible binding activity with HLA-A*0201. For example, the typical negative peptide (URLC-A2-9-58) were shown in FIG. 9a. In this invention, the peptide which could establish CTL line were selected as potent CTL stimulation peptide.

Specific CTL Activity Against the Target Cells Expressing URLC10 and HLA-A*0201

The established CTL line raised against these peptides were examined for their ability to recognize the target cells endogenously expressing URLC10 and HLA-A*0201. Specific CTL activity against COS7, Hek293 and 293T transfected with both full length URLC10 gene and the HLA-A*0201 molecule, which serves as a specific model for the target cells endogenously express URLC10 and HLA-A*0201, was tested using as effector cells the CTL line raised by URLC10-A02-10-211. COS7, Hek293 or 293T transfected with full length URLC10 but not HLA-A*0201 (replaced HLA-A*2402), COS7, Hek293 or 293T transfected with HLA-A*0201 but not full length URLC10 and COS7 transfected with HLA-A*0201 and pulsed with different target epitope peptide (URLC10-A02-10-64) were prepared as controls. The CTL line demonstrating the highest specific CTL activity against COS7, Hek293 or 293T was that transfected with both URLC10 and HLA-A*0201 (FIG. 9-2).

These results clearly demonstrate that URLC10-A02-10-211 is naturally expressed on the target cell surface with HLA-A*0201 molecule and recognizes CTL. Furthermore, this peptide was epitope peptides, which may utilize cancer vaccine targeting URLC10 expressed tumors.

Homology Analysis of the Antigen Peptides

The CTL clones established against the following peptides showed potent specific CTL activity.

CDH3-A24-9-513 (SEQ ID NO: 19),
CDH3-A24-9-406 (SEQ ID NO: 22),
CDH3-A24-10-807 (SEQ ID NO: 30),
CDH3-A24-10-332 (SEQ ID NO: 34),
CDH3-A24-10-655 (SEQ ID NO: 344),
CDH3-A24-10-470 (SEQ ID NO: 358),
EphA4-A24-9-453 (SEQ ID NO: 41),
EphA4-A24-9-5 (SEQ ID NO: 44),
EphA4-A24-9-869 (SEQ ID NO: 46),
EphA4-A24-9-420 (SEQ ID NO: 48),
EphA4-A24-10-24 (SEQ ID NO: 78),
EphA4-A02-9-501 (SEQ ID NO: 376),
EphA4-A02-9-165 (SEQ ID NO: 379),
ECT2-A24-9-515 (SEQ ID NO: 80),
ECT2-A24-10-40 (SEQ ID NO: 100),
ECT2-A24-10-101 (SEQ ID NO: 101),
HIG2-A24-9-19 (SEQ ID NO: 110),
HIG2-A24-9-22 (SEQ ID NO: 111),
HIG2-A24-9-8 (SEQ ID NO: 387),
HIG2-A24-10-7 (SEQ ID NO: 112),
HIG2-A24-10-18 (SEQ ID NO: 394),
HIG2-A02-9-8 (SEQ ID NO: 114),
HIG2-A02-9-15 (SEQ ID NO: 116),
HIG2-A02-9-4 (SEQ ID NO: 117),
HIG2-A02-10-8 (SEQ ID NO: 121),
INHBB-A24-9-180 (SEQ ID NO: 395),
INHBB-A24-10-180 (SEQ ID NO: 133),
INHBB-A24-10-305 (SEQ ID NO: 135),
INHBB-A24-10-7 (SEQ ID NO: 137),
INHBB-A24-10-212 (SEQ ID NO: 426),
KIF20A-A24-9-305 (SEQ ID NO: 174),
KIF20A-A24-9-383 (SEQ ID NO: 178),
KIF20A-A24-10-304 (SEQ ID NO: 186),
KIF20A-A24-10-66 (SEQ ID NO: 194),
KNTC2-A24-9-309 (SEQ ID NO: 196),
KNTC2-A24-9-124 (SEQ ID NO: 202),
KNTC2-A24-9-154 (SEQ ID NO: 210),
KNTC2-A24-9-150 (SEQ ID NO: 213),
KNTC2-A24-10-452 (SEQ ID NO: 214),
KNTC2-A24-10-227 (SEQ ID NO: 217),
KNTC2-A24-10-273 (SEQ ID NO: 223),
TTK-A02-9-462 (SEQ ID NO: 227),
TTK-A02-9-547 (SEQ ID NO: 228),
TTK-A02-9-719 (SEQ ID NO: 233),
TTK-A02-10-462 (SEQ ID NO: 254),
URLC-A02-9-206 (SEQ ID NO: 271),
URLC-A02-9-212 (SEQ ID NO: 272) and
URLC-A02-10-211 (SEQ ID NO: 288)

This suggests that the sequences of SEQ ID NO: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 174, 178, 186, 194, 196, 202, 210, 213, 214, 217, 223, 227, 228, 233, 254, 271, 272 or 288 are homologous to the peptides derived from other molecules, which are known to sensitize human immune system.

To exclude this possibility, homology analysis was performed with the peptide sequences as queries using BLAST algorithm (http://www.ncbi.nlm.nih.gov/blast/blast.cgi). No significant sequence homology was revealed.

These results suggest that the sequences of SEQ ID NO: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 174, 178, 186, 194, 196, 202, 210, 213, 214, 217, 223, 227, 228, 233, 254, 271, 272 or 288 are unique and thus possess a low risk of raising unintended immunologic response to any unrelated molecule.

Example 2

Materials and Methods

Cell Lines

H2 (HLA-A02), human B-lymphoblastoid cell line, and COST were purchased from ATCC.

Candidate Selection of Peptides Derived from INHBB 9-mer and 10-mer peptides derived from INHBB that bind to HLA-A*0201 molecules were predicted using binding prediction software "BIMAS" (www-bimas.cit.nih.gov/molbio/hla_bind), which algorithms had been described by Parker K C et al. (J Immunol 1994, 152(1): 163-75) and Kuzushima K et al. (Blood 2001, 98(6): 1872-81). These peptides were synthesized by Sigma (Sapporo, Japan) or Biosynthesis Inc. (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (GM-CSF) (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 mcg/ml of each of the synthesized peptides in the presence of 3 mcg/ml of beta2-microglobulin for 3 hr at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by Mitomycin C (MMC) (30 mcg/ml for 30 min) and mixed at a 1:20 ratio with autologous CD8+ T cells, obtained by positive selection with CD8 Positive Isolation Kit (Dynal). These cultures were set up in 48-well plates (Corning); each well contained $1.5 \times 10^4$ peptide-pulsed DCs, $3 \times 10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTL was tested against peptide-pulsed T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 February, 2(2): 216-23). A total of $5 \times 10^4$ CTLs were suspended in 25 ml of AIM-V/5% AS medium with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed T2 ($1 \times 10^4$/well) was prepared as stimulator cells. Cultured cells in 48 wells were used as responder cells. IFN-gamma ELISPOT assay and IFN-gamma ELISA assay were performed under manufacture procedure.

RESULTS

Stimulation of the T Cells Using the Predicted Peptides from INHBB Restricted with HLA-A0201 and Establishment for CTL Lines Stimulated with INHBB Derived Peptides CTLs for those peptides derived from INHBB were generated according to the protocols set forth in "Materials and Methods" section above. Resulting CTLs having detectable specific CTL activity, as determined by IFN-gamma ELISPOT assay, are shown in FIG. 10. INHBB-A02-9-213 (SEQ ID NO: 143), INHBB-A02-9-174 (SEQ ID NO: 147), INHBB-A02-9-257 (SEQ ID NO: 148), INHBB-A02-9-313 (SEQ ID NO: 149), INHBB-A02-9-139 (SEQ ID NO: 150), INHBB-A02-9-8 (SEQ ID NO: 152), INHBB-A02-9-250 (SEQ ID NO: 153), INHBB-A02-10-179 (SEQ ID NO: 154), INHBB-A02-10-237 (SEQ ID NO: 156), INHBB-A02-10-313 (SEQ ID NO: 160), INHBB-A02-10-173 (SEQ ID NO: 161), INHBB-A02-10-256 (SEQ ID NO: 162), INHBB-A02-10-162 (SEQ ID NO: 163) and INHBB-A02-10-85 (SEQ ID NO: 166) demonstrated potent IFN-gamma production as compared to the control by IFN-gamma ELISPOT assay. Furthermore, the cells in the positive well number #7 stimulated with SEQ ID NO: 147, were expanded and CTL line was established. The CTL line having higher specific CTL activity against the peptide-pulsed target as compared to the activity against target without peptide pulse was determined by IFN-gamma ELISA (FIG. 11). The results herein demonstrate that the CTL line demonstrated potent IFN-gamma production against the target cells pulsed with corresponding peptide as compared to target cells without peptide pulse. In the context of the present invention, the peptides which could establish CTL line were selected as potent CTL stimulation peptide.

In conclusion, novel HLA-A02 epitope peptides derived from INHBB were identified and demonstrated to be applicable for cancer immunotherapy.

DISCUSSION

Identification of new TAAs, particularly those that induce potent and specific anti-tumor immune responses, warrants further development of the clinical application of peptide vaccination strategies in various types of cancer (Boon T. et al., (1996) J Exp Med 183: 725-9.; van der Bruggen P et al., (1991) Science 254: 1643-7.; Brichard V et al., (1993) J Exp Med 178: 489-95.; Kawakami Y et al., (1994) J Exp Med 180: 347-52.; Shichijo S et al., (1998) J Exp Med 187:277-88.; Chen Y T et al., (1997) Proc. Natl. Acd. Sci. USA, 94: 1914-8.; Harris C C., (1996) J Natl Cancer Inst 88:1442-5.; Butterfield L H et al., (1999) Cancer Res 59:3134-42.; Vissers J L et al., (1999) Cancer Res 59: 5554-9.; van der Burg S H et al., (1996) J. Immunol. 156:3308-14.; Tanaka F et al., (1997) Cancer Res 57:4465-8.; Fujie T et al., (1999) Int J Cancer 80:169-72.; Kikuchi M et al., (1999) Int J Cancer 81: 459-66.; Oiso M et al., (1999) Int J Cancer 81:387-94.).

cDNA microarray technologies can disclose comprehensive profiles of gene expression of malignant cells (Lin Y M, et al., Oncogene. 2002 Jun. 13; 21:4120-8.; Kitahara O, et al., Cancer Res. 2001 May 1; 61:3544-9.; Suzuki C, et al., Cancer Res. 2003 Nov. 1; 63:7038-41.; Ashida S, Cancer Res. 2004 Sep. 1; 64:5963-72.; Ochi K, et al., Int J Oncol. 2004 March; 24(3):647-55.; Kaneta Y, et al., Int J Oncol. 2003 September; 23:681-91.; Obama K, Hepatology. 2005 June; 41:1339-48.; Kato T, et al., Cancer Res. 2005 Jul. 1; 65:5638-46.; Kitahara O, et al., Neoplasia. 2002 July-August; 4:295-303.; Saito-Hisaminato A et al., DNA Res 2002, 9: 35-45.) and, find utility in the identification of potential TAAs. Among the transcripts that are up-regulated in various cancers, novel human genes, termed CDH3, EPHA4, ECT2, HIG2, INHBB, KIF20A, KNTC2, TTK and URLC10, were identified using these technologies.

As demonstrated above, CDH3, EPHA4, ECT2, HIG2, INHBB, KIF20A, KNTC2, TTK and URLC10, are over-expressed in various cancers but show minimal expression in normal tissues. In addition, these genes have been shown to have a significant function related to cell proliferation. Thus, peptides derived from CDH3, EPHA4, ECT2, HIG2, INHBB, KIF20A, KNTC2, TTK and URLC10 can serve as TAA epitopes, which, in turn, can be used to induce significant and specific immune responses against cancer cells.

Thus, as CDH3, EPHA4, ECT2, HIG2, INHBB, KIF20A, KNTC2, TTK and URLC10 are novel TAAs, vaccines using these epitope peptides find utility as immunotherapeutics against various carcinomas or other disease expressing these molecules.

INDUSTRIAL APPLICABILITY

The present invention identifies new TAAs, particularly those which induce potent and specific anti-tumor immune responses. Such TAAs warrants further development as peptide vaccines against diseases associated with the over-expression of CDH3, EPHA4, ECT2, HIG2, INHBB, KIF20A, KNTC2, TTK and/or, URLC10 e.g. cancers. All patents, patent applications, and publications cited herein are incorporated by reference.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. A method of treating a cancer expressing URLC10 and HLA-A2 in a subject, said method comprising administering to said subject a composition comprising a peptide selected from the group consisting of the following (i) and (ii), or a polynucleotide encoding said peptide:
   (i) an isolated peptide of less than 15 amino acids having cytotoxic T cell inducibility, wherein said peptide comprises the amino acid sequence of SEQ ID NO: 288; and
   (ii) an isolated peptide of less than 15 amino acids having cytotoxic T cell inducibility, wherein said peptide comprises an amino acid sequence of SEQ ID NO: 288 in which 1 or 2 amino acids are substituted.

2. The method of treating cancer of claim 1, wherein the cancer is selected from the group consisting of bladder cancer, cervical cancer, cholangiocellular carcinoma, esophageal cancer, gastric cancer, NSCLC, osteosarcoma, pancreatic cancer, and soft tissue tumor.

3. The method of claim 1, wherein the peptide of (ii) has one or both of the following characteristics:
   (a) the second amino acid from the N-terminus of the amino acid sequence of SEQ ID NO: 288 is substituted with methionine; and
   (b) the C-terminal amino acid of the amino acid sequence of SEQ ID NO: 288 is substituted with valine.

4. A method of treating cancer expressing URLC10 and HLA-A2 in a subject, said method comprising administering to said subject a composition comprising a peptide selected from the group consisting of following (i) and (ii) or a polynucleotide encoding said peptide:
   (i) an isolated peptide consisting of the amino acid sequence of SEQ ID NO: 288; and
   (ii) an isolated peptide having cytotoxic T cell inducibility, wherein said peptide consists of an amino acid sequence of SEQ ID NO: 288 in which 1 or 2 amino acids are substituted.

* * * * *